(12) United States Patent
Jais

(10) Patent No.: US 9,540,671 B2
(45) Date of Patent: *Jan. 10, 2017

(54) CAPPING PRONE RNA POLYMERASE ENZYMES AND THEIR APPLICATIONS

(71) Applicant: EUKARYS, Beauvais (FR)

(72) Inventor: Philippe Jais, Issy les Moulineaux (FR)

(73) Assignee: EUKARYS, Evry (FR)

( * ) Notice: Subject to any disclaimer, the term of this patent is extended or adjusted under 35 U.S.C. 154(b) by 55 days.

This patent is subject to a terminal disclaimer.

(21) Appl. No.: 14/598,874

(22) Filed: Jan. 16, 2015

(65) Prior Publication Data
US 2015/0203888 A1 Jul. 23, 2015

Related U.S. Application Data

(63) Continuation of application No. 13/641,584, filed as application No. PCT/EP2011/056051 on Apr. 15, 2011, now Pat. No. 8,962,292.

(30) Foreign Application Priority Data

Apr. 16, 2010 (EP) .................................... 10305400

(51) Int. Cl.
| C12N 9/14 | (2006.01) |
|---|---|
| C12P 19/34 | (2006.01) |
| C12N 9/10 | (2006.01) |
| C12N 9/12 | (2006.01) |
| A61K 38/00 | (2006.01) |

(52) U.S. Cl.
CPC ............. *C12P 19/34* (2013.01); *C12N 9/1007* (2013.01); *C12N 9/1241* (2013.01); *C12N 9/1247* (2013.01); *C12N 9/14* (2013.01); *A61K 38/00* (2013.01); *C07K 2319/00* (2013.01); *C12Y 201/01056* (2013.01); *C12Y 306/04013* (2013.01)

(58) Field of Classification Search
CPC ................................ C12N 9/1247; C12N 9/14
See application file for complete search history.

(56) References Cited

U.S. PATENT DOCUMENTS

| 5,126,251 A | 6/1992 | Moss et al. |
|---|---|---|
| 6,312,926 B1 | 11/2001 | Shatkin et al. |
| 7,056,683 B2 | 6/2006 | Ting et al. |
| 8,962,292 B2 | 2/2015 | Jais |
| 2013/0042334 A1 | 2/2013 | Jais |

OTHER PUBLICATIONS

Brisson et al., "A Novel T7 RNA Polymerase Autogene for Efficient Cytoplasmic Expression of Target Genes", Gene Therapy, vol. 6, 1999, pp. 263-270.

Chimeric Enzyme Definition 2013; answers.yahoo.com/question/index?qid=1006030904934.

Deuschle et al. 1989; Regulated expression of foreign genes in mammalian cells under the control of coliphage T3 RNA polymerase and lac repressor. PNAS 86: 5400-5404.

Dower et al., "T7 RNA Polymerase-directed Transcripts are Processed in Yeast and Link 3' end Formation to mRNA Nuclear Export", Howard Hughes Medical Institute, Departement of Bioloav, Brandeis University, vol. 8, 2002, pp. 686-697.

Elroy-Stein et al. 1990; Cytoplasmic expression system based on constitutive synthesis bacteriophage T7 RNA polymerase in mammalian cells. PNAS 87: 6743-6747.

Elroy-Stein et al., "Cap-independent translation of mRNA conferred by encephalomyocarditis virus 5' sequence improves the performance of the vaccinia virus/bacteriophage T7 hybrid expression system", Proc. Natl. A cad. Sci. USA, vol. 86, pp. 6126-6130, Aug. 1989.

Fuerst et al. 1989; Structure and stability of mRNA synthesized by vaccinia virus-encoded bacteriophage T7 RNA polymerase in mammalian cells. J. Mol.Biol 206: 333-348.

Gallie, "The Cap and Poly(A) tail Function Synergistically to Regulate mRNA Translational Efficiency", Genes & Development, vol. 5, 1991, pp. 2108-2116.

Ho et al., "A Yeast-Based Genetic System for Functional Analysis of Viral mRNA Capping Enzymes", Journal of Virology, vol. 74, No. 12, Jun. 2000, pp. 5486-5494.

McCracken et al. 1997; 5'-capping enzymes are targeted to pre-mRNA by binding to the phosphorylated carboxy-terminal domain of RNA polymerase II. Genes & Development. 11:33-6-3318.

McCracken et al., "Role of RNA Polymerase II Carboxy-Terminal Domain in Coordinating Transcription with RNA Processing", vol. 63, 1998, pp. 301-309.

Natalizio et al., "The Carboxyl-terminal Domain of RNA Polymerase II is not Sufficient to Enhance the Efficiency of Pre-mRNA Capping or Splicing in the Context of a Different Polymerase", The Journal of Biological Chemistry, vol. 284, No. 13, Mar. 27, 2009, pp: 8692-8702.

RNA Polymerase. 2013; en.wikipedia.org/wiki/RNA_polymerase.

Shuman 2002. What messenger RNA capping tells us about eukaryotic evolution. Nature Reviews Molecular Cell Biology. 3:619-625.

Shuman et al. 1997; Origins of mRNA identify: capping enzymes bind to the phosphorylated C-terminal domain of RNA polymerase 11. PNAS 94: 12758-12760.

Vos et al. 1991; Vaccinia virus capping enzyme is a transcription initiation factor. EMBO J. 10(9): 2553-2558.

PCT International Search Report of PCT/EP2011/056051.

(Continued)

*Primary Examiner* — Karen Cochrane Carlson
(74) *Attorney, Agent, or Firm* — Fish & Richardson P.C.

(57) ABSTRACT

The invention provides a chimeric enzyme comprising at least one catalytic domain of a RNA triphosphatase, at least one catalytic domain of a guanylyltransferase, at least one catalytic domain of a $N^7$-guanine methyltransferase, and at least one catalytic domain of a DNA-dependant RNA polymerase. The invention also provides pharmaceutical composition comprising said chimeric enzyme and uses of said chimeric enzyme.

13 Claims, 17 Drawing Sheets

(56) References Cited

OTHER PUBLICATIONS

Bedzyk et al "Immunological and structural characterization of a high affinity anti-fluorescein single-chain antibody" J Biol Chem. 1990, 265(30):18615-18620.

Bengal et al "Role of the mammalian transcription factors IIF, IIS, and IIX during elongation by RNA polymerase II" Mol Cell Biol. 1991, 11(3):1195-1206.

Benton et al "Signal-mediated import of bacteriophage T7 RNA polymerase into the *Saccharomyces cerevisiae* nucleus and specific transcription of target genes" Mol Cell Biol. 1990, 10(1):353-360.

Bird et al "Single-chain antigen-binding proteins" Science. 1988, 242(4877):423-426.

Busch et al "Secondary structure composition and pH-dependent conformational changes of soluble recombinant HLA-DM" J Biol Chem. 1998, 273(42):27557-27564.

Busch et al "Stabilization of soluble, low-affinity HLA-DM/HLA-DR1 complexes by leucine zippers" J Immunol Methods. 2002, 263(1-2):111-121.

Bushnell et al "Structural basis of transcription: alpha-amanitin-RNA polymerase II cocrystal at 2.8 A resolution" Proc Natl Acad Sci U.S.A. 2002, 99(3):1218-1222.

Chang et al "A general method for facilitating heterodimeric pairing between two proteins: application to expression of alpha and beta T-cell receptor extracellular segments" Proc Natl Acad Sc U.S.A. 1994, 91(24):11408-11412.

Chen and Schneider "Information theory based T7-like promoter models: classification of bacteriophages and differential evolution of promoters and their polymerases" Nucleic Acids Res. 2005, 33(19):6172-6187.

Chen et al "A self-initiating eukaryotic transient gene expression system based on contransfection of bacteriophage T7 RNA polymerase and DNA vectors containing a T7 autogene" Nucleic Acids Res. 1994, 22(11):2114-2120.

Cho et al "mRNA capping enzyme is recruited to the transcription complex by phosphorylation of the RNA polymerase II carboxy-terminal domain" Genes Dev. 1997, 11(24):3319-3326.

Clayton "Replication and transcription of vertebrate mitochondrial DNA" Annu Rev Cell Biol. 1991, 7:453-478.

Cong and Shuman "Covalent catalysis in nucleotidyl transfer. A KTDG motif essential for enzyme-GMP complex formation by mRNA capping enzyme is conserved at the active sites of RNA and DNA ligases" J Biol Chem. 1993, 268(10):7256-7260.

Cong et al "Linear DNA plasmids from Pichia etchellsii, Debaryomyces hansenii and Wingea robertsiae" Microbiology. 1994, 140(Pt 6):1327-1335.

Crasto and Feng "LINKER: a program to generate linker sequences for fusion proteins" Protein Eng. 2000, 13(5):309-312.

Cronan "Biotination of proteins in vivo. A post-translational modification to label, purify, and study proteins" J Biol Chem. 1990, 265(18):10327-33.

Davanloo et al "Cloning and expression of the gene for bacteriophage T7 RNA polymerase" Proc Natl Acad Sci U.S.A. 1984, 81(7):2035-2039.

Dias and Stein "Antisense oligonucleotides: basic concepts and mechanisms" Mol Cancer Ther. 2002, 1(5):347-355.

Drummond et al "The effect of capping and polyadenylation on the stability, movement and translation of synthetic messenger RNAs in Xenopus oocytes" Nucleic Acids Res. 1985, 13(20):7375-7394.

Engleka et al "Mechanisms of replication-deficient vaccinia virus/T7 RNA polymerase hybrid expression: effect of T7 RNA polymerase levels and alpha-amanitin" Virology. 1998, 243(2):331-339.

Fancy and Kodadek "Chemistry for the analysis of protein-protein interactions: rapid and efficient cross-linking triggered by long wavelength light" Proc Natl Acad Sci U.S.A., 1999, 96(11):6020-6024.

Fernandez-Silva et al "The human mitochondrial transcription termination factor (mTERF) is a multizipper protein but binds to DNA as a monomer, with evidence pointing to intramolecular leucine zipper interactions" EMBO J. 1997, 16(5):1066-1079.

Finn et al "Factors limiting autogene-based cytoplasmic expression systems" Faseb J. 2005, 19(6):608-610.

Fire et al "Interactions between RNA polymerase II, factors, and template leading to accurate transcription" J Biol Chem; 1984, 259(4):2509-2516.

Fisher and Clayton "A transcription factor required for promoter recognition by human mitochondrial RNA polymerase. Accurate initiation at the heavy- and light-strand promoters dissected and reconstituted in vitro" J Biol Chem. 1985, 260(20):11330-11338.

Fisher and Clayton "Purification and characterization of human mitochondrial transcription factor 1" Mol Cell Biol. 1988, 8(8):3496-3509.

Fisher et al "Promoter selection in human mitochondria involves binding of a transcription factor to orientation-independent upstream regulatory elements" Cell. 1987, 50(2):247-258.

Fortes et al "Inhibiting expression of specific genes in mammalian cells with 5' end-mutated U1 small nuclear RNAs targeted to terminal exons of pre-mRNA." Proc Natl Acad Sci U.S.A., 2003, 100(14):8264-8269.

Fuerst et al "Eukaryotic transient-expression system based on recombinant vaccinia virus that synthesizes bacteriophage T7 RNA polymerase" Proc Natl Acad Sci U.S.A. 1986, 83(21):8122-8126.

Fuerst et al "Transfer of the inducible lac repressor/operator system from *Escherichia coli* to a vaccinia virus expression vector" Proc Natl Acad Sic U.S.A. 1989, 86(8):2549-2553.

Fuerst et al "Use of a hybrid vaccinia virus-T7 RNA polymerase system for expression of target genes" Mol Cell Biol. 1987, 7(7):2538-2544.

Furuichi and Shatkin "Viral and cellular mRNA capping: past and prospects" Adv Virus Res. 2000, 55:135-184.

Furuichi et al "5'-Terminal structure and mRNA stability" Nature. 1977, 266(5599):235-239.

Gao and Huang "Cytoplasmic expression of a reporter gene by co-delivery of T7 RNA polymerase and T7 promoter sequence with cationic liposomes" Nucleic Acids Res. 1993, 21(12):2867-2872.

Ghosh et al "Antiparallel Leucine Zipper-Directed Protein Reassembly: Application to the Green Fluorescent Protein" J Am Chem Soc. 2000, 122(23):5658-5659.

Gill et al "Increased persistence of lung gene expression using plasmids containing the ubiquitin C or elongation factor lalpha promote" Gene Ther. 2001, 8(20):1539-1546.

Gingras et al "eIF4 initiation factors: effectors of mRNA recruitment to ribosomes and regulators of translation" Annu Rev Biochem. 1999, 68:913-963.

Golomb and Chamberlin "Characterization of T7-specific ribonucleic acid polymerase. IV. Resolution of the major in vitro transcripts by gel electrophoresis" J Biol Chem. 1974, 249(9):2858-2863.

Gong and Shuman "Mapping the active site of vaccinia virus RNA triphosphatase" Virology. 2003, 309(1):125-134.

Gregoire et al "Covalent assembly of a soluble T cell receptor-peptide-major histocompatibility class I complex" Proc Natl Acad Sci U.S.A. 1996, 93(14):7184-7189.

Gustavsson et al "Stable linker peptides for a cellulose-binding domain-lipase fusion protein expressed in Pichia pastoris" Protein Eng. 2001, 14(9):711-715.

Han et al "Mutational analysis of a helicase motif-based RNA 5'-triphosphatase/NTPase from bamboo mosaic virus" Virology. 2007, 367(1):41-50.

Hennecke et al "Non-repetitive single-chain Fv linkers selected by selectively infective phage (SIP) technology" Protein Eng. 1998, 11(5):405-410.

Higman and Niles "Location of the S-adenosyl-L-methionine binding region of the vaccinia virus mRNA (guanine-7-)methyltransferase" J Biol Chem. 1994, 269(21):14982-14987.

Higman et al "The mRNA (guanine-7-)methyltransferase domain of the vaccinia virus mRNA capping enzyme. Expression in *Escherichia coli* and structural and kinetic comparison to the intact capping enzyme" J Biol Chem. 1994, 269(21):14974-14981.

Higman et al "The vaccinia virus mRNA (guanine-N7-)-methyltransferase requires both subunits of the mRNA capping enzyme for activity" J Biol Chem. 1992, 267(23):16430-16437.

(56) References Cited

OTHER PUBLICATIONS

Hu et al "A flexible peptide linker enhances the immunoreactivity of two copies HBsAg preS1 (21-47) fusion protein" J Biotechnol. 2004, 107(1):83-90.
Huang and Steitz "SRprises along a messenger's journey" Mol Cell. 2005, 17(5):613-615.
Huston et al "Protein engineering of antibody binding sites: recovery of specific activity in an anti-digoxin single-chain Fv analogue produced in *Escherichia coli*" Proc Natl Acad Sci U.S.A. 1988, 85(16):5879-5883.
Izban and Luse "Factor-stimulated RNA polymerase II transcribes at physiological elongation rates on naked DNA but very poorly on chromatin templates" J Biol Chem. 1992, 267(19):13647-13655.
Jacob et al "Specific action of alpha-amanitin on mammalian RNA polymerase protein" Nature. 1970, 225(5227):60-62.
Kedinger et al "Alpha-amanitin. A specific inhibitor of one of two DNA-pendent RNA polymerase activities from calf thymus" Biochem Biophys Res Commun. 1970, 38(1):165-171.
Kohler and Hurt "Exporting RNA from the nucleus to the cytoplasm" Nat Rev Mol Cell Biol. 2007, 8(10):761-773.
Komarnitsky et al "Different phosphorylated forms of RNA polymerase II and associated mRNA processing factors during transcription" Genes Dev. 2000, 14(19):2452-2460.
Kozak "Regulation of translation via mRNA structure in prokaryotes and eukaryotes" Gene. 2005, 361:13-37.
Kruse et al "Termination of transcription in human mitochondria: identification and purification of a DNA binding protein factor that promotes termination" Cell. 1989, 58(2):391-397.
Kuge et al "Cap ribose methylation of c-mos mRNA stimulates translation and oocyte maturation in Xenopus laevis" Nucleic Acids Res. 1998, 26(13):3208-3214.
Kupper et al "Comparison of *Escherichia coli* and T3 RNA polymerases. Differential inhibition of transcription by various drugs" Eur J Biochem. 1973, 38(3):581-586.
Lamla and Erdmann "The Nano-tag, a streptavidin-binding peptide for the purification and detection of recombinant proteins" Protein Expr Purif. 2004, 33(1):39-47.
Lang et al "Molecular mobility and nucleocytoplasmic flux in hepatoma cells" J Cell Biol. 1986, 102(4):1183-1190.
Langberg and Moss "Post-transcriptional modifications of mRNA. Purification and characterization of cap I and cap II RNA (nucleoside-2'-)-methyltransferases from HeLa cells" J Biol Chem. 1981, 256(19):10054-10060.
Lee et al "Transcription pausing by *Escherichia coli* RNA polymerase is modulated by downstream DNA sequences" J Biol Chem. 1990, 265(25):15145-15153.
Li et al "Characterization of the AdoMet-dependent guanylyltransferase activity that is associated with the N terminus of bamboo mosaic virus replicase" J Virol. 2001, 75(2):782-788.
Li et al "Identification and characterization of the *Escherichia coli*-expressed RNA-dependent RNA polymerase of bamboo mosaic virus" J Virol. 1998, 72(12):10093-10099.
Li et al "The helicase-like domain of plant potexvirus replicase participates in formation of RNA 5' cap structure by exhibiting RNA 5'-triphosphatase activity" J Virol. 2001, 75(24):12114-12120.
Lian et al "The sCYMV1 hairpin ribozyme: targeting rules and cleavage of heterologous RNA" Gene Ther. 1999, 6(6):1114-1119.
Lieschke et al "Bioactive murine and human interleukin-12 fusion proteins which retain antitumor activity in vivo" Nat Biotechnol. 1997, 15(1):35-40.
Lindell et al "Specific inhibition of nuclear RNA polymerase II by alpha-amanitin" Science. 1970, 170(956):447-449.
Lisser and Margalit "Compilation of *E. coli* mRNA promoter sequences" Nucleic Acids Res. 1993, 21(7):1507-1516.
Liu and Carmichael "Nuclear antisense RNA. An efficient new method to inhibit gene expression" Mol Biotechnol. 1994, 2(2):107-118.
Liu et al "Anti-proteolysis study of recombinant IIn-UK fusion protein in CHO cells" Prog Biochem Biophys. 2005, 32(6):544-550.
Lo et al "RNA polymerase I-promoted HIS4 expression yields uncapped, polyadenylated mRNA that is unstable and inefficiently translated in *Saccharomyces cerevisiae*" Mol Cell Biol. 1998, 18(2):665-675.
Loser et al "Reactivation of the previously silenced cytomegalovirus major immediate-early promoter in the mouse liver: involvement of NFkappaB" J Virol. 1998, 72(1):180-190.
Lumb and Kim "A buried polar interaction imparts structural uniqueness in a designed heterodimeric coiled coil" Biochemistry. 1995, 34(27):8642-8648.
Makarova et al "Transcribing of *Escherichia coli* genes with mutant T7 RNA polymerases: stability of lacZ mRNA inversely correlates with polymerase speed" Proc Natl Acad Sci U.S.A. 1995, 92(26):12250-12254.
Malone et al "Cationic liposome-mediated RNA transfection" Proc Natl Acad Sci U.S.A. 1989, 86(16):6077-6081.
Mantile et al "Stable, long-term bacterial production of soluble, dimeric, disulfide-bonded protein pharmaceuticals without antibiotic selection" Biotechnol Prog. 2000, 16(1):17-25.
Mao and Shuman "Intrinsic RNA (guanine-7) methyltransferase activity of the vaccinia virus capping enzyme D1 subunit is stimulated by the D12 subunit. Identification of amino acid residues in the D1 protein required for subunit association and methyl group transfer" J Biol Chem. 1994, 269(39):24472-24479.
Martinez-Costas et al "Guanylyltransferase and RNA 5'-triphosphatase activities of the purified expressed VP4 protein of bluetongue virus" J Mol Biol. 1998, 280(5):859-866.
McClain et al "Design and Characterization of a Heterodimeric Coiled Coil that Forms Exclusively with an Antiparallel Relative Helix Orientation" J Am Chem Soc. 2001, 123(13):3151-3152.
McCulloch et al "A human mitochondrial transcription factor is related to RNA adenine methyltransferases and binds S-adenosylmethionine" Mol Cell Biol. 2002, 22(4);1116-1125.
Miao et al "High-level factor VIII gene expression in vivo achieved by nonviral liver-specific gene therapy vectors" Hum Gen Ther. 2003, 14(14):1297-1305.
Miao et al "Long-term and therapeutic-level hepatic gene expression of human factor IX after naked plasmid transfer in vivo" Mol Ther. 2001, 3(6):947-957.
Mifflin and Kellems "Coupled transcription-polyadenylation in a cell-free system" J Biol Chem. 1991, 266(29):19593-19598.
Moffatt et al "Nucleotide sequence of the gene for bacteriophage T7 RNA polymerase" J Mol Biol. 1984, 173(2):265-269.
Moll et al "Designed heterodimerizing leucine zippers with a ranger of pIs and stabilities up to 10(-15) M" Protein Sci. 2001, 10(3):649-655.
Newton et al "Angiogenin single-chain immunofusions: influence of peptide linkers and spacers between fusion protein domains" Biochemistry. 1996, 35(2):545-553.
Nicol et al "Poly-L-glutamate, an anionic polymer, enhances transgene expression for plasmids delivered by intramuscular injection with in vivo electroporation" Gene Ther. 2002, 9(20):1351-1358.
Niles and Christen "Identification of the vaccinia virus mRNA guanyltransferase active site lysine" J Biol Chem. 1993, 268(33):24986-24989.
Oakley and Kim "A buried polar interaction can direct the relative orientation of helices in a coiled coil" Biochemistry. 1998, 37(36):12603-12610.
Ojala et al "tRNA punctuation model of RNA processing in human mitochondria" Nature. 1981, 290(5806):470-474.
O'Shea et al "Peptide 'Velcro': design of a heterodimeric coiled coil" Curr Biol. 1993, 3(10):658-667.
O'Shea et al "X-ray structure of the GCN4 leucine zipper, a two-stranded, parallel coiled coil" Science. 1991, 254(5031):539-544.
Osumi-Davis et al "Asp537, Asp812 are essential and Lys631, His811 are catalytically significant in bacteriophage T7 RNA polymerase activity" J Mol Biol. 1992, 225(1):37-45.
Osumi-Davis et al "Bacteriophage T7 RNA polymerase and its active-site mutants. Kinetic, spectroscopic and calorimetric characterization" J Mol Biol. 1994, 237(1):5-19.

(56) References Cited

OTHER PUBLICATIONS

Paguirigan and Beebe "Protocol for the fabrication of enzymatically crosslinked gelatin microchannels for microfluidic cell culture" Nat Protoc. 2007, 2(7):1782-1788.
Palancade and Bensaude "Investigating RNA polymerase II carboxyl-terminal domain (CTD) phosphorylation" Eur J Biochem. 2003, 270(19):3859-3870.
Pantoliano et al "Conformational stability, folding, and ligand-binding affinity of single-chain Fv immunoglobulin fragments expressed in *Escherichia coli*" Biochemistry. 1991, 30(42):10117-10125.
Pashine et al "Interaction of HLA-DR with an acidic face of HLA-DM disrupts sequence-dependent interactions with peptides" Immunity. 2003, 19(2):183-192.
Patil et al "Anionic liposomal delivery system for DNA transfection" AAPS J. 2004, 6(4):e29.
Pavlinkova et al "Pharmacokinetics and biodistribution of engineered single-chain antibody constructs of MAb CC49 in colon carcinoma xenografts" J Nucl Med. 1999, 40)9):1536-1546.
Prieto-Martin et al "A study on the human mitochondrial RNA polymerase activity points to existence of a transcription factor B-like protein" FEBS Lett. 2001, 503(1):51-55.
Ramadevi et al "A leucine zipper-like domain is essential for dimerization and encapsidation of bluetongue virus nucleocapsid protein VP4" J Virol. 1998, 72(4):2983-2990.
Ramadevi et al "Capping and methylation of mRNA by purified recombinant VP4 protein of bluetongue virus" Proc Natl Acad Sci U.S.A. 1998, 95(23):13537-13542.
Ramsey-Ewing and Moss "Recombinant protein synthesis in Chinese hamster ovary cells using a vaccinia virus/bacteriophage T7 hybrid expression system" J Biol Chem. 1996, 271(28):16962-16966.
Rhoads "Signal transduction pathways that regulate eukaryotic protein synthesis" J Biol Chem. 1999, 274(43):30337-30340.
Robinson and Sauer "Optimizing the stability of single-chain proteins by linker length and composition mutagenesis" Proc Natl Acad Sci U.S.A. 1998, 95(11):5929-5934.
Salehi-Ashtiani and Szostak "In vitro evolution suggests multiple origins for the hammerhead ribozyme" Nature. 2001, 414(6859):82-84.
Schmidt and Skerra "The random peptide library-assisted engineering of a C-terminal affinity peptide, useful for the detection and purification of a functional Ig Fv fragment" Protein Eng. 1993, 6(1):109-122.
Schroeder et al "Dynamic association of capping enzymes with transcribing RNA polymerase II" Genes Dev. 2000, 14(19):2435-2440.
Shao et al "Anchor-chain molecular system for orientation control in enzyme immobilization" Bioconjug Chem. 2000, 11(6):822-826.
Spehner et al "A cowpox virus gene required for multiplication in Chinese hamster ovary cells" J Virol. 1988, 62(4):1297-1304.
Studier et al "Use of T7 RNA polymerase to direct expression of cloned genes" Methods Enzymol. 1990, 185:60-89.
Tang et al "Selection of linkers for a catalytic single-chain antibody using phage display technology" J Biol Chem. 1996, 271(26):15682-15686.
Ting et al "Genetically encoded fluorescent reporters of protein tyrosine kinase activities in living cells" Proc Natl Acad Sci U.S.A. 2001, 98(26):15003-15008.
Tiranti et al "Identification of the gene encoding the human mitochondrial RNA polymerase (h-mtRPOL) by cyberscreening of the Expressed Sequence Tags database" Hum Mol Genet. 1997, 6(4):615-625.
Tommasino et al "Genome organization of the killer plasmid pGK12 from Kluyveromyces lactis" Nucleic Acids Res. 1988, 16(13):5863-5878.
Topper and Clayton "Identification of transcriptional regulatory elements in human mitochondrial DNA by linker substitution analysis" Mol Cell Biol. 1980, 9(3):1200-1211.
Turner et al "Importance of the linker in expression of single-chain Fv antibody fragments: optimisation of peptide sequence using phage display technology" J Immunol Methods. 1997, 205(1):43-54.
Ucker and Yamamoto "Early events in the stimulation of mammary tumor virus RNA synthesis by glucocorticoids. Novel assays of transcription rates" J Biol Chem. 1984, 259(12):74116-7420.
Uptain and Chamberlin "*Escherichia coli* RNA polymerase terminates transcription efficiently at rho-independent terminators on single-stranded DNA templates" Proc Natl Acad Sci U.S.A. 1997, 94(25):13548-13553.
Wells and Powers "In vivo formation and stability of engineered disulfide bonds in subtilisin" J Biol Chem. 1986, 261(14):66564-6570.
Whitlow et al "An improved linker for single-chain Fv with reduced aggregation and enhanced proteolytic stability" Protein Eng. 1993, 6(8):989-995.
Wickham et al "Targeting of adenovirus penton base to new receptors through replacement of its RGD motif with other receptor-specific peptide motifs" Gene Ther. 1995, 2(10):750-756.
Wu et al "Design, production, and characterization of an engineered biotin ligase (BirA) and its application for affinity purification of staphylokinase produced from Bacillus subtilis via secretion" Protein Expr Purif. 2002, 24(3):357-365.
Wyatt et al "Replication-deficient vaccinia virus encoding bacteriophage T7 RNA polymerase for transient gene expression in mammalian cells" Virology. 1995, 210(1):202-205.
Yue et al "Mammalian capping enzyme complements mutant *Saccharomyces cerevisiae* lacking mRNA guanylyltransferase and selectively binds the elongating form of RNA polymerase II" Proc Natl Acad Sci U.S.A. 1997, 94(24):12898-12903.
Zabner et al "Cellular and molecular barriers to gene transfer by a cationic lipid" J Biol Chem. 1995, 270(32):18997-19007.
Zhang and Studier "Mechanism of inhibition of bacteriophage T7 RNA polymerase by T7 lysozyme" J Mol Biol. 1997, 269(1):10-27.

**BamHI digested pT7p-Luciferase
7287 bp**

CAPPING PRONE RNA POLYMERASE ENZYMES AND THEIR APPLICATIONS

The sequence listing text file (65002US_Sequence_Listing.txt, created Mar. 31, 2014, 163,840 bytes) is incorporated by reference in its entirety herein.

The present invention relates to the field of transgenesis, particularly in eukaryotic cells.

In particular, the invention relates to a chimeric enzyme useful for the production of RNA molecules with 5'-terminal $m^7$GpppN cap structures.

Eukaryotic expression is very widely used in the life sciences, biotechnology and medicine. Thus, many methods for efficient transgenesis in eukaryotic cells have been developed. Common DNA sources and delivery mechanisms are viruses (e.g. baculovirus, retrovirus, or adenovirus) or non-viral vectors including plasmids and artificial chromosomes.

Because of their simplicity, the non-viral plasmids are commonly used as expression vectors for gene transfer into eukaryotic cells both in vitro and in vivo applications. However, the levels of transgene expression achieved by non-viral methods are usually modest and declines rapidly. A common explanation for this modest efficacy is the fact that DNA molecules, which are over approximately 40,000 Daltons, are too large to pass through the nuclear pores and enter the nucleus, where they are transcribed by the nuclear RNA polymerase II (Lang, Scholz et al. 1986; Zabner, Fasbender et al. 1995). In fact, only a very small amount (<0.1-0.001%) of large DNA molecules is actively transferred from the cytoplasm to the nucleus of eukaryotic cells. The mechanisms by which expression rapidly declines are also possibly nuclear-specific and related to the silencing of transgene expression by various epigenetic mechanisms (Loser, Jennings et al. 1998; Gill, Smyth et al. 2001; Miao, Thompson et al. 2001; Nicol, Wong et al. 2002; Miao, Ye et al. 2003).

Other drawbacks of transgenesis methods using endogenous RNA transcription system of eukaryotic cells also restrain their use. Firstly, the weak processivity of nuclear eukaryotic RNA polymerases (e.g. 10-20 nucleotides/second for RNA polymerase II) (Fire, Samuels et al. 1984; Ucker and Yamamoto 1984; Bengal, Flores et al. 1991; Izban and Luse 1992). Secondly, the competition between endogenous gene transcription and transgene transcription. Thirdly, the extreme complexity of eukaryotic RNA polymerases, which are made of several subunits (e.g. 12 subunits for RNA polymerase II and regulated by multiple transcription factors (Lodish, Berk et al. 2008).

In view of these disadvantages, some transgenesis methods based on bacteriophage DNA-dependent RNA polymerases have been developed. These methods have notably the advantage of not using the endogenous RNA transcription system of eukaryotic cells but some bacteriophage DNA-dependent RNA polymerases, which have a higher processivity than the eukaryotic RNA polymerases.

The pET expression system is a popular method for gene expression in prokaryotes (Studier, Rosenberg et al. 1990). It relies on the expression of the bacteriophage single-subunit T7 DNA-dependent RNA polymerase (T7 RNA polymerase, T7RNAP), the product of T7 gene 1, to transcribe genes of interest engineered to be expressed under the control of a T7 promoter. The pET expression system has been adapted to eukaryotic cells and is usually designated as the hybrid RNA polymerase. However, in an eukaryotic environment, the high enzymatic activity of the T7 DNA dependent RNA polymerase remarkably contrasts with very weak translation yields of the T7 transcripts (Fuerst, Niles et al. 1986). The absence of maturation of the transcripts in eukaryotic cells, which are neither modified by the addition of cap structures at their 5'-terminal (Benton, Eng et al. 1990; Dower and Rosbash 2002), nor strongly polyadenylated at their 3'-terminal (Mifflin and Kellems 1991; Dower and Rosbash 2002), provides an explanation for this discrepancy.

Methods for improving the translatability of uncapped transcripts produced by the hybrid system have thus been developed, like the vaccinia virus/bacteriophage RNAP hybrid expression system. This eukaryotic expression system is based on a recombinant vaccinia virus that synthesizes the bacteriophage T7 DNA dependent RNA polymerase in the cytoplasm of infected mammalian cells (Fuerst, Niles et al. 1986; Fuerst, Earl et al. 1987; Elroy-Stein, Fuerst et al. 1989; Fuerst, Fernandez et al. 1989; Fuerst and Moss 1989; Elroy-Stein and Moss 1990). The target gene for the bacteriophage RNA polymerase, flanked by T7 promoter and termination sequences, is introduced into infected cells either by transfection of a recombinant plasmid or by infection with a second recombinant vaccinia virus (Fuerst, Niles et al. 1986; Elroy-Stein, Fuerst et al. 1989; Elroy-Stein and Moss 1990). It was expected that the vaccinia virus-encoded cytoplasmic enzymes for mRNA capping would act on the T7 transcripts to improve their translatability. However, the capping of T7 transcripts remains infra-optimal (Fuerst and Moss 1989). For instance, using this expression system, it was found that T7 transcripts can comprise up to 30% of total cytoplasmic RNA after a 24 hour period, but only 5%-10% of T7 transcripts contained 5'-terminal cap structures (Fuerst and Moss 1989). Although rather efficient, technical drawbacks of the vaccinia virus/bacteriophage RNAP hybrid expression system clearly restrain its generalization and use at large-scale. Firstly, this system is based on recombinant vaccinia viruses, which are infectious for humans. Therefore, handling these recombinant viruses require specific laboratory facilities and practices. An attenuated avian host-range-restricted strain, i.e. the modified vaccinia Ankara (MVA), which aborts its replicative cycle at a late-stage packaging step in human cells, can be used to better control this hazard (Wyatt, Moss et al. 1995; Engleka, Lewis et al. 1998). Secondly, the recombinant vaccinia or MVA viruses are cytotoxic. Therefore, the vaccinia virus/bacteriophage RNAP hybrid expression system can only be used for transient transgenesis (Elroy-Stein, Fuerst et al. 1989; Elroy-Stein and Moss 1990). Thirdly, the vaccinia virus/bacteriophage RNAP hybrid expression system can be readily used in some cellular models that are permissive to vaccinia infection (e.g. BSC-1), whereas some are not (e.g. CHO). The insertion of the CP77 gene of cowpox virus into the genome of the recombinant vaccinia virus can overcome the vaccinia virus/bacteriophage RNAP hybrid expression system host range restriction of Chinese hamster ovary (CHO) cells by enabling the vaccinia virus to productively infect these cells (Spehner, Gillard et al. 1988; Ramsey-Ewing and Moss 1996). Fourthly, due to the complexity of the system, significant variability in its efficacy can be expected, even in the same cellular model. Fifthly, the vaccinia virus/bacteriophage RNAP hybrid expression system is a cost and labor-consuming technology, which is therefore poorly appropriate for large-scale assays and protein production.

In an attempt to couple capping to transcription and thus to improve the translatability of uncapped transcripts produced by the T7 RNA polymerase, this enzyme has been fused to the carboxyl-terminal domain (CTD) of the largest subunit of the RNA polymerase II (POLR2A), (Natalizio, Robson-Dixon et al. 2009). The CTD comprises 25-52 heptapeptide repeats of the consensus sequence $^1$YSPTSPS$^7$, which is highly conserved throughout evolution and subject to reversible phosphorylation during the transcription cycle (Palancade and Bensaude 2003). When phosphorylated, the CTD is thought to mediate the coupling of transcription and capping of nascent transcripts, by binding one or more subunits of the mRNA capping enzymes in yeast (Cho, Takagi et al. 1997; McCracken, Fong et al. 1997) and mammals (McCracken, Fong et al. 1997; Yue, Maldonado et al. 1997). Noticeably, RNA polymerase II with Ser$^5$-phosphorylated CTD repeats undergoes promoter proximal pausing which is coincident with the co-transcriptional capping of the nascent transcripts (Komarnitsky, Cho et al. 2000; Schroeder, Schwer et al. 2000). However, in contrast to what could be expected intuitively, the fusion of the CTD to the single-unit T7 RNA polymerase is not sufficient to enhance the capping of both constitutively and alternatively spliced substrates in vivo (Natalizio, Robson-Dixon et al. 2009).

The capping is a specialized structure found at the 5'-end of nearly all eukaryotic messenger RNAs. The simplest cap structure, cap0, results of the addition of a guanine nucleoside methylated at N$^7$ that is joined by 5'-5' triphosphate bound to the end of primary RNA (i.e. m$^7$GpppN where N is any base, p denotes a phosphate and m a methyl group). The formation of the cap0 involves a series of three enzymatic reactions: RNA triphosphatase (RTPase) removes the γ phosphate residue of 5' triphosphate end of nascent pre-mRNA to diphosphate, RNA guanylyltransferase (GTase) transfers GMP from GTP to the diphosphate nascent RNA terminus, and RNA N7-guanine methyltransferase (N7-MTase) adds a methyl residue on azote 7 of guanine to the GpppN cap (Furuichi and Shatkin 2000). In higher eukaryotes and some viruses, the 2'-hydroxyl group of the ribose of the first (i.e. cap1 structures; m$^7$GpppNm$^{2'-O}$pN) and second (i.e. cap2 structures; m$^7$GpppNm$^{2'-O}$pNm$^{2'-O}$ transcribed nucleotides can be methylated by two separate ribose-2'-O MTases, respectively named cap1- and cap2-specific MTases (Langberg and Moss 1981). However, In contrast to the cellular N7-MTase activity that is exclusively nuclear, cap1 ribose-2'-O MTase activity has been detected in both the cytoplasm and nucleus of HeLa cells, whereas cap2 MTase activity is exclusively found in their cytoplasm (Langberg and Moss 1981).

The formation of the 5'-terminal m$^7$GpppN cap is the first step of pre-mRNA processing. The m$^7$GpppN cap plays important roles in mRNA stability and its transport from the nucleus to the cytoplasm (Huang and Steitz 2005; Kohler and Hurt 2007). In addition, the 5'-terminal m$^7$GpppN cap is important for the translation of mRNA to protein by anchoring the eukaryotic translation initiation factor 4F (eIF4F) complex, which mediates the recruitment of the 16S portion of the small ribosomal subunit to mRNA (Furuichi, LaFiandra et al. 1977; Gingras, Raught et al. 1999; Rhoads 1999). The 5'-terminal m$^7$GpppN cap therefore enhances drastically the translation of mRNA both in vitro (Lo, Huang et al. 1998), and in vivo (Malone, Felgner et al. 1989; Gallie 1991; Lo, Huang et al. 1998; Kozak 2005). In contrast, the effects of 2'-O-methylation on mRNA translation appear to depend on the type of cells and the conditions of the experimentation (Epicentre Biotechnologies website; Drummond, Armstrong et al. 1985; Kuge, Brownlee et al. 1998).

There remains therefore a significant need in the art for new and improved systems for efficient transgenesis in eukaryotic cells, which are appropriate for gene therapy and large-scale protein production without cytotoxicity or induced-cytotoxicity. The present inventor has made a significant step forward with the invention disclosed herein.

The purpose of the invention is to fulfill this need by providing new chimeric enzymes, which make it possible to solve in whole or part the problems mentioned-above.

Unexpectedly, the inventor has demonstrated that chimeric enzymes comprising a catalytic domain of a RNA triphosphatase, a catalytic domain of a guanylyltransferase, a catalytic domain of a N$^7$-guanine methyltransferase, and a catalytic domain of a DNA-dependant RNA polymerase are able to synthesize RNA molecules with 5'-terminal m$^7$GpppN caps, which are highly translatable by the eukaryotic translational machinery, without cytotoxicity and while not inducing apoptosis.

These results are surprising since the capping of T7 transcripts remains infra-optimal with the vaccinia virus/bacteriophage RNAP hybrid expression system, and cannot be achieved by the fusion enzyme CTD-T7 RNA polymerase.

Thus, in one aspect, the invention relates to a chimeric enzyme comprising:
- at least one, in particular a catalytic domain of a RNA triphosphatase,
- at least one, in particular a catalytic domain of a guanylyltransferase,
- at least one, in particular a catalytic domain of a N$^7$-guanine methyltransferase, and,
- at least one, in particular a catalytic domain of a DNA-dependant RNA polymerase.

In particular the chimeric enzyme according to the invention is able to synthesize RNA molecules with 5'-terminal m$^7$GpppN caps.

The chimeric enzyme according to the invention has in particular the following advantages:
- There is no competition between the endogenous gene transcription and the transgene transcription;
- It is not expensive, quick and easy to implement and thus appropriate for large-scale assays and protein production;
- In contrast to the vaccinia virus/bacteriophage RNAP hybrid expression system, it has no obvious cytotoxicity or pro-apoptotic activities;
- It allows the production of RNA transcripts in any eukaryotic species (e.g. yeast, plants, rodents, dairy ruminants, primates, and humans).

Unless defined otherwise, all technical and scientific terms used herein have the same meaning as commonly understood to one skilled in the relevant art.

For convenience, the meaning of certain terms and phrases employed in the specification, examples, and claims are provided.

As used herein, the term "chimeric enzyme" refers to enzyme that is not a native enzyme that is found in nature. Accordingly, a chimeric enzyme may comprises catalytic domains that are derived from different sources (e.g. from different enzymes) or catalytic domains derived from the same source (e.g. from the same enzyme), but arranged in a different manner than that found in nature.

The term "chimeric enzyme" encompasses monomeric (i.e. single-unit) enzyme but also oligomeric (i.e. multi-unit) enzyme, in particular hetero-oligomeric enzyme.

As used herein, the term "monomeric enzyme" relates to a single-unit enzyme that consists of only one polypeptide chain.

As used herein, the term "oligomeric enzyme" refers to a multi-units enzyme that consists of at least two polypeptides chains, linked together covalently or noncovalently. The term "oligomeric enzyme" encompasses a multi-units enzyme, wherein at least two units of said enzyme are linked together covalently or noncovalently. The term "oligomeric enzyme" encompasses homo-oligomeric enzyme that is a multi-unit enzyme consisting of only one type of monomers (subunit) and hetero-oligomeric enzyme consisting of different types of monomers (subunits).

In particular, said catalytic domains of a RNA triphosphatase, of a guanylyltransferase, of a $N^7$-guanine methyltransferase and of a DNA-dependant RNA polymerase are linked together covalently and/or noncovalently.

In particular, said catalytic domains of a RNA triphosphatase, of a guanylyltransferase, of a $N^7$-guanine methyltransferase and of a DNA-dependant RNA polymerase are operatively linked together to synthesize RNA molecules with 5'-terminal $m^7$GpppN caps.

In particular, the chimeric enzyme according to the invention comprising:
  at least one, particularly a catalytic domain of a RNA triphosphatase,
  at least one, particularly a catalytic domain of a guanylyltransferase,
  at least one, particularly a catalytic domain of a $N^7$-guanine methyltransferase, and
  at least one, particularly a catalytic domain of a DNA-dependant RNA polymerase;
  wherein at least two of said catalytic domains are linked together, preferably at their extremity (N or C terminal end), covalently or non-covalently, more particularly wherein at least one of the catalytic domain chosen in the group consisting of:
    said at least one, particularly a catalytic domain of a RNA triphosphatase,
    said at least one, particularly a catalytic domain of a guanylyltransferase, and
    said at least one, particularly a catalytic domain of a $N^7$-guanine methyltransferase
  is linked, preferably at its extremity (N or C terminal end), covalently or non-covalently with
    said at least one, particularly a catalytic domain of a DNA-dependant RNA polymerase, preferably at its extremity (N or C terminal end).

In particular, the invention relates to the chimeric enzyme according to the invention comprising:
  at least one, particularly a catalytic domain of a RNA triphosphatase,
  at least one, particularly a catalytic domain of a guanylyltransferase,
  at least one, particularly a catalytic domain of a $N^7$-guanine methyltransferase, and
  at least one, particularly a catalytic domain of a DNA-dependant RNA polymerase;
  with the exception of chimeric enzyme comprising:
  a catalytic domain of a RNA triphosphatase,
  a catalytic domain of a guanylyltransferase,
  a catalytic domain of a $N^7$-guanine methyltransferase, and
  only catalytic domains of nuclear eukaryotic DNA-dependant RNA polymerase I, II and/or III; and more particularly, only catalytic domain(s) of the DNA-dependant RNA polymerase II.

In particular, the invention relates to the chimeric enzyme according to the invention comprising:
  at least one, particularly a catalytic domain of a RNA triphosphatase,
  at least one, particularly a catalytic domain of a guanylyltransferase,
  at least one, particularly a catalytic domain of a $N^7$-guanine methyltransferase, and
  at least one, particularly a catalytic domain of a DNA-dependant RNA polymerase;
  with the exception of chimeric enzyme comprising:
  a catalytic domain of a RNA triphosphatase,
  a catalytic domain of a guanylyltransferase,
  a catalytic domain of a $N^7$-guanine methyltransferase, and
  catalytic domains of nuclear eukaryotic DNA-dependant RNA polymerase I, II and/or III, more particularly, at least a catalytic domain of the DNA-dependant RNA polymerase II.

In particular, upon expression in a eukaryotic host cell, said chimeric enzyme according to the invention is able to synthesize RNA molecules with 5'-terminal $m^7$GpppN cap, which are preferably translatable by the eukaryotic translational machinery.

Particularly, upon expression in a eukaryotic host cell said catalytic domains of a RNA triphosphatase, of a guanylyltransferase and of a $N^7$-guanine methyltransferase are able to add a $m^7$GpppN cap at the 5'-terminal end of RNA molecules synthesized by said catalytic domain of a DNA-dependant RNA polymerase and preferably said RNA molecules with 5'-terminal $m^7$GpppN cap are translatable by the eukaryotic translational machinery.

Particularly, upon expression in a eukaryotic host cell, when said catalytic domain of a DNA-dependant RNA polymerase is a catalytic domain of a bacteriophage DNA-dependant RNA polymerase, said catalytic domains of a RNA triphosphatase, of a guanylyltransferase and of a $N^7$-guanine methyltransferase are able to add a $m^7$GpppN cap at the 5'-terminal end of RNA molecules that have a guanosine ribonucleotide at their 5' terminal end.

Particularly, upon expression in a eukaryotic host cell, when said catalytic domain of a DNA-dependant RNA polymerase is a catalytic domain of a bacterial DNA-dependant RNA polymerase, said catalytic domains of a RNA triphosphatase, of a guanylyltransferase and of a $N^7$-guanine methyltransferase are able to add a $m^7$GpppN cap at the 5'-terminal end of RNA molecules that have a guanosine or a adenosine ribonucleotide at their 5' terminal end.

Particularly, upon expression in a eukaryotic host cell, when said catalytic domain of a DNA-dependant RNA polymerase is a catalytic domain of a human or mouse mitochondrial DNA-dependant RNA polymerase, said catalytic domains of a RNA triphosphatase, of a guanylyltransferase and of a $N^7$-guanine methyltransferase are able to add a $m^7$GpppN cap at the 5'-terminal end of RNA molecules that have a adenosine or a thymidine ribonucleotide at their 5' terminal end.

A used herein the term "catalytic domain" of an enzyme relates to domain, which is necessary and sufficient, in particular in its three-dimensional structure, to assure the enzymatic function. For example, a catalytic domain of a RNA triphosphatase is the domain, which is necessary and sufficient to assure the RNA triphosphatase function. The term "catalytic domain" encompasses catalytic domain of wild type or mutant enzyme.

The chimeric enzyme according to the invention comprises at least said catalytic domains but can further comprise the whole or part of the enzymes containing said catalytic domains. In fact, according to one embodiment of the chimeric enzyme according to the invention, said catalytic domain of a DNA-dependant RNA polymerase can be included in the whole or part of a DNA-dependant RNA polymerase, preferably of a monomeric DNA-dependant RNA polymerase. Said catalytic domain of a RNA triphosphatase, said catalytic domain of a guanylyltransferase and said catalytic domain of a N[7]-guanine methyltransferase can also be included in the whole or part of a capping enzyme, preferably of a monomeric capping enzyme.

The chimeric enzyme according to the invention can be a nuclear enzyme, a subcellular compartment enzyme or a cytoplasmic enzyme. Thus, the chimeric enzyme according to the invention can comprise a signal peptide or a marker-signal well known by one skilled in the art, which directs the transport of the enzyme in cells. For example, the chimeric enzyme according to the invention can comprise a nuclear localization signal (NLS), which directs the enzyme to the nucleus. Such NLS is often a unit consisting of five basic, plus-charged amino acids. The NLS can be located anywhere on the peptide chain.

Preferably, the chimeric enzyme according to the invention is a cytoplasmic chimeric enzyme. In particular, it does not comprise signal peptide or marker-signal that directs the transport of the enzyme, except to the cytoplasm.

The cytoplasmic localisation of the chimeric enzyme according to the invention has the advantage that it optimizes the levels of transgene expression by avoiding the active transfer of large DNA molecules (i.e. transgene) from the cytoplasm to the nucleus of eukaryotic cells and the export of RNA molecules from the nucleus to the cytoplasm.

These cytoplasmic chimeric enzymes according to the invention can thus be useful to generate a host-independent, eukaryotic gene expression system that is able to work in the cytoplasm in which significantly higher amounts of transfected DNA are usually found as compared to the nucleus.

These cytoplasmic chimeric enzymes according to the invention are able to synthesize RNA molecules with 5'-terminal m[7]GpppN caps, which are highly translatable by the eukaryotic cytoplasmic translational machinery, without cytotoxicity and while not inducing apoptosis.

There is also no competition between the endogenous gene transcription and the transgene transcription, since the endogenous gene transcription occurs in the nucleus of eukaryotic cells in contrast to the transgene transcription, which occurs in the cytoplasm.

The cytoplasmic chimeric enzyme according to the invention is thus notably appropriate for large-scale assays and protein production.

In one embodiment of the chimeric enzyme according to the invention, said catalytic domain of a RNA triphosphatase, said catalytic domain of a guanylyltransferase, said catalytic domain of a N[7]-guanine methyltransferase, are included in a monomer, i.e. in one polypeptide. For example, said monomer can be a monomeric capping enzyme or a monomeric chimeric enzyme according to the invention.

In particular, said catalytic domain of a RNA triphosphatase, said catalytic domain of a guanylyltransferase, and said catalytic domain of a N[7]-guanine methyltransferase are included in a monomeric capping enzyme. In this case, the chimeric enzyme according to the invention comprise a monomeric capping enzyme, which includes said catalytic domain of a RNA triphosphatase, said catalytic domain of a guanylyltransferase, and said catalytic domain of a N[7]-guanine methyltransferase. Said monomeric capping enzyme can be a monomeric virus capping enzyme, in particular chosen in the group consisting of the wild type bluetongue virus capping enzyme, the wild type bamboo mosaic virus capping enzyme, the wild type African swine fever virus capping enzyme, the wild type acanthamoeba polyphaga mimivirus capping enzyme and mutants and derivatives thereof which are able to add a m[7]GpppN cap at the 5'-terminal end of RNA molecules and, more particularly of the wild type African swine fever virus capping enzyme and mutants and derivatives thereof which are able to add a m[7]GpppN cap at the 5'-terminal end of RNA molecules, and even more particularly the wild type African swine fever virus capping enzyme.

In particular, said catalytic domain of a DNA-dependant RNA polymerase can also be included in a monomer, i.e. in one polypeptide. For example, said monomer can be a monomeric DNA-dependent RNA polymerase or a monomeric chimeric enzyme according to the invention.

In particular, said catalytic domain of a DNA-dependant RNA polymerase is included in a monomeric DNA-dependent RNA polymerase. In this case, the chimeric enzyme according to the invention comprises a monomeric DNA-dependent RNA polymerase, which includes said catalytic domain of a DNA-dependant RNA polymerase. Said monomeric DNA-dependent RNA polymerase can be a monomeric phage DNA-dependent RNA polymerase, in particular chosen in the group consisting of T7 RNA polymerase, T3 RNA polymerase and SP6 RNA polymerase and mutants or derivatives thereof, which are able to synthesize single-stranded RNA complementary in sequence to the double-stranded template DNA in the 5'→3' direction, more particularly of T7 RNA polymerase and mutants or derivatives thereof, which are able to synthesize single-stranded RNA complementary in sequence to the double-stranded template DNA in the 5'→3' direction.

Said catalytic domain of a DNA-dependant RNA polymerase and at least one, preferably at least two and more preferably the whole catalytic domain chosen in the group consisting of:
  said catalytic domain of a RNA triphosphatase;
  said catalytic domain of a guanylyltransferase; and
  said catalytic domain of a N[7]-guanine methyltransferase;
can be included in a monomer.

The chimeric enzyme according to the invention can be monomeric or oligomeric. In fact, said catalytic domains of a RNA triphosphatase, of a guanylyltransferase, of a N[7]-guanine methyltransferase and of a DNA-dependant RNA polymerase can be included in one or several polypeptides.

Preferably, the chimeric enzyme according to the invention is monomeric.

In fact, the inventor has demonstrated that a monomeric chimeric enzyme comprising a catalytic domain of a RNA triphosphatase, a catalytic domain of a guanylyltransferase, a catalytic domain of a N[7]-guanine methyltransferase, and a catalytic domain of a DNA-dependant RNA polymerase are able to synthesize RNA molecules with 5'-terminal m[7]GpppN caps, which are highly translatable by the eukaryotic translational machinery, without cytotoxicity and while not inducing apoptosis.

It was not obvious that the capping of transcripts well occurred with a monomeric enzyme, due to steric hindrance and components and the enzyme, which have to remain in their native conformation. In fact, the capping of T7 transcripts cannot be achieved by the fusion enzyme CTD-T7 RNA polymerase, although it was supposed to trigger m[7]GpppN capping at the 5'-terminal end of nascent RNA molecules.

The monomeric chimeric enzyme according to the invention has in particular the advantages that it is not expensive, quick and easy to implement and thus appropriate notably for large-scale assays and protein production. In fact, the production of a monomeric enzyme is easier than of oligomeric enzyme. There is also no problem of unit assembly, since there is only a single-unit. The monomeric enzyme is also easier to manipulate than multimeric enzyme.

As used herein, the term "DNA-dependent RNA polymerase" (RNAPs) relates to nucleotidyl transferases that synthesize single-stranded RNA complementary in sequence to the double-stranded template DNA in the 5'→3' direction.

Preferably, said catalytic domain of a DNA-dependant RNA polymerase is a catalytic domain of an enzyme, which have a relatively simple structure and more preferably, which have characterized genomic enzymatic regulation elements (i.e. promoter, transcription termination signal and concatemer junction). Thus, in particular, said catalytic domain of a DNA-dependant RNA polymerase can be a catalytic domain of a bacteriophage DNA-dependent RNA polymerase, of a bacterial DNA-dependent RNA polymerase or of a DNA-dependent RNA polymerase of various eukaryotic organelles (e.g. mitochondria, chloroplast and proplastids).

In one embodiment, said catalytic domain of a DNA-dependant RNA polymerase is a catalytic domain of a bacteriophage DNA-dependant RNA polymerase.

The bacteriophage DNA-dependant RNA polymerases have notably the advantage that they optimize the levels of transgene expression, in particular by having a higher processivity than the eukaryotic RNA polymerases. The bacteriophage DNA-dependant RNA polymerases have also a much simpler structure than most nuclear eukaryotic polymerases, which have complex structure with multiple subunits (e.g. RNA polymerase II) (Chen and Schneider 2005). Most of the bacteriophage DNA-dependant RNA polymerases characterized so far are single-subunit enzymes, which require no accessory proteins for initiation, elongation, or termination of transcription (Chen and Schneider 2005). Several of these enzymes, which are named for the bacteriophages from which they have been cloned, have also well-characterized regulation genomic elements (i.e. promoter, termination signals, transcriptional pausing sequences), which are important for transgenesis.

There is also no competition between the endogenous gene transcription and the transgene transcription. The chimeric enzymes according to the invention, which comprise bacteriophage DNA dependant RNA-polymerase moieties allow the production of RNA transcripts in any eukaryotic species (e.g. yeast, rodents, and humans). They are not expensive, quick and easy to implement and thus appropriate for large-scale assays and protein productions; it allows the production of RNA transcripts in any biological system (e.g. acellular reaction mix, cultured cells, and living organisms), since in contrast to eukaryotic RNA polymerase such as RNA polymerase II, most of bacteriophage DNA dependant RNA polymerases do not require associated factors for initiation, elongation or termination of transcription.

Said catalytic domain of a bacteriophage DNA-dependant RNA polymerase can be a catalytic domain of a bacteriophage DNA-dependent RNA polymerase, in particular chosen in the group consisting of the wild type of the T7 RNA polymerase, the wild type of the T3 RNA polymerase (NCBI genomic sequence ID# NC_003298; GeneID#927437; UniProtKB/Swiss-Prot ID# Q778M8), the wild type of the K11 RNA polymerase (NCBI genomic K11 RNAP sequence ID# NC_004665; GeneID#1258850; UniProtKB/Swiss-Prot ID# Q859H5), the wild type of the φA1122 RNA polymerase (NCBI genomic sequence ID# NC_004777; GeneID#1733944; UniProtKB/Swiss-Prot protein ID# Q858N4), the wild type of the φYeo3-12 RNA polymerase (NCBI genomic sequence ID# NC_001271; GeneID#1262422; UniProtKB/Swiss-Prot ID# Q9T145) and the wild type of the gh-1 RNA polymerase (NCBI genomic sequence ID# NC_004665; GeneID#1258850; UniProtKB/Swiss-Prot protein ID# Q859H5), the wild type of the K1-5 RNAP RNA polymerase (NCBI genomic sequence ID# NC_008152; GeneID#5075932; UniProtKB/Swiss-Prot protein ID# Q8SCG8) and the wild type of the SP6 RNA polymerase (NCBI genomic sequence ID# NC_004831; GeneID#1481778; UniProtKB/Swiss-Prot protein ID# Q7Y5R1), and mutants or derivatives thereof, which are able to synthesize single-stranded RNA complementary in sequence to the double-stranded template DNA in the 5'→3' direction, more particularly of the wild type of T7 RNA polymerase.

As used herein, the term "T7 RNA polymerase" relates to the bacteriophage T7 DNA-dependant RNA polymerase. Preferably, the T7 RNA polymerase have the amino acid sequence of SEQ ID NO:1 (NCBI genomic sequence ID# NC_001604; GeneID#1261050; UniProtKB/Swiss-Prot ID# P00573) and is a 883 amino-acid protein with a molecular weight of 98.8 kDa (Davanloo, Rosenberg et al. 1984; Moffatt, Dunn et al. 1984).

The T7 RNA polymerase has in particular the advantage that, in vitro, the enzyme is extremely processive and elongates 240-250 nucleotides/s at 37° C. in the 5'→3' direction (Golomb and Chamberlin 1974; Lyakhov, He et al. 1997; Zhang and Studier 1997; Finn, MacLachlan et al. 2005). Moreover, when expressed in eukaryotic cells, the T7 RNA polymerase, remains largely in the cytoplasm (Elroy-Stein and Moss 1990; Gao and Huang 1993; Brisson, He et al. 1999), and thus optimizes the levels of transgene expression by avoiding the active transfer of large DNA molecules (i.e. transgene) from the cytoplasm to the nucleus of eukaryotic cells and the export of RNA molecules from the nucleus to the cytoplasm.

The catalytic domain of a DNA-dependant RNA polymerase can be the one of the wild-type of the T7 RNA polymerase but also of mutants of the T7 RNA polymerase, which are able to synthesize single-stranded RNA complementary in sequence to the double-stranded template DNA in the 5'→3' direction, even with reduced processivity. For example, said mutants can be chosen in the group comprising R551S, F644A, Q649S, G645A, R627S, I810S, and D812E (Makarova, Makarov et al. 1995), and K631M (Osumi-Davis, de Aguilera et al. 1992; Osumi-Davis, Sreerama et al. 1994).

In one embodiment of the chimeric enzyme according to the invention, said catalytic domain of a DNA-dependant RNA polymerase is located C-terminally with respect to said catalytic domain of a RNA triphosphatase, said catalytic domain of a guanylyltransferase, and said catalytic domain of a $N^7$-guanine methyltransferase.

In fact, when the catalytic domain of a DNA-dependent RNA polymerase is a catalytic domain of a bacteriophage DNA-dependant RNA polymerase, in particular of a bacteriophage DNA-dependant RNA polymerase chosen in the group consisting of T7, T3 and SP6-RNA polymerases, said catalytic domain preferably conserves its native carboxyl-terminal end. In particular, the C-terminal end of said catalytic domain of a DNA-dependant RNA polymerase, particularly of a bacteriophage DNA-dependant RNA polymerase corresponds to the C-terminal end of said chimeric enzyme. In particular, when the chimeric enzyme comprises a whole bacteriophage DNA-dependant RNA polymerase, in particular of a bacteriophage DNA-dependant RNA polymerase chosen in the group consisting of T7, T3 and SP6-RNA polymerases, said polymerase preferably conserves its native carboxyl-terminal end. In particular, the C-terminal end of said catalytic domain of a DNA-dependant RNA polymerase, particularly of a bacteriophage DNA-dependant RNA polymerase corresponds to the C-terminal end of said chimeric enzyme. Particularly, said catalytic domain of a DNA-dependant RNA polymerase, in particular of a bacteriophage DNA-dependant RNA polymerase chosen in the group consisting of T7, T3 and SP6-RNA polymerases, is included in the whole or part of a bacteriophage DNA-dependant RNA polymerase and wherein the C-terminal end of said bacteriophage DNA-dependant RNA polymerase corresponds to the C-terminal end of said chimeric enzyme.

In one embodiment of the chimeric enzyme according to the invention, said catalytic domain of a DNA-dependent RNA polymerase, particularly said catalytic domain of a bacteriophage DNA-dependent RNA polymerase, in particular of a bacteriophage DNA-dependent RNA polymerase chosen in the group consisting of T7, T3 and SP6-RNA polymerases, is located C-terminally with respect to said catalytic domain of a RNA triphosphatase, said catalytic domain of a guanylyltransferase, and said catalytic domain of a $N^7$-guanine methyltransferase.

In another embodiment, said catalytic domain of a DNA-dependant RNA polymerase is a catalytic domain of a bacterial DNA-dependant RNA polymerase.

Preferably said bacterial DNA-dependant RNA polymerase has a moderate structure complexity.

For example, said bacterial DNA-dependent RNA polymerase can be the *E. coli* DNA-dependent RNA polymerase (NCBI genomic sequence of K-12 substrain DH10B ID# NC_010473), which consists of four different subunits (α subunit: rpoA GeneID#6060938, UniProtKB/Swiss-Prot ID# B1X6E7; β subunit: rpoB GeneID#6058462, UniProtKB/Swiss-Prot ID# B1XBY9; β' subunit: rpoC GeneID#6058956, UniProtKB/Swiss-Prot ID# B1XBZ0; σ subunit: rpoE GeneID#6060683, UniProtKB/Swiss-Prot ID# B1XBQ0), which are assembled in a five ααββ'σ subunit complex (Lodish, Berk et al. 2008). The genomic elements involved in the regulation of the enzymatic activity are well-characterized, including *E. coli* RNA polymerase promoters (Lisser and Margalit 1993), termination signals including rho-dependant and -independent terminators (Platt 1986; Uptain and Chamberlin 1997), and transcriptional pausing sequences (Lee, Phung et al. 1990).

In another embodiment, said catalytic domain of a DNA-dependant RNA polymerase is a catalytic domain of a DNA-dependant RNA polymerase of a eukaryotic organelle, like mitochondria, chloroplast and proplastids. In fact, these polymerases can also have relatively simple structure.

In particular, said catalytic domain of a DNA-dependant RNA polymerase is a catalytic domain of a mitochondrial DNA-dependant RNA polymerase.

Particularly, said catalytic domain of a DNA-dependant RNA polymerase can be the catalytic domain of the mammalian mouse mitochondrial RNA polymerase, which is a single-unit 120 kDa protein (GeneID#216151, UniProtKB/Swiss-Prot ID# Q8BKF1), which shares homology with the bacteriophage RNA polymerases (Tiranti, Savoia et al. 1997). Several transcription factors are required for transcription initiation, elongation, or termination: TFB1M (mitochondrial transcription factor B1; mouse GeneID#224481, UniProtKB/Swiss-Prot ID# Q8JZM0) or TFB2M (mitochondrial transcription factor B2; mouse GeneID#15278, UniProtKB/Swiss-Prot ID# Q3TL26), TFAM (mitochondrial transcription factor A; mouse GeneID#21780, UniProtKB/Swiss-Prot ID# P40630), and mTERF (mitochondrial transcription termination factor; mouse GeneID#545725, UniProtKB/Swiss-Prot ID# Q8CHZ9) for termination of transcription (Fisher and Clayton 1985; Fisher, Topper et al. 1987; Fisher and Clayton 1988; Topper and Clayton 1989; Fernandez-Silva, Martinez-Azorin et al. 1997; Prieto-Martin, Montoya et al. 2001; McCulloch, Seidel-Rogol et al. 2002). The genomic elements involved in the regulation of the enzymatic activity of the mitochondrial RNA polymerase are well-characterized, including two promoters at light- and heavy-strands of the mitochondrial genome (Ojala, Montoya et al. 1981; Clayton 1991), as well as transcriptional termination signals (Kruse, Narasimhan et al. 1989).

As used herein, the term "RNA triphosphatase" (RTPase) relates to the enzyme, which removes the γ phosphate residue of 5' triphosphate end of nascent pre-mRNA to diphosphate (Furuichi and Shatkin 2000).

As used herein, the term "RNA guanylyltransferase" (GTase) refers to the enzyme, which transfers GMP from GTP to the diphosphate nascent RNA terminus (Furuichi and Shatkin 2000).

As used herein, the term "N7-guanine methyltransferase" (N7-MTase) relates to the enzyme, which adds a methyl residue on azote 7 of guanine to the GpppN cap (Furuichi and Shatkin 2000).

Said catalytic domains of a RNA triphosphatase, of a guanylyltransferase, of a $N^7$-guanine methyltransferase, can be of the same or of different capping enzymes. If said catalytic domains are of the same enzyme, said catalytic domain of a DNA-dependant RNA polymerase is of a different enzyme.

Preferably, said catalytic domains of a RNA triphosphatase, of a guanylyltransferase, of a $N^7$-guanine methyltransferase are from one or several cytoplasmic enzymes, which have advantageously relatively simple structure and well-characterized enzymatic activities. Thus, in particular, said catalytic domains of a RNA triphosphatase, of a guanylyltransferase, of a $N^7$-guanine methyltransferase can be catalytic domains of one or several virus capping enzymes, or of capping enzymes of cytoplasmic episomes.

In one embodiment, said catalytic domains of a RNA triphosphatase, of a guanylyltransferase, of a $N^7$-guanine methyltransferase are from one or several virus capping enzymes, in particular chosen in the group consisting of the wild type bluetongue virus capping enzyme, the wild type bamboo mosaic virus capping enzyme, the wild type African swine fever virus capping enzyme, the wild type acanthamoeba polyphaga mimivirus capping enzyme, and mutants or derivatives thereof which are able respectively to remove the γ phosphate residue of 5' triphosphate end of nascent pre-mRNA to diphosphate or transfer GMP from GTP to the diphosphate nascent RNA terminus or add a methyl residue on azote 7 of guanine to the GpppN cap, more particularly of the wild type African swine fever virus capping enzyme.

As used herein the term "bluetongue virus capping enzyme" relates to the single-unit VP4 capping enzyme of Bluetongue virus (BTV), which is a 76 kDa protein (644 amino-acids; for sequence, see for instance NCBI BTV serotype 10 genomic sequence ID# Y00421; GeneID#2943157; UniProtKB/Swiss-Prot ID# P07132, D0UZ45, Q5J7C0, Q65751, Q8BA65, P33428, P33429, P33427, C3TUP7, Q8BAD5, C5IWW0, B4E551, Q3KVQ2, Q3KVQ1, Q65732, Q3KVP8, Q3KVP9, Q3KVQ0). This capping enzyme is likely able to homodimerize through the leucine zipper located near its carboxyl-terminus (Ramadevi, Rodriguez et al. 1998). VP4 catalyze all three enzymatic steps required for mRNA $m^7$GpppN capping synthesis: RTPase (Martinez-Costas, Sutton et al. 1998), GTase (Martinez-Costas, Sutton et al. 1998; Ramadevi, Burroughs et al. 1998) and N7-MTase (Ramadevi, Burroughs et al. 1998).

As used herein, the term "bamboo mosaic virus capping enzyme" relates to ORF1, the Bamboo Mosaic Virus (BMV) mRNA capping enzyme, which is a single-unit 155-kDa protein (1365-amino acids; NCBI BMV isolate BaMV-O genomic sequence ID# NC_001642; GeneID#1497253; UniProtKB/Swiss-Prot ID# Q65005). ORF1 protein has all the enzymatic activities required to generate m$^7$GpppN mRNA capping, i.e. RTPase (Li, Shih et al. 2001; Han, Tsai et al. 2007), GTase and N7-MTase (Li, Chen et al. 2001; Li, Shih et al. 2001). In addition, ORF1 has RNA-dependent RNA-polymerase activity, which is not mandatory for chimeric enzymatic activities according to the invention and can be abolished by deletion of Asp$^{1229}$Asp$^{1230}$ residues of the mRNA capping enzyme (Li, Cheng et al. 1998). As used herein, the term "African swine fever virus capping enzyme" relates to the NP868R capping enzyme (G4R), (ASFV), which is a single-unit 100 kDa protein (868 amino-acids; NCBI ASFV genomic sequence strain BA71V ID# NC_001659; GeneID#1488865; UniProtKB/Swiss-Prot ID# P32094).

As used herein, the term "acanthamoeba polyphaga mimivirus capping enzyme" relates to R382, (APMV), which is another single-unit 136.5 kDa protein (1170 amino-acids; NCBI APMV genomic sequence ID# NC_006450; GeneID#3162607; UniProtKB/Swiss-Prot ID# Q5UQX1).

In one embodiment, said catalytic domains of a RNA triphosphatase, of a guanylyltransferase, of a N$^7$-guanine methyltransferase are from one or several capping enzymes of cytoplasmic episomes, like pGKL2. In particular, said catalytic domains of a RNA triphosphatase, of a guanylyltransferase, of a N$^7$-guanine methyltransferase are included in the whole or part of the capping enzyme of the yeast linear extra-chromosomal episome pGKL2.

Cytoplasmic linear episomes are double-stranded DNA structures, which stably replicate in the cytoplasm of various yeast strains (Cong, Yarrow et al. 1994). One prototype of yeast linear extra-chromosomal episome, pGKL2 (13,457 bp; also named pGK12), has been entirely sequenced from various yeast strains, including *Kluyveromyces lactis* CB 2359 and *Saccharomyces cerevisiae* F102-2 (Tommasino, Ricci et al. 1988). The capping enzyme encoded by the ORF3 gene of *Kluyveromyces lactis* pGKL2 (NCBI *Kluyveromyces lactis* CB 2359 pGKL2 genomic sequence ID# NC_010187; UniProtKB/Swiss-Prot ID# P05469) is a 594 amino-acid protein (70.6 kDa protein).

In one embodiment of the chimeric enzyme according to the invention, at least two, in particular at least three and more particularly the whole catalytic domains can be assembled, fused, or bound directly or indirectly by a linking peptide.

In particular at least two, particularly at least three and more particularly the whole catalytic domains chosen in the group consisting of:
 a catalytic domain of a RNA triphosphatase,
 a catalytic domain of a guanylyltransferase,
 a catalytic domain of a N$^7$-guanine methyltransferase, and
 a catalytic domain of a DNA-dependent RNA polymerase.
are bound directly or by a linking peptide.

Linking peptide has the advantage of generating fusion proteins in which steric hindrance is minimizes and enough space is provided for the components of the fusion protein to remain in their native conformation.

Preferably, at least said catalytic domain of a DNA-dependant RNA polymerase is bound by a linking peptide to at least one of the catalytic domain chosen in the group consisting of:
 said catalytic domain of a RNA triphosphatase;
 said catalytic domain of a guanylyltransferase; and
 said catalytic domain of a N$^7$-guanine methyltransferase.

Particularly, the linking peptide can be located N-terminally with respect to said catalytic domain of a DNA-dependant RNA polymerase, in particular of a bacteriophage DNA-dependant RNA polymerase chosen in the group consisting of T7, T3 and SP6-RNA polymerases, and C-terminally with respect to said catalytic domain of a RNA triphosphatase, said catalytic domain of a guanylyltransferase, and said catalytic domain of a N$^7$-guanine methyltransferase.

In particular, the N-terminal end of said catalytic domain of a DNA-dependant RNA polymerase, in particular of a bacteriophage DNA-dependant RNA polymerase chosen in the group consisting of T7, T3 and SP6-RNA polymerases, is linked by covalent linkage, in particular by a linking peptide, to the C-terminal end of one of the catalytic domain chosen in the group consisting of:
 said catalytic domain of a RNA triphosphatase,
 said catalytic domain of a guanylyltransferase, and
 said catalytic domain of a N$^7$-guanine methyltransferase.

Said linking peptide can be chosen from the group consisting of:
 peptides of formula $(Gly_mSer_p)_n$, in which:
  m represents an integer from 0 to 12, in particular from 1 to 8, and more particularly from 3 to 6 and even more particularly 4;
  p represents an integer from 0 to 6, in particular from 0 to 5, more particularly from 0 to 3 and more particularly 1; and
  n represents an integer from 0 to 30, in particular from 0 to 12, more particularly from 0 to 8 and even more particularly between 1 and 6 inclusive;
 peptides consisting of an amino acid sequence selected from the group consisting of SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18.

The flexible linker peptides of formula $(Gly_mSer_p)_n$ have the advantages that the glycine residues confer peptide flexibility, while the serine provide some solubility (Huston, Levinson et al. 1988). Furthermore, the absence of sensitive sites for chymotrypsin I, factor Xa, papain, plasmin, thrombin and trypsin in the $(Gly_mSer_p)_n$ linker sequences is supposed to increase the overall stability of the resulting fusion proteins (Crasto and Feng 2000).

$(Gly_mSer_p)_n$ linkers of variable lengths are commonly used to engineer single-chain Fv fragment (sFv) antibodies (Huston, Levinson et al. 1988). In addition, $(Gly_mSer_p)_n$ linkers have been used to generate various fusion proteins, which frequently retain the biological activities of each of their components (Newton, Xue et al. 1996; Lieschke, Rao et al. 1997; Shao, Zhang et al. 2000; Hu, Li et al. 2004).

Other types of peptide linkers can be also considered to generate chimeric enzymes according to the invention, such as GGGGIAPSMVGGGGS (SEQ ID NO:2) (Turner, Ritter et al. 1997), SPNGASNSGSAPDTSSAPGSQ (SEQ ID NO:3) (Hennecke, Krebber et al. 1998), EGKSSGSGSESK-STE (SEQ ID NO:4) (Bird, Hardman et al. 1988), EGKSSGSGSESKEF (SEQ ID NO:5) (Newton, Xue et al.

1996), GGGSGGGSGGGTGGGSGGG (SEQ ID NO:6) (Robinson and Sauer 1998), GSTSGSGKSSEGKG (SEQ ID NO:7) (Bedzyk, Weidner et al. 1990), YPRSIYIR-RRHPSPSLTT (SEQ ID NO:8) (Tang, Jiang et al. 1996), GSTSGSGKPGSGEGSTKG (SEQ ID NO:9) (Whitlow, Bell et al. 1993), GSTSGSGKPGSGEGS (SEQ ID NO:10) (Ting, Kain et al. 2001), SSADDAKKDAAKKDDAKKD-DAKKDA (SEQ ID NO:11) (Pantoliano, Bird et al. 1991), GSADDAXXDAAXKDDAKKDDAKKDGS (SEQ ID NO:12) (Gregoire, Lin et al. 1996), LSADDAKKDAAK-KDDAKKDDAKKDL (SEQ ID NO:13) (Pavlinkova, Beresford et al. 1999), AEAAAKEAAAKEAAAKA (SEQ ID NO:14) (Wickham, Carrion et al. 1995), GSHSGSGKP (SEQ ID NO:15) (Ting, Kain et al. 2001), GSTSGSGK-PGSGEGSTGAGGAGSTSGSGKPSGEG (SEQ ID NO:16) (Ting 2003), LSLEVAEEIARLEAEV (SEQ ID NO:17) (Liu, Jian-Bo et al. 2005), and GTPTPTPTPTGEF (SEQ ID NO:18) (Gustavsson, Lehtio et al. 2001).

Other types of covalent linkage include but are not limited to disulfide bounds (Mantile, Fuchs et al. 2000), transglutamination (Paguirigan and Beebe 2007), as well as protein trans-linking by chemical and/or physical agents, e.g. cross-linking by tris(bipyridine)ruthenium(II)-dichloride and ultraviolet light illumination (Fancy and Kodadek 1999).

Said catalytic domains of a RNA triphosphatase, of a guanylyltransferase, of a $N^7$-guanine methyltransferase, and of a DNA-dependant RNA polymerase can also be assembled by specific protein elements, like leucine zippers, like biotinylation domain to one of the catalytic domain (e.g. Avi-tag II (Cronan 1990) or PFB-tag (Wu, Yeung et al. 2002)) and a biotin binding domain to one of the other catalytic domain (e.g. Strep-tag II (Schmidt and Skerra 1993) or Nano-tag (Lamla and Erdmann 2004)) in the chimeric enzyme according to the invention.

In one embodiment of the chimeric enzyme according to the invention, at least two of said catalytic domains can be assembled, by non-covalent linkage, in particular by leucine zippers.

Preferably, at least said catalytic domain of a DNA-dependant RNA polymerase is assembled by non-covalent linkage, in particular by leucine zippers, to at least one of the catalytic domain chosen in the group consisting of:
said catalytic domain of a RNA triphosphatase;
said catalytic domain of a guanylyltransferase; and
said catalytic domain of a $N^7$-guanine methyltransferase.

The leucine zippers, which are dimeric coiled-coil protein structures composed of two amphipathic α-helices that interact with each other, are commonly used to homo- or hetero-dimerize proteins (O'Shea, Klemm et al. 1991). Each helices consist of repeats of seven amino acids, in which the first amino-acid (residue a) is hydrophobic, the fourth (residue d) is usually a Leucine, while the other residues are polar. The leucine zippers VELCRO ACID-p1 and BASE-p1, which form a parallel heterodimeric two-stranded coiled coil structures, have high propensity to form parallel protein hetero-dimers (O'Shea, Lumb et al. 1993). They have been used to heterodimerize membrane proteins (Chang, Bao et al. 1994; Pashine, Busch et al. 2003), as well as several soluble proteins (Busch, Reich et al. 1998; Busch, Pashine et al. 2002).

Other types of oligomerisation peptide domains can be also considered to generate chimeric enzyme according to the invention, to assemble at least two of said catalytic domains of the chimeric enzyme according to the invention, especially leucine zippers that form antiparallel heteromeric structures, such as the ACID-a1/BASE-a1 (Oakley and Kim 1998), ACID-Kg/BASE-Eg (McClain, Woods et al. 2001), NZ/CZ (Ghosh, Hamilton et al. 2000), ACID-pLL/BASE-pLL (Lumb and Kim 1995), and $EE_{1234}L$ and $RR_{1234}L$ (Moll, Ruvinov et al. 2001) leucine zippers. Disulfide-linked versions of leucine zippers can be also used to generate disulfide coiled coil-bound heterodimeric chimeric enzyme according to the invention (O'Shea, Lumb et al. 1993), as well as interchain disulfide bridges between cysteine residues under oxidizing conditions (Wells and Powers 1986).

At least two of said catalytic domains of a RNA triphosphatase, of a guanylyltransferase, of a $N^7$-guanine methyltransferase, and of a DNA-dependant RNA polymerase can thus be assembled by leucine zippers, in particular leucine zippers that form antiparallel heteromeric structures, such as the ACID-a1/BASE-a1 (Oakley and Kim 1998), ACID-Kg/BASE-Eg (McClain, Woods et al. 2001), NZ/CZ (Ghosh, Hamilton et al. 2000), and ACID-pLL/BASE-pLL leucine zippers, disulfide coiled coil-bound (O'Shea, Lumb et al. 1993), as well as disulfide bridges between cysteine residues (Wells and Powers 1986).

In one embodiment, the chimeric enzyme according to the invention comprises:
the wild type mRNA capping enzyme of the African Swine Fever virus or a mutant or a derivative thereof, which is able to add a $m^7$GpppN cap at the 5'-terminal end of RNA molecules, in particular the wild type African swine fever virus capping enzyme, fused to
the amino-terminal end of the wild type T7 RNA polymerase or mutant or derivative thereof which is able to synthesize single-stranded RNA complementary in sequence to the double-stranded template DNA in the 5'→3' direction, in particular the wild type of T7 RNA polymerase,
in particular via a linker, and more particularly via a $(Gly_3Ser)_4$ linker.

In another embodiment, the chimeric enzyme according to the invention comprises:
the wild type mRNA capping enzyme of the African Swine Fever virus or a mutant or a derivative thereof, which is able to add a $m^7$GpppN cap at the 5'-terminal end of RNA molecules, in particular the wild type African swine fever virus capping enzyme, fused to
the amino-terminal end of the wild type T3 RNA polymerase or mutant or derivative thereof which is able to synthetize single-stranded RNA complementary in sequence to the double-stranded template DNA in the 5'→3' direction, in particular the wild type of T3 RNA polymerase, in particular via a linker, and more particularly via a $(Gly_3Ser)_4$ linker.

In another embodiment, the chimeric enzyme according to the invention comprises:
the wild type mRNA capping enzyme of the African Swine Fever virus or a mutant or a derivative thereof, which is able to add a $m^7$GpppN cap at the 5'-terminal end of RNA molecules, in particular the wild type African swine fever virus capping enzyme, fused to
the amino-terminal end of the wild type SP6 RNA polymerase or mutant or derivative thereof which is able to synthetize single-stranded RNA complementary in sequence to the double-stranded template DNA in the 5'→3' direction, in particular the wild type of SP6 RNA polymerase,
in particular via a linker, and more particularly via a $(Gly_3Ser)_4$ linker.

In another embodiment, the chimeric enzyme according to the invention comprises
the wild type mRNA capping enzyme of the African Swine Fever virus or a mutant or a derivative thereof, which is able to add a m⁷GpppN cap at the 5'-terminal end of RNA molecules, in particular the wild type African swine fever virus capping enzyme, and the amino-terminal end of the wild type T7 RNA polymerase or mutant or derivative thereof which is able to synthetize single-stranded RNA complementary in sequence to the double-stranded template DNA in the 5'→3' direction, in particular the wild type of T7 RNA polymerase, assembled by leucine zippers.

The chimeric enzyme according to the invention can also further comprise a domain, which enhance the activity of at least one catalytic domain of the chimeric enzyme of the invention, in particular of at least one catalytic domain chosen in the group consisting of a catalytic domain of a RNA triphosphatase, a catalytic domain of a guanylyltransferase, a catalytic domain of a N⁷-guanine methyltransferase and a catalytic domain of a DNA-dependant RNA polymerase.

For example said domain, which enhance the activity of at least one catalytic domain of the chimeric enzyme of the invention, can be a 31-kDa subunit encoded by the vaccinia virus D12L gene (genomic sequence ID# NC_006998.1; GeneID#3707515; UniProtKB/Swiss-Prot ID#YP_232999.1), which has no intrinsic enzymatic activity, but enhances drastically the RNA N7-guanine methyltransferase activity of the D1R subunit of the vaccinia mRNA capping enzyme (Higman, Bourgeois et al. 1992; Higman, Christen et al. 1994; Mao and Shuman 1994).

In one embodiment, the chimeric enzyme of the invention comprises:

at least one catalytic domain of the vaccinia mRNA capping enzyme, in particular the 95 kDa subunit encoded by the vaccinia virus D1R gene (genomic sequence ID# NC_006998.1; GeneID#3707562; UniProtKB/Swiss-Prot ID# YP_232988.1), which has RNA-triphosphatase, RNA guanylyltransferase and RNA N7-guanine methyltransferase enzymatic activities (Cong and Shuman 1993; Niles and Christen 1993; Higman and Niles 1994; Mao and Shuman 1994; Gong and Shuman 2003);

at least one catalytic domain of a DNA-dependant RNA polymerase, in particular chosen in the group consisting of T7, T3 and SP6-RNA polymerases and more particularly the T7 RNA polymerase; and a 31-kDa subunit encoded by the vaccinia virus D12L gene, in particular assembled in whole or part via a linker, and more particularly via a (Gly₃Ser)₄ linker and/or by leucine zippers.

The invention also relates to an isolated nucleic acid molecule or a group of isolated nucleic acid molecules, said nucleic acid molecule(s) encoding a chimeric enzyme according to the invention.

Said group of isolated nucleic molecules encoding a chimeric enzyme according to the invention comprises or consists of all the nucleic acid molecules which are necessary and sufficient to obtain a chimeric enzyme according to the invention by their expression.

In one embodiment, said group of isolated nucleic acid molecules encoding a chimeric enzyme according to the invention comprises or consists of:

a nucleic acid molecule encoding at least one catalytic domain of a RNA triphosphatase, at least one catalytic domain of a guanylyltransferase and at least one catalytic domain of a N⁷-guanine methyltransferase; and a nucleic acid molecule encoding at least one catalytic domain of a DNA-dependant RNA polymerase.

In another embodiment, said group of isolated nucleic acid molecules encoding a chimeric enzyme according to the invention comprises or consists of:

a nucleic acid molecule encoding at least one catalytic domain of a RNA triphosphatase, a nucleic acid molecule encoding at least one catalytic domain of a guanylyltransferase, a nucleic acid molecule encoding at least one catalytic domain of a N⁷-guanine methyltransferase; and a nucleic acid molecule encoding at least one catalytic domain of a DNA-dependant RNA polymerase.

In particular, the nucleic acid molecule according to the invention can be operatively linked to at least one, preferably the whole promoter(s) chosen from the group consisting of:

a promoter for an eukaryotic DNA dependant RNA polymerase, preferably for RNA polymerase II; and a promoter for said catalytic domain of a DNA-dependant RNA polymerase.

The link of the nucleic acid to a promoter for a eukaryotic DNA dependant RNA polymerase, preferably for RNA polymerase II has notably the advantage that when the chimeric enzyme of the invention is expressed in an eukaryotic host cell, the expression of the chimeric enzymes is driven by the eukaryotic RNA polymerase, preferably the RNA polymerase II. These chimeric enzymes, in turn, can initiate transcription of the transgene. If tissue-specific RNA polymerase II promoters are used, the chimeric enzyme of the invention can be selectively expressed in the targeted tissues/cells.

Said promoter can be a constitutive promoter or an inducible promoter well known by one skilled in the art. The promoter can be developmentally regulated, inducible or tissue specific.

The invention also relates to a vector comprising a nucleic acid molecule according to the invention. Said vector can be appropriated for semi-stable or stable expression.

The invention also relates to a group of vectors comprising said group of isolated nucleic acid molecules according to the invention.

Particularly said vector according to the invention is a cloning or an expression vector.

The vectors can be viral vectors such as bacteriophages, or non-viral, such as plasmid vectors.

In one embodiment, said vector according to the invention is a bicistronic vector, in particular comprising a nucleic acid molecule according to the invention and a promoter for said catalytic domain of a DNA-dependant RNA polymerase and/or at least one DNA sequence of interest, wherein said DNA sequence is operatively linked to a promoter for said catalytic domain of a DNA-dependant RNA polymerase.

Said vector according to the invention can also comprise a promoter for said catalytic domain of a DNA-dependant RNA polymerase.

The invention also relates to a host cell comprising an isolated nucleic acid molecule according to the invention or a group of isolated nucleic acid molecules according to the invention or a vector according to the invention or a group of vectors according to the invention.

The host cell according to the invention can be useful for large-scale protein production.

Preferably, said catalytic domains of the DNA-polymerase RNA polymerase chimeric enzyme according to the invention are from different enzymes than those of the host cell to prevent the competition between the endogenous gene transcription and the transgene transcription.

The invention also relates to a genetically engineered non-human eukaryotic organism, which expresses a chimeric enzyme according to invention. Said non-human eukaryotic organism can be any non-human animals, plants.

The invention also relates to the use, particularly in vitro or ex vivo, of a chimeric enzyme according to the invention or an isolated nucleic acid molecule according to the invention or a group of isolated nucleic acid molecules according to the invention, for the production of RNA molecule with 5'-terminal m$^7$GpppN cap.

The invention also relates to the in vitro or ex vivo use of a chimeric enzyme according to the invention or an isolated nucleic acid molecule according to the invention or a group of isolated nucleic acid molecules according to the invention for the production of protein, in particular protein of therapeutic interest like antibody, particularly in eukaryotic systems, such as in vitro synthesized protein assay or cultured cells.

The invention also relates to a method, particularly in vitro or ex vivo, for producing a RNA molecule with 5'-terminal m$^7$GpppN cap encoded by a DNA sequence, in a host cell, said method comprising the step of expressing in the host cell a nucleic acid molecule or a group of nucleic acid molecules according to the invention, wherein said DNA sequence is operatively linked to a promoter for said catalytic domain of a DNA-dependant RNA polymerase, particularly said promoter being effective in said host cell.

Preferably, said catalytic domain of the DNA-dependent RNA-polymerase of the chimeric enzyme according to the invention is from different enzymes than those of the host cell to prevent the competition between the endogenous gene transcription and said DNA sequence transcription.

In particular, said method according to the invention can further comprise the step of introducing in the host cell said DNA sequence and/or the nucleic acid according to the invention, using well-known methods by one skilled in the art like by transfection using calcium phosphate, by electroporation or by mixing a cationic lipid with DNA to produce liposomes.

In one embodiment, said method according to the invention further comprises the step of inhibiting, in particular silencing (preferably by siRNA) the cellular transcription and post-transcriptional machineries of said host cell.

In one embodiment, said method according to the invention further comprises the step of inhibiting the expression of at least one of the subunits of the endogenous DNA-dependent RNA polymerase and/or of the endogenous capping enzyme in said host cell.

Said additional steps (i e inhibiting, in particular silencing (preferably by siRNA or shRNA) the cellular transcription and post-transcriptional machineries of said host cell and/or inhibiting the expression of one or several subunits of the endogenous DNA-dependent RNA polymerase and/or of the endogenous capping enzyme in said host cell) allow the optimization of RNA molecules with 5'-terminal m$^7$GpppN caps synthesis.

As used herein the term "endogenous DNA-dependent RNA polymerase" relates to the endogenous DNA-dependent RNA polymerase of said host cell. When the host cell is a eukaryotic cell, said endogenous DNA-dependent RNA polymerase is the RNA polymerase II.

As used herein the term "endogenous capping enzyme" refers to the endogenous capping enzyme of said host cell.

As used herein the term "inhibiting the expression of a protein" relates to a decrease of at least 20%, particularly at least 35%, at least 50% and more particularly at least 65%, at least 80%, at least 90% of expression of said protein Inhibition of protein expression can be determined by techniques well known to one skilled in the art, including but not limiting to Northern-Blot, Western-Blot, RT-PCR.

The step of inhibiting the expression of the endogenous DNA-dependent RNA polymerase and/or the endogenous capping enzyme in said host cell can be implemented by any techniques well known to one skilled in the art, including but not limiting to siRNA (small interfering RNA) techniques that target said endogenous DNA-dependent RNA polymerase and/or the endogenous capping enzyme, anti-sens RNA techniques that target said endogenous DNA-dependent RNA polymerase and/or the endogenous capping enzyme, shRNA (short hairpin RNA) techniques that target said endogenous DNA-dependent RNA polymerase and/or the endogenous capping enzyme.

In addition to siRNA (or shRNA; short hairpin RNA), other inhibitory sequences might be also considered for the same purpose including DNA or RNA antisense (Liu and Carmichael 1994; Dias and Stein 2002), hammerhead ribozyme (Salehi-Ashtiani and Szostak 2001), hairpin ribozyme (Lian, De Young et al. 1999) or chimeric snRNA U1-antisense targeting sequence (Fortes, Cuevas et al. 2003). In addition, other cellular target genes might be considered for inhibition, including other genes involved in the cellular transcription (e.g. other subunits of the RNA polymerase II or transcription factors), post-transcriptional processing (e.g. other subunit of the capping enzyme, as well as polyadenylation or spliceosome factors), and mRNA nuclear export pathway.

In one embodiment of the method according to the invention, said RNA molecule can encode a polypeptide of therapeutic interest.

In another embodiment, said RNA molecule can be a non-coding RNA molecule chosen in the group comprising siRNA, ribozyme, shRNA and antisense RNA. In particular, said DNA sequence can encode a RNA molecule chosen in the group consisting of mRNA, non-coding RNA, particularly siRNA, ribozyme, shRNA and antisense RNA.

The invention also relates to the use of a chimeric enzyme according to the invention as a capping enzyme and DNA-dependent RNA polymerase.

The invention also relates to a kit for the production of a RNA molecule with 5'-terminal m$^7$GpppN cap, comprising at least one chimeric enzyme according to the invention, and/or an isolated nucleic acid molecule and/or a group of nucleic acid molecules according to the invention, and/or a vector according to the invention and/or a group of vectors according to the invention.

In one embodiment the kit of the invention comprises a vector according to the invention and/or a group of vectors according to the invention, wherein said vector(s) comprising:
  a promoter for said catalytic domain of a DNA-dependant RNA polymerase, and/or
  at least one DNA sequence of interest, wherein said DNA sequence is operatively linked to a promoter for said catalytic domain of a DNA-dependant RNA polymerase.

The kit according to the invention can further comprise:
  a vector comprising a promoter for said catalytic domain of a DNA-dependant RNA polymerase; and/or
  at least one DNA sequence of interest, wherein said DNA sequence is operatively linked to a promoter for said catalytic domain of a DNA-dependant RNA polymerase.

The invention also relates to a chimeric enzyme according to the invention, an isolated nucleic acid molecule according to the invention, a group of nucleic acid molecules according to the invention or a vector according to the invention, for its use as a medicament, in particular for the prevention and/or treatment of human or animal pathologies, preferably by means of gene therapy.

The invention also relates to a pharmaceutical composition comprising a chimeric enzyme according to the invention, and/or an isolated nucleic acid molecule according to the invention and/or a group of nucleic acid molecules according to the invention, and/or a vector according to the invention. Preferably, said pharmaceutical composition according to the invention is formulated in a pharmaceutical acceptable carrier.

Pharmaceutical acceptable carriers are well known by one skilled in the art.

The pharmaceutical composition according to the invention can further comprise:
  at least one DNA sequence of interest, wherein said DNA sequence is operatively linked to a promoter for said catalytic domain of a DNA-dependant RNA polymerase.

Such components (in particular chosen in the group consisting of a chimeric enzyme according to the invention, an isolated nucleic acid molecule according to the invention, a group of isolated nucleic acid molecules according to the invention, a vector according to the invention, a group of vector(s) according to the invention and at least one DNA sequence of interest) can be present in the pharmaceutical composition or medicament according to the invention in a therapeutically amount (active and non-toxic amount).

Such therapeutically amount can be determined by one skilled in the art by routine tests including assessment of the effect of administration of said components on the pathologies and/or disorders which are sought to be prevent and/or to be treated by the administration of said pharmaceutical composition or medicament according to the invention.

For example, such tests can be implemented by analyzing both quantitative and qualitative effect of the administration of different amounts of said aforementioned components (in particular chosen in the group consisting of a chimeric enzyme according to the invention, an isolated nucleic acid molecule according to the invention, a group of isolated molecules according to the invention, a vector according to the invention, a group of vectors according to the invention and at least one DNA sequence of interest) on a set of markers (biological and/or clinical) characteristics of said pathologies and/or of said disorders, in particular from a biological sample of a subject.

The invention also relates to a therapeutic method comprising the administration of a chimeric enzyme according to the invention, and/or an isolated nucleic acid molecule according to the invention, and/or a group of nucleic acid molecules according to the invention and/or a vector according to the invention and/or a group of vectors according to the invention in a therapeutically amount to a subject in need thereof. The therapeutic method according to the invention can further comprise the administration of at least one DNA sequence of interest, wherein said DNA sequence is operatively linked to a promoter for said catalytic domain of a DNA-dependant RNA polymerase, in a therapeutically amount to a subject in need thereof.

Said chimeric enzyme, nucleic acid molecule and/or said vector according to the invention can be administrated simultaneously, separately or sequentially of said DNA sequence of interest, in particular before said DNA sequence of interest.

The invention also relates to a pharmaceutical composition according to the invention for its use for the prevention and/or treatment of human or animal pathologies, in particular by means of gene therapy.

Said pathologies can be chosen from the group consisting of pathologies, which can be improved by the administration of said at least one DNA sequence of interest.

The invention also relates to the use of a chimeric enzyme according to the invention, and/or an isolated nucleic acid molecule according to the invention, and/or a group of nucleic acid molecules according to the invention and/or a vector according to the invention, and/or a group of vectors according to the invention for the preparation of a medicament for the prevention and/or treatment of human or animal pathologies, in particular by means of gene therapy.

The invention also relates to a combination product, which comprises:
  at least one enzyme according to the invention and/or at least one nucleic acid molecule according to the invention and/or a group of nucleic acid molecules according to the invention and/or a at least one vector comprising and/or expressing a nucleic acid molecule according to the invention and/or a group of nucleic acid molecules according to the invention; and
  at least one DNA sequence of interest, wherein said DNA sequence is operatively linked to a promoter for said catalytic domain of a DNA-dependant RNA polymerase;
  for simultaneous, separate or sequential administration.

Said DNA sequence of interest can be an anti-oncogene (a tumor suppressor gene).

Said DNA sequence of interest can encode a polypeptide of therapeutic interest or a non-coding RNA chosen in the group comprising siRNA, ribozyme, shRNA and antisense RNA.

Said polypeptide of therapeutic interest can be selected from, a cytokine, a cell or nuclear receptor, a ligand, a coagulation factor, the CFTR protein, insulin, dystrophin, a growth hormone, an enzyme, an enzyme inhibitor, a polypeptide which has an antineoplastic effect, a polypeptide which is capable of inhibiting a bacterial, parasitic or viral, in particular HIV, infection, an antibody, a toxin, an immunotoxin, a subunit of RNA polymerase II (in particular the Rpb1 subunit of RNA polymerase II, which can be inhibited by the alpha-amanitin toxin) and a marker.

Preferably, the combination product according to the invention can be formulated in a pharmaceutical acceptable carrier.

In one embodiment of the combination product according to the invention, said vector is administrated before said DNA sequence of interest.

The invention also relates to a combination product according to the invention, for its use for the prevention and/or treatment of human or animal pathologies, in particular by means of gene therapy.

Said pathologies can be chosen from the group consisting of pathologies, which can be improved by the administration of at least one DNA sequence of interest, as described above.

For example, said pathologies, as well as their clinical, biological or genetic subtypes, can be chosen from the group comprising cancers and their predisposition (especially breast and colorectal cancers, melanoma), malignant hemopathies (in particular leukemias, Hodgkin's and non-Hodgkin's lymphomas, myeloma), coagulation and primary hemostasis disorders, hemoglobinopathies (especially sickle cell anemia and thalassemias), autoimmune disorders (including systemic lupus erythematosus and scleroderma), cardiovascular pathologies (in particular cardiac rhythm and conduction disorders, and hypertrophic cardiomyopathy), metabolic disorders (especially type I and type II diabetes mellitus and their complications, dsylipidemia, atherosclerosis and their complications, mucopolysaccharidoses, glycogen storage diseases, phenylketonuria), infectious disorders (including AIDS, viral hepatitis B, viral hepatitis C, influenza flu and other viral diseases; botulism, tetanus and other bacterial disorders; malaria and other parasitic disorders), muscular disorders (including Duchenne muscular dystrophy and Steinert myotonic muscular dystrophy), respiratory diseases (especially cystic fibrosis and alpha-1 antitrypsin deficiency), renal disease (especially polycystic kidney disease), liver diseases (including cirrhosis, Wilson disease, hepatotoxicity due to the alpha-amanitin, drug-related hepatotoxicity), colorectal disorders (including Crohn's disease and ulcerative colitis), ocular disorders especially retinal diseases (especially Leber's amaurosis, retinitis pigmentosa, age related macular degeneration), central nervous system disorders (especially Alzheimer's disease, Parkinson's disease, multiple sclerosis, Huntington's disease, neurofibromatosis, adrenoleukodystrophy, bipolar disease, schizophrenia and autism), and skin and connective tissue disorders (especially Marfan syndrome and psoriasis).

In one embodiment, the combination product of the invention comprises:

at least one vector comprising and expressing a nucleic acid molecule according to the invention and/or a group of nucleic acid molecules according to the invention, wherein said catalytic domain of a DNA-dependant RNA polymerase is a catalytic domain of a bacteriophage DNA-dependant RNA polymerase, particularly of a T7 bacteriophage DNA-dependant RNA polymerase; and at least one DNA sequence of interest, wherein said DNA sequence is operatively linked to a promoter for said catalytic domain of a bacteriophage DNA-dependant RNA polymerase, particularly of a T7 bacteriophage DNA-dependant RNA polymerase, wherein said DNA sequence of interest encodes the Rpb1 subunit of RNA polymerase II, which can be inhibited by the alpha-amanitin toxin.

The invention also relates to this combination product for its use for the prevention and/or treatment of human or animal hepatotoxicity due to the alpha-amanitin, by means of gene therapy.

The invention also relates to a method for producing the chimeric enzyme according to the invention comprising the step of expressing in at least one host cell said nucleic acid molecule or said group of nucleic acid molecules encoding the chimeric enzyme of the invention in conditions allowing the expression of said nucleic acid molecule(s) in said host cell.

The invention also relates to a method for producing the chimeric enzyme according to the invention comprising the steps of:

expressing a part of said group of nucleic acid molecules encoding a chimeric enzyme of the invention in a first host cell in conditions allowing the expression of said nucleic acid molecules in said host cell, to obtain a first part of the chimeric enzyme of the invention;

expressing the other part of said group of nucleic acid molecules encoding the chimeric enzyme of the invention in a second host cell in conditions allowing the expression of said nucleic acid molecules in said host cell to obtain a second part of the chimeric enzyme of the invention; and assembling said first part and said second part to obtain the chimeric enzyme of the invention.

The present invention will be explained in detail with examples in the following, but the technical scope of the present invention is not limited to these examples.

EXAMPLES

Example 1

Example of Active Monomeric Chimeric Enzyme Np868R-T7RNAP

I. Plasmids

Figure 1:
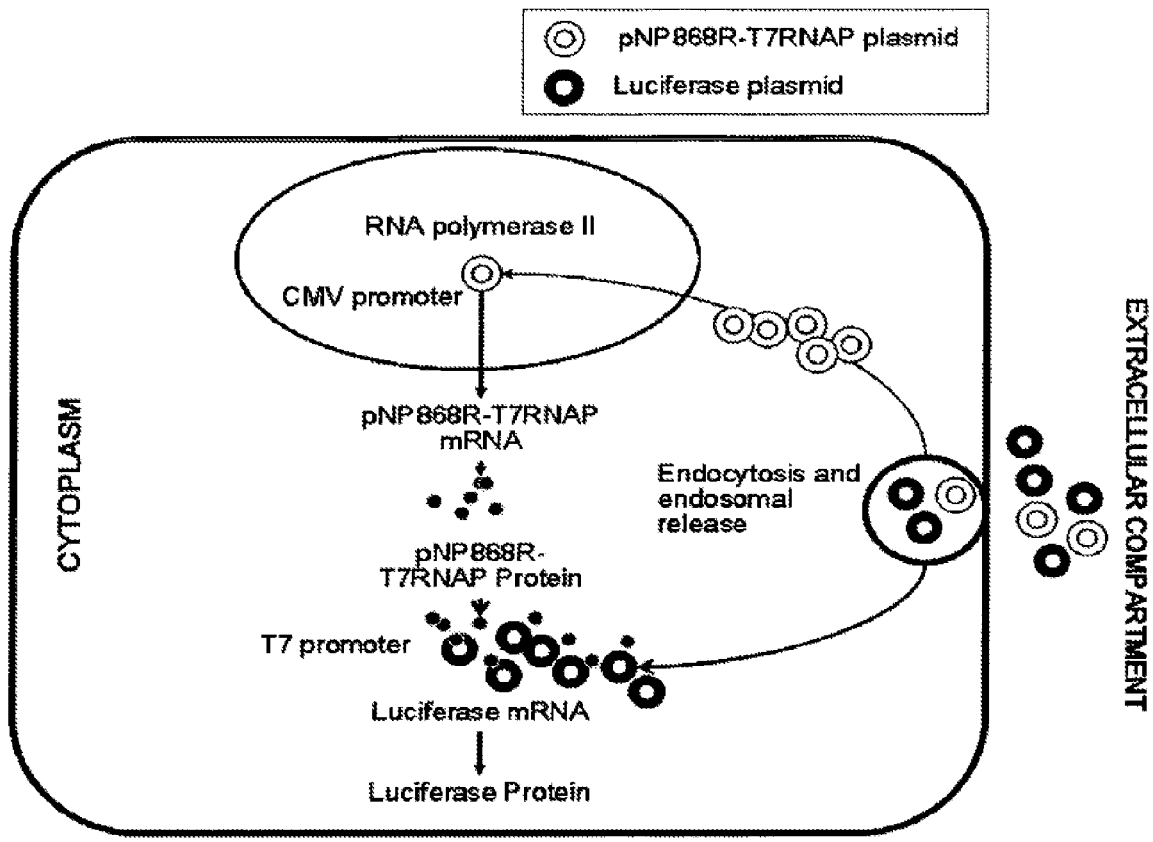
FIG. 1 represents a firefly luciferase gene reporter expression assay, which was used to monitor the translation yields triggered by a chimeric enzyme according to the invention the NP868R-T7RNAP. The pNP868R-T7RNAP or the pT7RNAP plasmids were co-transfected with the pT7p-Luciferase plasmid in the human HEK-293 cultured cells. The expression of NP868R-T7RNAP and T7RNAP enzymes is driven by the RNA polymerase II-dependent CMV promoter of the corresponding plasmids. The NP868R-T7RNAP and T7RNAP enzymes, in turn, are expected to initiate transcription at the T7 promoter of the pT7p-Luciferase gene reporter plasmid. If both the mRNA capping and DNA-dependent RNAP enzymatic activities of the NP868R-T7RNAP enzymes are retained, luciferase mRNA having a $m^7GpppGm$ cap structures are to be synthesized, which can be translated into firefly luciferase protein and detected by cell luminescence assay. In contrast, the T7RNAP enzyme is expected to synthesize RNA molecules without 5'-terminal $m^7GpppN$ cap, which are therefore poorly translated.

One plasmid has been synthesized, which encode for fusions between NP868R, the mRNA capping enzyme of the African Swine Fever Virus, and the wild-type phage DNA-dependent RNA polymerase of the bacteriophage T7. The capping enzyme was fused to the amino-terminal end of the T7 RNA polymerase via a (Gly$_3$Ser)$_4$ linker. The pNP868R-T7RNAP plasmid was used to assess the activity of the encoded enzyme by a firefly luciferase gene reporter expression assay (FIG. 1). In brief, pNP868R-T7RNAP and pT7p-Luciferase plasmids were co-transfected in the human HEK-293 cultured cells. The expression of the NP868R-T7RNAP enzyme is driven by the RNA polymerase II-dependent CMV promoter of the corresponding plasmid. NP868R-T7RNAP enzyme, in turn, is expected to initiate the transcription of the pT7p-Luciferase plasmid at its T7 promoter. If both the mRNA capping and DNA-dependent RNAP enzymatic activities of the NP868R-T7RNAP enzyme are retained, luciferase mRNA having m$^7$GpppGm cap structures are to be synthesized, which in turn can be translated into firefly luciferase protein and detected by cell luminescence assay. In addition, the pNP868R-T7RNAP plasmid was used to investigate the cellular distribution of the enzyme, as well as the cell viability, cytotoxicity and apoptosis related with the expression of the enzyme in the HEK-293 cells.

Figure 2:
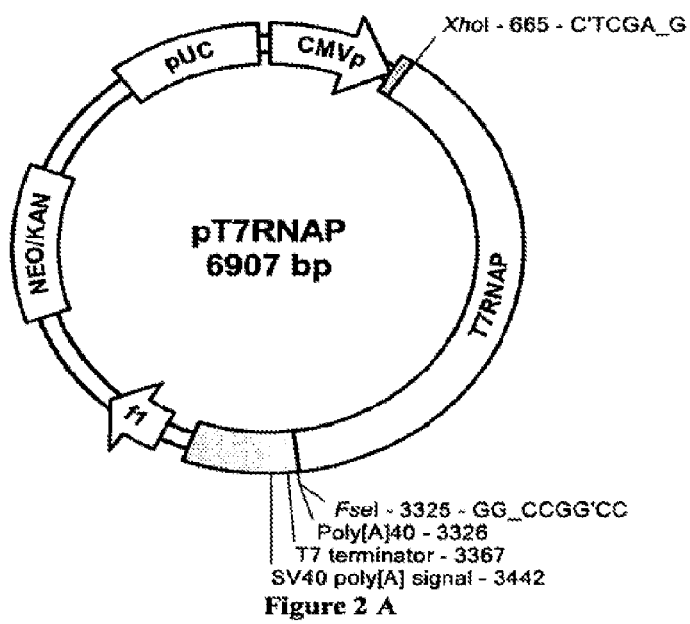
FIG. 2 (A-B) represents the physical maps of the pNP868R-T7RNAP and pT7RNAP plasmids. Physical maps of (A) pT7RNAP plasmid, which encodes for the wild-type phage DNA-dependent T7 RNA polymerase, (B) pNP868R-T7RNAP plasmids, which encodes for a fusion between the NP868R mRNA capping enzymes (African Swine Fever Virus) and the wild-type phage DNA-dependent T7 RNA polymerase (bacteriophage T7), via a flexible $(Gly_3Ser)_4$ linker. These two plasmids have the same design: CMV promoter, Kozak sequence followed by the NP868R-T7RNAP or T7RNAP open-reading frames (ORFs), poly [A]-track, TΦ terminator for phage RNA polymerase transcription, and SV40 polyadenylation signal.
Figure 2:
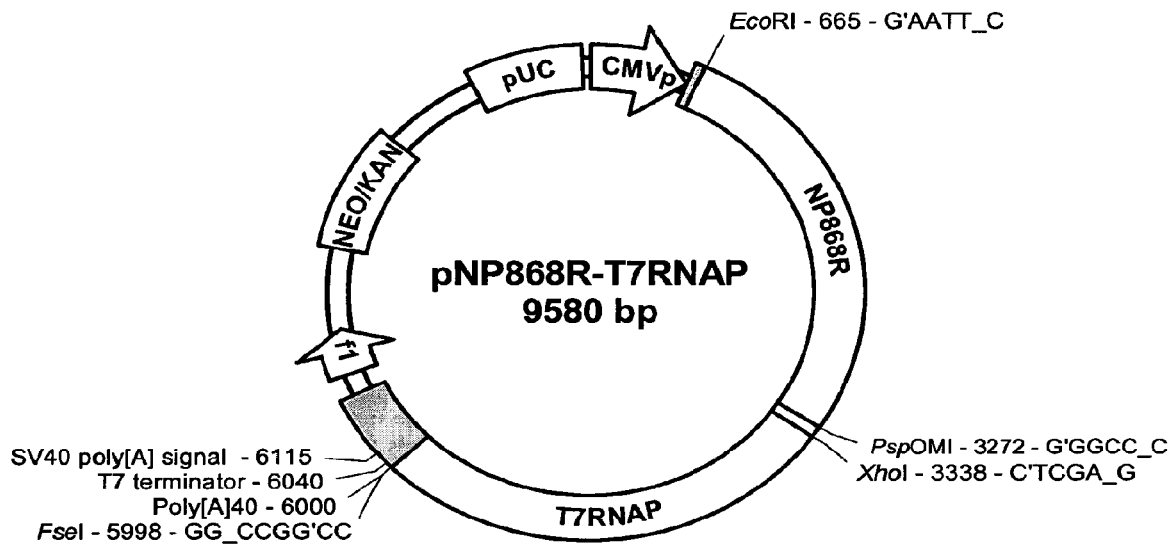

The plasmid encoding for the NP868R-T7RNAP and T7RNAP (T7 RNA polymerase) enzymes were synthesized in four steps by GeneArt AG (Regensburg, Germany). The protein sequence encoded by pT7RNA plasmid corresponds to SEQ ID NO:19. The protein sequence encoded by pNP868R-T7RNAP plasmid corresponds to SEQ ID NO:20. Firstly, a DNA fragment containing the T7 RNA polymerase promoter and the multiple cloning site (MCS) was removed from the pCMV-Script plasmid (Stratagene, La Jolla, Calif. USA). Secondly, a cassette was introduced in the pCMV-Script plasmid between its CMV promoter and its SV40 polyadenylation signal. This cassette consisted of the Lac operator stem-loop (Gilbert and Maxam 1973), a MCS, a poly[A]-tract, and a TΦ class-I hairpin terminator signal (Lyakhov, He et al. 1997). Thirdly, the Kozak consensus sequence for initiation of translation (Kozak 1987), followed by the entire open-reading frame (ORF) of the NP868R-T7RNAP or T7RNAP enzymes were assembled from synthetic oligonucleotides using a PCR-based method, cloned and fully sequence verified. The ORF of the NP868R-T7RNAP (SEQ ID NO:21) and of the ORF of the T7RNAP (SEQ ID NO:22) were optimized by altering for preferred codon usage, removing of cis-acting elements such as cryptic splice sites and poly(A) signals, as well as improving mRNA stability by removal of direct repeats and secondary structure elements. Fourthly, the entire ORFs of each NP868R-T7RNAP or T7RNAP were subcloned in the MCS of the cassette, resulting in the pNP868R-T7RNAP plasmid and the pT7RNAP plasmid. As a consequence of the construction strategy, two additional amino-acids (Glu, Phe) were added immediately downstream to the ATG of the Kozak sequence, two other were added immediately upstream to the $(Gly_3Ser)_4$ linker (Gly, Pro), and two immediately downstream to this linker (Leu, Glu) of the NP868R-T7RNAP enzyme. Finally, the pNP868R-T7RNAP and pT7RNAP plasmids had the following design (FIGS. 2A and 2B): CMV promoter, Kozak sequence followed by the NP868R-T7RNAP or T7RNAP ORFs, poly[A]-track, TΦ terminator for phage RNA polymerase transcription, and SV40 polyadenylation signal.

Figure 3:
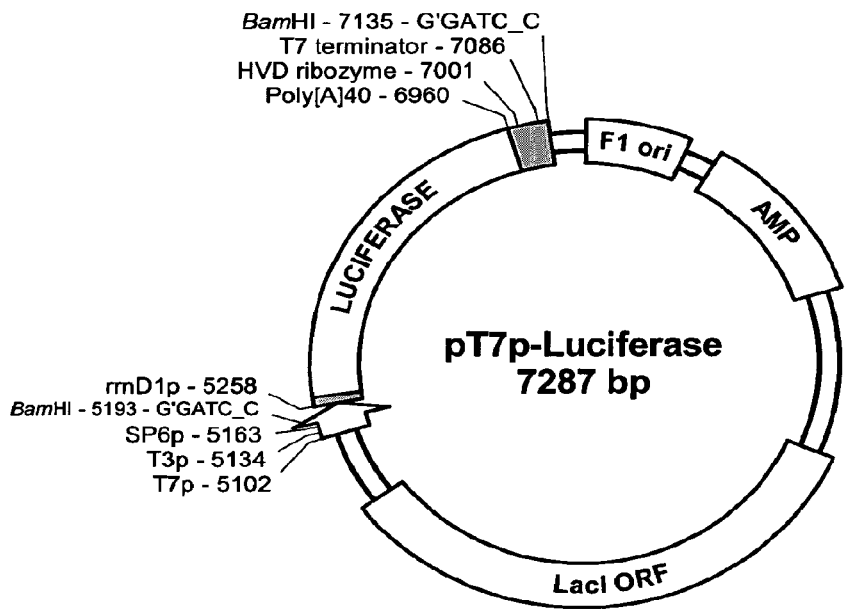
FIG. 3 (A-C) represents the physical maps of the firefly luciferase gene reporter plasmids. (A) pT7p-Luciferase: was designed to assay the activity of the NP868R-T7RNAP and the T7RNAP enzymes. It consist of an array of RNA polymerase promoters (T7, T3 and SP6 phage RNAP promoters, followed by the *E. coli* ribosomal rrnD1 promoter), a Lac operator sequence, the entire ORF of the firefly luciferase, a poly[A]-track, a hepatitis-D ribozyme encoding sequence for RNA auto-cleavage and the TΦ terminator in pET-22b(+) backbone, (B) BamHI-digested pT7p-Luciferase: in which the physical connection between the luciferase ORF and the promoter array is disrupted by the restriction enzyme digestion. This plasmid is used as a negative control. Arrows indicate the sites of digestion. (C) pCMV-Luciferase: in which the entire ORF of the firefly luciferase is under control of the CMV promoter. This plasmid is used as a positive comparator.
Figure 3:
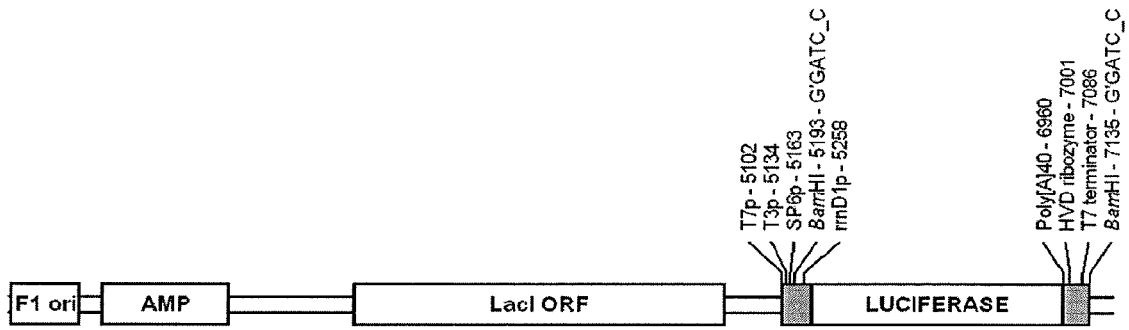
Figure 3:
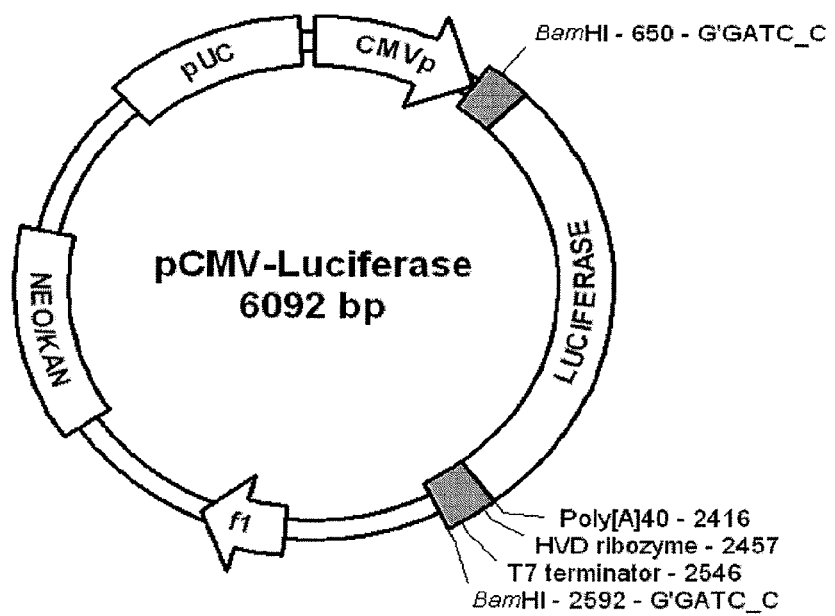

Two plasmids encoding for the firefly luciferase reporter gene were synthesized by Eurofins/MWG/Operon (Ebersberg, Germany). The pET-22b(+)RNAPp-Luciferase plasmid (named pT7p-Luciferase thereafter) was designed to assay the activity of the chimeric enzyme according to the invention. A test sequence was introduced in the pET-22b(+) backbone (Novagen, San Diego, Calif. USA), which consisted of an array of RNA polymerase promoters (T7, T3 and SP6 phage RNAP promoters, followed by the E. coli ribosomal rrnD1 promoter), a Lac operator stem-loop sequence, the entire ORF of the firefly luciferase, a poly[A]-track, a hepatitis-D ribozyme encoding sequence for RNA autocleavage (Conzelmann and Schnell 1994; Garcin, Pelet et al. 1995; Bridgen and Elliott 1996; Schurer, Lang et al. 2002; Walker, Avis et al. 2003) and the TΦ terminator for phage RNA polymerase transcription (FIG. 3A). A BamHI-digested version of the pT7p-Luciferase plasmid, which disrupts the physical connection between the luciferase ORF and the T7 promoter, was also used as negative control (FIG. 3B). Moreover, the pCMV-Luciferase plasmid, which was used as an active comparator, contained the firefly luciferase downstream to the RNA polymerase II-dependent CMV promoter of the pCMV-Script plasmid (FIG. 3C).

II. Cell Culture and Transfection

The Human Embryonic Kidney 293 cells (HEK-293, ATCC CRL 1573) were grown at 37° C. with 5% CO2. Cells were maintained in Dulbecco's Modified Eagle's Medium (DMEM) supplemented with 3.97 mM L-alanyl-L-glutamine (substituted on a molar equivalent basis for L-glutamine), 10% fetal bovine serum (FBS), 1% non-essential amino-acids, 1% penicillin and streptomycin, and 0.2% fungizone.

The day before transfection, HEK-293 cells were plated in 24 well plates at densities of approximately $8 \times 10^4$ cells per well. One hour prior to transfection, the medium was changed to fresh complete medium without antibiotics. Transfections were performed with Lipofectamine 2000 (Invitrogen, Carlsbad, Calif. USA) according to manufacturer's recommendations. In brief, plasmid DNA diluted in Opti-MEM I reduced serum medium (Invitrogen, Carlsbad, Calif. USA) and mixed with Lipofectamine 2000, were added to the cell medium. Following transfection, cells were incubated up to 120 hours prior to testing for luciferase and SEAP gene reporter expression.

Cells were co-transfected with the pT7RNAP or pNP868R-T7RNAP (0.4 μg DNA/well and 1 μL/well Lipofectamine 2000), together with the pT7p-Luciferase reporter plasmid (0.4 μg DNA/well and 1 μL/well Lipofectamine 2000). A series of other transfection conditions were used as negative controls and included: (a) the same co-transfection as before, except that the pT7p-Luciferase was digested by the BamHI restriction enzyme, which disrupts the physical connection between the luciferase ORF and the T7 promoter, (b) the pNP868R-T7RNAP or pT7RNAP plasmids alone, (c) the pT7p-Luciferase reporter plasmid digested or not alone, (d) the transfection reagent alone (i.e. Lipofectamine 2000). Cells were also transfected with the pORF-eSEAP plasmid (InvivoGen, San Diego, Calif.; used to normalize for transfection efficacy), as well as with the pCMV-T7RNAP plasmid (used as an active comparator).

III. Firefly Luciferase Luminescence and SEAP Colorimetric Assays

The firefly luciferase luminescence was assayed with the Luciferase Assay System according to manufacturer's recommendations (Promega, Madison Wis. USA). In brief, HEK-293 cells were lysed in Cell Culture Lysis Reagent (CCLR) lysis buffer, and then centrifuged at 12,000×g for 2 minutes at 4° C. Luciferase Assay Reagent (Promega; 100 μl/well) was added to supernatant (20 μl/well). Luminescence readout was taken on a luminometer reader (Fluostar; BMG Labtech, Offenburg Germany) according to the manufacturer's instructions.

The expression of pORF-eSEAP plasmid was used to normalize for transfection efficiency. This plasmid encodes for the secreted placental alkaline phosphatase (SEAP), which was assayed for enzymatic activity in cell culture medium using the Quanti-Blue colorimetric enzyme assay kit (InvivoGen, San Diego, Calif.) at selected time points. Gene reporter expression was expressed as the luciferase luminescence in studied cells subtracted for luminescence in cells treated with the transfection reagent only (RLU; relative light units), then divided by SEAP absorbance to normalize for transfection efficacy (OD, optic density) ratio.

IV. Statistical Analysis

All statistical analyses were performed using Student's t two-tailed test adjusted by Holm-Bonferroni correction for multiple testing, if appropriate. A p-value of less than 0.05 was regarded as being significant.

V. Gene Reporter Expression Assay

Figure 4:
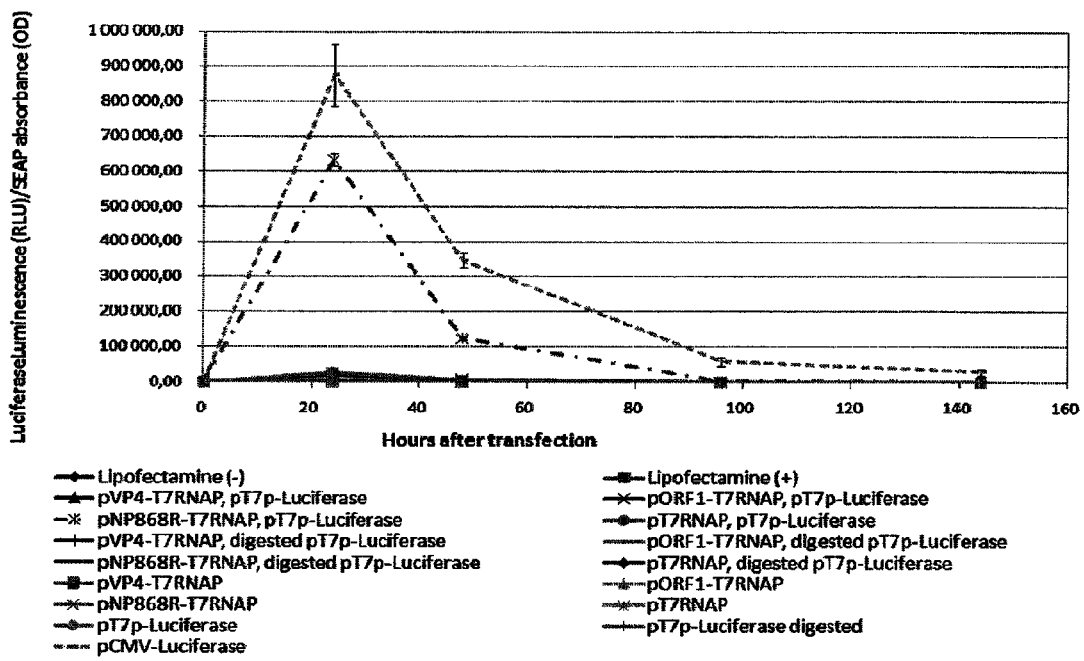
FIG. 4 (A-C) shows the Firefly luciferase gene reporter expression after plasmid transfection in HEK-293 cells. HEK-293 cells were cultured and transfected as described above. Cells were transfected with either the pNP868R-T7RNAP or the pT7RNAP plasmids (0.4 μg DNA/well and 1 μL/well Lipofectamine 2000), and/or the pT7p-Luciferase, BamHI-digested pT7p-Luciferase, or pCMV-T7RNAP (0.4 μg DNA/well and 1 μL/well Lipofectamine 2000), or none. The firefly luciferase luminescence was assayed at selected time points using the Luciferase Assay System (Promega, Madison Wis. USA). To normalize for transfection efficiency, cells were also transfected with the pORF-eSEAP plasmid, which encodes for the secreted placental alkaline phosphatase (SEAP) that was assayed in cell culture medium using the Quanti-Blue colorimetric enzyme assay kit (InvivoGen, San Diego, Calif.). Gene reporter expression was expressed as the luciferase luminescence in studied cells subtracted for luminescence in cells treated with the transfection reagent only (RLU; relative light units), then divided by SEAP absorbance (OD, optic density) ratio. Two independent repetitions of this experiment were performed. Errors bars represent standard error of the mean (SEM). Statistical analyses were performed using Student's t two-tailed test. (A) Firefly luciferase gene reporter expression in pNP868R-T7RNAP/pT7p-Luciferase, pT7RNAP/pT7p-Luciferase and pCMV-Luciferase transfected cells. Cells transfected with the pNP868R-T7RNAP/pT7p-Luciferase and the pCMV-Luciferase plasmids display 23- and 33-fold fold higher signal than the cells co-transfected with pT7RNAP/pT7p-Luciferase, respectively ($*p<0.05$). (B) Firefly luciferase gene reporter expression for cells transfected with pT7RNAP/pT7p-Luciferase, pT7RNAP/BamHI-digested pT7p-Luciferase ($*p<0.05$) and other control conditions (pT7RNAP alone, pT7p-Luciferase digested or not alone, or transfection reagent only). (C) Firefly luciferase gene reporter expression for the pNP868R-T7RNAP/pT7p-Luciferase, pNP868R-T7RNAP/BamHI-digested pT7p-Luciferase ($*p<0.05$) and other control conditions (pNP868R-T7RNAP alone, pT7p-Luciferase digested or not alone, or transfection reagent only).
Figure 4:
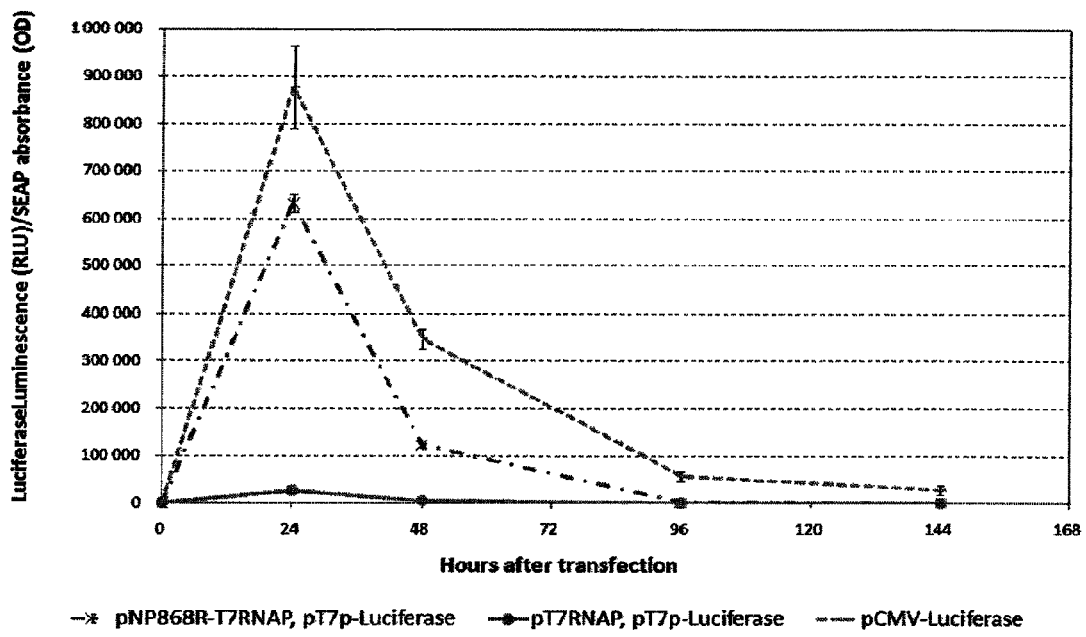
Figure 4:
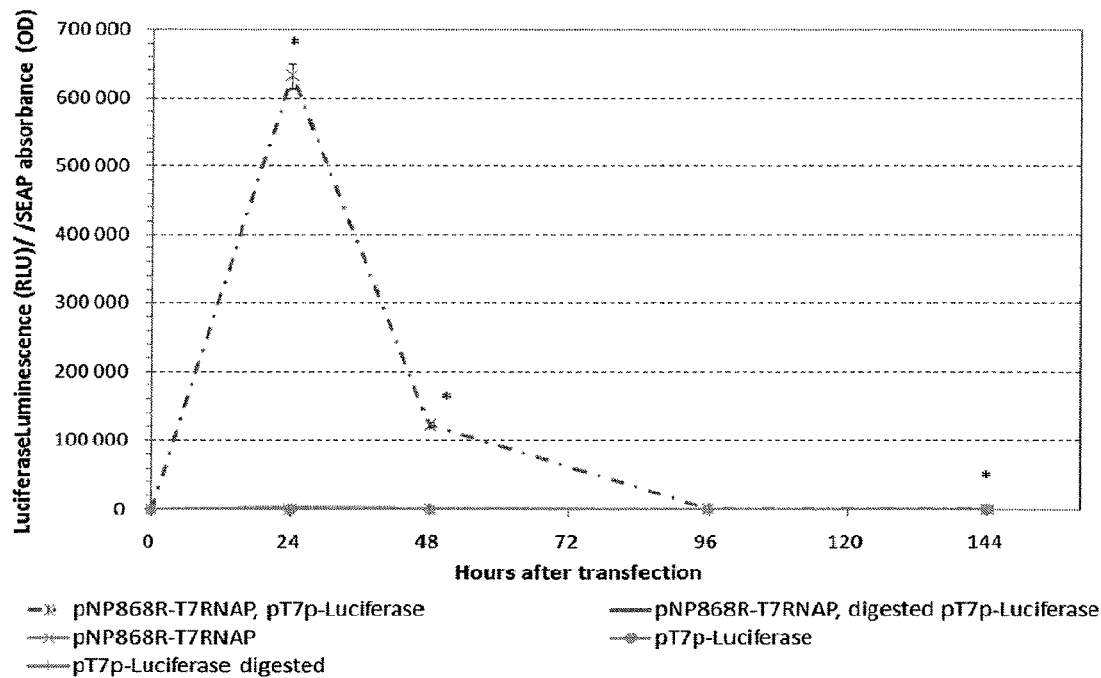

A firefly luciferase reporter luminescence assay was used to assess the translatability of mRNA generated by the chimeric enzyme according to the invention or T7RNAP enzyme. The co-transfection of the pT7RNAP and pT7p-Luciferase plasmids triggered low but detectable luciferase expression signal in comparison to cells co-transfected with the pT7RNAP/BamHI-digested version of the pT7p-Luciferase plasmid (which therefore demonstrate that luciferase gene reporter expression is driven by the phage T7 promoter; FIGS. 4A and 4B). This is in agreement with previously published reports, which have shown that the T7RNAP expressed in eukaryotic cells can synthesize RNA molecules which are poorly translated because of their absence of 5'-capping (Fuerst, Niles et al. 1986; Chen, Li et al. 1994). A drastic reduction of the firefly luciferase gene expression signal was also observed when the transfection was performed without the pT7RNAP plasmid (which confirm that luciferase expression require the presence of T7RNAP) or the pT7p-Luciferase plasmid (which confirm the specificity of the luminescence signal), or both.

The pNP868R-T7RNAP plasmid was cotransfected with the pT7p-Luciferase plasmid and tested under same conditions as above. At peak, approximately 23-fold higher luciferase expression signal was observed with pNP868R-T7RNAP/pT7p-Luciferase than with the pT7RNAP/pT7p-Luciferase plasmids (FIG. 4A). The specificity of the above findings was confirmed by the co-transfection of BamHI-digested version of the pT7p-Luciferase plasmid, as well as the transfection by pNP868R-T7RNAP or pT7p-Luciferase plasmids digested or not alone, which gave drastically reduced luciferase expression signal (FIG. 4C). At peak, co-transfection of pNP868R-T7RNAP/pT7p-Luciferase plasmids gave 72% of the luciferase expression signal to that of pCMV-T7RNAP plasmid (FIG. 4A).

In summary, the activity of the chimeric NP868R-T7RNAP enzyme according to the invention encoded by the pNP868R-T7RNAP plasmid has been demonstrated using a firefly luciferase reporter luminescence assay. The specificity of the present findings is supported by a series of controls, which suggest that both the mRNA capping and DNA-dependent RNA polymerase enzymatic activities of the NP868R-T7RNAP enzyme are retained when expressed in HEK-293 cells.

VI. Gene Reporter Expression Assay in Alpha-Amanitin Treated Cells

To further demonstrate that the transcription by pNP868R-T7RNAP is dependent of its phage DNA-dependent T7 RNA polymerase moiety, gene transfection assays were also performed in α-amanitin treated cells. Alpha-amanitin is a specific inhibitor of the nuclear RNA polymerase II (Jacob, Sajdel et al. 1970; Kedinger, Gniazdowski et al. 1970; Lindell, Weinberg et al. 1970), which binds its Rpb1 subunit (Bushnell, Cramer et al. 2002). In contrast, alpha-amanitin has no effect on transcription by the phage T7 RNA polymerase which was used to engineer the NP868R-T7RNAP chimeric enzyme according to the invention (Kupper, McAllister et al. 1973; Engleka, Lewis et al. 1998).

Figure 5:
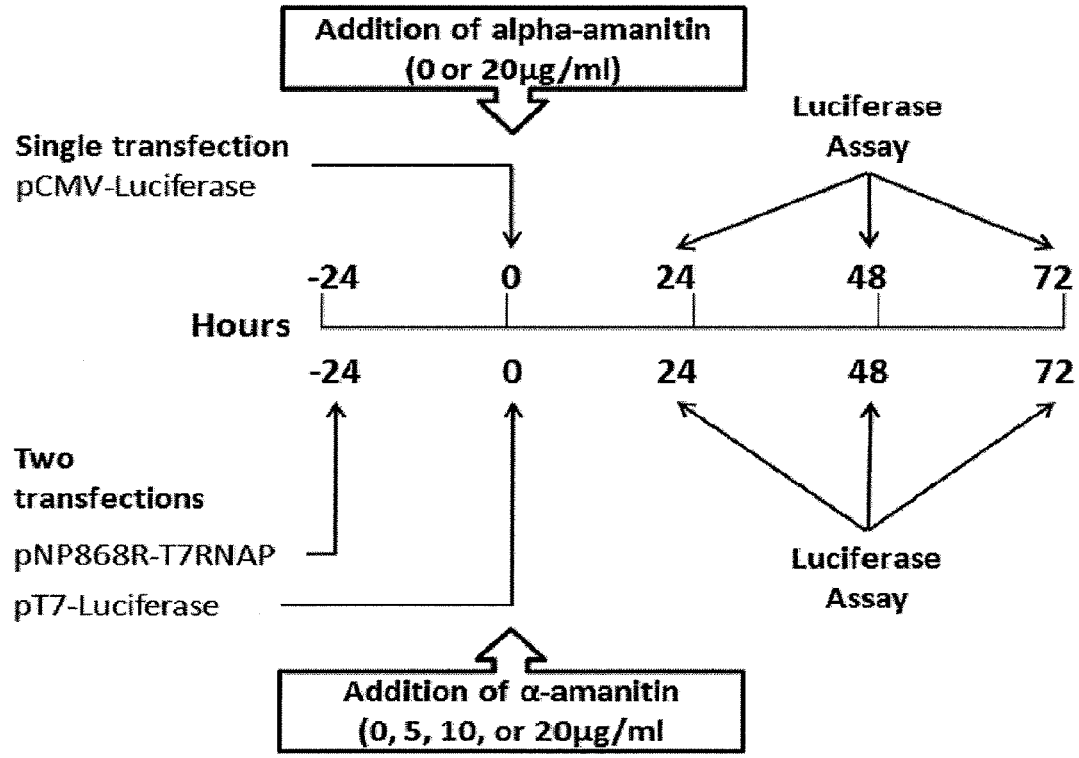
FIG. 5 (A-C) represents the Firefly luciferase gene reporter expression of HEK-293 transfected cells treated with α-amanitin. (A) Schematic diagram of the assay. For the pCMV-Luciferase plasmid (expression of luciferase is driven by the RNA polymerase II-dependent CMV promoter), α-amanitin was added to cell medium (at 0 or 20 μg/ml) simultaneously to cell transfection. For the pNP868R-T7RNAP/pT7p-Luciferase plasmids, a first transfection with the pNP868R-T7RNAP plasmid (expression of NP868R-T7RNAP is driven by the RNA polymerase II-dependent CMV promoter) was performed 24 hours before addition of α-amanitin to the cell medium (at concentrations ranging from 0 to 20 μg/ml) and a second transfection with the pT7p-Luciferase plasmid. Two repetitions of these experiments were performed. Errors bars represent standard error of the mean (SEM). Statistical analysis was performed as described above. (B) α-amanitin nearly completely abolished luciferase gene reporter expression of cells transfected with the pCMV-Luciferase plasmid; $*p<0.05$) (C) α-amanitin triggered only a mild decrease of luciferase expression signal in cells transfected with the pNP868R-T7RNAP/pT7p-Luciferase plasmids ($*p<0.05$), which therefore suggest that the transcription by the NP868R-T7RNAP enzyme is dependent of its phage DNA-dependent T7 RNA polymerase moiety.
Figure 5:
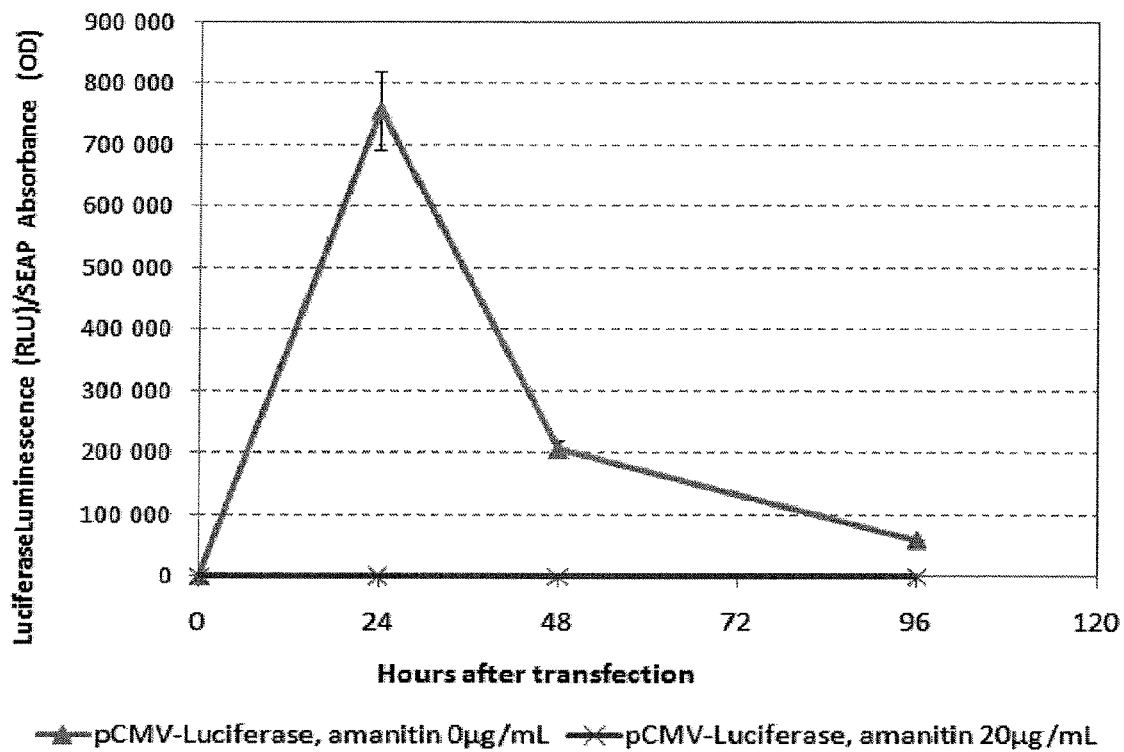
Figure 5:
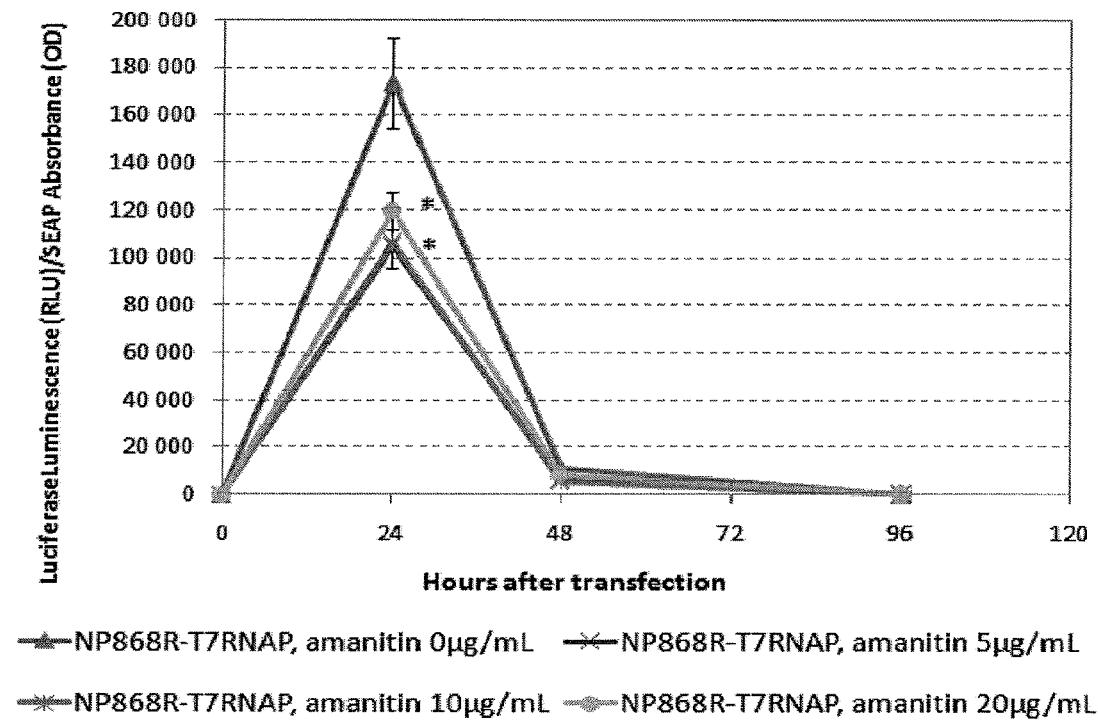

To initiate the expression of the NP868R-T7RNAP enzyme, which is driven by the RNA polymerase II-dependent CMV promoter, cells were transfected with the pNP868R-T7RNAP 24 hours before addition of α-amanitin to cell medium (at concentrations ranging from 0 to 20ηg/ml) and a second transfection with the pT7p-Luciferase plasmid (FIG. 5A). For the pCMV-Luciferase plasmid, cells were simultaneously transfected and treated with α-amanitin (at 0 or 20 μg/ml; FIG. 5A). Gene reporter expression was expressed as the luciferase luminescence in studied cells subtracted for luminescence in cells treated with the transfection reagent only (RLU; relative light units), then divided by SEAP absorbance to normalize for transfection efficacy (OD, optic density) ratio.

As expected, α-amanitin nearly completely abolished firefly luciferase gene reporter expression of pCMV-Luciferase transfected cells (FIG. 5B). In contrast, only a mild decrease of luciferase expression was triggered by α-amanitin at all concentrations in pNP868R-T7RNAP/pT7p-Luciferase transfected cells (FIG. 5C).

The present findings, therefore confirms that the transcription by NP868R-T7RNAP enzyme depends of the enzymatic activity of its phage T7 DNA-dependent RNA polymerase moiety.

VII. Immunofluorescence

The subcellular distribution of the NP868R-T7RNAP enzyme was investigated by indirect immunofluorescence. HEK-293 cells were plated in 24 well plates at $8 \times 10^4$ cells/well, on poly-L-lysine coated coverslips (BD BioCoat; Bioscience, Mississauga, ON USA), then transfected as previously described. Six and 24-hours after transfection, cells were washed in phosphate buffered saline (PBS), and then fixed in 4% paraformaldehyde for 15 minutes. After fixation, cells were washed with PBS, and then permeabilised for 30 minutes in PBS containing 5% goat serum (Invitrogen), 0.1% Triton X-100 and 0.02% sodium azide. Cells were incubated overnight at 4° C. with the mouse monoclonal antibody raised against T7 RNA Polymerase (1:200, Novagen). After extensive washing with PBS, cells were incubated for 3 hours at room temperature with fluorescein isothiocyanate-conjugated (FITC) goat anti-mouse IgG (Sigma-Aldrich). Cell nuclei were stained with 4'-6-Diamidino-2-phenylindole (DAPI) for 5 minutes. Cells were then washed and mounted in the anti-fade medium Mowiol 4-88 (Calbiochem, Gibbstown, N.J. USA). Cells were analyzed by using an epifluorescence microscope with appropriate filters.

As expected, a weak but detectable FITC signal was observed at both 6 and 24-hours in the cytoplasm of cells transfected with the pNP868R-T7RNAP plasmid, while their nuclei were stained by DAPI.

VIII. Cell Viability, Cytotoxicity and Apoptosis Assays

The ApoTox-Glo Triplex Assay (Promega, Madison Wis.) was used to investigate whether the expression of the NP868R-T7RNAP enzyme impair viability, or induce toxicity or apoptosis of transfected cells. Two protease activities were assayed by fluorescence: one is a marker of cell viability (i.e. the peptide substrate GF-AFC), and the other is a marker of cytotoxicity (i.e. the peptide substrate bis-AAF-R110). Apoptosis was assayed by the luminogenic caspase-3/7 substrate, which contains the tetrapeptide sequence DEVD, in a reagent optimized for caspase activity.

Cell culture and transfections were performed as previously, except that HEK-293 cells were plated in 96-well plates at densities ranging of $1.2 \times 10^4$ cells per well. Cells were transfected with the pNP868R-T7RNAP plasmid, the pT7RNAP plasmid, or the transfection reagent only. Apo-Tox-Glo Triplex Assay was performed according to manufacturer's recommendations. In brief, at selected time points, the viability/cytotoxicity reagent containing both GF-AFC Substrate and bis-AAF-R110 substrates were added to the wells and incubated for 30 minutes at 37° C., before fluorescence assessment at two different wavelength sets for viability and cytotoxicity. The caspase reagent was then added to all wells, and luminescence was measured after 30 minutes incubation at room temperature. Statistical analysis was performed as above. Cell viability, cytotoxicity and apoptosis levels were expressed as the luminescence/fluorescence signal in studied cells subtracted for luminescence/fluorescence in untreated cells.

Figure 6:
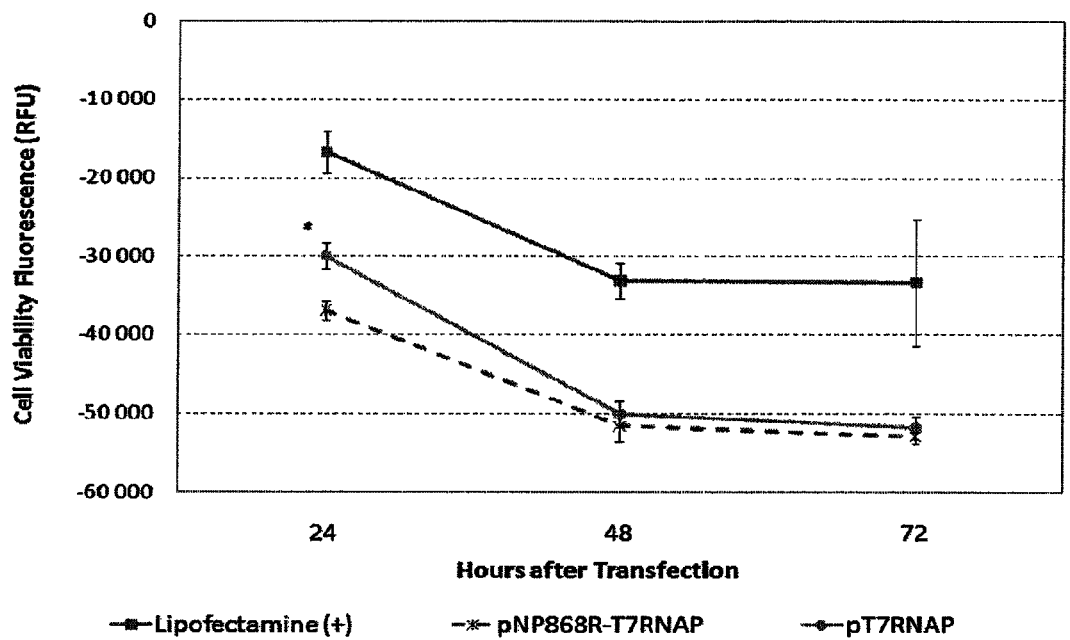
FIG. 6 (A-C) represents the cell viability, cytotoxicity and apoptosis assays of HEK-293 transfected cells. Cells were cultured and transfected as above with the pNP868R-T7RNAP or pT7RNAP plasmids. Cell viability, cytotoxicity and apoptosis were assessed at selected time points using the ApoTox-Glo Triplex Assay. Two repetitions of this experiment were performed. Errors bars represent standard error of the mean (SEM). Cell viability, cytotoxicity and apoptosis levels were expressed as the luminescence/fluorescence signal in studied cells subtracted for luminescence/fluorescence in untreated cells. Statistical analysis was performed as above. The transfection reagent (i.e. Lipofectamine 2000), with or without plasmid DNA, impairs cell viability, cytotoxicity and apoptosis. However, no statistically significant difference was observed between cells transfected with the pNP868R-T7RNAP plasmid and the pT7RNAP plasmid for (A) cell viability levels, at all time points, except at day 1 (two-tailed Student's t test, $*p<0.05$), (B) cytotoxicity levels at all time points, or (C) apoptosis levels at all time points.
Figure 6:
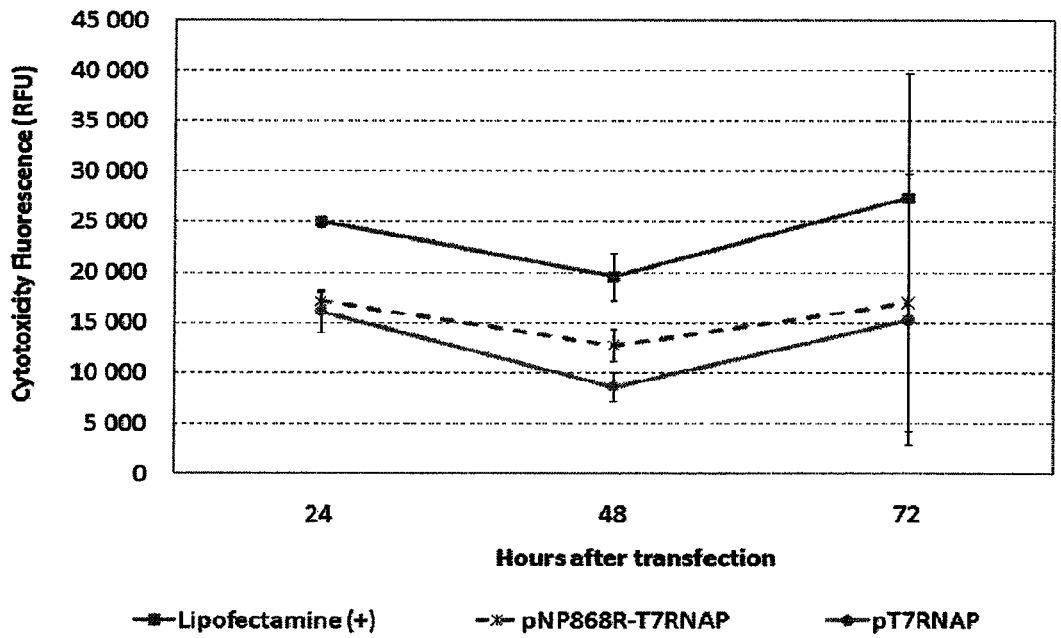
Figure 6:
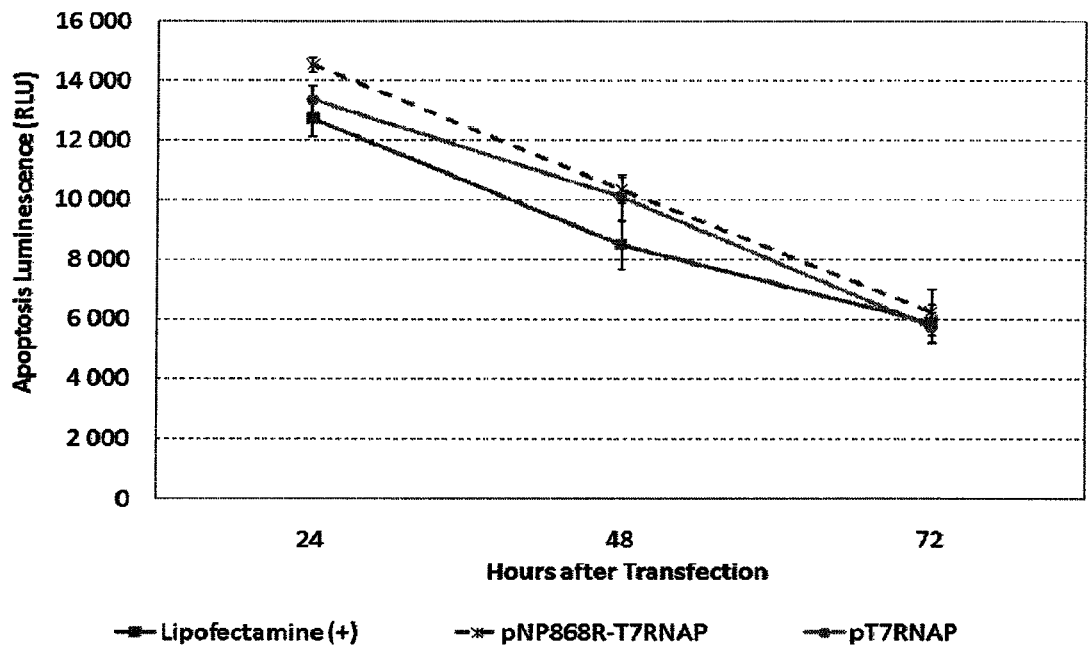

As previously reported (Patil, Rhodes et al. 2004), the cell viability, cytotoxicity and apoptosis were significantly impaired in cells treated with the transfection reagent (i.e. Lipofectamine 2000) as compared to untreated cells (FIGS. 6A, 6B and 6C). As also expected, cell viability, cytotoxicity and apoptosis were generally more impaired when plasmid DNA were added to transfection mixture (FIGS. 6A, 6B and 6C). However, at all studied time points, the cell viability, cytotoxicity or apoptosis markers of cells transfected with the pNP868R-T7RNAP plasmid were not statistically different to that of pT7RNAP plasmid, except 24 hours after transfection for cell viability only, which is possibly due to hazard only (FIGS. 6A, 6B and 6C; two-tailed Student's t test for individual time points, P-value<0.05).

In conclusion, no obvious difference in cytotoxicity, cell viability, and apoptosis of the NP868R-T7RNAP enzyme can be demonstrated in comparison to T7RNAP, which has no recognized capping enzymatic activity.

Example 2

Examples of Active Monomeric Chimeric ENZYMES NP868R-T3RNAP and NP868R-SP6RNAP

Two other types of monomeric chimeric enzymes according to the invention have been generated, which consist of NP868R, the monomeric mRNA capping enzyme of the African Swine Fever Virus, fused to the amino-terminal end of the wild type T3 or SP6 monomeric bacteriophage DNA-dependent RNA polymerases, via the flexible linker $(Gly_3Ser)_4$.

I. Methods

Figure 7:
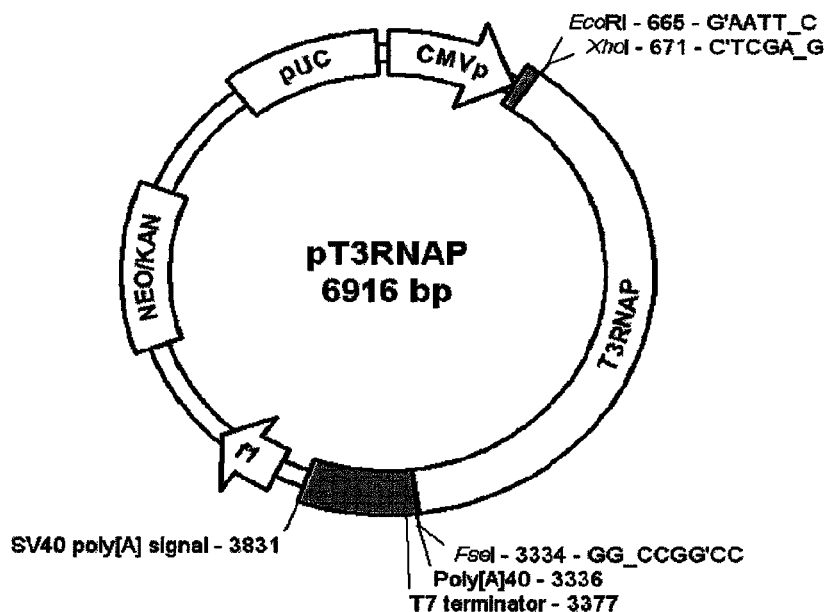
FIG. 7 (A-D) represents the physical maps of the plasmids used for the monomeric NP868R-T3RNAP and NP868R-SP6RNAP chimeric enzymes. Physical maps of: (A) pT3RNAP plasmid, which encodes for the phage DNA-dependent T3 RNA polymerase, (B) pSP6 RNAP plasmid, which encodes for the phage DNA-dependent SP6 RNA polymerase, (C) pNP868R-T3RNAP plasmid, which encodes for a fusion between the NP868R African Swine Fever Virus mRNA capping enzyme and the phage DNA-dependent T3 RNA polymerase, via the flexible $(Gly_3Ser)_4$ linker, (D) pNP868R-SP6RNAP plasmid, which encodes for a fusion between the NP868R African Swine Fever Virus mRNA capping enzyme and the phage DNA-dependent SP6 RNA polymerase, via the flexible $(Gly_3Ser)_4$ linker. These two plasmids have the same design: CMV promoter, Kozak sequence followed by the ORFs, poly[A]-track, TΦ terminator for phage RNA polymerase transcription, and SV40 polyadenylation signal.
Figure 7:
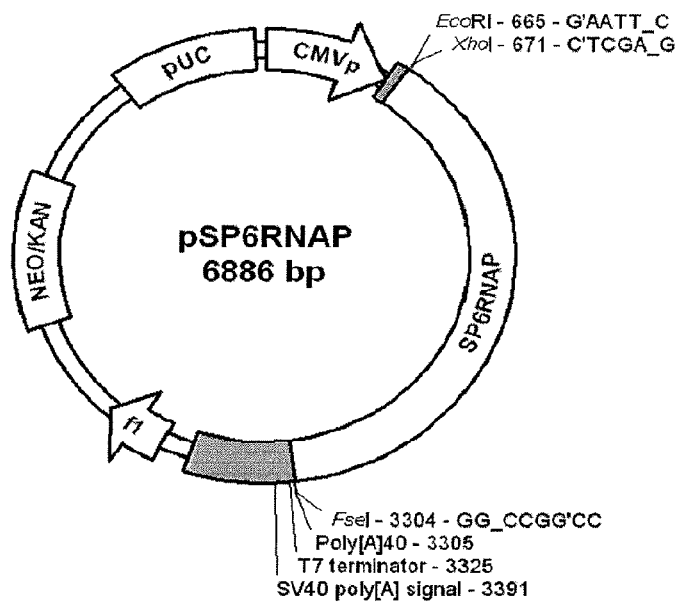
Figure 7:
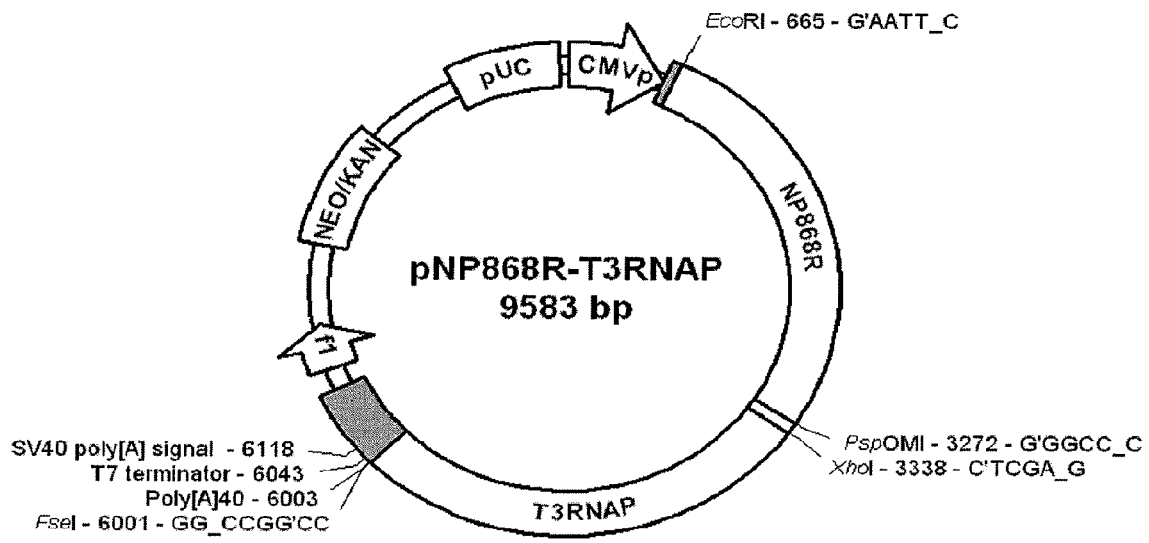
Figure 7:
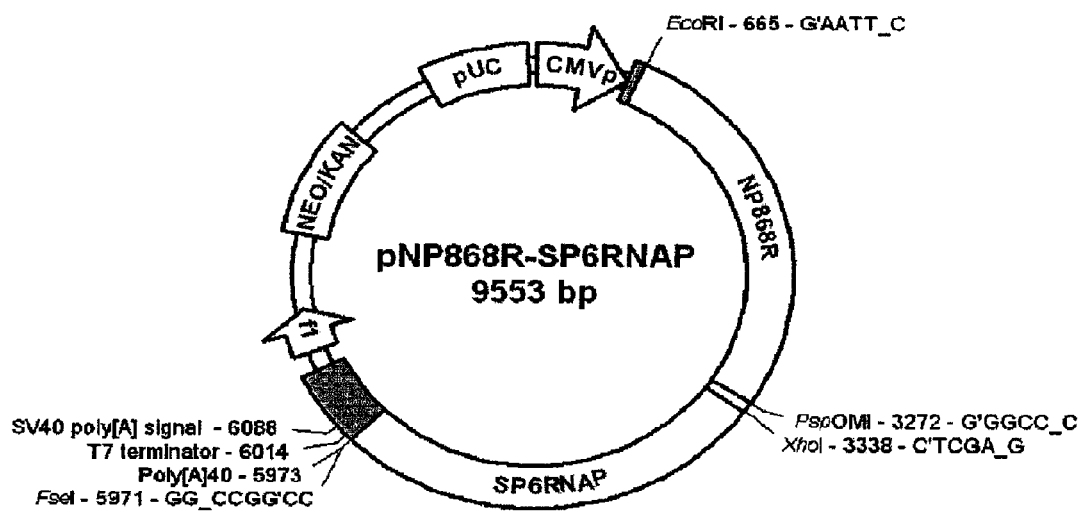

The sequences used to generate said monomeric chimeric enzymes were assembled from synthetic oligonucleotides using a PCR-based method, cloned and fully sequence verified. These sequences were subcloned in the pCMV-Script plasmid containing the subcloning cassette previously described. Finally, all the plasmids used for expression had the similar design: CMV IE1 promoter/enhancer promoter, Kozak sequence followed by the ORFs, poly[A]-track, TΦ terminator for phage RNA polymerase transcription, and SV40 polyadenylation signal (FIG. 7 (A-D)).

As a consequence of the subcloning strategy, amino-acids were added immediately downstream to the ATG of the Kozak sequence encoded by the plasmids (Glu-Phe-Leu-Glu for pT3RNAP and pSP6RNAP; Glu-Phe for pNP868R-T3RNAP and pNP868R-SP6RNAP). In addition, two amino-acids were added immediately upstream (Gly-Pro for pNP868R-T3RNAP and pNP868R-SP6RNAP) or downstream to the $(Gly_3Ser)_4$ linker (Leu-Glu for pNP868R-T3RNAP and pNP868R-SP6RNAP).

HEK-293 cells were grown as previously described in 24-wells plates and transfected using the Lipofectamine 2000 reagent, and the appropriate plasmids (0.4 μg DNA/well, plus 1 μL/well lipofectamine 2000, per transfected plasmid). The firefly luciferase luminescence was assayed as previously described using the pT7p-Luciferase (which also contains both the T3 and SP6 promoters) and the Luciferase Assay System. The expression of pORF-eSEAP plasmid was used to normalize for transfection efficacy as previously described. Statistical analyses were performed using Student's t two-tailed test adjusted by Holm-Bonferroni correction for multiple testing, if appropriate. A p-value of less than 0.05 was regarded as being statistically significant.

II. Results

Figure 8:
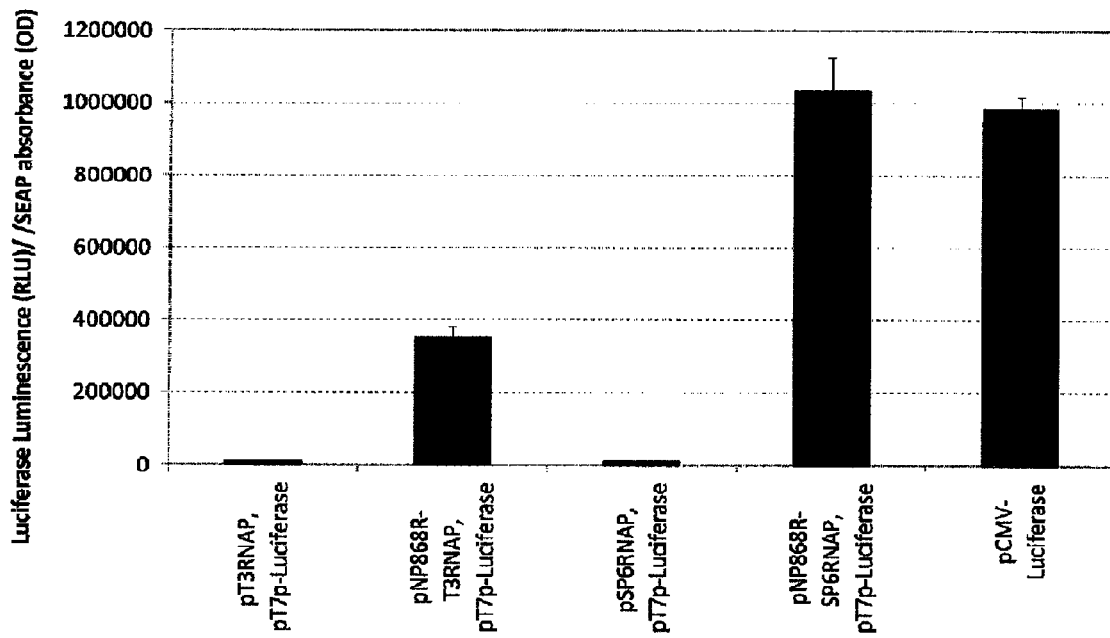
FIG. 8 represents the expression of the luciferase reporter gene by the monomeric NP868R-T3RNAP and NP868R-SP6RNAP chimeric enzymes. Transfection and luciferase assay were performed as previously described. Gene reporter expression was expressed as the luciferase luminescence in studied cells subtracted for luminescence in cells treated with the transfection reagent only (RLU, relative light units), then divided by SEAP absorbance (OD, optic density) ratio. Four repetitions of this experiment were performed. Errors bars represent standard error of the mean (SEM).

As shown in FIG. 8, when co-transfected with the reporter pT7p-luciferase plasmid, both pNP868R-T3RNAP and NP868R-SP6RNAP show strong luciferase gene reporter signal, which was 14- and 56-folds higher than pT3RNAP or pSP6RNAP, respectively (p<0.001 for each comparisons, Student's t-test). The NP868R-T3RNAP enzyme has 36% activity to that of pCMV-T7RNAP plasmid (p<0.001, Student's t-test), whereas or NP868R-SP6RNAP heterodimeric enzyme shows 1.1-fold luciferase reporter gene expression to that of pCMV-T7RNAP plasmid (non-statistically significant difference, Student's t-test).

These results demonstrate the activity of different types of monomeric chimeric enzymes according to the invention.

Example 3

Examples of Active Dimeric and Trimeric Chimeric Enzymes

Figure 9:
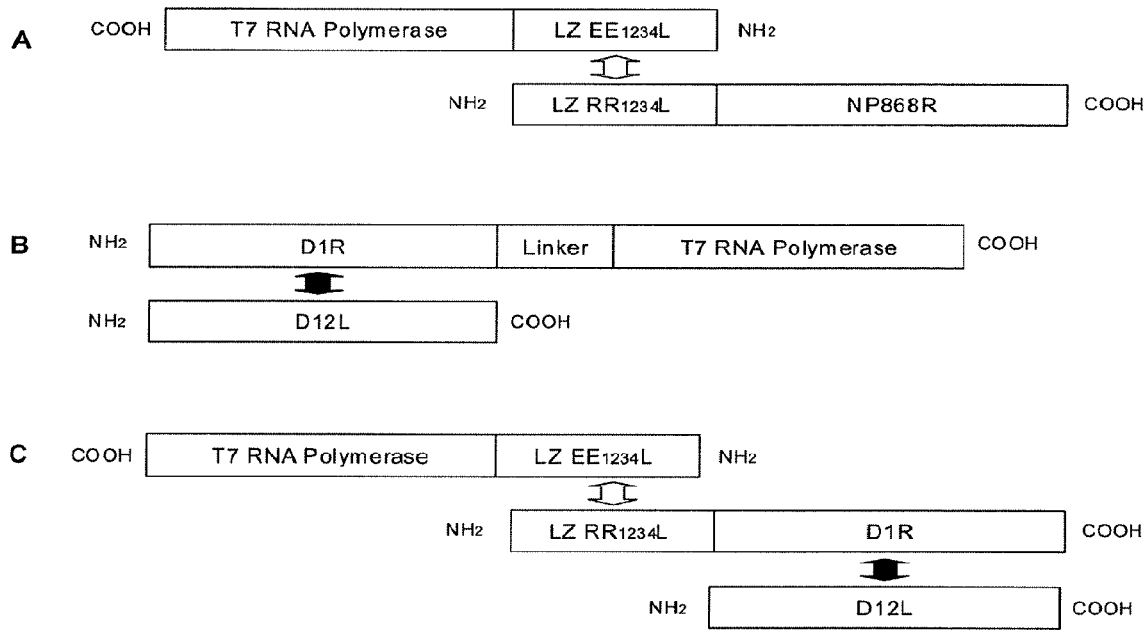
FIG. 9 (A-C) represents the schematic structure of heterodimeric and heterotrimeric chimeric enzymes. (A) Heterodimeric $RR_{1234}L$-NP868R/$EE_{1234}L$-T7RNAP enzyme. The leucine zippers $EE_{1234}L$ (acid) and $RR_{1234}L$ (basic) were added to the amino-terminal ends of NP868R and T7 RNA polymerase, respectively, which interact to form an heterodimer; (B) Heterodimeric D12L/D1R-T7RNAP CCPP enzyme. The D1R subunit of the vaccinia virus mRNA capping enzyme is fused to the amino-terminal end of the single-unit T7 RNA polymerase. When co-expressed with the D12L subunit of the mRNA capping enzyme, D1R-T7RNAP forms a heterodimer designated D12L/D1R-T7RNAP. For simplification, the other construction, i.e. D1R/D12L-T7RNAP chimeric enzyme, is not shown; (C) Heterotrimeric D12L/$RR_{1234}L$-D1R/$EE_{1234}L$-T7RNAP chimeric enzyme. The leucine zippers $EE_{1234}L$ (acid) and $RR_{1234}L$ (basic) were added to the amino-terminal ends of D1R and T7 RNA polymerase, respectively. The co-expression of $RR_{1234}L$-D1R together with $EE_{1234}L$-T7RNAP and the D12L subunit of the vaccinia virus mRNA capping enzyme form a heterotrimer. For simplification, the other construction, i.e. D1R/$RR_{1234}L$-D12L/$EE_{1234}L$-T7RNAP chimeric enzyme, is not shown. Open arrows indicate leucine-zipper binding in antiparallel orientation. Black arrows indicate other types of protein interaction.

Different types of active oligomeric chimeric enzymes according to the invention have been generated as shown in FIG. 9:

one heterodimeric chimeric enzyme, resulting of the non-covalent linkage between the monomeric African Swine Fever Virus mRNA capping enzyme NP868R and the monomeric T7 RNA polymerase, via the $EE_{1234}L$ and $RR_{1234}L$ leucine-zippers, which form the heterodimeric $RR_{1234}L$-pNP868R/$EE_{1234}L$-T7RNAP chimeric enzyme, two heterodimeric chimeric enzymes obtained by fusion between each of the two subunits of the vaccinia virus mRNA capping enzyme (i.e. D1R or D12L) with the monomeric T7 RNA polymerase, via the flexible $(Gly_3Ser)_4$ linker. Each fusion proteins are coexpressed with the other subunit of the vaccinia virus mRNA capping enzyme, in order to form the heterodimeric D12L/D1R-T7RNAP and D1R/D12L-T7RNAP chimeric enzymes, two heterotrimeric chimeric enzymes, which are generated by fusion of the $EE_{1234}L$ and $RR_{1234}L$ leucine-zippers to the amino-terminal ends of one of the subunits of the vaccinia virus mRNA capping enzyme and the T7 RNA polymerase, respectively. Co-expression of $RR_{1234}L$-D1R or $pRR_{1234}L$-D12L, with the other subunit of the vaccinia virus mRNA capping enzyme, plus $EE_{1234}L$-T7RNAP, form the heterotrimeric D1R/$RR_{1234}L$-D12L/$EE_{1234}L$-T7RNAP and D12L/$RR_{1234}L$-D1R/$EE_{1234}L$-T7RNAP chimeric enzymes.

I. Methods

Figure 10:
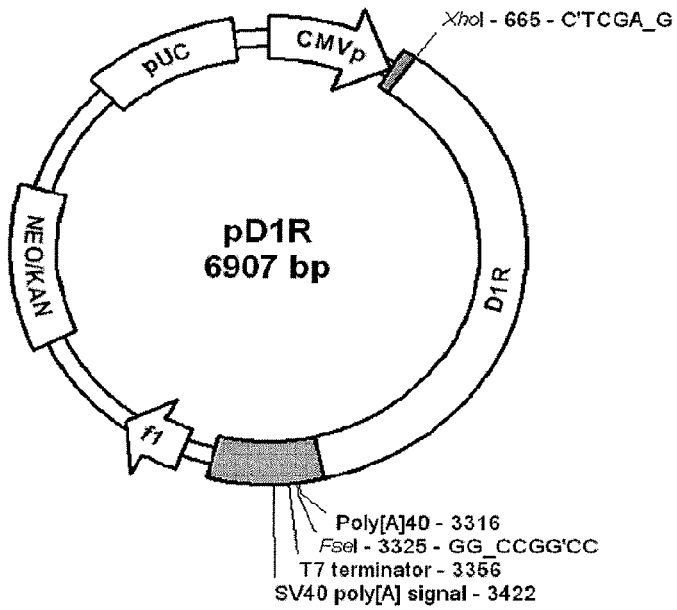
FIG. 10 (A-H) represents physical maps of the plasmids used for heterodimeric and heterotrimeric chimeric enzymes. Physical maps of (A) pD1R plasmid, which encodes for D1R, the large subunit of the vaccinia mRNA capping enzyme, (B) pD12L plasmid, which encodes for the D12L, the small subunit of the vaccinia mRNA capping enzyme, (C) pRR$_{1234}$L-NP868R plasmid, which encodes for the RR$_{1234}$L leucine-zipper fused to the amino-terminal end of NP868R, the African Swine Fever Virus mRNA capping enzyme, (D) pRR$_{1234}$L-D1R plasmid, which encodes for the RR$_{1234}$L leucine-zipper fused to the amino-terminal end of D1R, the large subunit of the vaccinia mRNA capping enzyme, (E) pRR$_{1234}$L-D12L plasmid, which encodes for the RR$_{1234}$L leucine-zipper fused to the amino-terminal end of D12L, the small subunit of the vaccinia mRNA capping enzyme, (F) pEE$_{1234}$L-T7RNA plasmid, which encodes for the pEE$_{1234}$L leucine-zipper fused to the phage DNA-dependent T7 RNA polymerase, (G) pD1R-T7RNAP plasmid, which encodes for a fusion between the large subunit of the vaccinia mRNA capping enzyme and the phage DNA-dependent T7 RNA polymerase, via the flexible (Gly$_3$Ser)$_4$ linker, (H) pD12L-T7RNAP plasmid, which encodes for a fusion between the small subunit of the vaccinia mRNA capping enzyme and the phage DNA-dependent T7 RNA polymerase, via the flexible (Gly$_3$Ser)$_4$ linker. All these plasmids have the same design: CMV promoter, Kozak sequence followed by the ORFs, poly[A]-track, TΦ terminator for phage RNA polymerase transcription, and SV40 polyadenylation signal.
Figure 10:
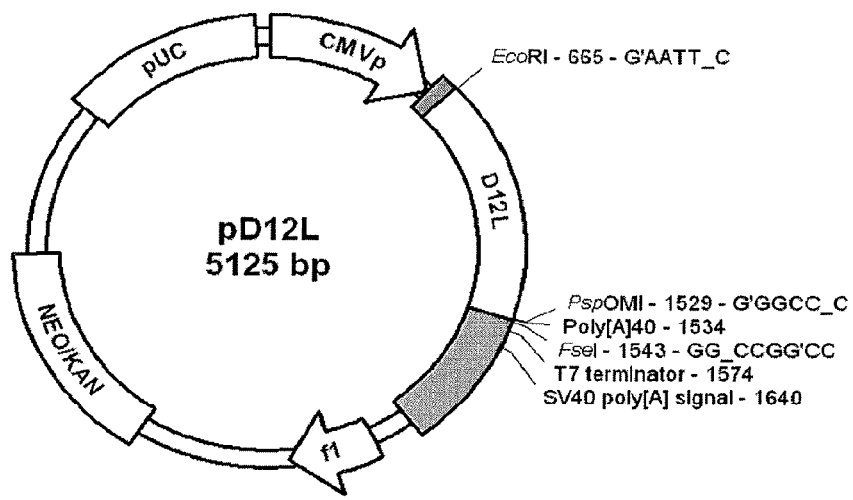
Figure 10:
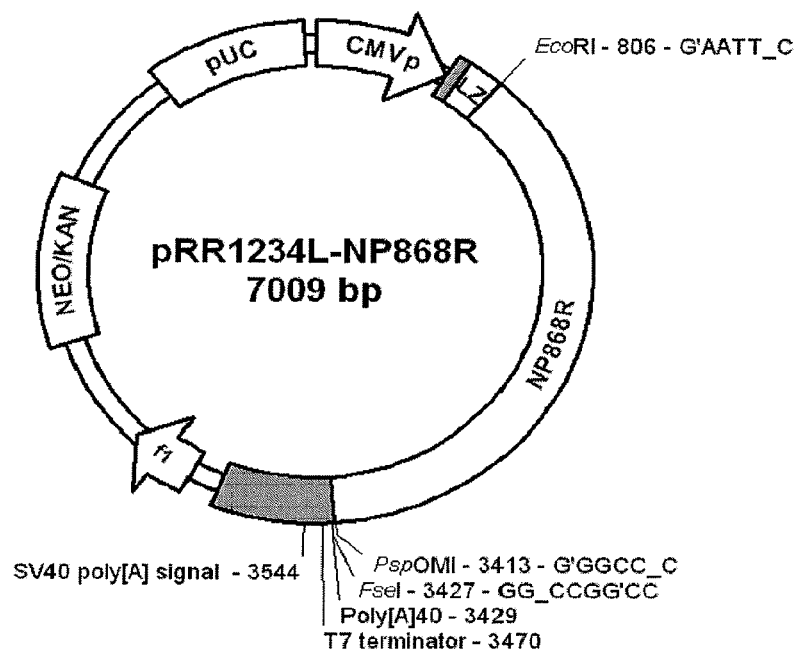
Figure 10:
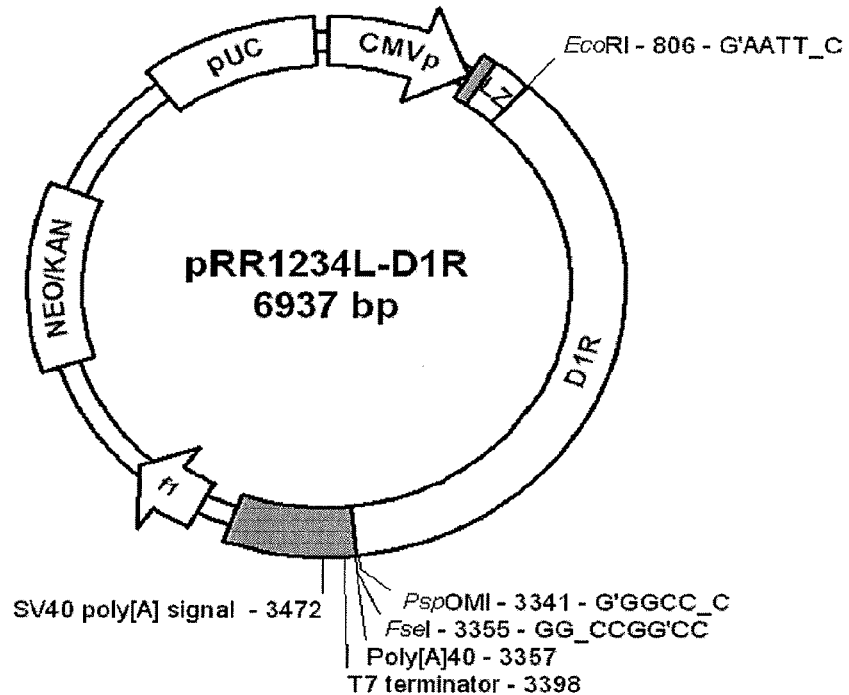
Figure 10:
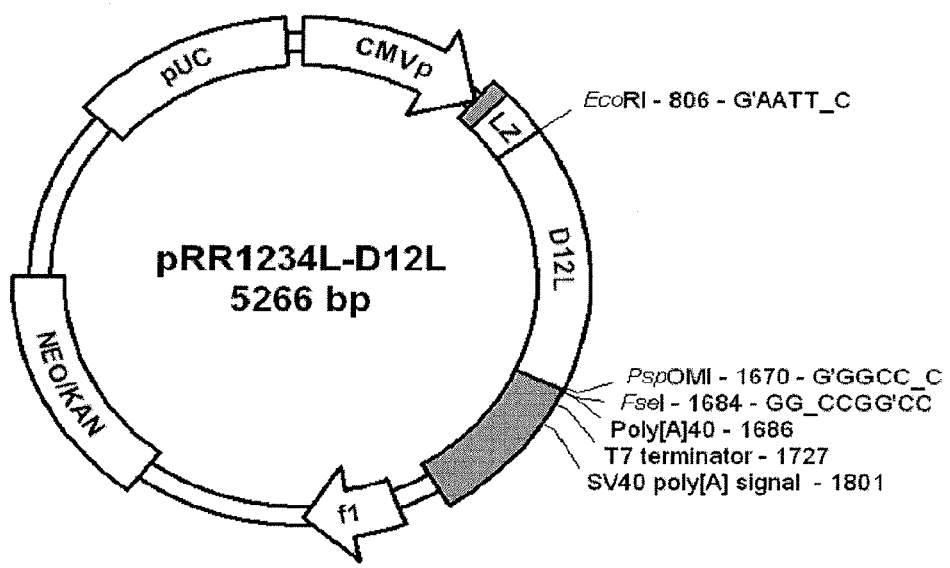
Figure 10:
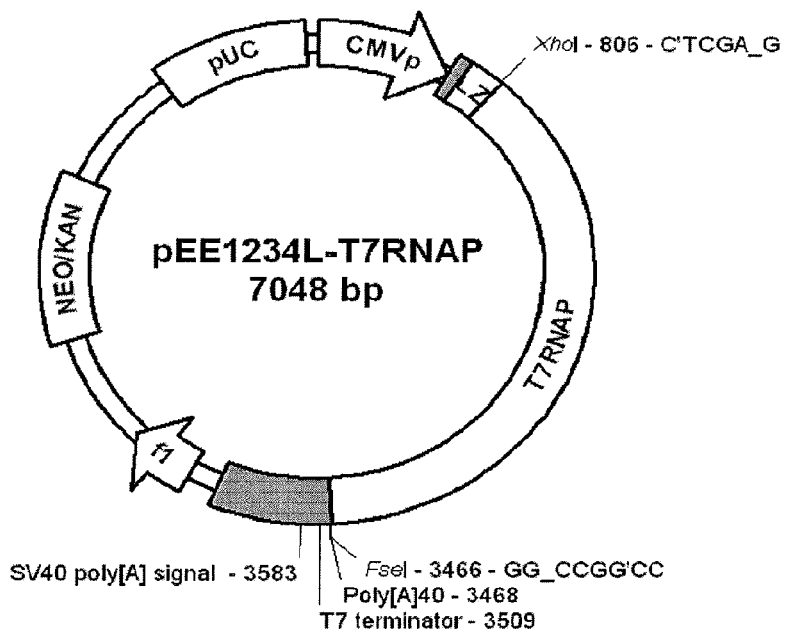
Figure 10:
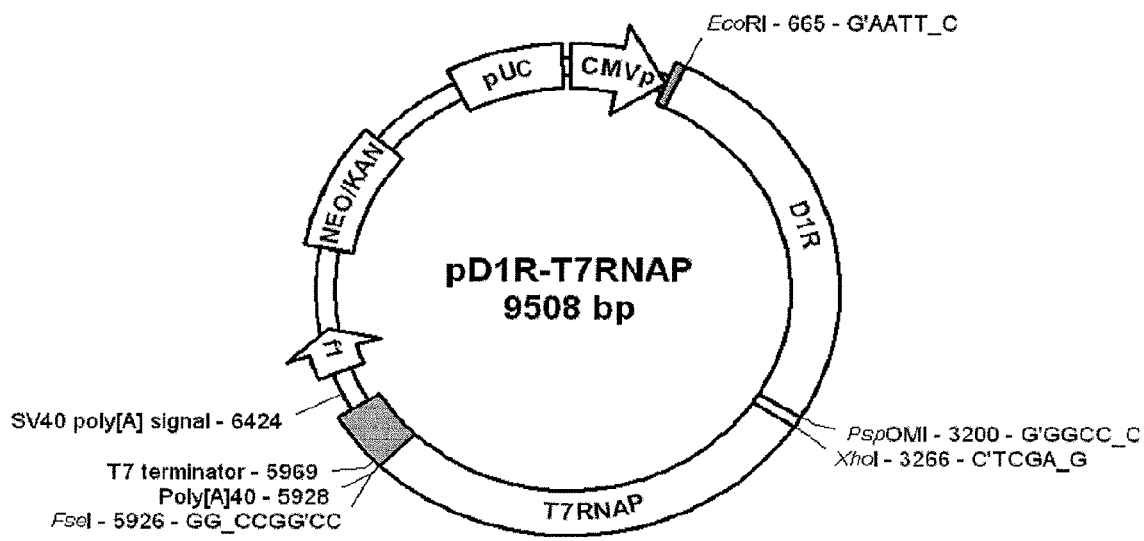
Figure 10:
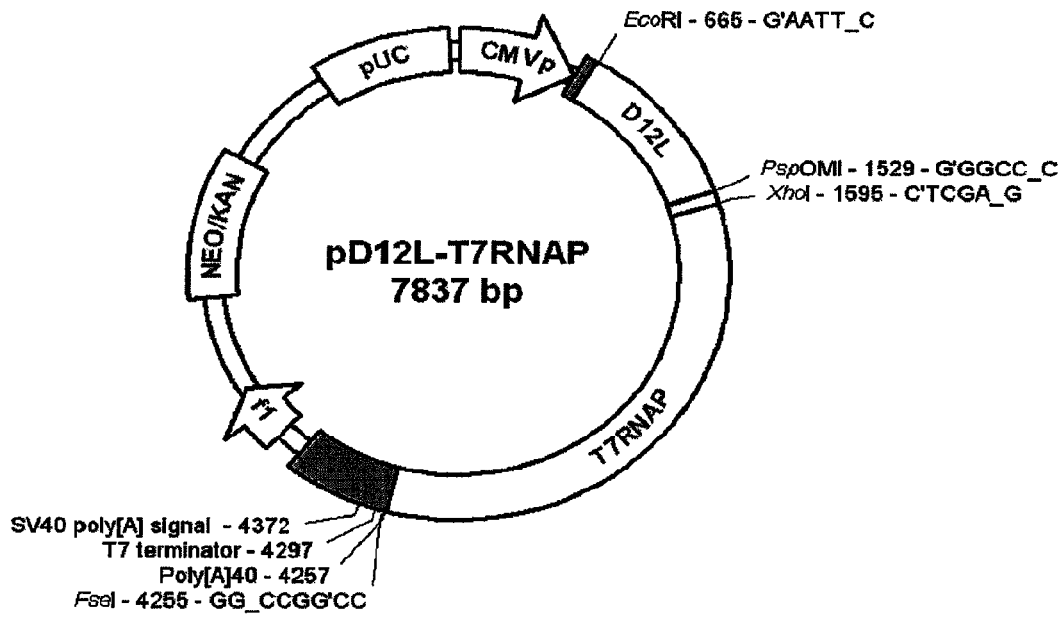

The sequences used to generate the chimeric enzymes were assembled from synthetic oligonucleotides using a PCR-based method, cloned and fully sequence verified. These sequences were subcloned in the pCMV-Script plasmid with the subcloning cassette previously described. Finally, all the plasmids used for expression had the similar design: CMV IE1 promoter/enhancer promoter, Kozak sequence followed by the open-reading frames (ORFs), poly[A]-track, TΦ terminator for phage RNA polymerase transcription, and SV40 polyadenylation signal (FIG. 10 (A-H)).

As a consequence of the subcloning strategy, two amino-acids were added immediately downstream to the ATG of the Kozak sequence of some plasmids (Leu-Glu for pT7RNAP; Glu-Phe for pNP868R, pD1R, pD12L, pD1R-T7RNAP, and pD12L-T7RNAP), immediately downstream to the leucine-zipper sequences (Leu-Glu for $pEE_{1234}L$-T7RNAP; Glu-Phe for $pRR_{1234}L$-NP868R, $pRR_{1234}L$-D1R and $pRR_{1234}L$-D12L), and at the carboxyl-terminal end of some encoded proteins (Gly-Pro for pNP868R, $pRR_{1234}L$-NP868R, pD1R, pD12L, $pRR_{1234}L$-D1R and $pRR_{1234}L$-D12L). In addition, two amino-acids were added immediately upstream (Gly-Pro for pD1R-T7RNAP and pD12L-

T7RNAP) or downstream to the (Gly$_3$Ser)$_4$ linker (Leu-Glu for pD1R-T7RNAP and pD12L-T7RNAP).

As previously described, the Human Embryonic Kidney 293 cells (HEK-293) were grown in 24-wells plates. HEK-293 cells were transfected using the lipofectamine 2000 reagent, and the appropriate plasmids (0.4 μg DNA/well, plus 1 μL/well lipofectamine 2000, per transfected plasmid) as previously described. The firefly luciferase luminescence was assayed as previously described using the pET-22b(+) T7RNAPp-Luciferase reporter plasmid (designated pT7p-Luciferase thereafter) and the Luciferase Assay System. The expression of pORF-eSEAP plasmid was used to normalize the transfection efficacy as previously described.

Gene reporter expression was expressed as the luciferase luminescence in studied condition subtracted by the luminescence in cells treated with the transfection reagent only (RLU, relative light units), then divided by SEAP absorbance (OD, optic density) ratio. Statistical analyses were performed using Student's t two-tailed test adjusted by Holm-Bonferroni correction for multiple testing, if appropriate. A p-value of less than 0.05 was regarded as being statistically significant.

II. Results

II.1 Heterodimeric RR$_{1234}$L-NP868R/EE$_{1234}$L-T7RNAP Chimeric Enzyme

The activity of the heterodimeric enzyme RR$_{1234}$L-NP868R/EE$_{1234}$L-T7RNA chimeric enzyme (encoded by pRR$_{1234}$L-pNP868R and pEE$_{1234}$L-T7RNAP plasmids, respectively) has been demonstrated. This heterodimeric enzyme is generated by non-covalent linkage between the monomeric African Swine Fever Virus mRNA capping enzyme pNP868R and the monomeric T7 RNA polymerase, via the EE$_{1234}$L and RR$_{1234}$L leucine-zippers (FIG. 9). The EE$_{1234}$L (acidic leucine-zipper; LEIAAFLEQENTALETE-VAELEQEVQRLENIVSQYETRYGPLGGGK (SEQ ID NO:51), one letter amino-acid code) and RR$_{1234}$L leucine-zippers (basic leucine-zipper with slight modification of the GGGK orientation, which is not involved in leucine-zipper dimerization (Moll, Ruvinov et al. 2001); LEIRAAFLR-RRNTALRTRVAELRQRVQRLRNIVSQYETRYG-PLGGGK (SEQ ID NO:52), one letter amino-acid code), which were respectively added to the amino-terminal end of NP868R and T7RNAP, respectively. The RR$_{1234}$L and EE$_{1234}$L leucine zippers are dimeric coiled-coil peptide structures consisting of two amphipathic α-helices that preferably melt as heterodimer in antiparallel orientation (Moll, Ruvinov et al. 2001).

Figure 11:
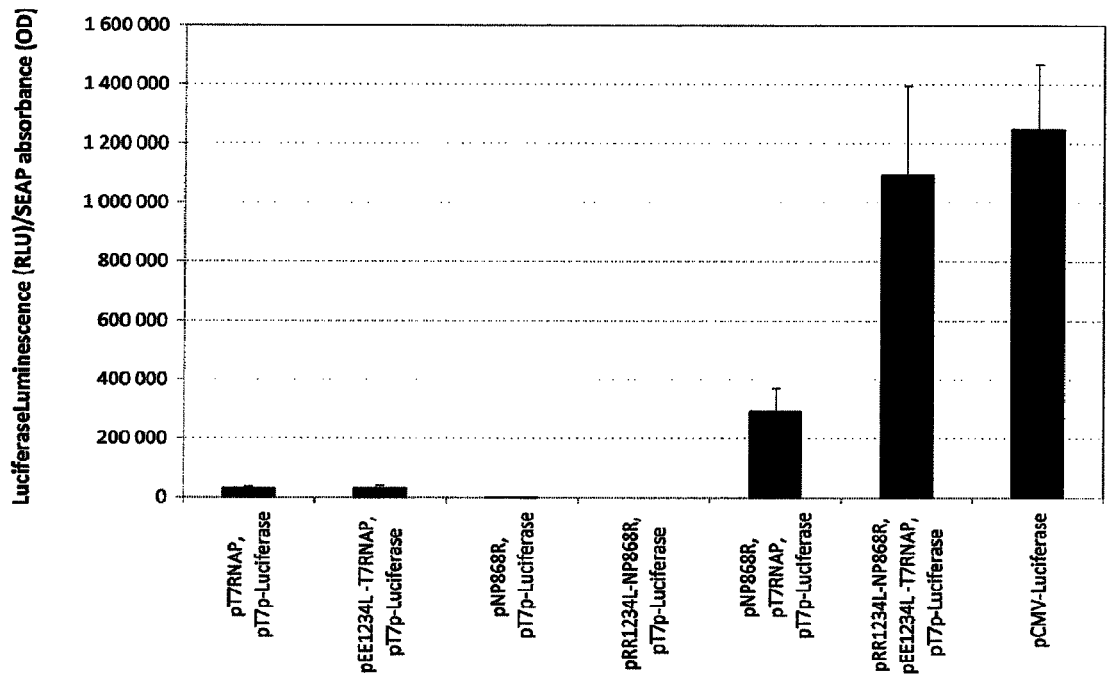
FIG. 11 represents the expression of the luciferase reporter gene by the heterodimeric RR$_{1234}$L-NP868R/EE$_{1234}$L-T7RNAP chimeric enzymes. HEK-293 cells were cultured and transfected as described above. Cells were transfected with either the corresponding plasmids (0.4 µg DNA/well and 1 µL/well lipofectamine 2000) and pT7p-Luciferase, or pCMV-T7RNAP (0.4 µg DNA/well and 1 µL/well lipofectamine 2000). Gene reporter expression was expressed as the luciferase luminescence in studied cells subtracted for luminescence in cells treated with the transfection reagent only (RLU, relative light units), then divided by SEAP absorbance (OD, optic density) ratio. Four repetitions of this experiment were performed. Errors bars represent standard error of the mean (SEM).

As expected, the transfection of the plasmid encoding for the African Swine Fever Virus mRNA capping enzyme alone with or without leucine-zipper sequences (i.e. pRR$_{1234}$L-NP868R and pNP868R, respectively) do not induce any detectable luciferase reporter gene expression (FIG. 11). As also expected, cells transfected with the plasmid encoding for the T7 RNA polymerase with the EE$_{1234}$L leucine zipper (encoded by pEE$_{1234}$L-T7RNA) show very similar activity to the T7 RNA polymerase without leucine-zipper (encoded by pT7RNA), which provide further evidence that the native amino-terminal end of the T7 RNA polymerase can be modified without major impairment of its enzymatic processivity.

The HEK293 cells co-transfected with the pRR$_{1234}$L-NP868R and pEE$_{1234}$L-T7RNA plasmids (encoding for NP868R and T7RNAP with leucine-zippers), together with the reporter pT7p-luciferase plasmid, show strong luciferase reporter gene expression signal, which is 87% to that of pCMV-T7RNAP plasmid (non-statistically significant difference, Student's t-test; (FIG. 11). Furthermore, cells co-transfected in presence of the reporter pT7p-luciferase plasmid with the pRR$_{1234}$L-NP868R and pEE$_{1234}$L-T7RNA plasmids, displays 3.7-fold higher luciferase reporter gene expression than cells cotransfected with pNP868R and pT7RNAP (encoding for NP868R and T7RNAP without leucine-zippers; p<0.05, Student's t-test).

These results demonstrate the activity of heterodimeric chimeric enzymes according to the invention and that the non-covalent linkage between NP868R and T7RNAP by leucine-zippers increases significantly the expression of the gene reporter driven by said chimeric enzymes.

II.2 Heterodimeric D1R/D12L-T7RNAP and D12L/D1R-T7RNAP Chimeric Enzymes

The activity of other types of heterodimeric chimeric enzyme has also been demonstrated, using the vaccinia mRNA capping enzyme.

By itself, the vaccinia mRNA capping enzyme is a heterodimer consisting of: (i) a 95 kDa subunit encoded by the vaccinia virus D1R gene (genomic sequence ID# NC_006998.1; GeneID#3707562; UniProtKB/Swiss-Prot ID# YP_232988.1), designated hereafter as D1R, which has RNA-triphosphatase, RNA guanylyltransferase and RNA N7-guanine methyltransferase enzymatic activities (Cong and Shuman 1993; Niles and Christen 1993; Higman and Niles 1994; Mao and Shuman 1994; Gong and Shuman 2003), (ii) and a 31-kDa subunit encoded by the vaccinia virus D12L gene (genomic sequence ID# NC_006998.1; GeneID#3707515; UniProtKB/Swiss-Prot ID#YP_232999.1), designated hereafter as D12L, which has no intrinsic enzymatic activity, but enhances drastically the RNA N7-guanine methyltransferase activity of the D1R subunit (Higman, Bourgeois et al. 1992; Higman, Christen et al. 1994; Mao and Shuman 1994).

Figure 12:
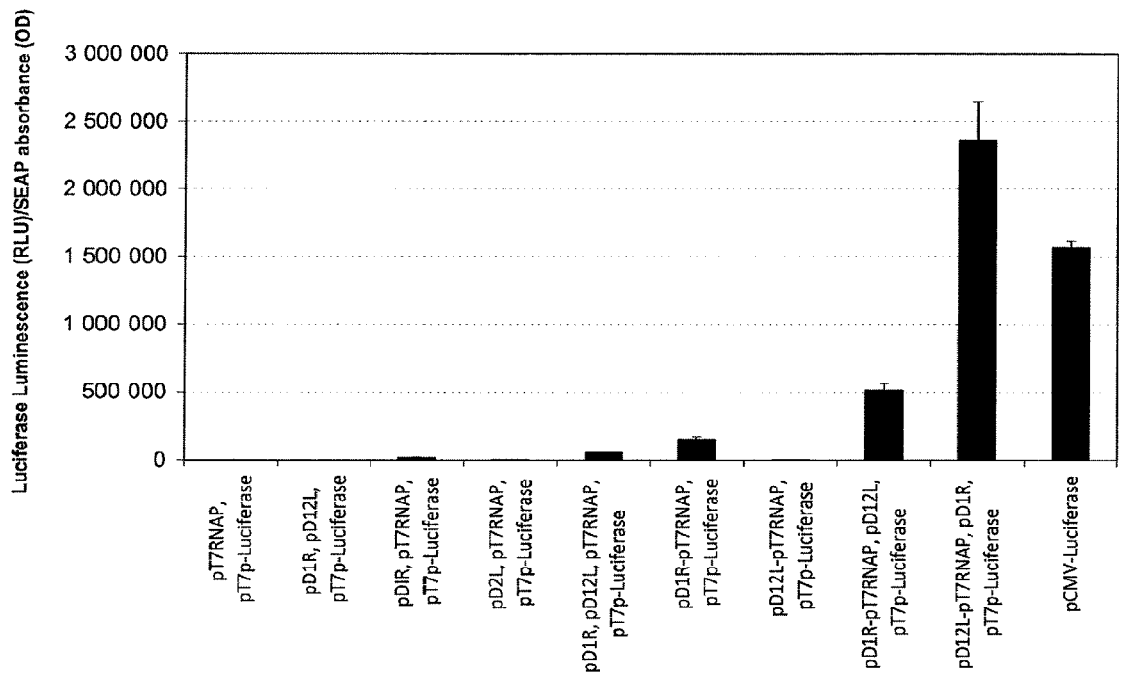
FIG. 12 represents the expression of the luciferase reporter gene by the heterodimeric D1R/D12L-T7RNAP and D12L/D1R-T7RNAP chimeric enzymes. Transfection and luciferase assay were performed as previously described. Gene reporter expression was expressed as the luciferase luminescence in studied cells subtracted for luminescence in cells treated with the transfection reagent only (RLU, relative light units), then divided by SEAP absorbance (OD, optic density) ratio. Two repetitions of this experiment were performed. Errors bars represent standard error of the mean (SEM).

D1R or D12L were fused to the amino-terminal end of the T7 RNA polymerase, via the (Gly$_3$Ser)$_4$ linker (encoded by D1R-T7RNAP or D12L-T7RNAP, respectively). When co-expressed, each fusion proteins, together with the other vaccinia mRNA capping enzyme subunit (encoded by pD12L or D1R, respectively), generate two different heterodimeric chimeric enzymes designated as D12L/D1R-T7RNAP and D1R/D12L-T7RNAP, respectively (FIG. 9). In presence of the reporter pT7p-luciferase plasmid, the heterodimeric chimeric enzymes generate a strong luciferase gene reporter signal in HEK293 cells (FIG. 12). The heterodimeric D12L/D1R-T7RNAP chimeric enzyme has 32% activity to that of pCMV-T7RNAP plasmid (p<0.01, Student's t-test), whereas the D1R/D12L-T7RNAP heterodimeric enzyme has 1.5-fold higher luciferase reporter gene expression than the pCMV-T7RNAP plasmid (non-statistically significant difference, Student's t-test). Furthermore, the coexpression of the two subunits of vaccinia mRNA capping enzyme unbound to the T7 RNA polymerase (encoded by pD1R, pD12L and pT7RNAP) shows 9- and 42-fold lower luciferase reporter gene expression signal than the heterodimeric D12L/D1R-T7RNAP and D1R/D12L-T7RNAP chimeric enzymes, respectively (P<0.05 for both statistical comparison, Student's t-test).

These results demonstrate the activity of different types of heterodimeric chimeric enzymes according to the invention and that covalent linkage between the subunits of the vaccinia mRNA capping enzyme and the T7RNAP stimulates significantly the gene reporter expression. As also expected, in presence of the reporter pT7p-luciferase plasmid, the expression of D1R and/or D12L without T7 RNA polymerase induces virtually no detectable luciferase expression.

II.3 Heterotrimeric D12L/RR$_{1234}$L-D1R/EE$_{1234}$L-T7RNAP and D1R/RR$_{1234}$L-D12L/EE$_{1234}$L-T7RNAP Chimeric Enzymes The activity of heterotrimeric chimeric enzyme has also been demonstrated.

The basic RR$_{1234}$L leucine zipper was fused to the amino-terminal ends of either the D1R or D12L subunits of the vaccinia virus mRNA capping enzyme (encoded by pRR$_{1234}$L-D1R and RR$_{1234}$L-D12L, respectively), while the complementary acidic EE$_{1234}$L leucine-zipper was added to the amino-terminal end of T7 RNA polymerase (encoded by the pEE$_{1234}$L-T7RNA plasmid). The co-expression of pEE$_{1234}$L-T7RNAP, together with either pRR$_{1234}$L-D1R or pRR$_{1234}$L-D12L, plus the other vaccinia mRNA capping enzyme subunit (pD12L and pD1R plasmids, respectively), therefore generate two different heterotrimeric CCPP enzymes, designated as D12L/RR$_{1234}$L-D1R/EE$_{1234}$L-T7RNAP and D1R/RR$_{1234}$L-D12L/EE$_{1234}$L-T7RNAP, respectively (FIG. 9).

The T7 RNA polymerase displayed 7-fold higher luciferase gene reporter signal when coexpressed with the D1R/D12L subunits of the vaccinia virus mRNA capping enzyme than in their absence. These results are therefore in line with those obtained by the vaccinia virus/bacteriophage RNAP hybrid expression system, in which the translatability of uncapped T7 transcripts is increased by the expression of the vaccinia mRNA capping enzyme provided by a recombinant virus (Fuerst, Niles et al. 1986; Fuerst, Earl et al. 1987; Elroy-Stein, Fuerst et al. 1989; Fuerst, Fernandez et al. 1989; Fuerst and Moss 1989; Elroy-Stein and Moss 1990).

Figure 13:
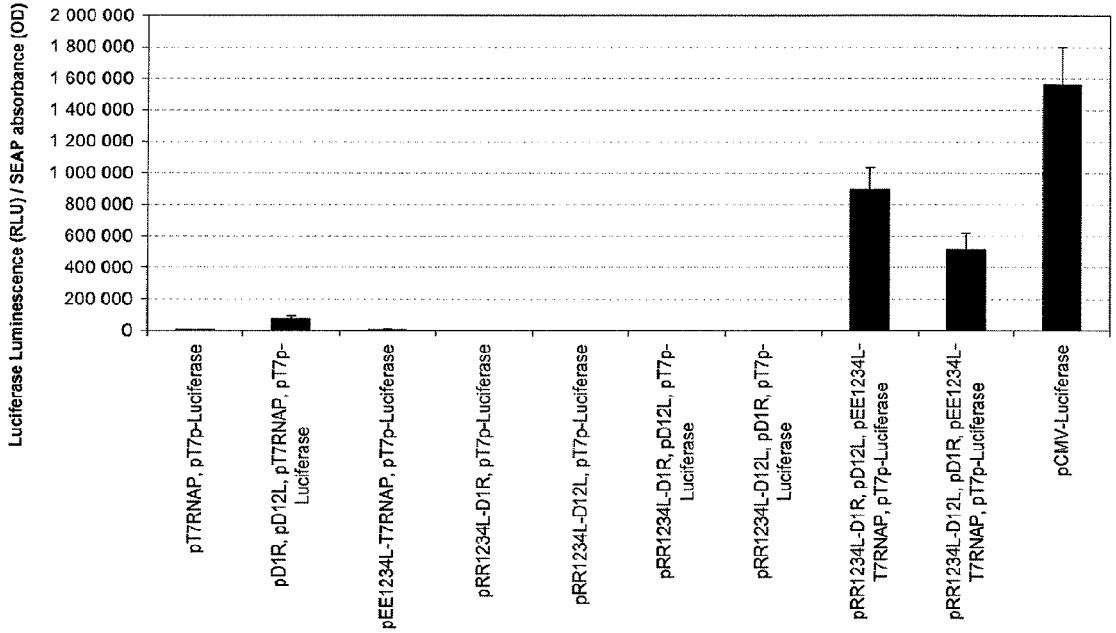
FIG. 13 represents the expression of the luciferase reporter gene by the heterotrimeric D1R/RR$_{1234}$L-D12L/EE$_{1234}$L-T7RNAP and D12L/EE$_{1234}$L-D1R/EE$_{1234}$L-T7RNAP chimeric enzymes. Transfection and luciferase assay were performed as previously described. Gene reporter expression was expressed as the luciferase luminescence in studied cells subtracted for luminescence in cells treated with the transfection reagent only (RLU, relative light units), then divided by SEAP absorbance (OD, optic density) ratio. Two repetitions of this experiment were performed. Errors bars represent standard error of the mean (SEM).

A strong luciferase gene reporter signal was shown in HEK-293 cells expressing either the D1R/RR$_{1234}$L-D12L/EE$_{1234}$L-T7RNAP or the D12L/RR$_{1234}$L-D1R/EE$_{1234}$L-T7RNAP CCPP enzymes, in presence of the reporter pT7p-luciferase plasmid (FIG. 13). The heterodimeric D12L/RR$_{1234}$L-D1R/EE$_{1234}$L-T7RNAP and D1R/RR$_{1234}$L-D12L/EE$_{1234}$L-T7RNAP chimeric enzymes have respectively 57% and 33% activity to that of pCMV-T7RNAP plasmid (non-statistically significant difference, Student's t-test). The heterodimeric D12L/RR$_{1234}$L-D1R/EE$_{1234}$L-T7RNAP and D1R/RR$_{1234}$L-D12L/EE$_{1234}$L-T7RNAP chimeric enzymes show respectively 11- and 6.7-fold stronger luciferase gene reporter expression signal than cells expressing D1, D12L and T7RNAP without leucine-zippers (p=0.05 and non-statistically significant difference, respectively; Student's t-test).

These results demonstrate the activity of heterotrimeric chimeric enzymes according to the invention and that the non-covalent linkage between any of the subunits of the vaccinia mRNA capping enzyme and the T7 RNA polymerase increases significantly the gene reporter expression.

III. Conclusion

These present results show the activity of different types of heterodimeric and heterotrimeric chimeric enzymes according to the invention, generated by covalent or non-covalent linkage.

The present results also provide evidences that covalent or non-covalent linkage between the different catalytic domain of the chimeric enzyme and in particular between capping enzymes and RNA polymerases allows the optimization of the gene reporter expression by the chimeric enzymes.

Example 4

Stimulation of Luciferase Reporter Gene Expression by Silencing Sequences Against the Cellular RNA Polymerase II and Capping Enzyme I. Methods HEK-293 cells were grown as previously described in 24-wells plates and transfected using the Lipofectamine 2000 reagent, and the appropriate concentration of siRNA (Qiagen; Hilden, Germany) and plasmids (0.4 μg DNA/well, plus 1 μL/well lipofectamine 2000, per transfected plasmid). The NP868R-SP6 chimeric enzyme, which has strong demonstrated activity, was used in the present experiment. The firefly luciferase luminescence was assayed as previously described using the pT7p-Luciferase (which also contains both the T3 and SP6 promoters) and the Luciferase Assay System. The expression of pORF-eSEAP plasmid was used to normalize for transfection efficacy as previously described.

Four siRNA that target the human POLR2A (NCBI Gene ID#5430; mRNA sequence ID# NM_000937.4; NCBI protein sequence ID# NP_000928.1) were used: SI04364381 (mRNA sequence 1255-1275: CAGCGGTT-GAAGGGCAAGGAA (SEQ ID NO:43)), SI04369344 (mRNA sequence 830-850: ATGCGGAATG-GAAGCACGTTA (SEQ ID NO:44)), SI04250162 (mRNA sequence 2539-2559: ATGGTCGTGTCCGGAGCTAAA (SEQ ID NO:45)), and SI04354420 (mRNA sequence 4896-4916: CAGCGGCTTCAGCCCAGGTTA (SEQ ID NO:46)).

In addition, four siRNA that target the human RNGTT (Gene ID#8732; mRNA sequence ID# NM_003800.3; NCBI protein sequence ID# NP_003791.3) were used: SI00055986 (mRNA sequence 3187-3207: ATGGATT-TAAAGGGCGGCTAA (SEQ ID NO:47)), SI03021508 (mRNA sequence 430-450: TTCAAGGTTCTATGAC-CGAAA (SEQ ID NO:48)), SI00055972 (mRNA sequence 2530-2550: CAGGGTTGTTAAGTTGTACTA (SEQ ID NO:49)) and SI00055979 (mRNA sequence 4132-4152: TACCATCTGCAGTATTATAAA (SEQ ID NO:50)).

II. Results

Figure 14:
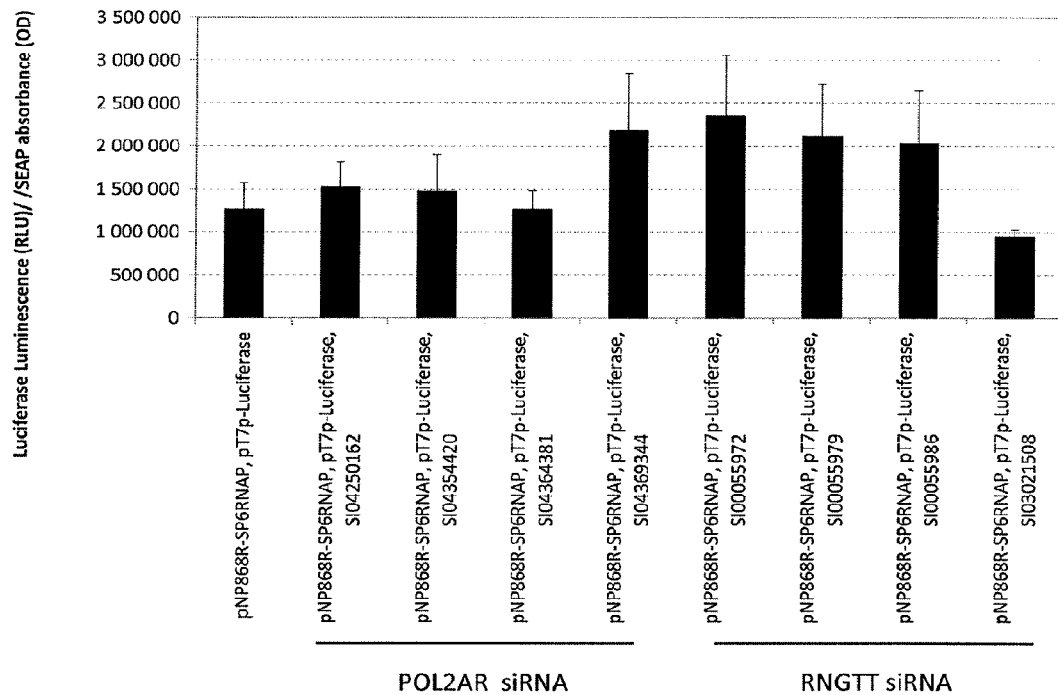
FIG. 14 represents the expression of the luciferase reporter gene by the monomeric NP868R-SP6RNAP chimeric enzymes in presence of siRNAs targeting the large subunit of RNA polymerase II (POL2AR) or the human capping enzyme (RNGTT). Transfection and luciferase assay were performed as previously described, except that siRNA at 25 nM final concentration were added to the transfection reagent. The siRNA SI04364381, SI04369344, SI04250162 and SI04354420 target the POLR2A gene, whereas the siRNA SI00055986, SI03021508, SI00055972, and SI00055979 target RNGTT. Gene reporter expression was expressed as the luciferase luminescence in studied cells subtracted for luminescence in cells treated with the transfection reagent only (RLU, relative light units), then divided by SEAP absorbance (OD, optic density) ratio. Two repetitions of this experiment were performed. Errors bars represent standard error of the mean (SEM).

In a first series of experiments, the effects of four POLR2A siRNA and four RNGTT siRNA were tested at 25 nM final concentration (FIG. 14). The siRNA were co-transfected with the pNP868R-SP6RNAP chimeric enzyme plasmid and the reporter pT7p-luciferase plasmid. Collectively, the POLR2A siRNA trend to increase the luciferase gene reporter expression by 127% on average, in comparison the same condition without siRNA. Similarly, the addition of RNGTT siRNA collectively increased the luciferase gene reporter expression to 147% on average in comparison the same condition without siRNA.

Figure 15:
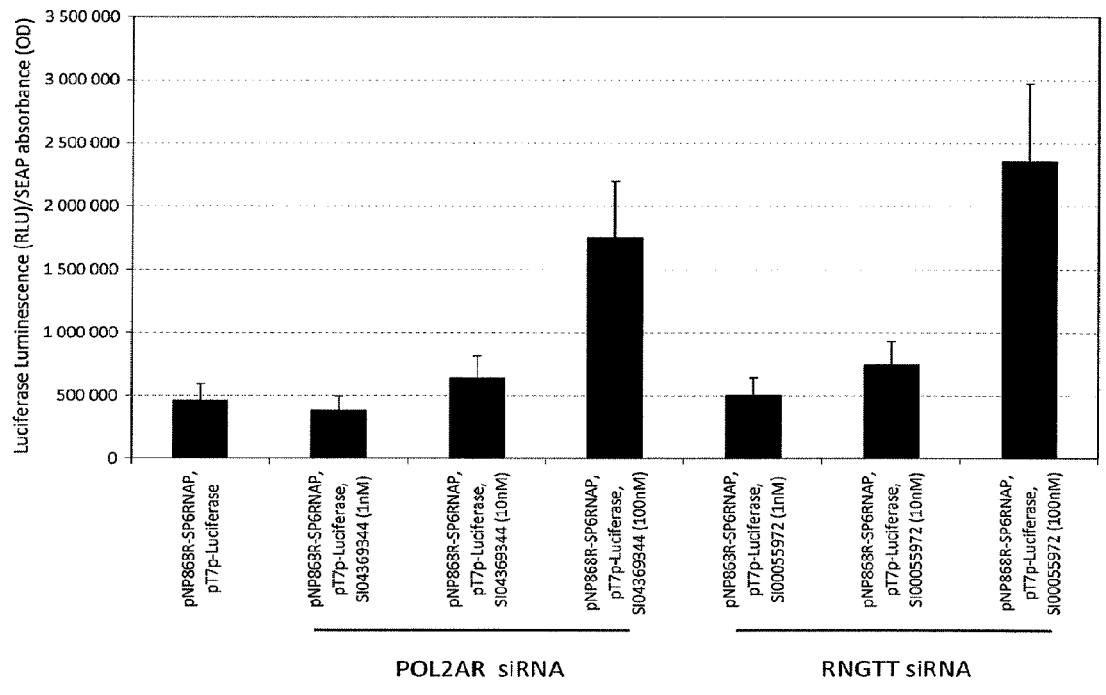
FIG. 15 represents the dose effect activity of siRNAs targeting the large subunit of RNA polymerase II (POL2AR) and the human capping enzyme (RNGTT). Transfection and luciferase assay were performed as previously described, except that siRNA were added at concentration ranging from 0 to 100 nM to the transfection reagent. The siRNA SI04369344 and SI00055972 target the POLR2A and RNGTT genes, respectively. Gene reporter expression was expressed as the luciferase luminescence in studied cells subtracted for luminescence in cells treated with the transfection reagent only (RLU, relative light units), then divided by SEAP absorbance (OD, optic density) ratio. Three repetitions of this experiment were performed. Errors bars represent standard error of the mean (SEM).

The POLR2A SI04369344 and the RNGTT SI00055972 siRNA, which have show the highest stimulation rate, were selected for a second series of experiments. Expression of the luciferase reporter gene driven by NP868R-SP6RNAP was assayed in presence of siRNA at concentrations ranging from 0 to 100 nM (FIG. 15). Dose-response was observed with both siRNA. The strongest expression stimulation of 3.8-folds was observed at 100 nM with POLR2A SI04369344, and of 5.1-folds with the RNGTT SI00055972 siRNA at 100 nM.

III. Conclusion

The present findings demonstrate that the silencing of the cellular transcription and post-transcriptional machineries by siRNA stimulate the reporter gene expression driven by the NP868R-SP6RNAP chimeric enzyme.

BIBLIOGRAPHIC REFERENCES

Bedzyk, W. D., K. M. Weidner, et al. (1990). "Immunological and structural characterization of a high affinity anti-fluorescein single-chain antibody." *J Biol Chem* 265(30): 18615-18620.

Bengal, E., O. Flores, et al. (1991). "Role of the mammalian transcription factors IIF, IIS, and IIX during elongation by RNA polymerase II." *Mol Cell Biol* 11(3): 1195-1206.

Benton, B. M., W. K. Eng, et al. (1990). "Signal-mediated import of bacteriophage T7 RNA polymerase into the *Saccharomyces cerevisiae* nucleus and specific transcription of target genes." *Mol Cell Biol* 10(1): 353-360.

Bird, R. E., K. D. Hardman, et al. (1988). "Single-chain antigen-binding proteins." *Science* 242(4877): 423-426.

Bridgen, A. and R. M. Elliott (1996). "Rescue of a segmented negative-strand RNA virus entirely from cloned complementary DNAs." *Proc Natl Acad Sci USA* 93(26): 15400-15404.

Brisson, M., Y. He, et al. (1999). "A novel T7 RNA polymerase autogene for efficient cytoplasmic expression of target genes." *Gene Ther* 6(2): 263-270.

Busch, R., A. Pashine, et al. (2002). "Stabilization of soluble, low-affinity HLA-DM/HLA-DR1 complexes by leucine zippers." *J Immunol Methods* 263(1-2): 111-121.

Busch, R., Z. Reich, et al. (1998). "Secondary structure composition and pH-dependent conformational changes of soluble recombinant HLA-DM." *J Biol Chem* 273(42): 27557-27564.

Bushnell, D. A., P. Cramer, et al. (2002). "Structural basis of transcription: alpha-amanitin-RNA polymerase II cocrystal at 2.8 A resolution." *Proc Natl Acad Sci USA* 99(3): 1218-1222.

Chang, H. C., Z. Bao, et al. (1994). "A general method for facilitating heterodimeric pairing between two proteins: application to expression of alpha and beta T-cell receptor extracellular segments." *Proc Natl Acad Sci USA* 91(24): 11408-11412.

Chen, X., Y. Li, et al. (1994). "A self-initiating eukaryotic transient gene expression system based on contransfection of bacteriophage T7 RNA polymerase and DNA vectors containing a T7 autogene." *Nucleic Acids Res* 22(11): 2114-2120.

Chen, Z. and T. D. Schneider (2005). "Information theory based T7-like promoter models: classification of bacteriophages and differential evolution of promoters and their polymerases." *Nucleic Acids Res* 33(19): 6172-6187.

Cho, E. J., T. Takagi, et al. (1997). "mRNA capping enzyme is recruited to the transcription complex by phosphorylation of the RNA polymerase II carboxy-terminal domain." *Genes Dev* 11(24): 3319-3326.

Clayton, D. A. (1991). "Replication and transcription of vertebrate mitochondrial DNA." *Annu Rev Cell Biol* 7: 453-478.

Cong, P. and S. Shuman (1993). "Covalent catalysis in nucleotidyl transfer. A KTDG motif essential for enzyme-GMP complex formation by mRNA capping enzyme is conserved at the active sites of RNA and DNA ligases." *J Biol Chem* 268(10): 7256-60.

Cong, Y. S., D. Yarrow, et al. (1994). "Linear DNA plasmids from *Pichia etchellsii, Debaryomyces hansenii* and *Wingea robertsiae*." *Microbiology* 140 (Pt 6): 1327-1335.

Conzelmann, K. K. and M. Schnell (1994). "Rescue of synthetic genomic RNA analogs of rabies virus by plasmid-encoded proteins." *J Virol* 68(2): 713-719.

Crasto, C. J. and J. A. Feng (2000). "LINKER: a program to generate linker sequences for fusion proteins." *Protein Eng* 13(5): 309-312.

Cronan, J. E., Jr. (1990). "Biotination of proteins in vivo. A post-translational modification to label, purify, and study proteins." *J Biol Chem* 265(18): 10327-33.

Davanloo, P., A. H. Rosenberg, et al. (1984). "Cloning and expression of the gene for bacteriophage T7 RNA polymerase." *Proc Natl Acad Sci USA* 81(7): 2035-2039.

Dias, N. and C. A. Stein (2002). "Antisense oligonucleotides: basic concepts and mechanisms." *Mol Cancer Ther* 1(5): 347-55.

Dower, K. and M. Rosbash (2002). "T7 RNA polymerase-directed transcripts are processed in yeast and link 3' end formation to mRNA nuclear export." *Rna* 8(5): 686-697.

Drummond, D. R., J. Armstrong, et al. (1985). "The effect of capping and polyadenylation on the stability, movement and translation of synthetic messenger RNAs in *Xenopus* oocytes." *Nucleic Acids Res* 13(20): 7375-7394.

Elroy-Stein, O., T. R. Fuerst, et al. (1989). "Cap-independent translation of mRNA conferred by encephalomyocarditis virus 5' sequence improves the performance of the vaccinia virus/bacteriophage T7 hybrid expression system." *Proc Natl Acad Sci USA* 86(16): 6126-6130.

Elroy-Stein, O. and B. Moss (1990). "Cytoplasmic expression system based on constitutive synthesis of bacteriophage T7 RNA polymerase in mammalian cells." *Proc Natl Acad Sci USA* 87(17): 6743-6747.

Engleka, K. A., E. W. Lewis, et al. (1998). "Mechanisms of replication-deficient vaccinia virus/T7 RNA polymerase hybrid expression: effect of T7 RNA polymerase levels and alpha-amanitin." *Virology* 243(2): 331-339.

Epicentre Biotechnologies website. "ScriptCap™ 2'-O-Methyltransferase."

Fancy, D. A. and T. Kodadek (1999). "Chemistry for the analysis of protein-protein interactions: rapid and efficient cross-linking triggered by long wavelength light." *Proc Natl Acad Sci USA* 96(11): 6020-4.

Fernandez-Silva, P., F. Martinez-Azorin, et al. (1997). "The human mitochondrial transcription termination factor (mTERF) is a multizipper protein but binds to DNA as a monomer, with evidence pointing to intramolecular leucine zipper interactions." *Embo J* 16(5): 1066-1079.

Finn, J., I. MacLachlan, et al. (2005). "Factors limiting autogene-based cytoplasmic expression systems." *Faseb J* 19(6): 608-610.

Fire, A., M. Samuels, et al. (1984). "Interactions between RNA polymerase II, factors, and template leading to accurate transcription." *J Biol Chem* 259(4): 2509-2516.

Fisher, R. P. and D. A. Clayton (1985). "A transcription factor required for promoter recognition by human mitochondrial RNA polymerase. Accurate initiation at the heavy- and light-strand promoters dissected and reconstituted in vitro." *J Biol Chem* 260(20): 11330-11338.

Fisher, R. P. and D. A. Clayton (1988). "Purification and characterization of human mitochondrial transcription factor 1." *Mol Cell Biol* 8(8): 3496-3509.

Fisher, R. P., J. N. Topper, et al. (1987). "Promoter selection in human mitochondria involves binding of a transcription factor to orientation-independent upstream regulatory elements." *Cell* 50(2): 247-258.

Fortes, P., Y. Cuevas, et al. (2003). "Inhibiting expression of specific genes in mammalian cells with 5' end-mutated U1 small nuclear RNAs targeted to terminal exons of pre-mRNA." *Proc Natl Acad Sci USA* 100(14): 8264-9.

Fuerst, T. R., P. L. Earl, et al. (1987). "Use of a hybrid vaccinia virus-T7 RNA polymerase system for expression of target genes." *Mol Cell Biol* 7(7): 2538-2544.

Fuerst, T. R., M. P. Fernandez, et al. (1989). "Transfer of the inducible lac repressor/operator system from *Escherichia coli* to a vaccinia virus expression vector." *Proc Natl Acad Sci USA* 86(8): 2549-2553.

Fuerst, T. R. and B. Moss (1989). "Structure and stability of mRNA synthesized by vaccinia virus-encoded bacteriophage T7 RNA polymerase in mammalian cells. Importance of the 5' untranslated leader." *J Mol Biol* 206(2): 333-348.

Fuerst, T. R., E. G. Niles, et al. (1986). "Eukaryotic transient-expression system based on recombinant vaccinia virus that synthesizes bacteriophage T7 RNA polymerase." *Proc Natl Acad Sci USA* 83(21): 8122-8126.

Furuichi, Y., A. LaFiandra, et al. (1977). "5'-Terminal structure and mRNA stability." *Nature* 266(5599): 235-239.

Furuichi, Y. and A. J. Shatkin (2000). "Viral and cellular mRNA capping: past and prospects." *Adv Virus Res* 55: 135-184.

Gallie, D. R. (1991). "The cap and poly(A) tail function synergistically to regulate mRNA translational efficiency." *Genes Dev* 5(11): 2108-2116.

Gao, X. and L. Huang (1993). "Cytoplasmic expression of a reporter gene by co-delivery of T7 RNA polymerase and T7 promoter sequence with cationic liposomes." *Nucleic Acids Res* 21(12): 2867-2872.

Garcin, D., T. Pelet, et al. (1995). "A highly recombinogenic system for the recovery of infectious Sendai paramyxovirus from cDNA: generation of a novel copy-back non-defective interfering virus." *Embo J* 14(24): 6087-6094.

Ghosh, I., A. D. Hamilton, et al. (2000). "Antiparallel Leucine Zipper-Directed Protein Reassembly: Application to the Green Fluorescent Protein." *Journal of the American Chemical Society* 122(23): 5658-5659.

Gilbert, W. and A. Maxam (1973). "The nucleotide sequence of the lac operator." *Proc Natl Acad Sci USA* 70(12): 3581-3584.

Gill, D. R., S. E. Smyth, et al. (2001). "Increased persistence of lung gene expression using plasmids containing the ubiquitin C or elongation factor 1alpha promoter." *Gene Ther* 8(20): 1539-1546.

Gingras, A. C., B. Raught, et al. (1999). "eIF4 initiation factors: effectors of mRNA recruitment to ribosomes and regulators of translation." *Annu Rev Biochem* 68: 913-963.

Golomb, M. and M. Chamberlin (1974). "Characterization of T7-specific ribonucleic acid polymerase. IV. Resolution of the major in vitro transcripts by gel electrophoresis." *J Biol Chem* 249(9): 2858-2863.

Gong, C. and S. Shuman (2003). "Mapping the active site of vaccinia virus RNA triphosphatase." *Virology* 309(1): 125-34.

Gregoire, C., S. Y. Lin, et al. (1996). "Covalent assembly of a soluble T cell receptor-peptide-major histocompatibility class I complex." *Proc Natl Acad Sci USA* 93(14): 7184-7189.

Gustavsson, M., J. Lehtio, et al. (2001). "Stable linker peptides for a cellulose-binding domain-lipase fusion protein expressed in *Pichia pastoris*." *Protein Eng* 14(9): 711-715.

Han, Y. T., C. S. Tsai, et al. (2007). "Mutational analysis of a helicase motif-based RNA 5'-triphosphatase/NTPase from bamboo mosaic virus." *Virology*.

Hennecke, F., C. Krebber, et al. (1998). "Non-repetitive single-chain Fv linkers selected by selectively infective phage (SIP) technology." *Protein Eng* 11(5): 405-410.

Higman, M. A., N. Bourgeois, et al. (1992). "The vaccinia virus mRNA (guanine-N7-)-methyltransferase requires both subunits of the mRNA capping enzyme for activity." *J Biol Chem* 267(23): 16430-7.

Higman, M. A., L. A. Christen, et al. (1994). "The mRNA (guanine-7-)methyltransferase domain of the vaccinia virus mRNA capping enzyme. Expression in *Escherichia coli* and structural and kinetic comparison to the intact capping enzyme." *J Biol Chem* 269(21): 14974-81.

Higman, M. A. and E. G. Niles (1994). "Location of the S-adenosyl-L-methionine binding region of the vaccinia virus mRNA (guanine-7-)methyltransferase." *J Biol Chem* 269(21): 14982-7.

Hu, W., F. Li, et al. (2004). "A flexible peptide linker enhances the immunoreactivity of two copies HBsAg preS1 (21-47) fusion protein." *J Biotechnol* 107(1): 83-90.

Huang, Y. and J. A. Steitz (2005). "SRprises along a messenger's journey." *Mol Cell* 17(5): 613-615.

Huston, J. S., D. Levinson, et al. (1988). "Protein engineering of antibody binding sites: recovery of specific activity in an anti-digoxin single-chain Fv analogue produced in *Escherichia coli*." *Proc Natl Acad Sci USA* 85(16): 5879-5883.

Izban, M. G. and D. S. Luse (1992). "Factor-stimulated RNA polymerase II transcribes at physiological elongation rates on naked DNA but very poorly on chromatin templates." *J Biol Chem* 267(19): 13647-13655.

Jacob, S. T., E. M. Sajdel, et al. (1970). "Specific action of alpha-amanitin on mammalian RNA polymerase protein." *Nature* 225(5227): 60-62.

Kedinger, C., M. Gniazdowski, et al. (1970). "Alpha-amanitin: a specific inhibitor of one of two DNA-pendent RNA polymerase activities from calf thymus." *Biochem Biophys Res Commun* 38(1): 165-171.

Kohler, A. and E. Hurt (2007). "Exporting RNA from the nucleus to the cytoplasm." *Nat Rev Mol Cell Biol* 8(10): 761-773.

Komarnitsky, P., E. J. Cho, et al. (2000). "Different phosphorylated forms of RNA polymerase II and associated mRNA processing factors during transcription." *Genes Dev* 14(19): 2452-2460.

Kozak, M. (1987). "At least six nucleotides preceding the AUG initiator codon enhance translation in mammalian cells." *J Mol Biol* 196(4): 947-950.

Kozak, M. (2005). "Regulation of translation via mRNA structure in prokaryotes and eukaryotes." *Gene* 361: 13-37.

Kruse, B., N. Narasimhan, et al. (1989). "Termination of transcription in human mitochondria: identification and purification of a DNA binding protein factor that promotes termination." *Cell* 58(2): 391-397.

Kuge, H., G. G. Brownlee, et al. (1998). "Cap ribose methylation of c-mos mRNA stimulates translation and oocyte maturation in *Xenopus laevis*." *Nucleic Acids Res* 26(13): 3208-3214.

Kupper, H. A., W. T. McAllister, et al. (1973). "Comparison of *Escherichia coli* and T3 RNA polymerases. Differential inhibition of transcription by various drugs." *Eur J Biochem* 38(3): 581-586.

Lamla, T. and V. A. Erdmann (2004). "The Nano-tag, a streptavidin-binding peptide for the purification and detection of recombinant proteins." *Protein Expr Purif* 33(1): 39-47.

Lang, I., M. Scholz, et al. (1986). "Molecular mobility and nucleocytoplasmic flux in hepatoma cells." *J Cell Biol* 102(4): 1183-1190.

Langberg, S. R. and B. Moss (1981). "Post-transcriptional modifications of mRNA. Purification and characterization of cap I and cap II RNA (nucleoside-2'-)-methyltransferases from HeLa cells." *J Biol Chem* 256(19): 10054-10060.

Lee, D. N., L. Phung, et al. (1990). "Transcription pausing by *Escherichia coli* RNA polymerase is modulated by downstream DNA sequences." *J Biol Chem* 265(25): 15145-15153.

Li, Y. I., Y. J. Chen, et al. (2001). "Characterization of the AdoMet-dependent guanylyltransferase activity that is associated with the N terminus of bamboo mosaic virus replicase." *J Virol* 75(2): 782-788.

Li, Y. I., Y. M. Cheng, et al. (1998). "Identification and characterization of the *Escherichia coli*-expressed RNA-dependent RNA polymerase of bamboo mosaic virus." *J Virol* 72(12): 10093-10099.

Li, Y. I., T. W. Shih, et al. (2001). "The helicase-like domain of plant potexvirus replicase participates in formation of RNA 5' cap structure by exhibiting RNA 5'-triphosphatase activity." *J Virol* 75(24): 12114-12120.

Lian, Y., M. B. De Young, et al. (1999). "The sCYMV1 hairpin ribozyme: targeting rules and cleavage of heterologous RNA." *Gene Ther* 6(6): 1114-9.

Lieschke, G. J., P. K. Rao, et al. (1997). "Bioactive murine and human interleukin-12 fusion proteins which retain antitumor activity in vivo." *Nat Biotechnol* 15(1): 35-40.

Lindell, T. J., F. Weinberg, et al. (1970). "Specific inhibition of nuclear RNA polymerase II by alpha-amanitin." *Science* 170(956): 447-449.

Lisser, S. and H. Margalit (1993). "Compilation of *E. coli* mRNA promoter sequences." *Nucleic Acids Res* 21(7): 1507-1516.

Liu, Z. and G. G. Carmichael (1994). "Nuclear antisense RNA. An efficient new method to inhibit gene expression." *Mol Biotechnol* 2(2): 107-18.

Liu, Z., J. Jian-Bo, et al. (2005). "Anti-proteolysis Study of Recombinant IIn-UK Fusion Protein in CHO Cell" *Prog. Biochem. Biophys* 32(6): 544-550.

Lo, H. J., H. K. Huang, et al. (1998). "RNA polymerase I-promoted HIS4 expression yields uncapped, polyadenylated mRNA that is unstable and inefficiently translated in *Saccharomyces cerevisiae*." *Mol Cell Biol* 18(2): 665-675.

Lodish, H., A. Berk, et al. (2008). *Molecular Cell Biology*. New York, USA, Freeman, W. H. and Co.

Loser, P., G. S. Jennings, et al. (1998). "Reactivation of the previously silenced cytomegalovirus major immediate-early promoter in the mouse liver: involvement of NFkappaB." *J Virol* 72(1): 180-190.

Lumb, K. J. and P. S. Kim (1995). "A buried polar interaction imparts structural uniqueness in a designed heterodimeric coiled coil." *Biochemistry* 34(27): 8642-8.

Lyakhov, D. L., B. He, et al. (1997). "Mutant bacteriophage T7 RNA polymerases with altered termination properties." *J Mol Biol* 269(1): 28-40.

Makarova, O. V., E. M. Makarov, et al. (1995). "Transcribing of *Escherichia coli* genes with mutant T7 RNA polymerases: stability of lacZ mRNA inversely correlates with polymerase speed." *Proc Natl Acad Sci USA* 92(26): 12250-12254.

Malone, R. W., P. L. Felgner, et al. (1989). "Cationic liposome-mediated RNA transfection." *Proc Natl Acad Sci USA* 86(16): 6077-6081.

Mantile, G., C. Fuchs, et al. (2000). "Stable, long-term bacterial production of soluble, dimeric, disulfide-bonded protein pharmaceuticals without antibiotic selection." *Biotechnol Prog* 16(1): 17-25.

Mao, X. and S. Shuman (1994). "Intrinsic RNA (guanine-7) methyltransferase activity of the vaccinia virus capping enzyme D1 subunit is stimulated by the D12 subunit. Identification of amino acid residues in the D1 protein required for subunit association and methyl group transfer." *J Biol Chem* 269(39): 24472-9.

Martinez-Costas, J., G. Sutton, et al. (1998). "Guanylyltransferase and RNA 5'-triphosphatase activities of the purified expressed VP4 protein of bluetongue virus." *J Mol Biol* 280(5): 859-866.

McClain, D. L., H. L. Woods, et al. (2001). "Design and characterization of a heterodimeric coiled coil that forms exclusively with an antiparallel relative helix orientation." *J Am Chem Soc* 123(13): 3151-3152.

McCracken, S., N. Fong, et al. (1997). "5'-Capping enzymes are targeted to pre-mRNA by binding to the phosphorylated carboxy-terminal domain of RNA polymerase II." *Genes Dev* 11(24): 3306-3318.

McCulloch, V., B. L. Seidel-Rogol, et al. (2002). "A human mitochondrial transcription factor is related to RNA adenine methyltransferases and binds S-adenosylmethionine." *Mol Cell Biol* 22(4): 1116-1125.

Miao, C. H., A. R. Thompson, et al. (2001). "Long-term and therapeutic-level hepatic gene expression of human factor IX after naked plasmid transfer in vivo." *Mol Ther* 3(6): 947-957.

Miao, C. H., X. Ye, et al. (2003). "High-level factor VIII gene expression in vivo achieved by nonviral liver-specific gene therapy vectors." *Hum Gene Ther* 14(14): 1297-1305.

Mifflin, R. C. and R. E. Kellems (1991). "Coupled transcription-polyadenylation in a cell-free system." *J Biol Chem* 266(29): 19593-19598.

Moffatt, B. A., J. J. Dunn, et al. (1984). "Nucleotide sequence of the gene for bacteriophage T7 RNA polymerase." *J Mol Biol* 173(2): 265-269.

Moll, J. R., S. B. Ruvinov, et al. (2001). "Designed heterodimerizing leucine zippers with a ranger of pls and stabilities up to 10(−15) M." *Protein Sci* 10(3): 649-55.

Natalizio, B. J., N. D. Robson-Dixon, et al. (2009). "The Carboxyl-terminal Domain of RNA Polymerase II Is Not Sufficient to Enhance the Efficiency of Pre-mRNA Capping or Splicing in the Context of a Different Polymerase." *J Biol Chem* 284(13): 8692-8702.

Newton, D. L., Y. Xue, et al. (1996). "Angiogenin single-chain immunofusions: influence of peptide linkers and spacers between fusion protein domains." *Biochemistry* 35(2): 545-553.

Nicol, F., M. Wong, et al. (2002). "Poly-L-glutamate, an anionic polymer, enhances transgene expression for plasmids delivered by intramuscular injection with in vivo electroporation." *Gene Ther* 9(20): 1351-1358.

Niles, E. G. and L. Christen (1993). "Identification of the vaccinia virus mRNA guanyltransferase active site lysine." *J Biol Chem* 268(33): 24986-9.

O'Shea, E. K., J. D. Klemm, et al. (1991). "X-ray structure of the GCN4 leucine zipper, a two-stranded, parallel coiled coil." *Science* 254(5031): 539-544.

O'Shea, E. K., K. J. Lumb, et al. (1993). "Peptide 'Velcro': design of a heterodimeric coiled coil." *Curr Biol* 3(10): 658-667.

Oakley, M. G. and P. S. Kim (1998). "A buried polar interaction can direct the relative orientation of helices in a coiled coil." *Biochemistry* 37(36): 12603-12610.

Ojala, D., J. Montoya, et al. (1981). "tRNA punctuation model of RNA processing in human mitochondria." *Nature* 290(5806): 470-474.

Osumi-Davis, P. A., M. C. de Aguilera, et al. (1992). "Asp537, Asp812 are essential and Lys631, His811 are catalytically significant in bacteriophage T7 RNA polymerase activity." *J Mol Biol* 226(1): 37-45.

Osumi-Davis, P. A., N. Sreerama, et al. (1994). "Bacteriophage T7 RNA polymerase and its active-site mutants. Kinetic, spectroscopic and calorimetric characterization." *J Mol Biol* 237(1): 5-19.

Paguirigan, A. L. and D. J. Beebe (2007). "Protocol for the fabrication of enzymatically crosslinked gelatin microchannels for microfluidic cell culture." *Nat Protoc* 2(7): 1782-8.

Palancade, B. and O. Bensaude (2003). "Investigating RNA polymerase II carboxyl-terminal domain (CTD) phosphorylation." *Eur J Biochem* 270(19): 3859-3870.

Pantoliano, M. W., R. E. Bird, et al. (1991). "Conformational stability, folding, and ligand-binding affinity of single-chain Fv immunoglobulin fragments expressed in *Escherichia coli*." *Biochemistry* 30(42): 10117-10125.

Pashine, A., R. Busch, et al. (2003). "Interaction of HLA-DR with an acidic face of HLA-DM disrupts sequence-dependent interactions with peptides." *Immunity* 19(2): 183-192.

Patil, S. D., D. G. Rhodes, et al. (2004). "Anionic liposomal delivery system for DNA transfection." *Aaps J* 6(4): e29.

Pavlinkova, G., G. W. Beresford, et al. (1999). "Pharmacokinetics and biodistribution of engineered single-chain antibody constructs of MAb CC49 in colon carcinoma xenografts." *J Nucl Med* 40(9): 1536-1546.

Platt, T. (1986). "Transcription termination and the regulation of gene expression." *Annu Rev Biochem* 55: 339-372.

Prieto-Martin, A., J. Montoya, et al. (2001). "A study on the human mitochondrial RNA polymerase activity points to existence of a transcription factor B-like protein." *FEBS Lett* 503(1): 51-55.

Ramadevi, N., N. J. Burroughs, et al. (1998). "Capping and methylation of mRNA by purified recombinant VP4 protein of bluetongue virus." *Proc Natl Acad Sci USA* 95(23): 13537-13542.

Ramadevi, N., J. Rodriguez, et al. (1998). "A leucine zipper-like domain is essential for dimerization and encapsidation of bluetongue virus nucleocapsid protein VP4." *J Virol* 72(4): 2983-2990.

Ramsey-Ewing, A. and B. Moss (1996). "Recombinant protein synthesis in Chinese hamster ovary cells using a vaccinia virus/bacteriophage T7 hybrid expression system." *J Biol Chem* 271(28): 16962-16966.

Rhoads, R. E. (1999). "Signal transduction pathways that regulate eukaryotic protein synthesis." *J Biol Chem* 274(43): 30337-30340.

Robinson, C. R. and R. T. Sauer (1998). "Optimizing the stability of single-chain proteins by linker length and composition mutagenesis." *Proc Natl Acad Sci USA* 95(11): 5929-5934.

Salehi-Ashtiani, K. and J. W. Szostak (2001). "In vitro evolution suggests multiple origins for the hammerhead ribozyme." *Nature* 414(6859): 82-4.

Schmidt, T. G. and A. Skerra (1993). "The random peptide library-assisted engineering of a C-terminal affinity peptide, useful for the detection and purification of a functional Ig Fv fragment." *Protein Eng* 6(1): 109-22.

Schroeder, S. C., B. Schwer, et al. (2000). "Dynamic association of capping enzymes with transcribing RNA polymerase II." *Genes Dev* 14(19): 2435-2440.

Schurer, H., K. Lang, et al. (2002). "A universal method to produce in vitro transcripts with homogeneous 3' ends." *Nucleic Acids Res* 30(12): e56.

Shao, W. H., X. E. Zhang, et al. (2000). "Anchor-chain molecular system for orientation control in enzyme immobilization." *Bioconjug Chem* 11(6): 822-826.

Spehner, D., S. Gillard, et al. (1988). "A cowpox virus gene required for multiplication in Chinese hamster ovary cells." *J Virol* 62(4): 1297-1304.

Studier, F. W., A. H. Rosenberg, et al. (1990). "Use of T7 RNA polymerase to direct expression of cloned genes." *Methods Enzymol* 185: 60-89.

Tang, Y., N. Jiang, et al. (1996). "Selection of linkers for a catalytic single-chain antibody using phage display technology." *J Biol Chem* 271(26): 15682-15686.

Ting, A. (2003). Genetically encoded fluorescent reporters of kinase, methyltransferase, and acetyl-transferase activities.

Ting, A. Y., K. H. Kain, et al. (2001). "Genetically encoded fluorescent reporters of protein tyrosine kinase activities in living cells." *Proc Natl Acad Sci USA* 98(26): 15003-15008.

Tiranti, V., A. Savoia, et al. (1997). "Identification of the gene encoding the human mitochondrial RNA polymerase (h-mtRPOL) by cyberscreening of the Expressed Sequence Tags database." *Hum Mol Genet* 6(4): 615-625.

Tommasino, M., S. Ricci, et al. (1988). "Genome organization of the killer plasmid pGK12 from *Kluyveromyces lactis*." *Nucleic Acids Res* 16(13): 5863-5878.

Topper, J. N. and D. A. Clayton (1989). "Identification of transcriptional regulatory elements in human mitochondrial DNA by linker substitution analysis." *Mol Cell Biol* 9(3): 1200-1211.

Turner, D. J., M. A. Ritter, et al. (1997). "Importance of the linker in expression of single-chain Fv antibody fragments: optimisation of peptide sequence using phage display technology." *J Immunol Methods* 205(1): 43-54.

Ucker, D. S. and K. R. Yamamoto (1984). "Early events in the stimulation of mammary tumor virus RNA synthesis by glucocorticoids. Novel assays of transcription rates." *J Biol Chem* 259(12): 7416-7420.

Uptain, S. M. and M. J. Chamberlin (1997). "*Escherichia coli* RNA polymerase terminates transcription efficiently at rho-independent terminators on single-stranded DNA templates." *Proc Natl Acad Sci USA* 94(25): 13548-13553.

Walker, S. C., J. M. Avis, et al. (2003). "General plasmids for producing RNA in vitro transcripts with homogeneous ends." *Nucleic Acids Res* 31(15): e82.

Wells, J. A. and D. B. Powers (1986). "In vivo formation and stability of engineered disulfide bonds in subtilisin." *J Biol Chem* 261(14): 6564-6570.

Whitlow, M., B. A. Bell, et al. (1993). "An improved linker for single-chain Fv with reduced aggregation and enhanced proteolytic stability." *Protein Eng* 6(8): 989-995.

Wickham, T. J., M. E. Carrion, et al. (1995). "Targeting of adenovirus penton base to new receptors through replacement of its RGD motif with other receptor-specific peptide motifs." *Gene Ther* 2(10): 750-756.

Wu, S. C., J. C. Yeung, et al. (2002). "Design, production, and characterization of an engineered biotin ligase (BirA) and its application for affinity purification of staphylokinase produced from *Bacillus subtilis* via secretion." *Protein Expr Purif* 24(3): 357-65.

Wyatt, L. S., B. Moss, et al. (1995). "Replication-deficient vaccinia virus encoding bacteriophage T7 RNA polymerase for transient gene expression in mammalian cells." *Virology* 210(1): 202-205.

Yue, Z., E. Maldonado, et al. (1997). "Mammalian capping enzyme complements mutant *Saccharomyces cerevisiae* lacking mRNA guanylyltransferase and selectively binds the elongating form of RNA polymerase II." *Proc Natl Acad Sci USA* 94(24): 12898-12903.

Zabner, J., A. J. Fasbender, et al. (1995). "Cellular and molecular barriers to gene transfer by a cationic lipid." *J Biol Chem* 270(32): 18997-19007.

Zhang, X. and F. W. Studier (1997). "Mechanism of inhibition of bacteriophage T7 RNA polymerase by T7 lysozyme." *J Mol Biol* 269(1): 10-27.

The invention claimed is:

1. A hetero-oligomeric enzyme comprising:
a catalytic domain of a RNA triphosphatase;
a catalytic domain of a guanylyltransferase;
a catalytic domain of a N7-guanine methyltransferase; and
a catalytic domain of a DNA-dependent RNA polymerase,
wherein the catalytic domain of a DNA-dependent RNA polymerase is linked covalently or non-covalently with the catalytic domain of a RNA triphosphatase, the catalytic domain of a guanylyltransferase, or the catalytic domain of a N7-guanine methyltransferase, and
wherein the hetero-oligomeric enzyme is non-natural.

2. The hetero-oligomeric enzyme according to claim 1, wherein the catalytic domain of a N7-guanine methyltransferase and the catalytic domain of a DNA-dependent RNA polymerase are included in a monomer.

3. The hetero-oligomeric enzyme according to claim 1, wherein the catalytic domain of a RNA triphosphatase and the catalytic domain of a guanylyltransferase are included in a monomer.

4. The hetero-oligomeric enzyme according to claim 1, wherein the catalytic domain of a RNA triphosphatase, the catalytic domain of a guanylyltransferase and the catalytic domain of a DNA-dependent RNA polymerase are included in a monomer.

5. The hetero-oligomeric enzyme according to claim 1, further comprising a domain that enhances the activity of at least one catalytic domain of the hetero-oligomeric enzyme.

6. The hetero-oligomeric enzyme according to claim 1, wherein at least one of the catalytic domain of a N7-guanine methyltransferase, the catalytic domain of a RNA triphosphatase and the catalytic domain of a guanylyltransferase is a catalytic domain of the vaccinia mRNA capping enzyme.

7. The hetero-oligomeric enzyme according to claim 1, comprising:
a first monomer comprising a catalytic domain of a N7-guanine methyltransferase and a catalytic domain of a DNA-dependent RNA polymerase, and
a second monomer comprising a catalytic domain of a RNA triphosphatase and a catalytic domain of a guanylyltransferase,
wherein the catalytic domain of a N7-guanine methyltransferase is a catalytic domain of the vaccinia mRNA capping enzyme encoded by the vaccinia virus D1R gene, and the catalytic domain of a RNA triphosphatase and the catalytic domain of a guanylyltransferase are catalytic domains of the vaccinia mRNA capping enzyme encoded by the vaccinia virus D1R gene, and
wherein the hetero-oligomeric enzyme further comprises a 31-kDa subunit encoded by the vaccinia virus D12L gene.

8. The hetero-oligomeric enzyme according to claim 1, comprising:
a first monomer comprising a catalytic domain of a N7-guanine methyltransferase, and
a second monomer comprising a catalytic domain of a RNA triphosphatase, a catalytic domain of a guanylyltransferase, and a catalytic domain of a DNA-dependent RNA polymerase,
wherein the catalytic domain of a N7-guanine methyltransferase is a catalytic domain of the vaccinia mRNA capping enzyme encoded by the vaccinia virus D1R gene, and the catalytic domain of a RNA triphosphatase and the catalytic domain of a guanylyltransferase are catalytic domains of the vaccinia mRNA capping enzyme encoded by the vaccinia virus D1R gene, and
wherein the hetero-oligomeric enzyme further comprises a 31-kDa subunit encoded by the vaccinia virus D12L gene.

9. A method for producing an RNA molecule with a 5'-terminal m$^7$GpppN cap, comprising
contacting a DNA sequence encoding the RNA molecule with the hetero-oligomeric enzyme according to claim 1,
wherein the DNA sequence is operatively linked to a promoter for the catalytic domain of a DNA-dependent RNA polymerase.

10. A hetero-oligomeric enzyme comprising:
a monomer comprising a catalytic domain of a RNA triphosphatase, a catalytic domain of a guanylyltransferase, and a catalytic domain of a N7-guanine methyltransferase; and
a complex comprising a catalytic domain of a DNA-dependent RNA polymerase,
wherein the monomer and the complex are linked covalently or non-covalently, and
wherein the hetero-oligomeric enzyme is non-natural.

11. The hetero-oligomeric enzyme according to claim 10, comprising a complex comprising a catalytic domain of a bacterial DNA-dependent RNA polymerase.

12. The hetero-oligomeric enzyme according to claim 10, comprising a complex comprising a catalytic domain of the DNA-dependent RNA polymerase of *Escherichia coli*.

13. A method for producing an RNA molecule with a 5'-terminal m⁷GpppN cap, comprising
contacting a DNA sequence encoding the RNA molecule with the hetero-oligomeric enzyme according to claim 10,
wherein the DNA sequence is operatively linked to a promoter for the catalytic domain of a DNA-dependent RNA polymerase.

* * * * *

SEQUENCE LISTING

```
<160> NUMBER OF SEQ ID NOS: 52

<210> SEQ ID NO 1
<211> LENGTH: 883
<212> TYPE: PRT
<213> ORGANISM: Enterobacteria phage T7

<400> SEQUENCE: 1

Met Asn Thr Ile Asn Ile Ala Lys Asn Asp Phe Ser Asp Ile Glu Leu
1               5                   10                  15

Ala Ala Ile Pro Phe Asn Thr Leu Ala Asp His Tyr Gly Glu Arg Leu
            20                  25                  30

Ala Arg Glu Gln Leu Ala Leu Glu His Glu Ser Tyr Glu Met Gly Glu
        35                  40                  45

Ala Arg Phe Arg Lys Met Phe Glu Arg Gln Leu Lys Ala Gly Glu Val
    50                  55                  60

Ala Asp Asn Ala Ala Ala Lys Pro Leu Ile Thr Thr Leu Leu Pro Lys
65                  70                  75                  80

Met Ile Ala Arg Ile Asn Asp Trp Phe Glu Glu Val Lys Ala Lys Arg
                85                  90                  95

Gly Lys Arg Pro Thr Ala Phe Gln Phe Leu Gln Glu Ile Lys Pro Glu
            100                 105                 110

Ala Val Ala Tyr Ile Thr Ile Lys Thr Thr Leu Ala Cys Leu Thr Ser
        115                 120                 125

Ala Asp Asn Thr Thr Val Gln Ala Val Ala Ser Ala Ile Gly Arg Ala
    130                 135                 140

Ile Glu Asp Glu Ala Arg Phe Gly Arg Ile Arg Asp Leu Glu Ala Lys
145                 150                 155                 160

His Phe Lys Lys Asn Val Glu Glu Gln Leu Asn Lys Arg Val Gly His
                165                 170                 175

Val Tyr Lys Lys Ala Phe Met Gln Val Val Glu Ala Asp Met Leu Ser
            180                 185                 190

Lys Gly Leu Leu Gly Gly Glu Ala Trp Ser Ser Trp His Lys Glu Asp
        195                 200                 205

Ser Ile His Val Gly Val Arg Cys Ile Glu Met Leu Ile Glu Ser Thr
    210                 215                 220

Gly Met Val Ser Leu His Arg Gln Asn Ala Gly Val Val Gly Gln Asp
225                 230                 235                 240

Ser Glu Thr Ile Glu Leu Ala Pro Glu Tyr Ala Glu Ala Ile Ala Thr
                245                 250                 255

Arg Ala Gly Ala Leu Ala Gly Ile Ser Pro Met Phe Gln Pro Cys Val
            260                 265                 270

Val Pro Pro Lys Pro Trp Thr Gly Ile Thr Gly Gly Gly Tyr Trp Ala
        275                 280                 285

Asn Gly Arg Arg Pro Leu Ala Leu Val Arg Thr His Ser Lys Lys Ala
    290                 295                 300
```

-continued

Leu Met Arg Tyr Glu Asp Val Tyr Met Pro Glu Val Tyr Lys Ala Ile
305                 310                 315                 320

Asn Ile Ala Gln Asn Thr Ala Trp Lys Ile Asn Lys Lys Val Leu Ala
            325                 330                 335

Val Ala Asn Val Ile Thr Lys Trp Lys His Cys Pro Val Glu Asp Ile
            340                 345                 350

Pro Ala Ile Glu Arg Glu Leu Pro Met Lys Pro Glu Asp Ile Asp
            355                 360                 365

Met Asn Pro Glu Ala Leu Thr Ala Trp Lys Arg Ala Ala Ala Val
370                 375                 380

Tyr Arg Lys Asp Lys Ala Arg Lys Ser Arg Arg Ile Ser Leu Glu Phe
385                 390                 395                 400

Met Leu Glu Gln Ala Asn Lys Phe Ala Asn His Lys Ala Ile Trp Phe
            405                 410                 415

Pro Tyr Asn Met Asp Trp Arg Gly Arg Val Tyr Ala Val Ser Met Phe
            420                 425                 430

Asn Pro Gln Gly Asn Asp Met Thr Lys Gly Leu Leu Thr Leu Ala Lys
            435                 440                 445

Gly Lys Pro Ile Gly Lys Glu Gly Tyr Tyr Trp Leu Lys Ile His Gly
450                 455                 460

Ala Asn Cys Ala Gly Val Asp Lys Val Pro Phe Pro Glu Arg Ile Lys
465                 470                 475                 480

Phe Ile Glu Glu Asn His Glu Asn Ile Met Ala Cys Ala Lys Ser Pro
            485                 490                 495

Leu Glu Asn Thr Trp Trp Ala Glu Gln Asp Ser Pro Phe Cys Phe Leu
            500                 505                 510

Ala Phe Cys Phe Glu Tyr Ala Gly Val Gln His His Gly Leu Ser Tyr
            515                 520                 525

Asn Cys Ser Leu Pro Leu Ala Phe Asp Gly Ser Cys Ser Gly Ile Gln
            530                 535                 540

His Phe Ser Ala Met Leu Arg Asp Glu Val Gly Gly Arg Ala Val Asn
545                 550                 555                 560

Leu Leu Pro Ser Glu Thr Val Gln Asp Ile Tyr Gly Ile Val Ala Lys
            565                 570                 575

Lys Val Asn Glu Ile Leu Gln Ala Asp Ala Ile Asn Gly Thr Asp Asn
            580                 585                 590

Glu Val Val Thr Val Thr Asp Glu Asn Thr Gly Glu Ile Ser Glu Lys
            595                 600                 605

Val Lys Leu Gly Thr Lys Ala Leu Ala Gly Gln Trp Leu Ala Tyr Gly
610                 615                 620

Val Thr Arg Ser Val Thr Lys Arg Ser Val Met Thr Leu Ala Tyr Gly
625                 630                 635                 640

Ser Lys Glu Phe Gly Phe Arg Gln Gln Val Leu Glu Asp Thr Ile Gln
            645                 650                 655

Pro Ala Ile Asp Ser Gly Lys Gly Leu Met Phe Thr Gln Pro Asn Gln
            660                 665                 670

Ala Ala Gly Tyr Met Ala Lys Leu Ile Trp Glu Ser Val Ser Val Thr
            675                 680                 685

Val Val Ala Ala Val Glu Ala Met Asn Trp Leu Lys Ser Ala Ala Lys
            690                 695                 700

Leu Leu Ala Ala Glu Val Lys Asp Lys Lys Thr Gly Glu Ile Leu Arg
705                 710                 715                 720

Lys Arg Cys Ala Val His Trp Val Thr Pro Asp Gly Phe Pro Val Trp

```
                    725                 730                 735
Gln Glu Tyr Lys Lys Pro Ile Gln Thr Arg Leu Asn Leu Met Phe Leu
            740                 745                 750

Gly Gln Phe Arg Leu Gln Pro Thr Ile Asn Thr Asn Lys Asp Ser Glu
        755                 760                 765

Ile Asp Ala His Lys Gln Glu Ser Gly Ile Ala Pro Asn Phe Val His
    770                 775                 780

Ser Gln Asp Gly Ser His Leu Arg Lys Thr Val Val Trp Ala His Glu
785                 790                 795                 800

Lys Tyr Gly Ile Glu Ser Phe Ala Leu Ile His Asp Ser Phe Gly Thr
                805                 810                 815

Ile Pro Ala Asp Ala Ala Asn Leu Phe Lys Ala Val Arg Glu Thr Met
            820                 825                 830

Val Asp Thr Tyr Glu Ser Cys Asp Val Leu Ala Asp Phe Tyr Asp Gln
        835                 840                 845

Phe Ala Asp Gln Leu His Glu Ser Gln Leu Asp Lys Met Pro Ala Leu
    850                 855                 860

Pro Ala Lys Gly Asn Leu Asn Leu Arg Asp Ile Leu Glu Ser Asp Phe
865                 870                 875                 880

Ala Phe Ala

<210> SEQ ID NO 2
<211> LENGTH: 15
<212> TYPE: PRT
<213> ORGANISM: artificial sequence
<220> FEATURE:
<223> OTHER INFORMATION: Peptide linker

<400> SEQUENCE: 2

Gly Gly Gly Gly Ile Ala Pro Ser Met Val Gly Gly Gly Gly Ser
1               5                   10                  15

<210> SEQ ID NO 3
<211> LENGTH: 21
<212> TYPE: PRT
<213> ORGANISM: artificial sequence
<220> FEATURE:
<223> OTHER INFORMATION: Peptide linker

<400> SEQUENCE: 3

Ser Pro Asn Gly Ala Ser Asn Ser Gly Ser Ala Pro Asp Thr Ser Ser
1               5                   10                  15

Ala Pro Gly Ser Gln
            20

<210> SEQ ID NO 4
<211> LENGTH: 15
<212> TYPE: PRT
<213> ORGANISM: artificial sequence
<220> FEATURE:
<223> OTHER INFORMATION: Peptide linker

<400> SEQUENCE: 4

Glu Gly Lys Ser Ser Gly Ser Gly Ser Glu Ser Lys Ser Thr Glu
1               5                   10                  15

<210> SEQ ID NO 5
<211> LENGTH: 14
<212> TYPE: PRT
<213> ORGANISM: artificial sequence
<220> FEATURE:
```

```
<223> OTHER INFORMATION: Peptide linker

<400> SEQUENCE: 5

Glu Gly Lys Ser Ser Gly Ser Gly Ser Glu Ser Lys Glu Phe
1               5                   10

<210> SEQ ID NO 6
<211> LENGTH: 19
<212> TYPE: PRT
<213> ORGANISM: artificial sequence
<220> FEATURE:
<223> OTHER INFORMATION: Peptide linker

<400> SEQUENCE: 6

Gly Gly Gly Ser Gly Gly Gly Ser Gly Gly Gly Thr Gly Gly Gly Ser
1               5                   10                  15

Gly Gly Gly

<210> SEQ ID NO 7
<211> LENGTH: 14
<212> TYPE: PRT
<213> ORGANISM: artificial sequence
<220> FEATURE:
<223> OTHER INFORMATION: Peptide linker

<400> SEQUENCE: 7

Gly Ser Thr Ser Gly Ser Gly Lys Ser Ser Glu Gly Lys Gly
1               5                   10

<210> SEQ ID NO 8
<211> LENGTH: 18
<212> TYPE: PRT
<213> ORGANISM: artificial sequence
<220> FEATURE:
<223> OTHER INFORMATION: Peptide linker

<400> SEQUENCE: 8

Tyr Pro Arg Ser Ile Tyr Ile Arg Arg Arg His Pro Ser Pro Ser Leu
1               5                   10                  15

Thr Thr

<210> SEQ ID NO 9
<211> LENGTH: 18
<212> TYPE: PRT
<213> ORGANISM: artificial sequence
<220> FEATURE:
<223> OTHER INFORMATION: Peptide linker

<400> SEQUENCE: 9

Gly Ser Thr Ser Gly Ser Gly Lys Pro Gly Ser Gly Glu Gly Ser Thr
1               5                   10                  15

Lys Gly

<210> SEQ ID NO 10
<211> LENGTH: 15
<212> TYPE: PRT
<213> ORGANISM: artificial sequence
<220> FEATURE:
<223> OTHER INFORMATION: Peptide linker

<400> SEQUENCE: 10

Gly Ser Thr Ser Gly Ser Gly Lys Pro Gly Ser Gly Glu Gly Ser
1               5                   10                  15
```

```
<210> SEQ ID NO 11
<211> LENGTH: 25
<212> TYPE: PRT
<213> ORGANISM: artificial sequence
<220> FEATURE:
<223> OTHER INFORMATION: Peptide linker

<400> SEQUENCE: 11

Ser Ser Ala Asp Asp Ala Lys Lys Asp Ala Ala Lys Lys Asp Ala
1               5                   10                  15

Lys Lys Asp Asp Ala Lys Lys Asp Ala
            20                  25

<210> SEQ ID NO 12
<211> LENGTH: 26
<212> TYPE: PRT
<213> ORGANISM: artificial sequence
<220> FEATURE:
<223> OTHER INFORMATION: Peptide linker
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 12

Gly Ser Ala Asp Asp Ala Xaa Xaa Asp Ala Ala Xaa Lys Asp Ala
1               5                   10                  15

Lys Lys Asp Asp Ala Lys Lys Asp Gly Ser
            20                  25

<210> SEQ ID NO 13
<211> LENGTH: 25
<212> TYPE: PRT
<213> ORGANISM: artificial sequence
<220> FEATURE:
<223> OTHER INFORMATION: Peptide linker

<400> SEQUENCE: 13

Leu Ser Ala Asp Asp Ala Lys Lys Asp Ala Ala Lys Lys Asp Ala
1               5                   10                  15

Lys Lys Asp Asp Ala Lys Lys Asp Leu
            20                  25

<210> SEQ ID NO 14
<211> LENGTH: 17
<212> TYPE: PRT
<213> ORGANISM: artificial sequence
<220> FEATURE:
<223> OTHER INFORMATION: Peptide linker

<400> SEQUENCE: 14

Ala Glu Ala Ala Ala Lys Glu Ala Ala Ala Lys Glu Ala Ala Ala Lys
1               5                   10                  15

Ala

<210> SEQ ID NO 15
<211> LENGTH: 9
<212> TYPE: PRT
<213> ORGANISM: artificial sequence
<220> FEATURE:
<223> OTHER INFORMATION: Peptide linker

<400> SEQUENCE: 15
```

-continued

Gly Ser His Ser Gly Ser Gly Lys Pro
1               5

<210> SEQ ID NO 16
<211> LENGTH: 34
<212> TYPE: PRT
<213> ORGANISM: artificial sequence
<220> FEATURE:
<223> OTHER INFORMATION: Peptide linker

<400> SEQUENCE: 16

Gly Ser Thr Ser Gly Ser Gly Lys Pro Gly Ser Gly Glu Ser Thr
1               5                   10                  15

Gly Ala Gly Gly Ala Gly Ser Thr Ser Gly Ser Gly Lys Pro Ser Gly
                20                  25                  30

Glu Gly

<210> SEQ ID NO 17
<211> LENGTH: 16
<212> TYPE: PRT
<213> ORGANISM: artificial sequence
<220> FEATURE:
<223> OTHER INFORMATION: Peptide linker

<400> SEQUENCE: 17

Leu Ser Leu Glu Val Ala Glu Glu Ile Ala Arg Leu Glu Ala Glu Val
1               5                   10                  15

<210> SEQ ID NO 18
<211> LENGTH: 13
<212> TYPE: PRT
<213> ORGANISM: artificial sequence
<220> FEATURE:
<223> OTHER INFORMATION: Peptide linker

<400> SEQUENCE: 18

Gly Thr Pro Thr Pro Thr Pro Thr Pro Thr Gly Glu Phe
1               5                   10

<210> SEQ ID NO 19
<211> LENGTH: 885
<212> TYPE: PRT
<213> ORGANISM: artificial sequence
<220> FEATURE:
<223> OTHER INFORMATION: Protein sequence encoded by pT7RNA plasmid

<400> SEQUENCE: 19

Met Leu Glu Asn Thr Ile Asn Ile Ala Lys Asn Asp Phe Ser Asp Ile
1               5                   10                  15

Glu Leu Ala Ala Ile Pro Phe Asn Thr Leu Ala Asp His Tyr Gly Glu
                20                  25                  30

Arg Leu Ala Arg Glu Gln Leu Ala Leu Glu His Glu Ser Tyr Glu Met
            35                  40                  45

Gly Glu Ala Arg Phe Arg Lys Met Phe Glu Arg Gln Leu Lys Ala Gly
        50                  55                  60

Glu Val Ala Asp Asn Ala Ala Ala Lys Pro Leu Ile Thr Thr Leu Leu
65                  70                  75                  80

Pro Lys Met Ile Ala Arg Ile Asn Asp Trp Phe Glu Glu Val Lys Ala
                85                  90                  95

Lys Arg Gly Lys Arg Pro Thr Ala Phe Gln Phe Leu Gln Glu Ile Lys
                100                 105                 110

```
Pro Glu Ala Val Ala Tyr Ile Thr Ile Lys Thr Thr Leu Ala Cys Leu
            115                 120                 125

Thr Ser Ala Asp Asn Thr Thr Val Gln Ala Val Ala Ser Ala Ile Gly
130                 135                 140

Arg Ala Ile Glu Asp Glu Ala Arg Phe Gly Arg Ile Arg Asp Leu Glu
145                 150                 155                 160

Ala Lys His Phe Lys Lys Asn Val Glu Glu Gln Leu Asn Lys Arg Val
                165                 170                 175

Gly His Val Tyr Lys Lys Ala Phe Met Gln Val Val Glu Ala Asp Met
            180                 185                 190

Leu Ser Lys Gly Leu Leu Gly Gly Glu Ala Trp Ser Ser Trp His Lys
        195                 200                 205

Glu Asp Ser Ile His Val Gly Val Arg Cys Ile Glu Met Leu Ile Glu
    210                 215                 220

Ser Thr Gly Met Val Ser Leu His Arg Gln Asn Ala Gly Val Val Gly
225                 230                 235                 240

Gln Asp Ser Glu Thr Ile Glu Leu Ala Pro Glu Tyr Ala Glu Ala Ile
                245                 250                 255

Ala Thr Arg Ala Gly Ala Leu Ala Gly Ile Ser Pro Met Phe Gln Pro
            260                 265                 270

Cys Val Val Pro Pro Lys Pro Trp Thr Gly Ile Thr Gly Gly Gly Tyr
        275                 280                 285

Trp Ala Asn Gly Arg Arg Pro Leu Ala Leu Val Arg Thr His Ser Lys
    290                 295                 300

Lys Ala Leu Met Arg Tyr Glu Asp Val Tyr Met Pro Glu Val Tyr Lys
305                 310                 315                 320

Ala Ile Asn Ile Ala Gln Asn Thr Ala Trp Lys Ile Asn Lys Lys Val
                325                 330                 335

Leu Ala Val Ala Asn Val Ile Thr Lys Trp Lys His Cys Pro Val Glu
            340                 345                 350

Asp Ile Pro Ala Ile Glu Arg Glu Leu Pro Met Lys Pro Glu Asp
        355                 360                 365

Ile Asp Met Asn Pro Glu Ala Leu Thr Ala Trp Lys Arg Ala Ala Ala
370                 375                 380

Ala Val Tyr Arg Lys Asp Lys Ala Arg Lys Ser Arg Arg Ile Ser Leu
385                 390                 395                 400

Glu Phe Met Leu Glu Gln Ala Asn Lys Phe Ala Asn His Lys Ala Ile
                405                 410                 415

Trp Phe Pro Tyr Asn Met Asp Trp Arg Gly Arg Val Tyr Ala Val Ser
            420                 425                 430

Met Phe Asn Pro Gln Gly Asn Asp Met Thr Lys Gly Leu Leu Thr Leu
        435                 440                 445

Ala Lys Gly Lys Pro Ile Gly Lys Glu Gly Tyr Tyr Trp Leu Lys Ile
    450                 455                 460

His Gly Ala Asn Cys Ala Gly Val Asp Lys Val Pro Phe Pro Glu Arg
465                 470                 475                 480

Ile Lys Phe Ile Glu Glu Asn His Glu Asn Ile Met Ala Cys Ala Lys
                485                 490                 495

Ser Pro Leu Glu Asn Thr Trp Trp Ala Glu Gln Asp Ser Pro Phe Cys
            500                 505                 510

Phe Leu Ala Phe Cys Phe Glu Tyr Ala Gly Val Gln His His Gly Leu
        515                 520                 525

Ser Tyr Asn Cys Ser Leu Pro Leu Ala Phe Asp Gly Ser Cys Ser Gly
```

```
            530                 535                 540
Ile Gln His Phe Ser Ala Met Leu Arg Asp Glu Val Gly Gly Arg Ala
545                 550                 555                 560

Val Asn Leu Leu Pro Ser Glu Thr Val Gln Asp Ile Tyr Gly Ile Val
                565                 570                 575

Ala Lys Lys Val Asn Glu Ile Leu Gln Ala Asp Ala Ile Asn Gly Thr
            580                 585                 590

Asp Asn Glu Val Val Thr Val Thr Asp Glu Asn Thr Gly Glu Ile Ser
        595                 600                 605

Glu Lys Val Lys Leu Gly Thr Lys Ala Leu Ala Gly Gln Trp Leu Ala
    610                 615                 620

Tyr Gly Val Thr Arg Ser Val Thr Lys Arg Ser Val Met Thr Leu Ala
625                 630                 635                 640

Tyr Gly Ser Lys Glu Phe Gly Phe Arg Gln Gln Val Leu Glu Asp Thr
                645                 650                 655

Ile Gln Pro Ala Ile Asp Ser Gly Lys Gly Leu Met Phe Thr Gln Pro
            660                 665                 670

Asn Gln Ala Ala Gly Tyr Met Ala Lys Leu Ile Trp Glu Ser Val Ser
        675                 680                 685

Val Thr Val Val Ala Ala Val Glu Ala Met Asn Trp Leu Lys Ser Ala
    690                 695                 700

Ala Lys Leu Leu Ala Ala Glu Val Lys Asp Lys Lys Thr Gly Glu Ile
705                 710                 715                 720

Leu Arg Lys Arg Cys Ala Val His Trp Val Thr Pro Asp Gly Phe Pro
                725                 730                 735

Val Trp Gln Glu Tyr Lys Lys Pro Ile Gln Thr Arg Leu Asn Leu Met
            740                 745                 750

Phe Leu Gly Gln Phe Arg Leu Gln Pro Thr Ile Asn Thr Asn Lys Asp
        755                 760                 765

Ser Glu Ile Asp Ala His Lys Gln Glu Ser Gly Ile Ala Pro Asn Phe
    770                 775                 780

Val His Ser Gln Asp Gly Ser His Leu Arg Lys Thr Val Val Trp Ala
785                 790                 795                 800

His Glu Lys Tyr Gly Ile Glu Ser Phe Ala Leu Ile His Asp Ser Phe
                805                 810                 815

Gly Thr Ile Pro Ala Asp Ala Ala Asn Leu Phe Lys Ala Val Arg Glu
            820                 825                 830

Thr Met Val Asp Thr Tyr Glu Ser Cys Asp Val Leu Ala Asp Phe Tyr
        835                 840                 845

Asp Gln Phe Ala Asp Gln Leu His Glu Ser Gln Leu Asp Lys Met Pro
    850                 855                 860

Ala Leu Pro Ala Lys Gly Asn Leu Asn Leu Arg Asp Ile Leu Glu Ser
865                 870                 875                 880

Asp Phe Ala Phe Ala
                885

<210> SEQ ID NO 20
<211> LENGTH: 1776
<212> TYPE: PRT
<213> ORGANISM: artificial sequence
<220> FEATURE:
<223> OTHER INFORMATION: Protein sequence encoded by pNP868R-pT7RNAP
      plasmid

<400> SEQUENCE: 20
```

```
Met Glu Phe Ala Ser Leu Asp Asn Leu Val Ala Arg Tyr Gln Arg Cys
1               5                   10                  15

Phe Asn Asp Gln Ser Leu Lys Asn Ser Thr Ile Glu Leu Glu Ile Arg
            20                  25                  30

Phe Gln Gln Ile Asn Phe Leu Leu Phe Lys Thr Val Tyr Glu Ala Leu
            35                  40                  45

Val Ala Gln Glu Ile Pro Ser Thr Ile Ser His Ser Ile Arg Cys Ile
50                  55                  60

Lys Lys Val His His Glu Asn His Cys Arg Glu Lys Ile Leu Pro Ser
65              70                  75                  80

Glu Asn Leu Tyr Phe Lys Lys Gln Pro Leu Met Phe Phe Lys Phe Ser
                85                  90                  95

Glu Pro Ala Ser Leu Gly Cys Lys Val Ser Leu Ala Ile Glu Gln Pro
            100                 105                 110

Ile Arg Lys Phe Ile Leu Asp Ser Ser Val Leu Val Arg Leu Lys Asn
        115                 120                 125

Arg Thr Thr Phe Arg Val Ser Glu Leu Trp Lys Ile Glu Leu Thr Ile
    130                 135                 140

Val Lys Gln Leu Met Gly Ser Glu Val Ser Ala Lys Leu Ala Ala Phe
145                 150                 155                 160

Lys Thr Leu Leu Phe Asp Thr Pro Glu Gln Gln Thr Lys Asn Met
                165                 170                 175

Met Thr Leu Ile Asn Pro Asp Asp Glu Tyr Leu Tyr Glu Ile Glu Ile
            180                 185                 190

Glu Tyr Thr Gly Lys Pro Glu Ser Leu Thr Ala Ala Asp Val Ile Lys
        195                 200                 205

Ile Lys Asn Thr Val Leu Thr Leu Ile Ser Pro Asn His Leu Met Leu
    210                 215                 220

Thr Ala Tyr His Gln Ala Ile Glu Phe Ile Ala Ser His Ile Leu Ser
225                 230                 235                 240

Ser Glu Ile Leu Leu Ala Arg Ile Lys Ser Gly Lys Trp Gly Leu Lys
                245                 250                 255

Arg Leu Leu Pro Gln Val Lys Ser Met Thr Lys Ala Asp Tyr Met Lys
            260                 265                 270

Phe Tyr Pro Pro Val Gly Tyr Tyr Val Thr Asp Lys Ala Asp Gly Ile
        275                 280                 285

Arg Gly Ile Ala Val Ile Gln Asp Thr Gln Ile Tyr Val Val Ala Asp
    290                 295                 300

Gln Leu Tyr Ser Leu Gly Thr Thr Gly Ile Glu Pro Leu Lys Pro Thr
305                 310                 315                 320

Ile Leu Asp Gly Glu Phe Met Pro Glu Lys Lys Glu Phe Tyr Gly Phe
                325                 330                 335

Asp Val Ile Met Tyr Glu Gly Asn Leu Leu Thr Gln Gln Gly Phe Glu
            340                 345                 350

Thr Arg Ile Glu Ser Leu Ser Lys Gly Ile Lys Val Leu Gln Ala Phe
        355                 360                 365

Asn Ile Lys Ala Glu Met Lys Pro Phe Ile Ser Leu Thr Ser Ala Asp
    370                 375                 380

Pro Asn Val Leu Leu Lys Asn Phe Glu Ser Ile Phe Lys Lys Lys Thr
385                 390                 395                 400

Arg Pro Tyr Ser Ile Asp Gly Ile Ile Leu Val Glu Pro Gly Asn Ser
                405                 410                 415

Tyr Leu Asn Thr Asn Thr Phe Lys Trp Lys Pro Thr Trp Asp Asn Thr
```

```
                420             425             430
Leu Asp Phe Leu Val Arg Lys Cys Pro Glu Ser Leu Asn Val Pro Glu
            435             440             445
Tyr Ala Pro Lys Lys Gly Phe Ser Leu His Leu Leu Phe Val Gly Ile
        450             455             460
Ser Gly Glu Leu Phe Lys Leu Ala Leu Asn Trp Cys Pro Gly Tyr
465             470             475             480
Thr Lys Leu Phe Pro Val Thr Gln Arg Asn Gln Asn Tyr Phe Pro Val
            485             490             495
Gln Phe Gln Pro Ser Asp Phe Pro Leu Ala Phe Leu Tyr Tyr His Pro
            500             505             510
Asp Thr Ser Ser Phe Ser Asn Ile Asp Gly Lys Val Leu Glu Met Arg
            515             520             525
Cys Leu Lys Arg Glu Ile Asn Tyr Val Arg Trp Glu Ile Val Lys Ile
            530             535             540
Arg Glu Asp Arg Gln Gln Asp Leu Lys Thr Gly Gly Tyr Phe Gly Asn
545             550             555             560
Asp Phe Lys Thr Ala Glu Leu Thr Trp Leu Asn Tyr Met Asp Pro Phe
                565             570             575
Ser Phe Glu Glu Leu Ala Lys Gly Pro Ser Gly Met Tyr Phe Ala Gly
            580             585             590
Ala Lys Thr Gly Ile Tyr Arg Ala Gln Thr Ala Leu Ile Ser Phe Ile
            595             600             605
Lys Gln Glu Ile Ile Gln Lys Ile Ser His Gln Ser Trp Val Ile Asp
            610             615             620
Leu Gly Ile Gly Lys Gly Gln Asp Leu Gly Arg Tyr Leu Asp Ala Gly
625             630             635             640
Val Arg His Leu Val Gly Ile Asp Lys Asp Gln Thr Ala Leu Ala Glu
                645             650             655
Leu Val Tyr Arg Lys Phe Ser His Ala Thr Thr Arg Gln His Lys His
                660             665             670
Ala Thr Asn Ile Tyr Val Leu His Gln Asp Leu Ala Glu Pro Ala Lys
            675             680             685
Glu Ile Ser Glu Lys Val His Gln Ile Tyr Gly Phe Pro Lys Glu Gly
            690             695             700
Ala Ser Ser Ile Val Ser Asn Leu Phe Ile His Tyr Leu Met Lys Asn
705             710             715             720
Thr Gln Gln Val Glu Asn Leu Ala Val Leu Cys His Lys Leu Leu Gln
                725             730             735
Pro Gly Gly Met Val Trp Phe Thr Thr Met Leu Gly Glu Gln Val Leu
            740             745             750
Glu Leu Leu His Glu Asn Arg Ile Glu Leu Asn Glu Val Trp Glu Ala
            755             760             765
Arg Glu Asn Glu Val Val Lys Phe Ala Ile Lys Arg Leu Phe Lys Glu
            770             775             780
Asp Ile Leu Gln Glu Thr Gly Gln Glu Ile Gly Val Leu Leu Pro Phe
785             790             795             800
Ser Asn Gly Asp Phe Tyr Asn Glu Tyr Leu Val Asn Thr Ala Phe Leu
                805             810             815
Ile Lys Ile Phe Lys His His Gly Phe Ser Leu Val Gln Lys Gln Ser
            820             825             830
Phe Lys Asp Trp Ile Pro Glu Phe Gln Asn Phe Ser Lys Ser Leu Tyr
            835             840             845
```

```
Lys Ile Leu Thr Glu Ala Asp Lys Thr Trp Thr Ser Leu Phe Gly Phe
    850                 855                 860

Ile Cys Leu Arg Lys Asn Gly Pro Gly Gly Gly Ser Gly Gly Gly
865                 870                 875                 880

Gly Ser Gly Gly Gly Ser Gly Gly Gly Ser Leu Glu Asn Thr
                885                 890                 895

Ile Asn Ile Ala Lys Asn Asp Phe Ser Asp Ile Glu Leu Ala Ala Ile
            900                 905                 910

Pro Phe Asn Thr Leu Ala Asp His Tyr Gly Glu Arg Leu Ala Arg Glu
                915                 920                 925

Gln Leu Ala Leu Glu His Glu Ser Tyr Glu Met Gly Glu Ala Arg Phe
    930                 935                 940

Arg Lys Met Phe Glu Arg Gln Leu Lys Ala Gly Glu Val Ala Asp Asn
945                 950                 955                 960

Ala Ala Ala Lys Pro Leu Ile Thr Thr Leu Leu Pro Lys Met Ile Ala
                965                 970                 975

Arg Ile Asn Asp Trp Phe Glu Glu Val Lys Ala Lys Arg Gly Lys Arg
                980                 985                 990

Pro Thr Ala Phe Gln Phe Leu Gln Glu Ile Lys Pro Glu Ala Val Ala
            995                 1000                1005

Tyr Ile Thr Ile Lys Thr Thr Leu Ala Cys Leu Thr Ser Ala Asp
    1010                1015                1020

Asn Thr Thr Val Gln Ala Val Ala Ser Ala Ile Gly Arg Ala Ile
    1025                1030                1035

Glu Asp Glu Ala Arg Phe Gly Arg Ile Arg Asp Leu Glu Ala Lys
    1040                1045                1050

His Phe Lys Lys Asn Val Glu Gln Leu Asn Lys Arg Val Gly
    1055                1060                1065

His Val Tyr Lys Lys Ala Phe Met Gln Val Val Glu Ala Asp Met
    1070                1075                1080

Leu Ser Lys Gly Leu Leu Gly Gly Glu Ala Trp Ser Ser Trp His
    1085                1090                1095

Lys Glu Asp Ser Ile His Val Gly Val Arg Cys Ile Glu Met Leu
    1100                1105                1110

Ile Glu Ser Thr Gly Met Val Ser Leu His Arg Gln Asn Ala Gly
    1115                1120                1125

Val Val Gly Gln Asp Ser Glu Thr Ile Glu Leu Ala Pro Glu Tyr
    1130                1135                1140

Ala Glu Ala Ile Ala Thr Arg Ala Gly Ala Leu Ala Gly Ile Ser
    1145                1150                1155

Pro Met Phe Gln Pro Cys Val Val Pro Pro Lys Pro Trp Thr Gly
    1160                1165                1170

Ile Thr Gly Gly Gly Tyr Trp Ala Asn Gly Arg Arg Pro Leu Ala
    1175                1180                1185

Leu Val Arg Thr His Ser Lys Lys Ala Leu Met Arg Tyr Glu Asp
    1190                1195                1200

Val Tyr Met Pro Glu Val Tyr Lys Ala Ile Asn Ile Ala Gln Asn
    1205                1210                1215

Thr Ala Trp Lys Ile Asn Lys Lys Val Leu Ala Val Ala Asn Val
    1220                1225                1230

Ile Thr Lys Trp Lys His Cys Pro Val Glu Asp Ile Pro Ala Ile
    1235                1240                1245
```

-continued

| | | | | | | | | | |
|---|---|---|---|---|---|---|---|---|---|
| Glu Arg 1250 | Glu | Glu | Leu | Pro Met 1255 | Lys | Pro | Glu | Asp Ile 1260 | Asp Met Asn |

Pro Glu Ala Leu Thr Ala Trp Lys Arg Ala Ala Ala Val Tyr
1265            1270            1275

Arg Lys Asp Lys Ala Arg Lys Ser Arg Arg Ile Ser Leu Glu Phe
1280            1285            1290

Met Leu Glu Gln Ala Asn Lys Phe Ala Asn His Lys Ala Ile Trp
1295            1300            1305

Phe Pro Tyr Asn Met Asp Trp Arg Gly Arg Val Tyr Ala Val Ser
1310            1315            1320

Met Phe Asn Pro Gln Gly Asn Asp Met Thr Lys Gly Leu Leu Thr
1325            1330            1335

Leu Ala Lys Gly Lys Pro Ile Gly Lys Glu Gly Tyr Tyr Trp Leu
1340            1345            1350

Lys Ile His Gly Ala Asn Cys Ala Gly Val Asp Lys Val Pro Phe
1355            1360            1365

Pro Glu Arg Ile Lys Phe Ile Glu Glu Asn His Glu Asn Ile Met
1370            1375            1380

Ala Cys Ala Lys Ser Pro Leu Glu Asn Thr Trp Trp Ala Glu Gln
1385            1390            1395

Asp Ser Pro Phe Cys Phe Leu Ala Phe Cys Phe Glu Tyr Ala Gly
1400            1405            1410

Val Gln His His Gly Leu Ser Tyr Asn Cys Ser Leu Pro Leu Ala
1415            1420            1425

Phe Asp Gly Ser Cys Ser Gly Ile Gln His Phe Ser Ala Met Leu
1430            1435            1440

Arg Asp Glu Val Gly Gly Arg Ala Val Asn Leu Leu Pro Ser Glu
1445            1450            1455

Thr Val Gln Asp Ile Tyr Gly Ile Val Ala Lys Lys Val Asn Glu
1460            1465            1470

Ile Leu Gln Ala Asp Ala Ile Asn Gly Thr Asp Asn Glu Val Val
1475            1480            1485

Thr Val Thr Asp Glu Asn Thr Gly Glu Ile Ser Glu Lys Val Lys
1490            1495            1500

Leu Gly Thr Lys Ala Leu Ala Gly Gln Trp Leu Ala Tyr Gly Val
1505            1510            1515

Thr Arg Ser Val Thr Lys Arg Ser Val Met Thr Leu Ala Tyr Gly
1520            1525            1530

Ser Lys Glu Phe Gly Phe Arg Gln Gln Val Leu Glu Asp Thr Ile
1535            1540            1545

Gln Pro Ala Ile Asp Ser Gly Lys Gly Leu Met Phe Thr Gln Pro
1550            1555            1560

Asn Gln Ala Ala Gly Tyr Met Ala Lys Leu Ile Trp Glu Ser Val
1565            1570            1575

Ser Val Thr Val Val Ala Ala Val Glu Ala Met Asn Trp Leu Lys
1580            1585            1590

Ser Ala Ala Lys Leu Leu Ala Ala Glu Val Lys Asp Lys Lys Thr
1595            1600            1605

Gly Glu Ile Leu Arg Lys Arg Cys Ala Val His Trp Val Thr Pro
1610            1615            1620

Asp Gly Phe Pro Val Trp Gln Glu Tyr Lys Lys Pro Ile Gln Thr
1625            1630            1635

Arg Leu Asn Leu Met Phe Leu Gly Gln Phe Arg Leu Gln Pro Thr

```
                      1640            1645             1650
Ile  Asn  Thr  Asn  Lys  Asp  Ser  Glu  Ile  Asp  Ala  His  Lys  Gln  Glu
         1655                 1660                1665

Ser  Gly  Ile  Ala  Pro  Asn  Phe  Val  His  Ser  Gln  Asp  Gly  Ser  His
         1670                 1675                1680

Leu  Arg  Lys  Thr  Val  Val  Trp  Ala  His  Glu  Lys  Tyr  Gly  Ile  Glu
         1685                 1690                1695

Ser  Phe  Ala  Leu  Ile  His  Asp  Ser  Phe  Gly  Thr  Ile  Pro  Ala  Asp
         1700                 1705                1710

Ala  Ala  Asn  Leu  Phe  Lys  Ala  Val  Arg  Glu  Thr  Met  Val  Asp  Thr
         1715                 1720                1725

Tyr  Glu  Ser  Cys  Asp  Val  Leu  Ala  Asp  Phe  Tyr  Asp  Gln  Phe  Ala
         1730                 1735                1740

Asp  Gln  Leu  His  Glu  Ser  Gln  Leu  Asp  Lys  Met  Pro  Ala  Leu  Pro
         1745                 1750                1755

Ala  Lys  Gly  Asn  Leu  Asn  Leu  Arg  Asp  Ile  Leu  Glu  Ser  Asp  Phe
         1760                 1765                1770

Ala  Phe  Ala
         1775

<210> SEQ ID NO 21
<211> LENGTH: 5331
<212> TYPE: DNA
<213> ORGANISM: artificial sequence
<220> FEATURE:
<223> OTHER INFORMATION: ORF of the NP868R-T7RNAP

<400> SEQUENCE: 21
atggaattcg ccagcctgga caacctggtg gccagatacc agcggtgctt caacgaccag      60
agcctgaaga acagcaccat cgagctggaa atccggttcc agcagatcaa cttcctgctg     120
ttcaagaccg tgtacgaggc cctggtcgcc caggaaatcc ccagcaccat cagccacagc     180
atccggtgca tcaagaaggt gcaccacgag aaccactgcc gggagaagat cctgcccagc     240
gagaacctgt acttcaagaa acagcccctg atgttcttca gttcagcga gccgccagc      300 ctgggctgta aagtgtccct ggccatcgag cagcccatcc ggaagttcat cctggacagc     360
agcgtgctgg tccggctgaa gaaccggacc accttccggg tgtccgagct gtggaagatc     420
gagctgacca tcgtgaagca gctgatgggc agcgaggtgt cagccaagct ggccgccttc     480
aagaccctgc tgttcgacac ccccgagcag cagaccacca gaacatgat gaccctgatc      540 aaccccgacg acgagtacct gtacgagatc gagatcgagt acaccggcaa gcctgagagc     600
ctgacagccg ccgacgtgat caagatcaag aacaccgtgc tgacactgat cagccccaac     660
cacctgatgc tgaccgccta ccaccaggcc atcgagttta cgccagcca atcctgagc      720 agcgagatcc tgctggcccg gatcaagagc ggcaagtggg gcctgaagag actgctgccc     780
caggtcaagt ccatgaccaa ggccgactac atgaagttct accccccgt gggctactac     840 gtgaccgaca aggccgacgg catccggggc attgccgtga tccaggacac ccagatctac     900
gtggtggccg accagctgta cagcctgggc accaccggca tcgagcccct gaagcccacc     960
atcctggacg cgagttcat gcccgagaag aaagagttct acggctttga cgtgatcatg    1020
tacgagggca acctgctgac ccagcagggc ttcgagacac ggatcgagag cctgagcaag    1080
ggcatcaagg tgctgcaggc cttcaacatc aaggccgaga tgaagccctt catcagcctg    1140
acctccgccg accccaacgt gctgctgaag aatttcgaga gcatcttcaa gaagaaaacc    1200
```

-continued

| | |
|---|---|
| cggccctaca gcatcgacgg catcatcctg gtggagcccg gcaacagcta cctgaacacc | 1260 |
| aacaccttca gtggaagcc cacctgggac aacaccctgg actttctggt ccggaagtgc | 1320 |
| cccgagtccc tgaacgtgcc cgagtacgcc cccaagaagg gcttcagcct gcatctgctg | 1380 |
| ttcgtgggca tcagcggcga gctgtttaag aagctggccc tgaactggtg ccccggctac | 1440 |
| accaagctgt tccccgtgac ccagcggaac cagaactact tccccgtgca gttccagccc | 1500 |
| agcgacttcc ccctggcctt cctgtactac caccccgaca ccagcagctt cagcaacatc | 1560 |
| gatggcaagg tgctggaaat gcggtgcctg aagcgggaga tcaactacgt gcgctgggag | 1620 |
| atcgtgaaga tccgggagga ccggcagcag gatctgaaaa ccggcggcta cttcggcaac | 1680 |
| gacttcaaga ccgccgagct gacctggctg aactacatgg accccttcag cttcgaggaa | 1740 |
| ctggccaagg gacccagcgg catgtacttc gctggcgcca agaccggcat ctacagagcc | 1800 |
| cagaccgccc tgatcagctt catcaagcag gaaatcatcc agaagatcag ccaccagagc | 1860 |
| tgggtgatcg acctgggcat cggcaagggc caggacctgg gcagataccc tggacgccggc | 1920 |
| gtgagacacc tggtcggcat cgataaggac cagacagccc tggccgagct ggtgtaccgg | 1980 |
| aagttctccc acgccaccac cagacagcac aagcacgcca ccaacatcta cgtgctgcac | 2040 |
| caggatctgg ccgagcctgc caaagaaatc agcgagaaag tgcaccagat ctatggcttc | 2100 |
| cccaaagagg gcgccagcag catcgtgtcc aacctgttca tccactacct gatgaagaac | 2160 |
| acccagcagg tcgagaacct ggctgtgctg tgccacaagc tgctgcagcc tggcggcatg | 2220 |
| gtctggttca ccaccatgct gggcgaacag gtgctggaac tgctgcacga gaaccggatc | 2280 |
| gaactgaacg aagtgtggga ggcccgggag aacgaggtgg tcaagttcgc catcaagcgg | 2340 |
| ctgttcaaag aggacatcct gcaggaaacc ggccaggaaa tcggcgtcct gctgcccttc | 2400 |
| agcaacggcg acttctacaa tgagtacctg gtcaacaccg cctttctgat caagattttc | 2460 |
| aagcaccatg gctttagcct cgtgcagaag cagagcttca aggactggat ccccgagttc | 2520 |
| cagaacttca gcaagagcct gtacaagatc ctgaccgagg ccgacaagac ctggaccagc | 2580 |
| ctgttcggct tcatctgcct gcggaagaac gggcccggcg aggcggaag tggaggcgga | 2640 |
| ggaagcggag ggggaggatc tggcggcgga ggcagcctcg agaacaccat caatatcgcc | 2700 |
| aagaacgact tcagcgacat cgagctggcc gccatcccct tcaacaccct ggccgaccac | 2760 |
| tatggcgagc ggctggccag agaacagctg gccctggaac acgagagcta cgaaatgggc | 2820 |
| gaggcccggt tccggaagat gttcgagaga cagctgaagg ccggcgaggt ggccgataat | 2880 |
| gccgccgcta agcccctgat caccaccctg ctgcccaaga tgatcgcccg gatcaacgat | 2940 |
| tggttcgagg aagtgaaggc caagcgggc aagaggccca ccgccttcca gtttctgcag | 3000 |
| gaaatcaagc ccgaggccgt ggcctacatc accatcaaga ccaccctggc ctgcctgacc | 3060 |
| agcgccgaca ataccaccgt gcaggctgtc gcttctgcca tcggcagagc catcgaggac | 3120 |
| gaggccagat cggcagaat ccgggacctg gaagccaagc acttcaagaa aaacgtggag | 3180 |
| gaacagctga acaagcgcgt gggccacgtg tacaagaaag ccttcatgca ggtggtggag | 3240 |
| gccgacatgc tgagcaaggg cctgctgggc ggagaagcct ggtccagctg gcacaaagag | 3300 |
| gacagcatcc acgtcggcgt gcggtgcatc gagatgctga tcgagtcgac cggcatggtg | 3360 |
| tccctgcaca ggcagaatgc cggcgtggtg gccaggaca gcgagacaat cgaactggcc | 3420 |
| cccgagtatg ccgaggccat tgccacaaga gccggcgctc tggccggcat cagccccatg | 3480 |
| ttccagcccct gcgtggtgcc tcctaagccc tggacaggca tcacaggcgg cggatactgg | 3540 |
| gccaacggca gacgccctct ggctctggtg cggacccaca gcaagaaagc cctgatgcgc | 3600 |

-continued

```
tacgaggacg tgtacatgcc cgaggtgtac aaggccatca acattgccca gaacaccgcc    3660
tggaagatca acaagaaagt gctggccgtg gccaatgtga tcaccaagtg gaagcactgc    3720
cccgtggagg catccccgc catcgagcgg gaggaactgc ccatgaagcc cgaggacatc    3780
gacatgaacc ccgaggccct gacagcctgg aaaagggccg ctgccgccgt gtaccggaag    3840
gacaaggccc ggaagtcccg gcggatcagc ctggagttca tgctggaaca ggccaacaag    3900
ttcgccaacc acaaggccat ttggttccct tacaacatgg actggcgggg cagagtgtac    3960
gccgtgagca tgttcaatcc acaaggcaac gacatgacca aggggctgct gaccctggcc    4020
aagggcaagc ccatcggcaa agagggctac tactggctga agatccacgg cgccaactgc    4080
gctggcgtgg acaaggtgcc cttcccagag cggatcaagt tcatcgagga aaaccacgag    4140
aacatcatgg cctgcgccaa gagccctcta gaaaacactt ggtgggccga gcaggacagc    4200
cccttctgct tcctggcctt ctgctttgag tacgccggag tgcagcacca cggcctgagc    4260
tacaactgca gcctgccct ggccttcgat ggcagctgca gcggcatcca gcacttcagc    4320
gccatgctga gggacgaagt gggcggcaga gccgtgaatc tgctgccaag cgagacagtg    4380
caggacatct acgggatcgt ggccaagaaa gtgaacgaga tcctgcaggc cgacgccatc    4440
aacggcaccg acaacgaggt ggtgaccgtg accgatgaga caccggcga gatcagcgag    4500 aaagtgaagc tcggcaccaa ggccctggct ggccagtggc tggcctacgg cgtgaccaga    4560
tccgtgacca gcggagcgt gatgacactg gcctatggca gcaaagagtt cggcttccgg    4620
cagcaggtgc tggaagatac catccagcct gccatcgaca gcggcaaggg gctgatgttc    4680
acccagccca ccaggccgc tggctacatg gccaagctca tatgggagag cgtgtccgtg    4740
acagtggtgg ccgccgtgga ggccatgaat tggctgaagt ccgccgccaa actgctggcc    4800
gctgaagtga aggacaaaaa gaccggcgaa atcctgcgga gagatgcgc cgtgcactgg    4860 gtgaccccg atggcttccc cgtgtggcag gagtacaaga agcccatcca gacccggctg    4920
aacctgatgt tcctgggcca gttcagactg cagcccacca tcaacaccaa caaggactcc    4980
gagatcgacg cccacaagca ggaaagcggc attgccccca acttcgtgca cagccaggac    5040
ggcagccacc tgagaaagac cgtggtgtgg gctcacgaga agtacggcat cgagagcttc    5100
gccctgatcc acgacagctt cggcaccatt cccgccgacg ccgccaacct gttcaaggcc    5160
gtgcgggaga caatggtgga cacctacgag agctgcgacg tgctggccga cttctacgac    5220
cagttcgccg accagctgca cgagagccag ctggacaaga tgcccgccct gcccgccaag    5280
gggaacctga acctgcggga catcctggaa agcgacttcg ccttcgcctg a    5331
```

<210> SEQ ID NO 22
<211> LENGTH: 2658
<212> TYPE: DNA
<213> ORGANISM: artificial sequence
<220> FEATURE:
<223> OTHER INFORMATION: ORF of the T7RNAP

<400> SEQUENCE: 22

```
atgctcgaga caccatcaa tatcgccaag aacgacttca gcgacatcga gctggccgcc      60 atcccttca acaccctggc cgaccactat ggcgagcggc tggccagaga acagctggcc     120
ctggaacacg agagctacga aatgggcgag gcccggttcc ggaagatgtt cgagagacag     180
ctgaaggccg cgaggtggc cgataatgcc gccgctaagc ccctgatcac caccctgctg     240
cccaagatga tcgcccggat caacgattgg ttcgaggaag tgaaggccaa gcggggcaag     300
```

```
aggcccaccg ccttccagtt tctgcaggaa atcaagcccg aggccgtggc ctacatcacc    360
atcaagacca ccctggcctg cctgaccagc gccgacaata ccaccgtgca ggctgtcgct    420
tctgccatcg gcagagccat cgaggacgag gccagattcg gcagaatccg ggacctggaa    480
gccaagcact tcaagaaaaa cgtggaggaa cagctgaaca agcgcgtggg ccacgtgtac    540
aagaaagcct tcatgcaggt ggtggaggcc gacatgctga gcaagggcct gctgggcgga    600
gaagcctggt ccagctggca caaagaggac agcatccacg tcggcgtgcg gtgcatcgag    660
atgctgatcg agtcgaccgg catggtgtcc ctgcacaggc agaatgccgg cgtggtgggc    720
caggacagcg agacaatcga actggccccc gagtatgccg aggccattgc cacaagagcc    780
ggcgctctgg ccggcatcag ccccatgttc cagccctgcg tggtgcctcc taagccctgg    840
acaggcatca caggcggcgg atactgggcc aacggcagac gccctctggc tctggtgcgg    900
acccacagca agaaagccct gatgcgctac gaggacgtgt acatgcccga ggtgtacaag    960
gccatcaaca ttgcccagaa caccgcctgg aagatcaaca agaaagtgct ggccgtggcc   1020
aatgtgatca ccaagtggaa gcactgcccc gtggaggaca tccccgccat cgagcgggag   1080
gaactgccca tgaagcccga ggacatcgac atgaaccccg aggccctgac agcctggaaa   1140
agggccgctg ccgccgtgta ccggaaggac aaggcccgga gtcccggcg atcagcctg   1200
gagttcatgc tggaacaggc caacaagttc gccaaccaca aggccatttg gttcccttac   1260
aacatggact ggcggggcag agtgtacgcc gtgagcatgt tcaatccaca aggcaacgac   1320
atgaccaagg ggctgctgac cctggccaag ggcaagccca tcggcaaaga gggctactac   1380
tggctgaaga tccacggcgc caactgcgct ggcgtggaca aggtgccctt cccagagcgg   1440
atcaagttca tcgaggaaaa ccacgagaac atcatggcct gcgccaagag ccctctagaa   1500
aacacttggt gggccgagca ggacagcccc ttctgcttcc tggccttctg ctttgagtac   1560
gccggagtgc agcaccacgg cctgagctac aactgcagcc tgcccctggc cttcgatggc   1620
agctgcagcg catccagca cttcagcgcc atgctgaggg acgaagtggg cggcagagcc   1680
gtgaatctgc tgccaagcga cagtgcag gacatctacg ggatcgtggc caagaaagtg   1740
aacgagatcc tgcaggccga cgccatcaac ggcaccgaca acgaggtggt gaccgtgacc   1800
gatgagaaca ccggcgagat cagcgagaaa gtgaagctcg gcaccaaggc cctggctggc   1860
cagtggctgg cctacggcgt gaccagatcc gtgaccaagc ggagcgtgat gacactggcc   1920
tatggcagca agagttcgg cttccggcag caggtgctgg aagataccat ccagcctgcc   1980
atcgacagcg gcaaggggct gatgttcacc cagcccaacc aggccgctgg ctacatggcc   2040
aagctcatat gggagagcgt gtccgtgaca gtggtggccg ccgtggaggc catgaattgg   2100
ctgaagtccg ccgccaaact gctggccgct gaagtgaagg acaaaaagac cggcgaaatc   2160
ctgcggaaga gatgcgccgt gcactgggtg acccccgatg cttcccgt gtggcaggag   2220
tacaagaagc ccatccagac ccggctgaac ctgatgttcc tgggccagtt cagactgcag   2280
cccaccatca acaccaacaa ggactccgag atcgacgccc acaagcagga aagcggcatt   2340
gcccccaact tcgtgcacag ccaggacggc agccacctga aaagaccgt ggtgtgggct   2400
cacgagaagt acggcatcga gagcttcgcc ctgatccacg acagcttcgg caccattccc   2460
gccgacgccg ccaacctgtt caaggccgtg cgggagacaa tggtggacac ctacgagagc   2520
tgcgacgtgc tggccgactt ctacgaccag ttcgccgacc agctgcacga gagccagctg   2580
gacaagatgc ccgccctgcc cgccaagggg aacctgaacc tgcgggacat cctggaaagc   2640
gacttcgcct tcgcctga                                                 2658
```

<210> SEQ ID NO 23
<211> LENGTH: 2667
<212> TYPE: DNA
<213> ORGANISM: Artificial
<220> FEATURE:
<223> OTHER INFORMATION: Open-reading frame of the pT3RNAP plasmid

<400> SEQUENCE: 23

| | | | | | |
|---|---|---|---|---|---|
| atggaattcc | tcgagaacat | catcgagaat | atcgagaaga | acgacttctc | cgagatcgag | 60 |
| ctggccgcca | tccccttcaa | caccctggcc | gaccactacg | gctccgccct | ggccaaagag | 120 |
| cagctggccc | tggaacatga | gtcctacgag | ctgggcgagc | ggcggttcct | gaagatgctg | 180 |
| gaacggcagg | ccaaggccgg | cgagatcgcc | gataacgccg | ctgccaagcc | cctgctggcc | 240 |
| accctgctgc | ctaagctgac | cacccggatc | gtggaatggc | tggaagagta | cgcctccaag | 300 |
| aagggccgga | agccctccgc | ctacgcccct | ctgcagctgc | tgaagcctga | agcctccgcc | 360 |
| ttcattaccc | tgaaagtgat | cctggcctcc | ctgacctcca | ccaacatgac | caccatccag | 420 |
| gccgctgccg | gcatgctggg | caaggccatc | gaggacgagg | ccagattcgg | ccggattcgg | 480 |
| gacctggaag | ccaagcactt | caagaagcac | gtcgaggaac | agctgaacaa | gcggcacggc | 540 |
| caggtgtaca | agaaagcctt | catgcaggtc | gtggaagccg | acatgatcgg | cagaggactg | 600 |
| ctggaggag | aggcttggtc | ctcctgggac | aaagaaacca | ccatgcacgt | gggcatccgg | 660 |
| ctgatcgaga | tgctgatcga | gtcaaccggg | ctggtggaac | tgcagcggca | caacgcaggc | 720 |
| aatgctggct | ctgatcacga | ggccctgcag | ctggctcagg | aatacgtgga | cgtgctggcc | 780 |
| aagcgggctg | gcgctctggc | tggcatctcc | cccatgttcc | agccctgcgt | ggtgccccca | 840 |
| aagccatggg | tggccatcac | cggcggaggc | tactgggcca | acggcagacg | acctctggcc | 900 |
| ctggtccgaa | cccactccaa | gaaaggcctg | atgagatacg | aggacgtgta | catgcccgaa | 960 |
| gtgtacaagg | ccgtgaacct | ggcccagaat | accgcctgga | agatcaacaa | gaaagtgctg | 1020 |
| gccgtggtca | cgagatcgt | gaactggaag | aactgccccg | tggccgacat | ccccagcctg | 1080 |
| gaaagacagg | aactgccccc | taagcccgac | gacatcgaca | ccaacgaggc | cgccctgaaa | 1140 |
| gagtggaaga | aggctgccgc | tggcatctac | cggctggaca | aggcccgggt | gtcacggcgg | 1200 |
| atctccctgg | agttcatgct | ggaacaggcc | aacaagttcg | ccagcaagaa | ggccatctgg | 1260 |
| ttcccttaca | acatggactg | gcggggcaga | gtgtacgccg | tgcccatgtt | caatccacag | 1320 |
| ggcaacgaca | tgaccaaggg | cctgctgacc | ctggccaagg | gcaagcccat | cggcgaggaa | 1380 |
| ggcttctact | ggctgaagat | ccacggcgcc | aactgtgccg | gggtggacaa | ggtgcccttc | 1440 |
| ccagagcgga | tcgccttcat | cgagaagcac | gtggacgaca | tcctggcctg | cgccaaggac | 1500 |
| cccatcaaca | cacttggtg | ggccgagcag | gactcccct | tctgcttcct | ggccttctgt | 1560 |
| ttcgagtacg | caggcgtgac | ccaccacggc | ctgtcctaca | actgctccct | gccctggc | 1620 |
| ttcgacggct | cctgctctgg | catccagcac | ttctccgcca | tgctgcggga | cgaagtgggc | 1680 |
| ggcagagccg | tgaatctgct | gccctccgag | acagtgcagg | acatctacgg | catcgtggcc | 1740 |
| cagaaagtga | acgagatcct | gaagcaggac | gccatcaacg | gcaccccaa | cgagatgatc | 1800 |
| accgtgaccg | acaaggacac | aggcgagatc | tccgagaagc | tgaagctggg | cacctccacc | 1860 |
| ctggctcagc | agtggctggc | ctacggcgtg | accagatccg | tgaccaagcg | gagcgtgatg | 1920 |
| accctggctt | acggctccaa | agagttcggc | ttccggcagc | aggtcctgga | cgacaccatc | 1980 |
| cagcctgcca | tcgactccgg | caagggcctg | atgttcaccc | agcccaacca | ggctgccggc | 2040 |

-continued

```
tacatggcca agctgatctg ggacgccgtg tccgtgactg tggtggccgc cgtggaagcc    2100
atgaattggc tgaagtccgc cgcaaagctg ctggccgccg aagtgaagga caaaaagacc    2160
aaagagatcc tgcggcacag atgcgccgtg cactggacca cccccgacgg ctttcccgtg    2220
tggcaggaat accggaagcc cctgcagaaa cggctggata tgatcttcct gggccagttc    2280
cgactgcagc ccaccatcaa taccctgaag gactccggca tcgacgccca caagcaggaa    2340
agcggaatcg cccccaactt cgtgcacagc caggacggct cccacctgag aatgacagtg    2400
gtgtacgccc acgagaagta cggcatcgag tccttcgccc tgatccacga ctccttcggc    2460
accatccctg ccgacgccgg aaagctgttc aaggccgtgc gggaaaccat ggtcatcacc    2520
tacgagaaca cgatgtgct ggccgacttc tacagccagt cgccgacca gctgcacgag    2580 acacagctgg acaagatgcc cccctgcct aagaagggca acctgaacct gcaggatatt    2640
ctgaagtccg acttcgcctt cgcttga                                        2667
```

<210> SEQ ID NO 24
<211> LENGTH: 888
<212> TYPE: PRT
<213> ORGANISM: Artificial
<220> FEATURE:
<223> OTHER INFORMATION: Protein sequence encoded by pT3RNAP plasmid

<400> SEQUENCE: 24

```
Met Glu Phe Leu Glu Asn Ile Ile Glu Asn Ile Glu Lys Asn Asp Phe
1               5                  10                  15

Ser Glu Ile Glu Leu Ala Ala Ile Pro Phe Asn Thr Leu Ala Asp His
            20                  25                  30

Tyr Gly Ser Ala Leu Ala Lys Glu Gln Leu Ala Leu Glu His Glu Ser
        35                  40                  45

Tyr Glu Leu Gly Glu Arg Arg Phe Leu Lys Met Leu Glu Arg Gln Ala
    50                  55                  60

Lys Ala Gly Glu Ile Ala Asp Asn Ala Ala Lys Pro Leu Leu Ala
65                  70                  75                  80

Thr Leu Leu Pro Lys Leu Thr Thr Arg Ile Val Glu Trp Leu Glu Glu
                85                  90                  95

Tyr Ala Ser Lys Lys Gly Arg Lys Pro Ser Ala Tyr Ala Pro Leu Gln
            100                 105                 110

Leu Leu Lys Pro Glu Ala Ser Ala Phe Ile Thr Leu Lys Val Ile Leu
        115                 120                 125

Ala Ser Leu Thr Ser Thr Asn Met Thr Thr Ile Gln Ala Ala Ala Gly
    130                 135                 140

Met Leu Gly Lys Ala Ile Glu Asp Glu Ala Arg Phe Gly Arg Ile Arg
145                 150                 155                 160

Asp Leu Glu Ala Lys His Phe Lys Lys His Val Glu Glu Gln Leu Asn
                165                 170                 175

Lys Arg His Gly Gln Val Tyr Lys Lys Ala Phe Met Gln Val Val Glu
            180                 185                 190

Ala Asp Met Ile Gly Arg Gly Leu Leu Gly Gly Glu Ala Trp Ser Ser
        195                 200                 205

Trp Asp Lys Glu Thr Thr Met His Val Gly Ile Arg Leu Ile Glu Met
    210                 215                 220

Leu Ile Glu Ser Thr Gly Leu Val Glu Leu Gln Arg His Asn Ala Gly
225                 230                 235                 240

Asn Ala Gly Ser Asp His Glu Ala Leu Gln Leu Ala Gln Glu Tyr Val
                245                 250                 255
```

```
Asp Val Leu Ala Lys Arg Ala Gly Ala Leu Ala Gly Ile Ser Pro Met
        260                 265                 270

Phe Gln Pro Cys Val Val Pro Lys Pro Trp Val Ala Ile Thr Gly
        275                 280                 285

Gly Gly Tyr Trp Ala Asn Gly Arg Arg Pro Leu Ala Leu Val Arg Thr
        290                 295                 300

His Ser Lys Lys Gly Leu Met Arg Tyr Glu Asp Val Tyr Met Pro Glu
305                 310                 315                 320

Val Tyr Lys Ala Val Asn Leu Ala Gln Asn Thr Ala Trp Lys Ile Asn
                325                 330                 335

Lys Lys Val Leu Ala Val Asn Glu Ile Val Asn Trp Lys Asn Cys
        340                 345                 350

Pro Val Ala Asp Ile Pro Ser Leu Glu Arg Gln Glu Leu Pro Pro Lys
        355                 360                 365

Pro Asp Asp Ile Asp Thr Asn Glu Ala Ala Leu Lys Glu Trp Lys Lys
    370                 375                 380

Ala Ala Ala Gly Ile Tyr Arg Leu Asp Lys Ala Arg Val Ser Arg Arg
385                 390                 395                 400

Ile Ser Leu Glu Phe Met Leu Glu Gln Ala Asn Lys Phe Ala Ser Lys
                405                 410                 415

Lys Ala Ile Trp Phe Pro Tyr Asn Met Asp Trp Arg Gly Arg Val Tyr
        420                 425                 430

Ala Val Pro Met Phe Asn Pro Gln Gly Asn Asp Met Thr Lys Gly Leu
        435                 440                 445

Leu Thr Leu Ala Lys Gly Lys Pro Ile Gly Glu Glu Gly Phe Tyr Trp
    450                 455                 460

Leu Lys Ile His Gly Ala Asn Cys Ala Gly Val Asp Lys Val Pro Phe
465                 470                 475                 480

Pro Glu Arg Ile Ala Phe Ile Glu Lys His Val Asp Ile Leu Ala
                485                 490                 495

Cys Ala Lys Asp Pro Ile Asn Asn Thr Trp Trp Ala Glu Gln Asp Ser
        500                 505                 510

Pro Phe Cys Phe Leu Ala Phe Cys Phe Glu Tyr Ala Gly Val Thr His
        515                 520                 525

His Gly Leu Ser Tyr Asn Cys Ser Leu Pro Leu Ala Phe Asp Gly Ser
    530                 535                 540

Cys Ser Gly Ile Gln His Phe Ser Ala Met Leu Arg Asp Glu Val Gly
545                 550                 555                 560

Gly Arg Ala Val Asn Leu Leu Pro Ser Glu Thr Val Gln Asp Ile Tyr
                565                 570                 575

Gly Ile Val Ala Gln Lys Val Asn Glu Ile Leu Lys Gln Asp Ala Ile
        580                 585                 590

Asn Gly Thr Pro Asn Glu Met Ile Thr Val Thr Asp Lys Asp Thr Gly
        595                 600                 605

Glu Ile Ser Glu Lys Leu Lys Leu Gly Thr Ser Thr Leu Ala Gln Gln
    610                 615                 620

Trp Leu Ala Tyr Gly Val Thr Arg Ser Val Thr Lys Arg Ser Val Met
625                 630                 635                 640

Thr Leu Ala Tyr Gly Ser Lys Glu Phe Gly Phe Arg Gln Gln Val Leu
                645                 650                 655

Asp Asp Thr Ile Gln Pro Ala Ile Asp Ser Gly Lys Gly Leu Met Phe
        660                 665                 670
```

```
Thr Gln Pro Asn Gln Ala Ala Gly Tyr Met Ala Lys Leu Ile Trp Asp
            675                 680                 685
Ala Val Ser Val Thr Val Val Ala Ala Val Glu Ala Met Asn Trp Leu
        690                 695                 700
Lys Ser Ala Ala Lys Leu Leu Ala Ala Glu Val Lys Asp Lys Lys Thr
705                 710                 715                 720
Lys Glu Ile Leu Arg His Arg Cys Ala Val His Trp Thr Thr Pro Asp
                725                 730                 735
Gly Phe Pro Val Trp Gln Glu Tyr Arg Lys Pro Leu Gln Lys Arg Leu
            740                 745                 750
Asp Met Ile Phe Leu Gly Gln Phe Arg Leu Gln Pro Thr Ile Asn Thr
        755                 760                 765
Leu Lys Asp Ser Gly Ile Asp Ala His Lys Gln Glu Ser Gly Ile Ala
770                 775                 780
Pro Asn Phe Val His Ser Gln Asp Gly Ser His Leu Arg Met Thr Val
785                 790                 795                 800
Val Tyr Ala His Glu Lys Tyr Gly Ile Glu Ser Phe Ala Leu Ile His
                805                 810                 815
Asp Ser Phe Gly Thr Ile Pro Ala Asp Ala Gly Lys Leu Phe Lys Ala
            820                 825                 830
Val Arg Glu Thr Met Val Ile Thr Tyr Glu Asn Asn Asp Val Leu Ala
        835                 840                 845
Asp Phe Tyr Ser Gln Phe Ala Asp Gln Leu His Glu Thr Gln Leu Asp
    850                 855                 860
Lys Met Pro Pro Leu Pro Lys Lys Gly Asn Leu Asn Leu Gln Asp Ile
865                 870                 875                 880
Leu Lys Ser Asp Phe Ala Phe Ala
                885
```

<210> SEQ ID NO 25
<211> LENGTH: 2637
<212> TYPE: DNA
<213> ORGANISM: Artificial
<220> FEATURE:
<223> OTHER INFORMATION: Open-reading frame of the pSP6RNAP plasmid

<400> SEQUENCE: 25

```
atggaattcc tcgagcagga cctgcacgcc attcagctgc agctggaaga ggaaatgttc    60
aacggcggca tcagaagatt cgaggccgac cagcagcgac agattgccgc tggctccgag   120
tctgacacag cctggaaccg gcggctgctg tctgagctga tcgcccctat ggccgagggc   180
atccaggcct acaaagagga atacgagggc aagaagggca gagcccccag agccctggcc   240
ttcctgcagt gcgtggaaaa tgaggtcgcc gcctacatca ccatgaaggt ggtcatggac   300
atgctgaaca ccgacgccac cctgcaggct atcgccatgt ctgtggccga gcggatcgag   360
gaccaggtcc gattctccaa gctggaaggc cacgccgcca agtacttcga aaagtgaag   420
aagtccctga aggcctcccg gaccaagtcc taccggcacg cccacaacgt ggccgtggtg   480
gccgagaagt ccgtggctga aaggacgcc gacttcgaca atgggaggc ctggcccaaa    540
gagacacagc tgcagatcgg caccaccctg ctggaaattc tggaaggctc cgtgttctac   600
aacggcgagc ccgtgttcat gcgggccatg agaacctacg gcggcaagac catctactac   660
ctgcagacct ccgagtccgt gggccagtgg atctccgcct tcaaagaaca cgtggcccag   720
ctgtcccccg cctacgcccc ttgtgtgatc cctccccgac cttggcggac ccccttcaat   780
ggcggcttcc acaccgagaa ggtggcctct cggatccggc tggtcaaggg caaccgcgag   840
```

```
cacgtgcgga agctgaccca gaaacagatg cccaaggtgt acaaggccat caacgccctg      900
cagaacaccc agtggcagat caacaaggac gtgctggccg tgatcgagga agtgatcaga      960
ctggacctgg gctacggcgt gcccagcttc aagcccctga tcgacaaaga gaacaagccc     1020
gccaaccccg tgcccgtgga atttcagcac ctgagaggcc gcgagctgaa agagatgctg     1080
tcccctgagc agtggcagca gttcatcaac tggaagggcg agtgcgccag actgtacacc     1140
gccgagacaa agcggggctc caagtctgcc gccgtcgtgc aatggtcgg acaggcccgg      1200 aagtactccg ccttcgagtc catctacttc gtgtacgcca tggactcccg gtcccgggtg     1260
tacgtgcagt cctccaccct gtcccccag tccaacgacc tgggcaaggc cctgctgcgg      1320
ttcaccgagg gcagacctgt gaacggcgtg aagccctga agtggttctg catcaatggc      1380
gccaacctgt ggggctggga caagaaaacc ttcgacgtgc gggtgtccaa cgtgctggac     1440
gaagagttcc aggacatgtg ccgggatatc gccgccgacc ccctgacctt acccagtgg     1500 gccaaggccg acgcccccta cgagttcctg gcctggtgct cgagtacgc ccagtacctg      1560 gacctggtgg acgagggcag ggccgacgag ttccggaccc atctgcccgt gcaccaggac     1620
ggcagctgct ctggcatcca gcactactcc gccatgctgc gggacgaagt gggcgctaag     1680
gccgtgaacc tgaagccttc cgatgcccct caggacatct acggagccgt ggctcaggtg     1740
gtcatcaaga aaacgccct gtacatggac gccgacgacg ccaccacctt cacctccggc      1800
tccgtgaccc tgtccggcac cgagctgaga gctatggcct ccgcctggga ctccatcggc     1860
atcacccggt ccctgaccaa gaaacccgtg atgaccctgc cctacggctc caccagactg     1920
acctgccgcg agtccgtgat cgactacatc gtggacctgg aagagaaaga ggcccagaag     1980
gccgtcgccg agggcaggac cgccaacaag gtgcaccct cgaggacga ccggcaggac       2040 tacctgaccc ctggcgccgc ttacaactac atgaccgccc tgatctggcc ctccatctcc     2100
gaggtggtca aggcccccat gtgccatg aagatgatcc ggcagctggc cagattcgcc       2160
gccaagagaa acgagggcct gatgtacacc ctgcccaccg gcttcattct ggaacagaaa     2220
atcatggcca ccgagatgct gagagtgcgg acctgcctga tgggcgacat caagatgtcc     2280
ctgcaggtcg agacagacat cgtggatgag ccgccatga tgggcgctgc cgcccctaac     2340
ttcgtgcacg ccacgacgc ctcccacctg atcctgaccg tgtgcgagct ggtggataag      2400
ggcgtgacct ctatcgccgt gatccacgac tccttcggca cccacgccga caacacactg     2460
accctgcggg tggccctgaa gggccagatg gtggccatgt acatcgacgg caatgctctg     2520
cagaagctgc tggaagaaca cgaagtgcgg tggatggtgg acaccggcat cgaggtcccc     2580
gagcagggag agttcgacct gaacgagatc atggactccg agtacgtgtt cgcttga        2637
```

<210> SEQ ID NO 26
<211> LENGTH: 878
<212> TYPE: PRT
<213> ORGANISM: Artificial
<220> FEATURE:
<223> OTHER INFORMATION: Protein sequence encoded by pSP6RNAP plasmid

<400> SEQUENCE: 26

```
Met Glu Phe Leu Glu Gln Asp Leu His Ala Ile Gln Leu Gln Leu Glu
1               5                   10                  15

Glu Glu Met Phe Asn Gly Gly Ile Arg Arg Phe Glu Ala Asp Gln Gln
            20                  25                  30

Arg Gln Ile Ala Ala Gly Ser Glu Ser Asp Thr Ala Trp Asn Arg Arg
        35                  40                  45
```

Leu Leu Ser Glu Leu Ile Ala Pro Met Ala Glu Gly Ile Gln Ala Tyr
            50                  55                  60

Lys Glu Glu Tyr Glu Gly Lys Lys Gly Arg Ala Pro Arg Ala Leu Ala
 65                  70                  75                  80

Phe Leu Gln Cys Val Glu Asn Glu Val Ala Ala Tyr Ile Thr Met Lys
                 85                  90                  95

Val Val Met Asp Met Leu Asn Thr Asp Ala Thr Leu Gln Ala Ile Ala
            100                 105                 110

Met Ser Val Ala Glu Arg Ile Glu Asp Gln Val Arg Phe Ser Lys Leu
            115                 120                 125

Glu Gly His Ala Ala Lys Tyr Phe Glu Lys Val Lys Lys Ser Leu Lys
            130                 135                 140

Ala Ser Arg Thr Lys Ser Tyr Arg His Ala His Asn Val Ala Val Val
145                 150                 155                 160

Ala Glu Lys Ser Val Ala Glu Lys Asp Ala Asp Phe Asp Arg Trp Glu
                165                 170                 175

Ala Trp Pro Lys Glu Thr Gln Leu Gln Ile Gly Thr Thr Leu Leu Glu
            180                 185                 190

Ile Leu Glu Gly Ser Val Phe Tyr Asn Gly Pro Val Phe Met Arg
            195                 200                 205

Ala Met Arg Thr Tyr Gly Gly Lys Thr Ile Tyr Tyr Leu Gln Thr Ser
            210                 215                 220

Glu Ser Val Gly Gln Trp Ile Ser Ala Phe Lys Glu His Val Ala Gln
225                 230                 235                 240

Leu Ser Pro Ala Tyr Ala Pro Cys Val Ile Pro Pro Arg Pro Trp Arg
                245                 250                 255

Thr Pro Phe Asn Gly Gly Phe His Thr Glu Lys Val Ala Ser Arg Ile
            260                 265                 270

Arg Leu Val Lys Gly Asn Arg Glu His Val Arg Lys Leu Thr Gln Lys
            275                 280                 285

Gln Met Pro Lys Val Tyr Lys Ala Ile Asn Ala Leu Gln Asn Thr Gln
            290                 295                 300

Trp Gln Ile Asn Lys Asp Val Leu Ala Val Ile Glu Glu Val Ile Arg
305                 310                 315                 320

Leu Asp Leu Gly Tyr Gly Val Pro Ser Phe Lys Pro Leu Ile Asp Lys
                325                 330                 335

Glu Asn Lys Pro Ala Asn Pro Val Pro Val Glu Phe Gln His Leu Arg
            340                 345                 350

Gly Arg Glu Leu Lys Glu Met Leu Ser Pro Glu Gln Trp Gln Gln Phe
            355                 360                 365

Ile Asn Trp Lys Gly Glu Cys Ala Arg Leu Tyr Thr Ala Glu Thr Lys
            370                 375                 380

Arg Gly Ser Lys Ser Ala Ala Val Val Arg Met Val Gly Gln Ala Arg
385                 390                 395                 400

Lys Tyr Ser Ala Phe Glu Ser Ile Tyr Phe Val Tyr Ala Met Asp Ser
                405                 410                 415

Arg Ser Arg Val Tyr Val Gln Ser Ser Thr Leu Ser Pro Gln Ser Asn
            420                 425                 430

Asp Leu Gly Lys Ala Leu Leu Arg Phe Thr Glu Gly Arg Pro Val Asn
            435                 440                 445

Gly Val Glu Ala Leu Lys Trp Phe Cys Ile Asn Gly Ala Asn Leu Trp
450                 455                 460

-continued

```
Gly Trp Asp Lys Lys Thr Phe Asp Val Arg Val Ser Asn Val Leu Asp
465                 470                 475                 480

Glu Glu Phe Gln Asp Met Cys Arg Asp Ile Ala Ala Asp Pro Leu Thr
            485                 490                 495

Phe Thr Gln Trp Ala Lys Ala Asp Ala Pro Tyr Glu Phe Leu Ala Trp
                500                 505                 510

Cys Phe Glu Tyr Ala Gln Tyr Leu Asp Leu Val Asp Glu Gly Arg Ala
            515                 520                 525

Asp Glu Phe Arg Thr His Leu Pro Val His Gln Asp Gly Ser Cys Ser
            530                 535                 540

Gly Ile Gln His Tyr Ser Ala Met Leu Arg Asp Glu Val Gly Ala Lys
545                 550                 555                 560

Ala Val Asn Leu Lys Pro Ser Asp Ala Pro Gln Asp Ile Tyr Gly Ala
                565                 570                 575

Val Ala Gln Val Val Ile Lys Lys Asn Ala Leu Tyr Met Asp Ala Asp
            580                 585                 590

Asp Ala Thr Thr Phe Thr Ser Gly Ser Val Thr Leu Ser Gly Thr Glu
            595                 600                 605

Leu Arg Ala Met Ala Ser Ala Trp Asp Ser Ile Gly Ile Thr Arg Ser
610                 615                 620

Leu Thr Lys Lys Pro Val Met Thr Leu Pro Tyr Gly Ser Thr Arg Leu
625                 630                 635                 640

Thr Cys Arg Glu Ser Val Ile Asp Tyr Ile Val Asp Leu Glu Glu Lys
                645                 650                 655

Glu Ala Gln Lys Ala Val Ala Glu Gly Arg Thr Ala Asn Lys Val His
                660                 665                 670

Pro Phe Glu Asp Asp Arg Gln Asp Tyr Leu Thr Pro Gly Ala Ala Tyr
            675                 680                 685

Asn Tyr Met Thr Ala Leu Ile Trp Pro Ser Ile Ser Glu Val Val Lys
            690                 695                 700

Ala Pro Ile Val Ala Met Lys Met Ile Arg Gln Leu Ala Arg Phe Ala
705                 710                 715                 720

Ala Lys Arg Asn Glu Gly Leu Met Tyr Thr Leu Pro Thr Gly Phe Ile
                725                 730                 735

Leu Glu Gln Lys Ile Met Ala Thr Glu Met Leu Arg Val Arg Thr Cys
            740                 745                 750

Leu Met Gly Asp Ile Lys Met Ser Leu Gln Val Glu Thr Asp Ile Val
            755                 760                 765

Asp Glu Ala Ala Met Met Gly Ala Ala Pro Asn Phe Val His Gly
770                 775                 780

His Asp Ala Ser His Leu Ile Leu Thr Val Cys Glu Leu Val Asp Lys
785                 790                 795                 800

Gly Val Thr Ser Ile Ala Val Ile His Asp Ser Phe Gly Thr His Ala
                805                 810                 815

Asp Asn Thr Leu Thr Leu Arg Val Ala Leu Lys Gly Gln Met Val Ala
            820                 825                 830

Met Tyr Ile Asp Gly Asn Ala Leu Gln Lys Leu Leu Glu Glu His Glu
            835                 840                 845

Val Arg Trp Met Val Asp Thr Gly Ile Glu Val Pro Glu Gln Gly Glu
            850                 855                 860

Phe Asp Leu Asn Glu Ile Met Asp Ser Glu Tyr Val Phe Ala
865                 870                 875
```

<210> SEQ ID NO 27
<211> LENGTH: 2547
<212> TYPE: DNA
<213> ORGANISM: Artificial
<220> FEATURE:
<223> OTHER INFORMATION: Open-reading frame of the pD1R plasmid

<400> SEQUENCE: 27

| | | | | | |
|---|---|---|---|---|---|
| atggaattcg | acgccaacgt | ggtgtcctcc | tccacaatcg | ccacctacat | cgacgccctg | 60 |
| gccaagaacg | cctccgagct | ggaacagcgg | tccaccgcct | acgagatcaa | caatgagctg | 120 |
| gaactggtgt | tcatcaagcc | ccccctgatc | accctgacca | acgtggtcaa | catcagcacc | 180 |
| atccaggaat | ccttcatccg | gttcaccgtg | accaacaaag | aaggcgtgaa | gatccggacc | 240 |
| aagatccccc | tgtccaaggt | gcacggcctg | gacgtgaaga | acgtgcagct | ggtggacgcc | 300 |
| atcgacaaca | tcgtgtggga | gaagaagtcc | ctggtcaccg | agaaccggct | gcacaaagag | 360 |
| tgcctgctgc | ggctgtccac | cgaggaacgg | cacatctttc | tggactacaa | gaagtacggc | 420 |
| tcctccatca | gactgaaact | ggtcaacctg | atccaggcca | agaccaagaa | cttcaccatc | 480 |
| gacttcaagc | tgaagtactt | cctgggctct | ggcgcccagt | ccaagtcctc | tctgctgcac | 540 |
| gccatcaacc | cccccaagtc | ccggcccaac | acctccctgg | aaatcgagtt | cacccctcgg | 600 |
| gacaacgaga | cagtgcccta | cgacgagctg | atcaaagagc | tgaccaccct | gtccagacac | 660 |
| atcttcatgg | cctcccccga | gaacgtgatc | ctgtcccccc | ccatcaacgc | ccccatcaag | 720 |
| accttcatgc | tgcccaagca | ggacatcgtg | ggcctggacc | tggaaaacct | gtacgccgtg | 780 |
| accaagaccg | acggcatccc | catcaccatc | agagtgacct | ccaacggcct | gtactgctac | 840 |
| ttcacccacc | tgggctacat | catcagatac | cccgtgaagc | ggatcatcga | ctccgaggtg | 900 |
| gtggtgttcg | gcgaggccgt | gaaggacaag | aactggaccg | tgtacctgat | caagctgatc | 960 |
| gagcccgtga | acgccatcaa | tgaccggctg | gaagagtcca | atacgtggaa | tccaagctg  | 1020 |
| gtggatatct | gcgaccggat | cgtgttcaag | tctaagaagt | acgagggacc | cttcactaca | 1080 |
| acttcagagg | tggtcgacat | gctgtccacc | tacctgccta | agcagcccga | gggcgtcatc | 1140 |
| ctgttctact | ccaagggacc | caagtccaac | atcgatttca | agatcaagaa | agagaacacc | 1200 |
| atcgaccaga | ccgccaatgt | ggtgttccgg | tacatgtcct | ccgagcccat | catcttcggc | 1260 |
| gagtcctcca | tcttcgtcga | gtacaagaag | ttctccaacg | acaagggctt | ccccaaagag | 1320 |
| tacggcagcg | gcaagatcgt | gctgtacaac | ggcgtgaact | acctgaacaa | catctactgc | 1380 |
| ctggagtaca | tcaacacccca | caacgaagtg | ggcatcaagt | ccgtggtggt | gcccatcaag | 1440 |
| tttatcgccg | agttcctggt | caacggcgag | atcctgaagc | cccggatcga | caagaccatg | 1500 |
| aagtacatca | attccgagga | ctactacggc | aaccagcaca | acatcatcgt | ggaacacctg | 1560 |
| agggaccagt | ccatcaagat | cggcgacatc | ttcaacgagg | acaagctgtc | cgacgtgggc | 1620 |
| caccagtacg | ccaacaacga | caagttccgg | ctgaaccccg | aggtgtccta | cttcaccaac | 1680 |
| aagagaaccc | gaggcccact | gggcatcctg | tccaactacg | tgaaaaccct | gctgatctcc | 1740 |
| atgtactgct | ccaagacctt | cctggacgac | tccaacaagc | ggaaggtgct | ggccatcgat | 1800 |
| ttcggcaacg | cgccgatct  | ggaaaagtac | ttctatggcg | agatcgccct | gctggtggct | 1860 |
| accgaccctg | acgccgacgc | tatcgccaga | ggcaacgagc | ggtacaacaa | gctgaactcc | 1920 |
| ggcatcaaga | ccaagtacta | caagttcgac | tacatccagg | aaaccatccg | ctccgacacc | 1980 |
| ttcgtgtcct | ccgtgcgcga | ggtgttctat | ttcggcaagt | tcaatatcat | cgactggcag | 2040 |
| ttcgccatcc | actacagctt | ccaccccggg | cactacgcca | ccgtgatgaa | caacctgtcc | 2100 |

-continued

```
gagctgaccg cctccggcgg caaggtgctg atcaccacca tggacggcga caagctgagc    2160
aagctgaccg acaagaaaac cttcatcatc cacaagaacc tgccctccag cgagaactac    2220
atgtccgtgg aaaagatcgc cgacgacaga atcgtggtgt acaatccctc caccatgtcc    2280
acccccatga ccgagtacat catcaagaag aacgacatcg tccgggtgtt caacgagtac    2340
ggcttcgtgc tggtggacaa cgtggacttc gccaccatca tcgagcggtc caaaaagttc    2400
atcaatggag ccagcaccat ggaagatcgg ccctctaccc ggaacttctt cgagctgaac    2460
agaggcgcca tcaagtgcga gggcctggat gtggaagatc tgctgagcta ctacgtggtg    2520
tacgtgttct ccaagagagg gccctga                                        2547
```

<210> SEQ ID NO 28
<211> LENGTH: 848
<212> TYPE: PRT
<213> ORGANISM: Artificial
<220> FEATURE:
<223> OTHER INFORMATION: Protein sequence encoded by pD1R plasmid

<400> SEQUENCE: 28

```
Met Glu Phe Asp Ala Asn Val Val Ser Ser Thr Ile Ala Thr Tyr
1               5                   10                  15

Ile Asp Ala Leu Ala Lys Asn Ala Ser Glu Leu Glu Gln Arg Ser Thr
                20                  25                  30

Ala Tyr Glu Ile Asn Asn Glu Leu Glu Leu Val Phe Ile Lys Pro Pro
            35                  40                  45

Leu Ile Thr Leu Thr Asn Val Val Asn Ile Ser Thr Ile Gln Glu Ser
        50                  55                  60

Phe Ile Arg Phe Thr Val Thr Asn Lys Glu Gly Val Lys Ile Arg Thr
65                  70                  75                  80

Lys Ile Pro Leu Ser Lys Val His Gly Leu Asp Val Lys Asn Val Gln
                85                  90                  95

Leu Val Asp Ala Ile Asp Asn Ile Val Trp Glu Lys Lys Ser Leu Val
            100                 105                 110

Thr Glu Asn Arg Leu His Lys Glu Cys Leu Leu Arg Leu Ser Thr Glu
        115                 120                 125

Glu Arg His Ile Phe Leu Asp Tyr Lys Lys Tyr Gly Ser Ser Ile Arg
    130                 135                 140

Leu Glu Leu Val Asn Leu Ile Gln Ala Lys Thr Lys Asn Phe Thr Ile
145                 150                 155                 160

Asp Phe Lys Leu Lys Tyr Phe Leu Gly Ser Gly Ala Gln Ser Lys Ser
                165                 170                 175

Ser Leu Leu His Ala Ile Asn His Pro Lys Ser Arg Pro Asn Thr Ser
            180                 185                 190

Leu Glu Ile Glu Phe Thr Pro Arg Asp Asn Glu Thr Val Pro Tyr Asp
        195                 200                 205

Glu Leu Ile Lys Glu Leu Thr Thr Leu Ser Arg His Ile Phe Met Ala
    210                 215                 220

Ser Pro Glu Asn Val Ile Leu Ser Pro Pro Ile Asn Ala Pro Ile Lys
225                 230                 235                 240

Thr Phe Met Leu Pro Lys Gln Asp Ile Val Gly Leu Asp Leu Glu Asn
                245                 250                 255

Leu Tyr Ala Val Thr Lys Thr Asp Gly Ile Pro Ile Thr Ile Arg Val
            260                 265                 270

Thr Ser Asn Gly Leu Tyr Cys Tyr Phe Thr His Leu Gly Tyr Ile Ile
        275                 280                 285
```

-continued

Arg Tyr Pro Val Lys Arg Ile Ile Asp Ser Glu Val Val Phe Gly
    290             295             300
Glu Ala Val Lys Asp Lys Asn Trp Thr Val Tyr Leu Ile Lys Leu Ile
305             310             315             320
Glu Pro Val Asn Ala Ile Asn Asp Arg Leu Glu Glu Ser Lys Tyr Val
                325             330             335
Glu Ser Lys Leu Val Asp Ile Cys Asp Arg Ile Val Phe Lys Ser Lys
            340             345             350
Lys Tyr Glu Gly Pro Phe Thr Thr Thr Ser Glu Val Val Asp Met Leu
        355             360             365
Ser Thr Tyr Leu Pro Lys Gln Pro Glu Gly Val Ile Leu Phe Tyr Ser
    370             375             380
Lys Gly Pro Lys Ser Asn Ile Asp Phe Lys Ile Lys Lys Glu Asn Thr
385             390             395             400
Ile Asp Gln Thr Ala Asn Val Val Phe Arg Tyr Met Ser Ser Glu Pro
                405             410             415
Ile Ile Phe Gly Glu Ser Ser Ile Phe Val Glu Tyr Lys Lys Phe Ser
            420             425             430
Asn Asp Lys Gly Phe Pro Lys Glu Tyr Gly Ser Gly Lys Ile Val Leu
        435             440             445
Tyr Asn Gly Val Asn Tyr Leu Asn Asn Ile Tyr Cys Leu Glu Tyr Ile
    450             455             460
Asn Thr His Asn Glu Val Gly Ile Lys Ser Val Val Pro Ile Lys
465             470             475             480
Phe Ile Ala Glu Phe Leu Val Asn Gly Glu Ile Leu Lys Pro Arg Ile
                485             490             495
Asp Lys Thr Met Lys Tyr Ile Asn Ser Glu Asp Tyr Tyr Gly Asn Gln
            500             505             510
His Asn Ile Ile Val Glu His Leu Arg Asp Gln Ser Ile Lys Ile Gly
        515             520             525
Asp Ile Phe Asn Glu Asp Lys Leu Ser Asp Val Gly His Gln Tyr Ala
    530             535             540
Asn Asn Asp Lys Phe Arg Leu Asn Pro Glu Val Ser Tyr Phe Thr Asn
545             550             555             560
Lys Arg Thr Arg Gly Pro Leu Gly Ile Leu Ser Asn Tyr Val Lys Thr
                565             570             575
Leu Leu Ile Ser Met Tyr Cys Ser Lys Thr Phe Leu Asp Asp Ser Asn
            580             585             590
Lys Arg Lys Val Leu Ala Ile Asp Phe Gly Asn Gly Ala Asp Leu Glu
        595             600             605
Lys Tyr Phe Tyr Gly Glu Ile Ala Leu Leu Val Ala Thr Asp Pro Asp
    610             615             620
Ala Asp Ala Ile Ala Arg Gly Asn Glu Arg Tyr Asn Lys Leu Asn Ser
625             630             635             640
Gly Ile Lys Thr Lys Tyr Tyr Lys Phe Asp Tyr Ile Gln Glu Thr Ile
                645             650             655
Arg Ser Asp Thr Phe Val Ser Ser Val Arg Glu Val Phe Tyr Phe Gly
            660             665             670
Lys Phe Asn Ile Ile Asp Trp Gln Phe Ala Ile His Tyr Ser Phe His
        675             680             685
Pro Arg His Tyr Ala Thr Val Met Asn Asn Leu Ser Glu Leu Thr Ala
    690             695             700

```
Ser Gly Gly Lys Val Leu Ile Thr Thr Met Asp Gly Asp Lys Leu Ser
705                 710                 715                 720

Lys Leu Thr Asp Lys Lys Thr Phe Ile Ile His Lys Asn Leu Pro Ser
            725                 730                 735

Ser Glu Asn Tyr Met Ser Val Glu Lys Ile Ala Asp Asp Arg Ile Val
        740                 745                 750

Val Tyr Asn Pro Ser Thr Met Ser Thr Pro Met Thr Glu Tyr Ile Ile
    755                 760                 765

Lys Lys Asn Asp Ile Val Arg Val Phe Asn Glu Tyr Gly Phe Val Leu
770                 775                 780

Val Asp Asn Val Asp Phe Ala Thr Ile Ile Glu Arg Ser Lys Lys Phe
785                 790                 795                 800

Ile Asn Gly Ala Ser Thr Met Glu Asp Arg Pro Ser Thr Arg Asn Phe
                805                 810                 815

Phe Glu Leu Asn Arg Gly Ala Ile Lys Cys Glu Gly Leu Asp Val Glu
            820                 825                 830

Asp Leu Leu Ser Tyr Tyr Val Val Tyr Val Phe Ser Lys Arg Gly Pro
        835                 840                 845

<210> SEQ ID NO 29
<211> LENGTH: 876
<212> TYPE: DNA
<213> ORGANISM: Artificial
<220> FEATURE:
<223> OTHER INFORMATION: Open-reading frame of the pD12L plasmid

<400> SEQUENCE: 29
atggaattcg acgagatcgt gaagaacatc cgcgagggca cccacgtgct gctgcccttc      60
tacgagacac tgcccgagct gaacctgtcc ctgggcaagt cccccctgcc ctccctggaa     120
tacggcgcca actacttcct gcagatctcc agagtgaacg acctgaaccg gatgcccacc     180
gacatgctga gctgttcac ccacgacatc atgctgcccg agtccgacct ggacaaggtg     240
tacgagattc tgaagatcaa ctccgtgaag tactacggcc ggtccacaaa ggctgacgcc     300
gtggtggccg acctgtctgc ccggaacaag ctgttcaaga gagagcggga cgccatcaag     360
tccaacaacc cctgaccga gaacaacctg tacatctccg actacaagat gctgaccttc     420
gacgtgttcc ggcccctgtt cgacttcgtg aacgagaagt actgcatcat caagctgccc     480
accctgttcg gcagaggcgt gatcgacacc atgcggatct actgctccct gttcaagaac     540
gtgcggctgc tgaagtgcgt gtccgactcc tggctgaagg actccgccat catggtggcc     600
tccgacgtgt gcaagaagaa cctggacctg ttcatgtccc acgtgaagtc cgtgaccaag     660
tcatccagct ggaaggacgt gaactccgtg cagttctcca tcctgaacaa ccccgtggac     720
accgagttca tcaacaagtt tctggaattt tccaaccggg tgtacgaggc cctgtactac     780
gtgcactccc tgctgtactc ctccatgacc tccgactcca gtccatcga gaacaaacat     840 cagcgacggc tggtcaagct gctgctgggg ccctga                              876

<210> SEQ ID NO 30
<211> LENGTH: 291
<212> TYPE: PRT
<213> ORGANISM: Artificial
<220> FEATURE:
<223> OTHER INFORMATION: Protein sequence encoded by pD12L plasmid

<400> SEQUENCE: 30

Met Glu Phe Asp Glu Ile Val Lys Asn Ile Arg Glu Gly Thr His Val
1               5                   10                  15
```

Leu Leu Pro Phe Tyr Glu Thr Leu Pro Glu Leu Asn Leu Ser Leu Gly
           20                  25                  30

Lys Ser Pro Leu Pro Ser Leu Glu Tyr Gly Ala Asn Tyr Phe Leu Gln
           35                  40                  45

Ile Ser Arg Val Asn Asp Leu Asn Arg Met Pro Thr Asp Met Leu Lys
 50                  55                  60

Leu Phe Thr His Asp Ile Met Leu Pro Glu Ser Asp Leu Asp Lys Val
65                   70                  75                  80

Tyr Glu Ile Leu Lys Ile Asn Ser Val Lys Tyr Tyr Gly Arg Ser Thr
                85                  90                  95

Lys Ala Asp Ala Val Val Ala Asp Leu Ser Ala Arg Asn Lys Leu Phe
            100                 105                 110

Lys Arg Glu Arg Asp Ala Ile Lys Ser Asn Asn His Leu Thr Glu Asn
        115                 120                 125

Asn Leu Tyr Ile Ser Asp Tyr Lys Met Leu Thr Phe Asp Val Phe Arg
130                 135                 140

Pro Leu Phe Asp Phe Val Asn Glu Lys Tyr Cys Ile Ile Lys Leu Pro
145                 150                 155                 160

Thr Leu Phe Gly Arg Gly Val Ile Asp Thr Met Arg Ile Tyr Cys Ser
                165                 170                 175

Leu Phe Lys Asn Val Arg Leu Leu Lys Cys Val Ser Asp Ser Trp Leu
            180                 185                 190

Lys Asp Ser Ala Ile Met Val Ala Ser Asp Val Cys Lys Lys Asn Leu
        195                 200                 205

Asp Leu Phe Met Ser His Val Lys Ser Val Thr Lys Ser Ser Ser Trp
210                 215                 220

Lys Asp Val Asn Ser Val Gln Phe Ser Ile Leu Asn Asn Pro Val Asp
225                 230                 235                 240

Thr Glu Phe Ile Asn Lys Phe Leu Glu Phe Ser Asn Arg Val Tyr Glu
                245                 250                 255

Ala Leu Tyr Tyr Val His Ser Leu Leu Tyr Ser Ser Met Thr Ser Asp
            260                 265                 270

Ser Lys Ser Ile Glu Asn Lys His Gln Arg Arg Leu Val Lys Leu Leu
        275                 280                 285

Leu Gly Pro
    290

<210> SEQ ID NO 31
<211> LENGTH: 2760
<212> TYPE: DNA
<213> ORGANISM: Artificial
<220> FEATURE:
<223> OTHER INFORMATION: Open-reading frame of the pRR1234L-NP868R
      plasmid

<400> SEQUENCE: 31
atgctggaaa tcagggccgc cttcctgcgg agaagaaaca ccgccctgcg gaccagagtg     60
gccgagctga cagcggggt gcagcggctg cggaacatcg tgtcccagta cgagacaaga    120
tacggccccc tgggcggagg caaagaattc gccagcctgg acaacctggt ggccagatac    180
cagcggtgct tcaacgacca gagcctgaag aacagcacca tcgagctgga aatccggttc    240
cagcagatca acttcctgct gttcaagacc gtgtacgagg ccctggtcgc ccaggaaatc    300
cccagcacca tcagccacag catccggtgc atcaagaagg tgcaccacga gaaccactgc    360
cgggagaaga tcctgcccag cgagaacctg tacttcaaga acagcccct gatgttcttc    420

```
aagttcagcg agcccgccag cctgggctgt aaagtgtccc tggccatcga gcagcccatc    480
cggaagttca tcctggacag cagcgtgctg gtccggctga agaaccggac caccttccgg    540
gtgtccgagc tgtggaagat cgagctgacc atcgtgaagc agctgatggg cagcgaggtg    600
tcagccaagc tggccgcctt caagaccctg ctgttcgaca cccccgagca gcagaccacc    660
aagaacatga tgaccctgat caaccccgac gacgagtacc tgtacgagat cgagatcgag    720
tacaccggca agcctgagag cctgacagcc gccgacgtga tcaagatcaa gaacaccgtg    780
ctgacactga tcagccccaa ccacctgatg ctgaccgcct accaccaggc catcgagttt    840
atcgccagcc acatcctgag cagcgagatc ctgctggccc ggatcaagag cggcaagtgg    900
ggcctgaaga gactgctgcc ccaggtcaag tccatgacca aggccgacta catgaagttc    960
taccccccg tgggctacta cgtgaccgac aaggccgacg catccgggg cattgccgtg    1020
atccaggaca cccagatcta cgtggtggcc gaccagctgt acagcctggg caccaccggc    1080
atcgagcccc tgaagcccac catcctggac ggcgagttca tgcccgagaa gaaagagttc    1140
tacggctttg acgtgatcat gtacgagggc aacctgctga cccagcaggg cttcgagaca    1200
cggatcgaga gctgagcaa gggcatcaag gtgctgcagg ccttcaacat caaggccgag    1260
atgaagccct tcatcagcct gacctccgcc gaccccaacg tgctgctgaa gaatttcgag    1320
agcatcttca agaagaaaac ccggccctac agcatcgacg gcatcatcct ggtggagccc    1380
ggcaacagct acctgaacac caacaccttc aagtggaagc ccacctggga caacaccctg    1440
gactttctgg tccggaagtg cccgagtcc ctgaacgtgc ccgagtacgc ccccaagaag    1500
ggcttcagcc tgcatctgct gttcgtgggc atcagcggcg agctgtttaa gaagctggcc    1560
ctgaactggt gccccggcta caccaagctg ttccccgtga cccagcggaa ccagaactac    1620
ttccccgtgc agttccagcc cagcgacttc ccctggcct cctgtacta ccaccccgac    1680
accagcagct tcagcaacat cgatggcaag gtgctggaaa tgcggtgcct gaagcgggag    1740
atcaactacg tgcgctggga gatcgtgaag atccgggagg accggcagca ggatctgaaa    1800
accggcggct acttcggcaa cgacttcaag accgccgagc tgacctggct gaactacatg    1860
gaccccttca gcttcgagga actggccaag ggacccagcg gcatgtactt cgctggcgcc    1920
aagaccggca tctacagagc ccagaccgcc ctgatcagct tcatcaagca ggaaatcatc    1980
cagaagatca gccaccagag ctgggtgatc gacctgggca tcggcaaggg ccaggacctg    2040
ggcagatacc tggacgccgg cgtgagacac ctggtcggca tcgataagga ccagacagcc    2100
ctggccgagc tggtgtaccg gaagttctcc cacgccacca ccagacagca aagcacgcc    2160
accaacatct acgtgctgca ccaggatctg gccgagcctg ccaaagaaat cagcgagaaa    2220
gtgcaccaga tctatggctt ccccaaagag ggcgccagca gcatcgtgtc caacctgttc    2280
atccactacc tgatgaagaa cacccagcag gtcgagaacc tggctgtgct gtgccacaag    2340
ctgctgcagc ctggcggcat ggtctggttc accaccatgc tgggcaacaa ggtgctggaa    2400
ctgctgcacg agaaccggat cgaactgaac gaagtgtggg aggcccggga aacgaggtg    2460
gtcaagttcg ccatcaagcg gctgttcaaa gaggacatcc tgcaggaaac cggcaggaa    2520
atcggcgtcc tgctgccctt cagcaacggc gacttctaca tgagtacct ggtcaacacc    2580
gcctttctga tcaagatttt caagcaccat ggctttagcc tcgtgcagaa gcagagcttc    2640
aaggactgga tccccgagtt ccagaacttc agcaagagcc tgtacaagat cctgaccgag    2700
gccgacaaga cctggaccag cctgttcggc ttcatctgcc tgcggaagaa cgggccctga    2760
```

<210> SEQ ID NO 32
<211> LENGTH: 919
<212> TYPE: PRT
<213> ORGANISM: Artificial
<220> FEATURE:
<223> OTHER INFORMATION: Protein sequence encoded by pRR1234L-NP868R
    plasmid

<400> SEQUENCE: 32

```
Met Leu Glu Ile Arg Ala Ala Phe Leu Arg Arg Asn Thr Ala Leu
1               5                   10                  15

Arg Thr Arg Val Ala Glu Leu Arg Gln Arg Val Gln Arg Leu Arg Asn
                20                  25                  30

Ile Val Ser Gln Tyr Glu Thr Arg Tyr Gly Pro Leu Gly Gly Gly Lys
            35                  40                  45

Glu Phe Ala Ser Leu Asp Asn Leu Val Ala Arg Tyr Gln Arg Cys Phe
    50                  55                  60

Asn Asp Gln Ser Leu Lys Asn Ser Thr Ile Glu Leu Glu Ile Arg Phe
65                  70                  75                  80

Gln Gln Ile Asn Phe Leu Leu Phe Lys Thr Val Tyr Glu Ala Leu Val
                85                  90                  95

Ala Gln Glu Ile Pro Ser Thr Ile Ser His Ser Ile Arg Cys Ile Lys
            100                 105                 110

Lys Val His His Glu Asn His Cys Arg Glu Lys Ile Leu Pro Ser Glu
        115                 120                 125

Asn Leu Tyr Phe Lys Lys Gln Pro Leu Met Phe Phe Lys Phe Ser Glu
    130                 135                 140

Pro Ala Ser Leu Gly Cys Lys Val Ser Leu Ala Ile Glu Gln Pro Ile
145                 150                 155                 160

Arg Lys Phe Ile Leu Asp Ser Ser Val Leu Val Arg Leu Lys Asn Arg
                165                 170                 175

Thr Thr Phe Arg Val Ser Glu Leu Trp Lys Ile Glu Leu Thr Ile Val
            180                 185                 190

Lys Gln Leu Met Gly Ser Glu Val Ser Ala Lys Leu Ala Ala Phe Lys
        195                 200                 205

Thr Leu Leu Phe Asp Thr Pro Glu Gln Gln Thr Thr Lys Asn Met Met
    210                 215                 220

Thr Leu Ile Asn Pro Asp Asp Glu Tyr Leu Tyr Glu Ile Glu Ile Glu
225                 230                 235                 240

Tyr Thr Gly Lys Pro Glu Ser Leu Thr Ala Ala Asp Val Ile Lys Ile
                245                 250                 255

Lys Asn Thr Val Leu Thr Leu Ile Ser Pro Asn His Leu Met Leu Thr
            260                 265                 270

Ala Tyr His Gln Ala Ile Glu Phe Ile Ala Ser His Ile Leu Ser Ser
        275                 280                 285

Glu Ile Leu Leu Ala Arg Ile Lys Ser Gly Lys Trp Gly Leu Lys Arg
    290                 295                 300

Leu Leu Pro Gln Val Lys Ser Met Thr Lys Ala Asp Tyr Met Lys Phe
305                 310                 315                 320

Tyr Pro Pro Val Gly Tyr Tyr Val Thr Asp Lys Ala Asp Gly Ile Arg
                325                 330                 335

Gly Ile Ala Val Ile Gln Asp Thr Gln Ile Tyr Val Val Ala Asp Gln
            340                 345                 350

Leu Tyr Ser Leu Gly Thr Thr Gly Ile Glu Pro Leu Lys Pro Thr Ile
        355                 360                 365
```

```
Leu Asp Gly Glu Phe Met Pro Glu Lys Lys Glu Phe Tyr Gly Phe Asp
    370                 375                 380

Val Ile Met Tyr Glu Gly Asn Leu Leu Thr Gln Gln Gly Phe Glu Thr
385                 390                 395                 400

Arg Ile Glu Ser Leu Ser Lys Gly Ile Lys Val Leu Gln Ala Phe Asn
                405                 410                 415

Ile Lys Ala Glu Met Lys Pro Phe Ile Ser Leu Thr Ser Ala Asp Pro
                420                 425                 430

Asn Val Leu Leu Lys Asn Phe Glu Ser Ile Phe Lys Lys Lys Thr Arg
            435                 440                 445

Pro Tyr Ser Ile Asp Gly Ile Ile Leu Val Glu Pro Gly Asn Ser Tyr
    450                 455                 460

Leu Asn Thr Asn Thr Phe Lys Trp Lys Pro Thr Trp Asp Asn Thr Leu
465                 470                 475                 480

Asp Phe Leu Val Arg Lys Cys Pro Glu Ser Leu Asn Val Pro Glu Tyr
                485                 490                 495

Ala Pro Lys Lys Gly Phe Ser Leu His Leu Leu Phe Val Gly Ile Ser
                500                 505                 510

Gly Glu Leu Phe Lys Lys Leu Ala Leu Asn Trp Cys Pro Gly Tyr Thr
            515                 520                 525

Lys Leu Phe Pro Val Thr Gln Arg Asn Gln Asn Tyr Phe Pro Val Gln
    530                 535                 540

Phe Gln Pro Ser Asp Phe Pro Leu Ala Phe Leu Tyr Tyr His Pro Asp
545                 550                 555                 560

Thr Ser Ser Phe Ser Asn Ile Asp Gly Lys Val Leu Glu Met Arg Cys
                565                 570                 575

Leu Lys Arg Glu Ile Asn Tyr Val Arg Trp Glu Ile Val Lys Ile Arg
            580                 585                 590

Glu Asp Arg Gln Gln Asp Leu Lys Thr Gly Gly Tyr Phe Gly Asn Asp
    595                 600                 605

Phe Lys Thr Ala Glu Leu Thr Trp Leu Asn Tyr Met Asp Pro Phe Ser
610                 615                 620

Phe Glu Glu Leu Ala Lys Gly Pro Ser Gly Met Tyr Phe Ala Gly Ala
625                 630                 635                 640

Lys Thr Gly Ile Tyr Arg Ala Gln Thr Ala Leu Ile Ser Phe Ile Lys
                645                 650                 655

Gln Glu Ile Ile Gln Lys Ile Ser His Gln Ser Trp Val Ile Asp Leu
                660                 665                 670

Gly Ile Gly Lys Gly Gln Asp Leu Gly Arg Tyr Leu Asp Ala Gly Val
            675                 680                 685

Arg His Leu Val Gly Ile Asp Lys Asp Gln Thr Ala Leu Ala Glu Leu
    690                 695                 700

Val Tyr Arg Lys Phe Ser His Ala Thr Thr Arg Gln His Lys His Ala
705                 710                 715                 720

Thr Asn Ile Tyr Val Leu His Gln Asp Leu Ala Glu Pro Ala Lys Glu
                725                 730                 735

Ile Ser Glu Lys Val His Gln Ile Tyr Gly Phe Pro Lys Glu Gly Ala
                740                 745                 750

Ser Ser Ile Val Ser Asn Leu Phe Ile His Tyr Leu Met Lys Asn Thr
            755                 760                 765

Gln Gln Val Glu Asn Leu Ala Val Leu Cys His Lys Leu Leu Gln Pro
    770                 775                 780
```

| | | | | | | | | | | | | | | | |
|---|---|---|---|---|---|---|---|---|---|---|---|---|---|---|---|
|Gly|Gly|Met|Val|Trp|Phe|Thr|Thr|Met|Leu|Gly|Glu|Gln|Val|Leu|Glu|
|785| | | |790| | | |795| | | |800| | | |
|Leu|Leu|His|Glu|Asn|Arg|Ile|Glu|Leu|Asn|Glu|Val|Trp|Glu|Ala|Arg|
| | | | |805| | | |810| | | | |815| | |
|Glu|Asn|Glu|Val|Val|Lys|Phe|Ala|Ile|Lys|Arg|Leu|Phe|Lys|Glu|Asp|
| | | | |820| | | | |825| | | | |830| |
|Ile|Leu|Gln|Glu|Thr|Gly|Gln|Glu|Ile|Gly|Val|Leu|Leu|Pro|Phe|Ser|
| | |835| | | | | |840| | | | |845| | |
|Asn|Gly|Asp|Phe|Tyr|Asn|Glu|Tyr|Leu|Val|Asn|Thr|Ala|Phe|Leu|Ile|
| |850| | | | |855| | | | |860| | | | |
|Lys|Ile|Phe|Lys|His|His|Gly|Phe|Ser|Leu|Val|Gln|Lys|Gln|Ser|Phe|
|865| | | |870| | | |875| | | | |880| | |
|Lys|Asp|Trp|Ile|Pro|Glu|Phe|Gln|Asn|Phe|Ser|Lys|Ser|Leu|Tyr|Lys|
| | | | |885| | | |890| | | | |895| | |
|Ile|Leu|Thr|Glu|Ala|Asp|Lys|Thr|Trp|Thr|Ser|Leu|Phe|Gly|Phe|Ile|
| | | |900| | | | |905| | | | |910| | |
|Cys|Leu|Arg|Lys|Asn|Gly|Pro| | | | | | | | | |
| |915| | | | | | | | | | | | | | |

```
<210> SEQ ID NO 33
<211> LENGTH: 2688
<212> TYPE: DNA
<213> ORGANISM: Artificial
<220> FEATURE:
<223> OTHER INFORMATION: Open-reading frame of the pRR1234L-D1R plasmid

<400> SEQUENCE: 33
```

| | |
|---|---|
|atgctggaaa tcagggccgc cttcctgcgg agaagaaaca ccgccctgcg gaccagagtg|60|
|gccgagctga cacagcgggt gcagcggctg cggaacatcg tgtcccagta cgagacaaga|120|
|tacggccccc tgggcggagg caaagaattc gacgccaacg tggtgtcctc ctccacaatc|180|
|gccacctaca tcgacgccct ggccaagaac gcctccgagc tggaacagcg gtccaccgcc|240|
|tacgagatca acaatgagct ggaactggtg ttcatcaagc cccccctgat caccctgacc|300|
|aacgtggtca acatcagcac catccaggaa tccttcatcc ggttcaccgt gaccaacaaa|360|
|gaaggcgtga agatccggac caagatcccc ctgtccaagg tgcacggcct ggacgtgaag|420|
|aacgtgcagc tggtggacgc catcgacaac atcgtgtggg agaagaagtc cctggtcacc|480|
|gagaaccggc tgcacaaaga gtgcctgctg cggctgtcca ccgaggaacg gcacatcttt|540|
|ctggactaca gaagtacgg ctcctccatc agactggaac tggtcaacct gatccaggcc|600|
|aagaccaaga acttcaccat cgacttcaag ctgaagtact cctgggctc tggcgcccag|660|
|tccaagtcct ctctgctgca cgccatcaac caccccaagt cccggcccaa cacctccctg|720|
|gaaatcgagt tcacccctcg ggacaacgag acagtgccct acgacgagct gatcaaagag|780|
|ctgaccaccc tgtccagaca catcttcatg gcctccccg agaacgtgat cctgtcccc|840|
|cccatcaacg cccccatcaa gaccttcatg ctgcccaagc aggacatcgt gggcctggac|900|
|ctggaaaacc tgtacgccgt gaccaagacc gacggcatcc ccatcaccat cagagtgacc|960|
|tccaacggcc tgtactgcta cttcacccac ctgggctaca tcatcagata ccccgtgaag|1020|
|cggatcatcg actccgaggt ggtggtgttc ggcgaggccg tgaaggacaa gaactggacc|1080|
|gtgtacctga tcaagctgat cgagcccgtg aacgccatca tgaccggct ggaagagtcc|1140|
|aaatacgtgg aatccaagct ggtggatatc tgcgaccgga tcgtgttcaa gtctaagaag|1200|
|tacgagggac ccttcactac aacttcagag gtggtcgaca tgctgtccac ctacctgcct|1260|

| | | |
|---|---|---|
| aagcagcccg agggcgtcat cctgttctac tccaagggac ccaagtccaa catcgatttc | 1320 | |
| aagatcaaga aagagaacac catcgaccag accgccaatg tggtgttccg gtacatgtcc | 1380 | |
| tccgagccca tcatcttcgg cgagtcctcc atcttcgtcg agtacaagaa gttctccaac | 1440 | |
| gacaagggct tccccaaaga gtacggcagc ggcaagatcg tgctgtacaa cggcgtgaac | 1500 | |
| tacctgaaca acatctactg cctggagtac atcaacaccc acaacgaagt gggcatcaag | 1560 | |
| tccgtggtgg tgcccatcaa gtttatcgcc gagttcctgg tcaacggcga gatcctgaag | 1620 | |
| ccccggatcg acaagaccat gaagtacatc aattccgagg actactacgg caaccagcac | 1680 | |
| aacatcatcg tggaacacct gagggaccag tccatcaaga tcggcgacat cttcaacgag | 1740 | |
| gacaagctgt ccgacgtggg ccaccagtac gccaacaacg acaagttccg gctgaacccc | 1800 | |
| gaggtgtcct acttcaccaa caagagaacc cgaggcccac tgggcatcct gtccaactac | 1860 | |
| gtgaaaaccc tgctgatctc catgtactgc tccaagacct tcctggacga ctccaacaag | 1920 | |
| cggaaggtgc tggccatcga tttcggcaac ggcgccgatc tggaaaagta cttctatggc | 1980 | |
| gagatcgccc tgctggtggc taccgaccct gacgccgacg ctatcgccag aggcaacgag | 2040 | |
| cggtacaaca agctgaactc cggcatcaag accaagtact acaagttcga ctacatccag | 2100 | |
| gaaaccatcg gctccgacac cttcgtgtcc tccgtgcgcg aggtgttcta tttcggcaag | 2160 | |
| ttcaatatca tcgactggca gttcgccatc cactacagct tccaccccg gcactacgcc | 2220 | |
| accgtgatga acaacctgtc cgagctgacc gcctccggcg caaggtgct gatcaccacc | 2280 | |
| atggacggcg acaagctgag caagctgacc gacaagaaaa ccttcatcat ccacaagaac | 2340 | |
| ctgcccctcca gcgagaacta catgtccgtg gaaaagatcg ccgacgacag aatcgtggtg | 2400 | |
| tacaatccct ccaccatgtc cacccccatg accgagtaca tcatcaagaa gaacgacatc | 2460 | |
| gtccgggtgt tcaacgagta cggcttcgtg ctggtggaca acgtggactt cgccaccatc | 2520 | |
| atcgagcggt ccaaaaagtt catcaatgga gccagcacca tggaagatcg ccctctacc | 2580 | |
| cggaacttct tcgagctgaa cagaggcgcc atcaagtgcg agggcctgga tgtggaagat | 2640 | |
| ctgctgagct actacgtggt gtacgtgttc tccaagagag ggccctga | 2688 | |

<210> SEQ ID NO 34
<211> LENGTH: 895
<212> TYPE: PRT
<213> ORGANISM: Artificial
<220> FEATURE:
<223> OTHER INFORMATION: Protein sequence encoded by pRR1234L-D1R
      plasmid

<400> SEQUENCE: 34

Met Leu Glu Ile Arg Ala Ala Phe Leu Arg Arg Arg Asn Thr Ala Leu
1               5                   10                  15

Arg Thr Arg Val Ala Glu Leu Arg Gln Arg Val Gln Arg Leu Arg Asn
            20                  25                  30

Ile Val Ser Gln Tyr Glu Thr Arg Tyr Gly Pro Leu Gly Gly Gly Lys
        35                  40                  45

Glu Phe Asp Ala Asn Val Val Ser Ser Thr Ile Ala Thr Tyr Ile
    50                  55                  60

Asp Ala Leu Ala Lys Asn Ala Ser Glu Leu Glu Gln Arg Ser Thr Ala
65                  70                  75                  80

Tyr Glu Ile Asn Asn Glu Leu Glu Leu Val Phe Ile Lys Pro Pro Leu
                85                  90                  95

Ile Thr Leu Thr Asn Val Val Asn Ile Ser Thr Ile Gln Glu Ser Phe
            100                 105                 110

-continued

```
Ile Arg Phe Thr Val Thr Asn Lys Glu Gly Val Lys Ile Arg Thr Lys
            115                 120                 125
Ile Pro Leu Ser Lys Val His Gly Leu Asp Val Lys Asn Val Gln Leu
130                 135                 140
Val Asp Ala Ile Asp Asn Ile Val Trp Glu Lys Lys Ser Leu Val Thr
145                 150                 155                 160
Glu Asn Arg Leu His Lys Glu Cys Leu Leu Arg Leu Ser Thr Glu Glu
                165                 170                 175
Arg His Ile Phe Leu Asp Tyr Lys Lys Tyr Gly Ser Ser Ile Arg Leu
            180                 185                 190
Glu Leu Val Asn Leu Ile Gln Ala Lys Thr Lys Asn Phe Thr Ile Asp
        195                 200                 205
Phe Lys Leu Lys Tyr Phe Leu Gly Ser Gly Ala Gln Ser Lys Ser Ser
    210                 215                 220
Leu Leu His Ala Ile Asn His Pro Lys Ser Arg Pro Asn Thr Ser Leu
225                 230                 235                 240
Glu Ile Glu Phe Thr Pro Arg Asp Asn Glu Thr Val Pro Tyr Asp Glu
                245                 250                 255
Leu Ile Lys Glu Leu Thr Thr Leu Ser Arg His Ile Phe Met Ala Ser
            260                 265                 270
Pro Glu Asn Val Ile Leu Ser Pro Pro Ile Asn Ala Pro Ile Lys Thr
        275                 280                 285
Phe Met Leu Pro Lys Gln Asp Ile Val Gly Leu Asp Leu Glu Asn Leu
    290                 295                 300
Tyr Ala Val Thr Lys Thr Asp Gly Ile Pro Ile Thr Ile Arg Val Thr
305                 310                 315                 320
Ser Asn Gly Leu Tyr Cys Tyr Phe Thr His Leu Gly Tyr Ile Ile Arg
                325                 330                 335
Tyr Pro Val Lys Arg Ile Ile Asp Ser Glu Val Val Phe Gly Glu
            340                 345                 350
Ala Val Lys Asp Lys Asn Trp Thr Val Tyr Leu Ile Lys Leu Ile Glu
        355                 360                 365
Pro Val Asn Ala Ile Asn Asp Arg Leu Glu Glu Ser Lys Tyr Val Glu
    370                 375                 380
Ser Lys Leu Val Asp Ile Cys Asp Arg Ile Val Phe Lys Ser Lys Lys
385                 390                 395                 400
Tyr Glu Gly Pro Phe Thr Thr Thr Ser Glu Val Val Asp Met Leu Ser
                405                 410                 415
Thr Tyr Leu Pro Lys Gln Pro Glu Gly Val Ile Leu Phe Tyr Ser Lys
            420                 425                 430
Gly Pro Lys Ser Asn Ile Asp Phe Lys Ile Lys Lys Glu Asn Thr Ile
        435                 440                 445
Asp Gln Thr Ala Asn Val Val Phe Arg Tyr Met Ser Ser Glu Pro Ile
    450                 455                 460
Ile Phe Gly Glu Ser Ser Ile Phe Val Glu Tyr Lys Lys Phe Ser Asn
465                 470                 475                 480
Asp Lys Gly Phe Pro Lys Glu Tyr Gly Ser Gly Lys Ile Val Leu Tyr
                485                 490                 495
Asn Gly Val Asn Tyr Leu Asn Asn Ile Tyr Cys Leu Glu Tyr Ile Asn
            500                 505                 510
Thr His Asn Glu Val Gly Ile Lys Ser Val Val Pro Ile Lys Phe
        515                 520                 525
```

```
Ile Ala Glu Phe Leu Val Asn Gly Glu Ile Leu Lys Pro Arg Ile Asp
            530                 535                 540

Lys Thr Met Lys Tyr Ile Asn Ser Glu Asp Tyr Tyr Gly Asn Gln His
545                 550                 555                 560

Asn Ile Ile Val Glu His Leu Arg Asp Gln Ser Ile Lys Ile Gly Asp
                565                 570                 575

Ile Phe Asn Glu Asp Lys Leu Ser Asp Val Gly His Gln Tyr Ala Asn
            580                 585                 590

Asn Asp Lys Phe Arg Leu Asn Pro Glu Val Ser Tyr Phe Thr Asn Lys
                595                 600                 605

Arg Thr Arg Gly Pro Leu Gly Ile Leu Ser Asn Tyr Val Lys Thr Leu
            610                 615                 620

Leu Ile Ser Met Tyr Cys Ser Lys Thr Phe Leu Asp Asp Ser Asn Lys
625                 630                 635                 640

Arg Lys Val Leu Ala Ile Asp Phe Gly Asn Gly Ala Asp Leu Glu Lys
                645                 650                 655

Tyr Phe Tyr Gly Glu Ile Ala Leu Leu Val Ala Thr Asp Pro Asp Ala
            660                 665                 670

Asp Ala Ile Ala Arg Gly Asn Glu Arg Tyr Asn Lys Leu Asn Ser Gly
                675                 680                 685

Ile Lys Thr Lys Tyr Tyr Lys Phe Asp Tyr Ile Gln Glu Thr Ile Arg
            690                 695                 700

Ser Asp Thr Phe Val Ser Val Arg Glu Val Phe Tyr Phe Gly Lys
705                 710                 715                 720

Phe Asn Ile Ile Asp Trp Gln Phe Ala Ile His Tyr Ser Phe His Pro
                725                 730                 735

Arg His Tyr Ala Thr Val Met Asn Asn Leu Ser Glu Leu Thr Ala Ser
            740                 745                 750

Gly Gly Lys Val Leu Ile Thr Thr Met Asp Gly Asp Lys Leu Ser Lys
                755                 760                 765

Leu Thr Asp Lys Lys Thr Phe Ile Ile His Lys Asn Leu Pro Ser Ser
            770                 775                 780

Glu Asn Tyr Met Ser Val Glu Lys Ile Ala Asp Asp Arg Ile Val Val
785                 790                 795                 800

Tyr Asn Pro Ser Thr Met Ser Thr Pro Met Thr Glu Tyr Ile Ile Lys
                805                 810                 815

Lys Asn Asp Ile Val Arg Val Phe Asn Glu Tyr Gly Phe Val Leu Val
                820                 825                 830

Asp Asn Val Asp Phe Ala Thr Ile Ile Glu Arg Ser Lys Lys Phe Ile
            835                 840                 845

Asn Gly Ala Ser Thr Met Glu Asp Arg Pro Ser Thr Arg Asn Phe Phe
850                 855                 860

Glu Leu Asn Arg Gly Ala Ile Lys Cys Glu Gly Leu Asp Val Glu Asp
865                 870                 875                 880

Leu Leu Ser Tyr Tyr Val Val Tyr Val Phe Ser Lys Arg Gly Pro
                885                 890                 895

<210> SEQ ID NO 35
<211> LENGTH: 1017
<212> TYPE: DNA
<213> ORGANISM: Artificial
<220> FEATURE:
<223> OTHER INFORMATION: Open-reading frame of the pRR1234L-D12L plasmid

<400> SEQUENCE: 35
```

-continued

```
atgctggaaa tcagagccgc cttcctgcgg cggagaaaca ccgccctgcg gaccagagtg    60
gccgagctga cagcgggt gcagcggctg cggaacatcg tgtcccagta cgagacaaga    120
tacgccccc tgggcggagg caaagaattc gacgagatcg tgaagaacat ccgcgagggc    180
acccacgtgc tgctgccctt ctacgagaca ctgcccgagc tgaacctgtc cctgggcaag    240
tcccccctgc cctccctgga atacggcgcc aactacttcc tgcagatctc cagagtgaac    300
gacctgaacc ggatgcccac cgacatgctg aagctgttca cccacgacat catgctgccc    360
gagtccgacc tggacaaggt gtacgagatt ctgaagatca actccgtgaa gtactacggc    420
cggtccacaa aggctgacgc cgtggtggcc gacctgtctg cccggaacaa gctgttcaag    480
agagagcggg acgccatcaa gtccaacaac cacctgaccg agaacaacct gtacatctcc    540
gactacaaga tgctgacctt cgacgtgttc cggcccctgt cgacttcgt gaacgagaag    600
tactgcatca tcaagctgcc caccctgttc ggcagaggcg tgatcgacac catgcggatc    660
tactgctccc tgttcaagaa cgtgcggctg ctgaagtgcg tgtccgactc ctggctgaag    720
gactccgcca tcatggtggc ctccgacgtg tgcaagaaga acctggacct gttcatgtcc    780
cacgtgaagt ccgtgaccaa gtcatccagc tggaaggacg tgaactccgt gcagttctcc    840
atcctgaaca ccccgtgga caccgagttc atcaacaagt ttctggaatt ttccaaccgg    900
gtgtacgagg ccctgtacta cgtgcactcc ctgctgtact cctccatgac ctccgactcc    960
aagtccatcg agaacaaaca tcagcgacgg ctggtcaagc tgctgctggg gccctga    1017
```

<210> SEQ ID NO 36
<211> LENGTH: 338
<212> TYPE: PRT
<213> ORGANISM: Artificial
<220> FEATURE:
<223> OTHER INFORMATION: Protein sequence encoded by pRR1234L-D12L
    plasmid

<400> SEQUENCE: 36

```
Met Leu Glu Ile Arg Ala Ala Phe Leu Arg Arg Arg Asn Thr Ala Leu
1               5                   10                  15

Arg Thr Arg Val Ala Glu Leu Arg Gln Arg Val Gln Arg Leu Arg Asn
            20                  25                  30

Ile Val Ser Gln Tyr Glu Thr Arg Tyr Gly Pro Leu Gly Gly Gly Lys
        35                  40                  45

Glu Phe Asp Glu Ile Val Lys Asn Ile Arg Glu Gly Thr His Val Leu
    50                  55                  60

Leu Pro Phe Tyr Glu Thr Leu Pro Glu Leu Asn Leu Ser Leu Gly Lys
65                  70                  75                  80

Ser Pro Leu Pro Ser Leu Glu Tyr Gly Ala Asn Tyr Phe Leu Gln Ile
                85                  90                  95

Ser Arg Val Asn Asp Leu Asn Arg Met Pro Thr Asp Met Leu Lys Leu
            100                 105                 110

Phe Thr His Asp Ile Met Leu Pro Glu Ser Asp Leu Asp Lys Val Tyr
        115                 120                 125

Glu Ile Leu Lys Ile Asn Ser Val Lys Tyr Tyr Gly Arg Ser Thr Lys
    130                 135                 140

Ala Asp Ala Val Val Ala Asp Leu Ser Ala Arg Asn Lys Leu Phe Lys
145                 150                 155                 160

Arg Glu Arg Asp Ala Ile Lys Ser Asn Asn His Leu Thr Glu Asn Asn
                165                 170                 175

Leu Tyr Ile Ser Asp Tyr Lys Met Leu Thr Phe Asp Val Phe Arg Pro
```

```
                180                 185                 190
Leu Phe Asp Phe Val Asn Glu Lys Tyr Cys Ile Ile Lys Leu Pro Thr
            195                 200                 205
Leu Phe Gly Arg Gly Val Ile Asp Thr Met Arg Ile Tyr Cys Ser Leu
        210                 215                 220
Phe Lys Asn Val Arg Leu Leu Lys Cys Val Ser Asp Ser Trp Leu Lys
225                 230                 235                 240
Asp Ser Ala Ile Met Val Ala Ser Asp Val Cys Lys Lys Asn Leu Asp
            245                 250                 255
Leu Phe Met Ser His Val Lys Ser Val Thr Lys Ser Ser Ser Trp Lys
        260                 265                 270
Asp Val Asn Ser Val Gln Phe Ser Ile Leu Asn Asn Pro Val Asp Thr
            275                 280                 285
Glu Phe Ile Asn Lys Phe Leu Glu Phe Ser Asn Arg Val Tyr Glu Ala
        290                 295                 300
Leu Tyr Tyr Val His Ser Leu Leu Tyr Ser Ser Met Thr Ser Asp Ser
305                 310                 315                 320
Lys Ser Ile Glu Asn Lys His Gln Arg Arg Leu Val Lys Leu Leu Leu
            325                 330                 335
Gly Pro

<210> SEQ ID NO 37
<211> LENGTH: 2799
<212> TYPE: DNA
<213> ORGANISM: Artificial
<220> FEATURE:
<223> OTHER INFORMATION: Open-reading frame of the pEE1234L-T7RNA
      plasmid

<400> SEQUENCE: 37
atgctggaaa tcgaggccgc cttcctggaa caggaaaaca ccgccctgga aaccgaggtg      60
gccgagctgg aacaggaagt gcagcggctg gaaaacatcg tgtcccagta cgagacaaga     120
tacggccccc tgggcggagg caaactcgag aacaccatca atatcgccaa gaacgacttc     180
agcgacatcg agctggccgc catccctttc aacaccctgg ccgaccacta tggcgagcgg     240
ctggccagag aacagctggc cctggaacac gagagctacg aaatgggcga ggcccggttc     300
cggaagatgt tcgagagaca gctgaaggcc ggcgaggtgg ccgataatgc cgccgctaag     360
cccctgatca ccaccctgct gcccaagatg atcgcccgga tcaacgattg gttcgaggaa     420
gtgaaggcca gcggggcaa gaggcccacc gccttccagt ttctgcagga aatcaagccc     480
gaggccgtgg cctacatcac catcaagacc accctggcct gctgaccag cgccgacaat     540 accaccgtgc aggctgtcgc ttctgccatc ggcagagcca tcgaggacga ggccagattc     600
ggcagaatcc gggacctgga agccaagcac ttcaagaaaa acgtggagga acagctgaac     660
aagcgcgtgg ccacgtgta caagaaagcc ttcatgcagg tggtggaggc cgacatgctg     720
agcaagggcc tgctgggcgg agaagcctgg tccagctggc acaaagagga cagcatccac     780
gtcggcgtgc ggtgcatcga gatgctgatc gagtcgaccg gcatggtgtc cctgcacagg     840
cagaatgccg cgtggtggg ccaggacagc gagacaatcg aactggcccc cgagtatgcc     900
gaggccattg ccacaagagc cggcgctctg gccggcatca gccccatgtt ccagccctgc     960
gtggtgcctc ctaagccctg gacaggcatc acaggcggcg gatactgggc aacggcaga    1020 cgccctctgg ctctggtgcg gacccacagc aagaaagccc tgatgcgcta cgaggacgtg    1080
tacatgcccg aggtgtacaa ggccatcaac attgcccaga acaccgcctg gaagatcaac    1140
```

```
aagaaagtgc tggccgtggc caatgtgatc accaagtgga agcactgccc cgtggaggac   1200
atccccgcca tcgagcggga ggaactgccc atgaagcccg aggacatcga catgaacccc   1260
gaggccctga cagcctggaa aagggccgct gccgccgtgt accggaagga caaggcccgg   1320
aagtcccggc ggatcagcct ggagttcatg ctggaacagg ccaacaagtt cgccaaccac   1380
aaggccattt ggttcccctta acatggac tggcggggca gagtgtacgc cgtgagcatg   1440
ttcaatccac aaggcaacga catgaccaag gggctgctga ccctggccaa gggcaagccc   1500
atcggcaaag agggctacta ctggctgaag atccacggcg ccaactgcgc tggcgtggac   1560
aaggtgccct cccagagcg gatcaagttc atcgaggaaa accacgagaa catcatggcc   1620
tgcgccaaga gccctctaga aaacacttgg tgggccgagc aggacagccc cttctgcttc   1680 ctggcctttct gctttgagta cgccggagtg cagcaccacg gcctgagcta caactgcagc   1740
ctgcccctgg ccttcgatgg cagctgcagc ggcatccagc acttcagcgc catgctgagg   1800
gacgaagtgg gcggcagagc cgtgaatctg ctgccaagcg agacagtgca ggacatctac   1860
gggatcgtgg ccaagaaagt gaacgagatc ctgcaggccg acgccatcaa cggcaccgac   1920
aacgaggtgg tgaccgtgac cgatgagaac accggcgaga tcagcgagaa agtgaagctc   1980
ggcaccaagg ccctggctgg ccagtggctg gcctacggcg tgaccagatc cgtgaccaag   2040
cggagcgtga tgacactggc ctatggcagc aaagagttcg gcttccggca gcaggtgctg   2100
gaagatacca tccagcctgc catcgacagc ggcaaggggc tgatgttcac ccagcccaac   2160
caggccgctg gctacatggc caagctcata tgggagagcg tgtccgtgac agtggtggcc   2220
gccgtggagg ccatgaattg gctgaagtcc gccgccaaac tgctggccgc tgaagtgaag   2280
gacaaaaaga ccggcgaaat cctgcggaag agatgcgccg tgcactgggt gaccccccgat   2340 ggcttccccg tgtggcagga gtacaagaag cccatccaga cccggctgaa cctgatgttc   2400
ctgggccagt tcagactgca gcccaccatc aacaccaaca aggactccga gatcgacgcc   2460
cacaagcagg aaagcggcat tgcccccaac ttcgtgcaca gccaggacgg cagccacctg   2520
agaaagaccg tggtgtgggc tcacgagaag tacggcatcg agagcttcgc cctgatccac   2580
gacagcttcg gcaccattcc cgccgacgcc gccaacctgt tcaaggccgt gcgggagaca   2640
atggtggaca cctacgagag ctgcgacgtg ctggccgact tctacgacca gttcgccgac   2700
cagctgcacg agagccagct ggacaagatg cccgccctgc cgccaaggg gaacctgaac   2760 ctgcgggaca tcctggaaag cgacttcgcc ttcgcctga                          2799
```

<210> SEQ ID NO 38  
<211> LENGTH: 932  
<212> TYPE: PRT  
<213> ORGANISM: Artificial  
<220> FEATURE:  
<223> OTHER INFORMATION: Protein sequence encoded by pEE1234L-T7RNA plasmid

<400> SEQUENCE: 38

```
Met Leu Glu Ile Glu Ala Ala Phe Leu Glu Gln Glu Asn Thr Ala Leu
1               5                   10                  15

Glu Thr Glu Val Ala Glu Leu Glu Gln Glu Val Gln Arg Leu Glu Asn
            20                  25                  30

Ile Val Ser Gln Tyr Glu Thr Arg Tyr Gly Pro Leu Gly Gly Gly Lys
        35                  40                  45

Leu Glu Asn Thr Ile Asn Ile Ala Lys Asn Asp Phe Ser Asp Ile Glu
    50                  55                  60
```

-continued

Leu Ala Ala Ile Pro Phe Asn Thr Leu Ala Asp His Tyr Gly Glu Arg
65                  70                  75                  80

Leu Ala Arg Glu Gln Leu Ala Leu Glu His Glu Ser Tyr Glu Met Gly
                85                  90                  95

Glu Ala Arg Phe Arg Lys Met Phe Glu Arg Gln Leu Lys Ala Gly Glu
            100                 105                 110

Val Ala Asp Asn Ala Ala Lys Pro Leu Ile Thr Thr Leu Leu Pro
            115                 120                 125

Lys Met Ile Ala Arg Ile Asn Asp Trp Phe Glu Val Lys Ala Lys
130                 135                 140

Arg Gly Lys Arg Pro Thr Ala Phe Gln Phe Leu Gln Glu Ile Lys Pro
145                 150                 155                 160

Glu Ala Val Ala Tyr Ile Thr Ile Lys Thr Thr Leu Ala Cys Leu Thr
                165                 170                 175

Ser Ala Asp Asn Thr Thr Val Gln Ala Val Ala Ser Ala Ile Gly Arg
                180                 185                 190

Ala Ile Glu Asp Glu Ala Arg Phe Gly Arg Ile Arg Asp Leu Glu Ala
            195                 200                 205

Lys His Phe Lys Lys Asn Val Glu Glu Gln Leu Asn Lys Arg Val Gly
210                 215                 220

His Val Tyr Lys Lys Ala Phe Met Gln Val Val Glu Ala Asp Met Leu
225                 230                 235                 240

Ser Lys Gly Leu Leu Gly Gly Glu Ala Trp Ser Ser Trp His Lys Glu
                245                 250                 255

Asp Ser Ile His Val Gly Val Arg Cys Ile Glu Met Leu Ile Glu Ser
            260                 265                 270

Thr Gly Met Val Ser Leu His Arg Gln Asn Ala Gly Val Val Gly Gln
            275                 280                 285

Asp Ser Glu Thr Ile Glu Leu Ala Pro Glu Tyr Ala Glu Ala Ile Ala
            290                 295                 300

Thr Arg Ala Gly Ala Leu Ala Gly Ile Ser Pro Met Phe Gln Pro Cys
305                 310                 315                 320

Val Val Pro Pro Lys Pro Trp Thr Gly Ile Thr Gly Gly Gly Tyr Trp
                325                 330                 335

Ala Asn Gly Arg Arg Pro Leu Ala Leu Val Arg Thr His Ser Lys Lys
            340                 345                 350

Ala Leu Met Arg Tyr Glu Asp Val Tyr Met Pro Glu Val Tyr Lys Ala
            355                 360                 365

Ile Asn Ile Ala Gln Asn Thr Ala Trp Lys Ile Asn Lys Lys Val Leu
            370                 375                 380

Ala Val Ala Asn Val Ile Thr Lys Trp Lys His Cys Pro Val Glu Asp
385                 390                 395                 400

Ile Pro Ala Ile Glu Arg Glu Glu Leu Pro Met Lys Pro Glu Asp Ile
                405                 410                 415

Asp Met Asn Pro Glu Ala Leu Thr Ala Trp Lys Arg Ala Ala Ala
            420                 425                 430

Val Tyr Arg Lys Asp Lys Ala Arg Lys Ser Arg Arg Ile Ser Leu Glu
            435                 440                 445

Phe Met Leu Glu Gln Ala Asn Lys Phe Ala Asn His Lys Ala Ile Trp
450                 455                 460

Phe Pro Tyr Asn Met Asp Trp Arg Gly Arg Val Tyr Ala Val Ser Met
465                 470                 475                 480

```
Phe Asn Pro Gln Gly Asn Asp Met Thr Lys Gly Leu Leu Thr Leu Ala
                485                 490                 495
Lys Gly Lys Pro Ile Gly Lys Glu Gly Tyr Tyr Trp Leu Lys Ile His
            500                 505                 510
Gly Ala Asn Cys Ala Gly Val Asp Lys Val Pro Phe Pro Glu Arg Ile
            515                 520                 525
Lys Phe Ile Glu Glu Asn His Glu Asn Ile Met Ala Cys Ala Lys Ser
530                 535                 540
Pro Leu Glu Asn Thr Trp Trp Ala Glu Gln Asp Ser Pro Phe Cys Phe
545                 550                 555                 560
Leu Ala Phe Cys Phe Glu Tyr Ala Gly Val Gln His His Gly Leu Ser
                565                 570                 575
Tyr Asn Cys Ser Leu Pro Leu Ala Phe Asp Gly Ser Cys Ser Gly Ile
            580                 585                 590
Gln His Phe Ser Ala Met Leu Arg Asp Glu Val Gly Gly Arg Ala Val
        595                 600                 605
Asn Leu Leu Pro Ser Glu Thr Val Gln Asp Ile Tyr Gly Ile Val Ala
    610                 615                 620
Lys Lys Val Asn Glu Ile Leu Gln Ala Asp Ala Ile Asn Gly Thr Asp
625                 630                 635                 640
Asn Glu Val Val Thr Val Thr Asp Glu Asn Thr Gly Glu Ile Ser Glu
                645                 650                 655
Lys Val Lys Leu Gly Thr Lys Ala Leu Ala Gly Gln Trp Leu Ala Tyr
            660                 665                 670
Gly Val Thr Arg Ser Val Thr Lys Arg Ser Val Met Thr Leu Ala Tyr
            675                 680                 685
Gly Ser Lys Glu Phe Gly Phe Arg Gln Gln Val Leu Glu Asp Thr Ile
        690                 695                 700
Gln Pro Ala Ile Asp Ser Gly Lys Gly Leu Met Phe Thr Gln Pro Asn
705                 710                 715                 720
Gln Ala Ala Gly Tyr Met Ala Lys Leu Ile Trp Glu Ser Val Ser Val
                725                 730                 735
Thr Val Val Ala Ala Val Glu Ala Met Asn Trp Leu Lys Ser Ala Ala
                740                 745                 750
Lys Leu Leu Ala Ala Glu Val Lys Asp Lys Thr Gly Glu Ile Leu
            755                 760                 765
Arg Lys Arg Cys Ala Val His Trp Val Thr Pro Asp Gly Phe Pro Val
            770                 775                 780
Trp Gln Glu Tyr Lys Lys Pro Ile Gln Thr Arg Leu Asn Leu Met Phe
785                 790                 795                 800
Leu Gly Gln Phe Arg Leu Gln Pro Thr Ile Asn Thr Asn Lys Asp Ser
                805                 810                 815
Glu Ile Asp Ala His Lys Gln Glu Ser Gly Ile Ala Pro Asn Phe Val
            820                 825                 830
His Ser Gln Asp Gly Ser His Leu Arg Lys Thr Val Val Trp Ala His
        835                 840                 845
Glu Lys Tyr Gly Ile Glu Ser Phe Ala Leu Ile His Asp Ser Phe Gly
    850                 855                 860
Thr Ile Pro Ala Asp Ala Ala Asn Leu Phe Lys Ala Val Arg Glu Thr
865                 870                 875                 880
Met Val Asp Thr Tyr Glu Ser Cys Asp Val Leu Ala Asp Phe Tyr Asp
                885                 890                 895
Gln Phe Ala Asp Gln Leu His Glu Ser Gln Leu Asp Lys Met Pro Ala
```

```
                900           905           910
Leu Pro Ala Lys Gly Asn Leu Asn Leu Arg Asp Ile Leu Glu Ser Asp
        915           920           925

Phe Ala Phe Ala
    930

<210> SEQ ID NO 39
<211> LENGTH: 5259
<212> TYPE: DNA
<213> ORGANISM: Artificial
<220> FEATURE:
<223> OTHER INFORMATION: Open-reading frame of the pD1R-T7RNAP plasmid

<400> SEQUENCE: 39
atggaattcg acgccaacgt ggtgtcctcc tccacaatcg ccacctacat cgacgccctg      60
gccaagaacg cctccgagct ggaacagcgg tccaccgcct acgagatcaa caatgagctg     120
gaactggtgt tcatcaagcc cccctgatc accctgacca acgtggtcaa catcagcacc      180
atccaggaat ccttcatccg gttcaccgtg accaacaaag aaggcgtgaa gatccggacc     240
aagatccccc tgtccaaggt gcacggcctg gacgtgaaga acgtgcagct ggtggacgcc     300
atcgacaaca tcgtgtggga agaagagtcc ctggtcaccg agaaccggct gcacaaagag     360
tgcctgctgc ggctgtccac cgaggaacgg cacatctttc tggactacaa gaagtacggc     420
tcctccatca gactggaact ggtcaacctg atccaggcca agaccaagaa cttcaccatc     480
gacttcaagc tgaagtactt cctgggctct ggcgcccagt ccaagtcctc tctgctgcac     540
gccatcaacc accccaagtc ccggcccaac acctccctgg aaatcgagtt caccccctcgg    600 gacaacgaga cagtgcccta cgacgagctg atcaagagc tgaccaccct gtccagacac     660
atcttcatgg cctcccccga aacgtgatc ctgtcccccc ccatcaacgc ccccatcaag      720
accttcatgc tgcccaagca ggacatcgtg gcctggacc tggaaaacct gtacgccgtg      780
accaagaccg acggcatccc catcaccatc agagtgacct ccaacggcct gtactgctac    840
ttcacccacc tgggctacat catcagatac cccgtgaagc ggatcatcga ctccgaggtg     900
gtggtgttcg cgaggccgt gaaggacaag aactggaccg tgtacctgat caagctgatc      960
gagcccgtga acgccatcaa tgaccggctg gaagagtcca atacgtgga atccaagctg     1020 gtggatatct cgaccggat cgtgttcaag tctaagaagt acgagggacc cttcactaca    1080
acttcagagg tggtcgacat gctgtccacc tacctgccta agcagcccga gggcgtcatc    1140
ctgttctact ccaagggacc caagtccaac atcgatttca agatcaagaa agagaacacc    1200
atcgaccaga ccgccaatgt ggtgttccgg tacatgtcct ccgagcccat catcttcggc    1260
gagtcctcca tcttcgtcga gtacaagaag ttctccaacg acaagggctt ccccaaagag    1320
tacggcagcg gcaagatcgt gctgtacaac ggcgtgaact acctgaacaa catctactgc    1380
ctggagtaca tcaacacccca caacgaagtg gcatcaagt ccgtggtggt gcccatcaag    1440
tttatcgccg agttcctggt caacggcgag atcctgaagc cccggatcga caagaccatg    1500
aagtacatca attccgagga ctactacggc aaccagcaca acatcatcgt ggaacacctg    1560
agggaccagt ccatcaagat cggcgacatc ttcaacgagg acaagctgtc cgacgtgggc    1620
caccagtacg ccaacaacga caagttccgg ctgaacccgg aggtgtccta cttcaccaac    1680
aagagaaccc gaggcccact gggcatcctg tccaactacg tgaaaaccct gctgatctcc    1740
atgtactgct ccaagacctt cctggacgac tccaacaagc ggaaggtgct ggccatcgat    1800
ttcggcaacg gcgccgatct ggaaaagtac ttctatggcg agatcgccct gctggtggct    1860
```

```
accgaccctg acgccgacgc tatcgccaga ggcaacgagc ggtacaacaa gctgaactcc   1920
ggcatcaaga ccaagtacta caagttcgac tacatccagg aaaccatccg ctccgacacc   1980
ttcgtgtcct ccgtgcgcga ggtgttctat ttcggcaagt tcaatatcat cgactggcag   2040
ttcgccatcc actacagctt ccaccccggg cactacgcca ccgtgatgaa caacctgtcc   2100
gagctgaccg cctccggcgg caaggtgctg atcaccacca tggacggcga caagctgagc   2160
aagctgaccg acaagaaaac cttcatcatc cacaagaacc tgccctccag cgagaactac   2220
atgtccgtgg aaaagatcgc cgacgacaga atcgtggtgt acaatcccta ccaccatgtcc  2280
accccatga ccgagtacat catcaagaag aacgacatcg tccgggtgtt caacgagtac   2340
ggcttcgtgc tggtggacaa cgtggacttc gccaccatca tcgagcggtc caaaaagttc   2400
atcaatggag ccagcaccat ggaagatcgg ccctctaccc ggaacttctt cgagctgaac   2460
agaggcgcca tcaagtgcga gggcctggat gtggaagatc tgctgagcta ctacgtggtg   2520
tacgtgttct ccaagagagg gcccggcgga ggcggaagtg gaggcggagg aagcggaggg   2580
ggaggatctg gcggcggagg cagcctcgag aacaccatca atatcgccaa gaacgacttc   2640
agcgacatcg agctggccgc catcccttc aacaccctgg ccgaccacta tggcgagcgg   2700
ctggccagag aacagctggc cctggaacac gagagctacg aaatgggcga ggcccggttc   2760
cggaagatgt tcgagagaca gctgaaggcc ggcgaggtgg ccgataatgc cgccgctaag   2820
cccctgatca ccaccctgct gcccaagatg atcgcccgga tcaacgattg gttcgaggaa   2880
gtgaaggcca gcggggcaa gaggcccacc gccttccagt ttctgcagga aatcaagccc   2940
gaggccgtgg cctacatcac catcaagacc accctggcct gcctgaccag cgccgacaat   3000
accaccgtgc aggctgtcgc ttctgccatc ggcagagcca tcgaggacga ggccagattc   3060
ggcagaatcc gggacctgga agccaagcac ttcaagaaaa acgtggagga acagctgaac   3120
aagcgcgtgg ccacgtgta caagaaagcc ttcatgcagg tggtggaggc cgacatgctg   3180
agcaagggcc tgctgggcgg agaagcctgg tccagctggc acaaagagga cagcatccac   3240
gtcggcgtgc ggtgcatcga gatgctgatc gagtcgaccg gcatggtgtc cctgcacagg   3300
cagaatgccg gcgtggtggg ccaggacagc gagacaatcg aactggcccc cgagtatgcc   3360
gaggccattg ccacaagagc cggcgctctg gccggcatca gccccatgtt ccagccctgc   3420
gtggtgcctc ctaagccctg acaggcatc acaggcggcg gatactgggc caacggcaga   3480
cgccctctgg ctctggtgcg gacccacagc aagaaagccc tgatgcgcta cgaggacgtg   3540
tacatgcccg aggtgtacaa ggccatcaac attgcccaga acaccgcctg gaagatcaac   3600
aagaaagtgc tggccgtggc caatgtgatc accaagtgga agcactgccc cgtggaggac   3660
atccccgcca tcgagcggga ggaactgccc atgaagcccg aggacatcga catgaacccc   3720
gaggccctga cagcctggaa aagggccgct gccgccgtgt accggaagga caaggcccgg   3780
aagtcccggc ggatcagcct ggagttcatg ctggaacagg ccaacaagtt cgccaaccac   3840
aaggccattt ggttcccttac aacatggac tggcggggca gagtgtacgc cgtgagcatg   3900
ttcaatccac aaggcaacga catgaccaag gggctgctga ccctggccaa gggcaagccc   3960
atcggcaaag agggctacta ctggctgaag atccacggcg ccaactgcgc tggcgtggac   4020
aaggtgccct tcccagagcg gatcaagttc atcgaggaaa accacgagaa catcatggcc   4080
tgcgccaaga gccctctaga aaacacttgg tgggccgagc aggacagccc cttctgcttc   4140
ctggccttct gctttgagta cgccggagtg cagcaccacg gcctgagcta caactgcagc   4200
```

-continued

```
ctgcccctgg ccttcgatgg cagctgcagc ggcatccagc acttcagcgc catgctgagg    4260
gacgaagtgg gcggcagagc cgtgaatctg ctgccaagcg agacagtgca ggacatctac    4320
gggatcgtgg ccaagaaagt gaacgagatc ctgcaggccg acgccatcaa cggcaccgac    4380
aacgaggtgt tgaccgtgac cgatgagaac accggcgaga tcagcgagaa agtgaagctc    4440
ggcaccaagg ccctggctgg ccagtggctg gcctacggcg tgaccagatc cgtgaccaag    4500
cggagcgtga tgcactggc ctatggcagc aaagagttcg gcttccggca gcaggtgctg    4560
gaagatacca tccagcctgc catcgacagc ggcaaggggc tgatgttcac ccagcccaac    4620
caggccgctg gctacatggc caagctcata tgggagagcg tgtccgtgac agtggtggcc    4680
gccgtggagg ccatgaattg gctgaagtcc gccgccaaac tgctggccgc tgaagtgaag    4740
gacaaaaaga ccggcgaaat cctgcggaag agatgcgccg tgcactgggt gaccccgat   4800 ggcttccccg tgtggcagga gtacaagaag cccatccaga cccggctgaa cctgatgttc    4860
ctgggccagt tcagactgca gcccaccatc aacaccaaca aggactccga gatcgacgcc    4920
cacaagcagg aaagcggcat tgccccccaac ttcgtgcaca gccaggacgg cagccacctg    4980
agaaagaccg tggtgtgggc tcacgagaag tacggcatcg agagcttcgc cctgatccac    5040
gacagcttcg gcaccattcc cgccgacgcc gccaacctgt tcaaggccgt gcgggagaca    5100
atggtggaca cctacgagag ctgcgacgtg ctggccgact tctacgacca gttcgccgac    5160 cagctgcacag agaccagct ggacaagatg cccgccctgc cgccaaggg gaacctgaac    5220 ctgcgggaca tcctggaaag cgacttcgcc ttcgcctga                          5259
```

<210> SEQ ID NO 40
<211> LENGTH: 1752
<212> TYPE: PRT
<213> ORGANISM: Artificial
<220> FEATURE:
<223> OTHER INFORMATION: Protein sequence encoded by pD1R-T7RNAP plasmid

<400> SEQUENCE: 40

```
Met Glu Phe Asp Ala Asn Val Val Ser Ser Thr Ile Ala Thr Tyr
1               5                   10                  15

Ile Asp Ala Leu Ala Lys Asn Ala Ser Glu Leu Glu Gln Arg Ser Thr
            20                  25                  30

Ala Tyr Glu Ile Asn Asn Glu Leu Glu Leu Val Phe Ile Lys Pro Pro
        35                  40                  45

Leu Ile Thr Leu Thr Asn Val Val Asn Ile Ser Thr Ile Gln Glu Ser
    50                  55                  60

Phe Ile Arg Phe Thr Val Thr Asn Lys Glu Gly Val Lys Ile Arg Thr
65                  70                  75                  80

Lys Ile Pro Leu Ser Lys Val His Gly Leu Asp Val Lys Asn Val Gln
                85                  90                  95

Leu Val Asp Ala Ile Asp Asn Ile Val Trp Glu Lys Lys Ser Leu Val
            100                 105                 110

Thr Glu Asn Arg Leu His Lys Glu Cys Leu Leu Arg Leu Ser Thr Glu
        115                 120                 125

Glu Arg His Ile Phe Leu Asp Tyr Lys Lys Tyr Gly Ser Ser Ile Arg
    130                 135                 140

Leu Glu Leu Val Asn Leu Ile Gln Ala Lys Thr Lys Asn Phe Thr Ile
145                 150                 155                 160

Asp Phe Lys Leu Lys Tyr Phe Leu Gly Ser Gly Ala Gln Ser Lys Ser
                165                 170                 175
```

-continued

```
Ser Leu Leu His Ala Ile Asn His Pro Lys Ser Arg Pro Asn Thr Ser
            180                 185                 190
Leu Glu Ile Glu Phe Thr Pro Arg Asp Asn Glu Thr Val Pro Tyr Asp
        195                 200                 205
Glu Leu Ile Lys Glu Leu Thr Thr Leu Ser Arg His Ile Phe Met Ala
    210                 215                 220
Ser Pro Glu Asn Val Ile Leu Ser Pro Ile Asn Ala Pro Ile Lys
225                 230                 235                 240
Thr Phe Met Leu Pro Lys Gln Asp Ile Val Gly Leu Asp Leu Glu Asn
                245                 250                 255
Leu Tyr Ala Val Thr Lys Thr Asp Gly Ile Pro Ile Thr Ile Arg Val
            260                 265                 270
Thr Ser Asn Gly Leu Tyr Cys Tyr Phe Thr His Leu Gly Tyr Ile Ile
        275                 280                 285
Arg Tyr Pro Val Lys Arg Ile Ile Asp Ser Glu Val Val Phe Gly
    290                 295                 300
Glu Ala Val Lys Asp Lys Asn Trp Thr Val Tyr Leu Ile Lys Leu Ile
305                 310                 315                 320
Glu Pro Val Asn Ala Ile Asn Asp Arg Leu Glu Glu Ser Lys Tyr Val
                325                 330                 335
Glu Ser Lys Leu Val Asp Ile Cys Asp Arg Ile Val Phe Lys Ser Lys
            340                 345                 350
Lys Tyr Glu Gly Pro Phe Thr Thr Thr Ser Glu Val Val Asp Met Leu
        355                 360                 365
Ser Thr Tyr Leu Pro Lys Gln Pro Glu Gly Val Ile Leu Phe Tyr Ser
    370                 375                 380
Lys Gly Pro Lys Ser Asn Ile Asp Phe Lys Ile Lys Lys Glu Asn Thr
385                 390                 395                 400
Ile Asp Gln Thr Ala Asn Val Val Phe Arg Tyr Met Ser Ser Glu Pro
                405                 410                 415
Ile Ile Phe Gly Glu Ser Ser Ile Phe Val Glu Tyr Lys Lys Phe Ser
            420                 425                 430
Asn Asp Lys Gly Phe Pro Lys Glu Tyr Gly Ser Gly Lys Ile Val Leu
        435                 440                 445
Tyr Asn Gly Val Asn Tyr Leu Asn Asn Ile Tyr Cys Leu Glu Tyr Ile
    450                 455                 460
Asn Thr His Asn Glu Val Gly Ile Lys Ser Val Val Pro Ile Lys
465                 470                 475                 480
Phe Ile Ala Glu Phe Leu Val Asn Gly Glu Ile Leu Lys Pro Arg Ile
                485                 490                 495
Asp Lys Thr Met Lys Tyr Ile Asn Ser Glu Asp Tyr Tyr Gly Asn Gln
            500                 505                 510
His Asn Ile Ile Val Glu His Leu Arg Asp Gln Ser Ile Lys Ile Gly
        515                 520                 525
Asp Ile Phe Asn Glu Asp Lys Leu Ser Asp Val Gly His Gln Tyr Ala
    530                 535                 540
Asn Asn Asp Lys Phe Arg Leu Asn Pro Glu Val Ser Tyr Phe Thr Asn
545                 550                 555                 560
Lys Arg Thr Arg Gly Pro Leu Gly Ile Leu Ser Asn Tyr Val Lys Thr
                565                 570                 575
Leu Leu Ile Ser Met Tyr Cys Ser Lys Thr Phe Leu Asp Asp Ser Asn
            580                 585                 590
Lys Arg Lys Val Leu Ala Ile Asp Phe Gly Asn Gly Ala Asp Leu Glu
```

-continued

```
            595                 600                 605
Lys Tyr Phe Tyr Gly Glu Ile Ala Leu Leu Val Ala Thr Asp Pro Asp
610                 615                 620

Ala Asp Ala Ile Ala Arg Gly Asn Glu Arg Tyr Asn Lys Leu Asn Ser
625                 630                 635                 640

Gly Ile Lys Thr Lys Tyr Tyr Lys Phe Asp Tyr Ile Gln Glu Thr Ile
                    645                 650                 655

Arg Ser Asp Thr Phe Val Ser Ser Val Arg Glu Val Phe Tyr Phe Gly
                660                 665                 670

Lys Phe Asn Ile Ile Asp Trp Gln Phe Ala Ile His Tyr Ser Phe His
            675                 680                 685

Pro Arg His Tyr Ala Thr Val Met Asn Asn Leu Ser Glu Leu Thr Ala
        690                 695                 700

Ser Gly Gly Lys Val Leu Ile Thr Thr Met Asp Gly Asp Lys Leu Ser
705                 710                 715                 720

Lys Leu Thr Asp Lys Lys Thr Phe Ile Ile His Lys Asn Leu Pro Ser
                725                 730                 735

Ser Glu Asn Tyr Met Ser Val Glu Lys Ile Ala Asp Arg Ile Val
                740                 745                 750

Val Tyr Asn Pro Ser Thr Met Ser Thr Pro Met Thr Glu Tyr Ile Ile
            755                 760                 765

Lys Lys Asn Asp Ile Val Arg Val Phe Asn Glu Tyr Gly Phe Val Leu
770                 775                 780

Val Asp Asn Val Asp Phe Ala Thr Ile Ile Glu Arg Ser Lys Lys Phe
785                 790                 795                 800

Ile Asn Gly Ala Ser Thr Met Glu Asp Arg Pro Ser Thr Arg Asn Phe
                805                 810                 815

Phe Glu Leu Asn Arg Gly Ala Ile Lys Cys Glu Gly Leu Asp Val Glu
                820                 825                 830

Asp Leu Leu Ser Tyr Tyr Val Val Tyr Val Phe Ser Lys Arg Gly Pro
            835                 840                 845

Gly Gly Gly Gly Ser Gly Gly Gly Ser Gly Gly Gly Ser Gly
850                 855                 860

Gly Gly Gly Ser Leu Glu Asn Thr Ile Asn Ile Ala Lys Asn Asp Phe
865                 870                 875                 880

Ser Asp Ile Glu Leu Ala Ala Ile Pro Phe Asn Thr Leu Ala Asp His
                885                 890                 895

Tyr Gly Glu Arg Leu Ala Arg Glu Gln Leu Ala Leu Glu His Glu Ser
            900                 905                 910

Tyr Glu Met Gly Glu Ala Arg Phe Arg Lys Met Phe Glu Arg Gln Leu
        915                 920                 925

Lys Ala Gly Glu Val Ala Asp Asn Ala Ala Ala Lys Pro Leu Ile Thr
    930                 935                 940

Thr Leu Leu Pro Lys Met Ile Ala Arg Ile Asn Asp Trp Phe Glu Glu
945                 950                 955                 960

Val Lys Ala Lys Arg Gly Lys Arg Pro Thr Ala Phe Gln Phe Leu Gln
                965                 970                 975

Glu Ile Lys Pro Glu Ala Val Ala Tyr Ile Thr Ile Lys Thr Thr Leu
            980                 985                 990

Ala Cys Leu Thr Ser Ala Asp Asn  Thr Thr Val Gln Ala  Val Ala Ser
        995                 1000                 1005

Ala Ile  Gly Arg Ala Ile Glu  Asp Glu Ala Arg Phe  Gly Arg Ile
    1010                 1015                 1020
```

```
Arg Asp Leu Glu Ala Lys His Phe Lys Asn Val Glu Glu Gln
    1025            1030            1035

Leu Asn Lys Arg Val Gly His Val Tyr Lys Lys Ala Phe Met Gln
    1040            1045            1050

Val Val Glu Ala Asp Met Leu Ser Lys Gly Leu Leu Gly Gly Glu
    1055            1060            1065

Ala Trp Ser Ser Trp His Lys Glu Asp Ser Ile His Val Gly Val
    1070            1075            1080

Arg Cys Ile Glu Met Leu Ile Glu Ser Thr Gly Met Val Ser Leu
    1085            1090            1095

His Arg Gln Asn Ala Gly Val Val Gly Gln Asp Ser Glu Thr Ile
    1100            1105            1110

Glu Leu Ala Pro Glu Tyr Ala Glu Ala Ile Ala Thr Arg Ala Gly
    1115            1120            1125

Ala Leu Ala Gly Ile Ser Pro Met Phe Gln Pro Cys Val Val Pro
    1130            1135            1140

Pro Lys Pro Trp Thr Gly Ile Thr Gly Gly Gly Tyr Trp Ala Asn
    1145            1150            1155

Gly Arg Arg Pro Leu Ala Leu Val Arg Thr His Ser Lys Lys Ala
    1160            1165            1170

Leu Met Arg Tyr Glu Asp Val Tyr Met Pro Glu Val Tyr Lys Ala
    1175            1180            1185

Ile Asn Ile Ala Gln Asn Thr Ala Trp Lys Ile Asn Lys Lys Val
    1190            1195            1200

Leu Ala Val Ala Asn Val Ile Thr Lys Trp Lys His Cys Pro Val
    1205            1210            1215

Glu Asp Ile Pro Ala Ile Glu Arg Glu Glu Leu Pro Met Lys Pro
    1220            1225            1230

Glu Asp Ile Asp Met Asn Pro Glu Ala Leu Thr Ala Trp Lys Arg
    1235            1240            1245

Ala Ala Ala Ala Val Tyr Arg Lys Asp Lys Ala Arg Lys Ser Arg
    1250            1255            1260

Arg Ile Ser Leu Glu Phe Met Leu Glu Gln Ala Asn Lys Phe Ala
    1265            1270            1275

Asn His Lys Ala Ile Trp Phe Pro Tyr Asn Met Asp Trp Arg Gly
    1280            1285            1290

Arg Val Tyr Ala Val Ser Met Phe Asn Pro Gln Gly Asn Asp Met
    1295            1300            1305

Thr Lys Gly Leu Leu Thr Leu Ala Lys Gly Lys Pro Ile Gly Lys
    1310            1315            1320

Glu Gly Tyr Tyr Trp Leu Lys Ile His Gly Ala Asn Cys Ala Gly
    1325            1330            1335

Val Asp Lys Val Pro Phe Pro Glu Arg Ile Lys Phe Ile Glu Glu
    1340            1345            1350

Asn His Glu Asn Ile Met Ala Cys Ala Lys Ser Pro Leu Glu Asn
    1355            1360            1365

Thr Trp Trp Ala Glu Gln Asp Ser Pro Phe Cys Phe Leu Ala Phe
    1370            1375            1380

Cys Phe Glu Tyr Ala Gly Val Gln His His Gly Leu Ser Tyr Asn
    1385            1390            1395

Cys Ser Leu Pro Leu Ala Phe Asp Gly Ser Cys Ser Gly Ile Gln
    1400            1405            1410
```

```
His Phe Ser Ala Met Leu Arg Asp Glu Val Gly Gly Arg Ala Val
1415                1420                1425

Asn Leu Leu Pro Ser Glu Thr Val Gln Asp Ile Tyr Gly Ile Val
    1430                1435                1440

Ala Lys Lys Val Asn Glu Ile Leu Gln Ala Asp Ala Ile Asn Gly
1445                1450                1455

Thr Asp Asn Glu Val Val Thr Val Thr Asp Glu Asn Thr Gly Glu
1460                1465                1470

Ile Ser Glu Lys Val Lys Leu Gly Thr Lys Ala Leu Ala Gly Gln
1475                1480                1485

Trp Leu Ala Tyr Gly Val Thr Arg Ser Val Thr Lys Arg Ser Val
    1490                1495                1500

Met Thr Leu Ala Tyr Gly Ser Lys Glu Phe Gly Phe Arg Gln Gln
1505                1510                1515

Val Leu Glu Asp Thr Ile Gln Pro Ala Ile Asp Ser Gly Lys Gly
1520                1525                1530

Leu Met Phe Thr Gln Pro Asn Gln Ala Ala Gly Tyr Met Ala Lys
1535                1540                1545

Leu Ile Trp Glu Ser Val Ser Val Thr Val Val Ala Ala Val Glu
1550                1555                1560

Ala Met Asn Trp Leu Lys Ser Ala Ala Lys Leu Leu Ala Ala Glu
1565                1570                1575

Val Lys Asp Lys Lys Thr Gly Glu Ile Leu Arg Lys Arg Cys Ala
1580                1585                1590

Val His Trp Val Thr Pro Asp Gly Phe Pro Val Trp Gln Glu Tyr
1595                1600                1605

Lys Lys Pro Ile Gln Thr Arg Leu Asn Leu Met Phe Leu Gly Gln
1610                1615                1620

Phe Arg Leu Gln Pro Thr Ile Asn Thr Asn Lys Asp Ser Glu Ile
1625                1630                1635

Asp Ala His Lys Gln Glu Ser Gly Ile Ala Pro Asn Phe Val His
1640                1645                1650

Ser Gln Asp Gly Ser His Leu Arg Lys Thr Val Val Trp Ala His
1655                1660                1665

Glu Lys Tyr Gly Ile Glu Ser Phe Ala Leu Ile His Asp Ser Phe
1670                1675                1680

Gly Thr Ile Pro Ala Asp Ala Ala Asn Leu Phe Lys Ala Val Arg
1685                1690                1695

Glu Thr Met Val Asp Thr Tyr Glu Ser Cys Asp Val Leu Ala Asp
1700                1705                1710

Phe Tyr Asp Gln Phe Ala Asp Gln Leu His Glu Ser Gln Leu Asp
1715                1720                1725

Lys Met Pro Ala Leu Pro Ala Lys Gly Asn Leu Asn Leu Arg Asp
1730                1735                1740

Ile Leu Glu Ser Asp Phe Ala Phe Ala
1745                1750

<210> SEQ ID NO 41
<211> LENGTH: 3588
<212> TYPE: DNA
<213> ORGANISM: Artificial
<220> FEATURE:
<223> OTHER INFORMATION: Open-reading frame of the pD12L-T7RNAP plasmid

<400> SEQUENCE: 41
```

```
atggaattcg acgagatcgt gaagaacatc cgcgagggca cccacgtgct gctgcccttc    60
tacgagacac tgcccgagct gaacctgtcc ctgggcaagt ccccccctgcc ctccctggaa   120
tacggcgcca actacttcct gcagatctcc agagtgaacg acctgaaccg gatgcccacc   180
gacatgctga agctgttcac ccacgacatc atgctgcccg agtccgacct ggacaaggtg   240
tacgagattc tgaagatcaa ctccgtgaag tactacggcc ggtccacaaa ggctgacgcc   300
gtggtggccg acctgtctgc ccggaacaag ctgttcaaga gagagcggga cgccatcaag   360
tccaacaacc acctgaccga gaacaacctg tacatctccg actacaagat gctgaccttc   420
gacgtgttcc ggcccctgtt cgacttcgtg aacgagaagt actgcatcat caagctgccc   480
accctgttcg gcagaggcgt gatcgacacc atgcggatct actgctccct gttcaagaac   540
gtgcggctgc tgaagtgcgt gtccgactcc tggctgaagg actccgccat catggtggcc   600
tccgacgtgt gcaagaagaa cctggacctg ttcatgtccc acgtgaagtc cgtgaccaag   660
tcatccagct ggaaggacgt gaactccgtg cagttctcca tcctgaacaa ccccgtggac   720
accgagttca tcaacaagtt tctggaattt tccaaccggg tgtacgaggc cctgtactac   780
gtgcactccc tgctgtactc ctccatgacc tccgactcca gtccatcga gaacaaacat    840
cagcgacggc tggtcaagct gctgctgggg cccggcggag gcgaagtgg aggcggagga    900
agcggagggg gaggatctgg cggcggaggc agcctcgaga caccatcaa tatcgccaag   960
aacgacttca gcgacatcga gctggccgcc atccctttca cacccctggc cgaccactat  1020
ggcgagcggc tggccagaga acagctggcc ctggaacacg agagctacga aatgggcgag  1080
gcccggttcc ggaagatgtt cgagagacag ctgaaggccg cgaggtggc cgataatgcc  1140
gccgctaagc ccctgatcac caccctgctg cccaagatga tcgcccggat caacgattgg  1200
ttcgaggaag tgaaggccaa gcggggcaag aggcccaccg ccttccagtt tctgcaggaa  1260
atcaagcccg aggccgtggc ctacatcacc atcaagacca cctggcctg cctgaccagc  1320
gccgacaata ccaccgtgca ggctgtcgct tctgccatcg gcagagccat cgaggacgag  1380
gccagattcg gcagaatccg ggacctggaa gccaagcact tcaagaaaaa cgtggaggaa  1440
cagctgaaca gcgcgtggg ccacgtgtac aagaaagcct tcatgcaggt ggtggaggcc  1500
gacatgctga gcaagggcct gctgggcgga gaagcctggt ccagctggca caaagaggac  1560
agcatccacg tcggcgtgcg gtgcatcgag atgctgatcg agtcgaccgg catggtgtcc  1620
ctgcacaggc agaatgccgg cgtggtgggc caggacagcg agacaatcga actggccccc  1680
gagtatgccg aggccattgc cacaagagcc ggcgctctgg ccggcatcag ccccatgttc  1740
cagccctgcg tggtgcctcc taagccctgg acaggcatca caggcggcgg atactgggcc  1800
aacggcagac gccctctggc tctggtgcgg acccacagca gaaaagccct gatgcgctac  1860
gaggacgtgt acatgcccga ggtgtacaag gccatcaaca ttgcccagaa caccgcctgg  1920
aagatcaaca gaaagtgct ggccgtggcc aatgtgatca ccaagtggaa gcactgccc   1980
gtggaggaca tccccgccat cgagcgggag gaactgccca tgaagcccga ggacatcgac  2040
atgaaccccg aggccctgac agcctggaaa agggccgctg ccgccgtgta ccggaaggac  2100
aaggcccgga gtccggcg gatcagcctg gagttcatgc tggaacaggc caacaagttc  2160
gccaaccaca aggccatttg gttccccttac aacatggact ggcggggcag agtgtacgcc  2220
gtgagcatgt tcaatccaca aggcaacgac atgaccaagg gctgctgac cctggccaag  2280
ggcaagccca tcggcaaaga gggctactac tggctgaaga tccacggcgc caactgcgct  2340
ggcgtggaca aggtgcccctt cccagagcgg atcagttca tcgaggaaaa ccacgagaac  2400
```

```
atcatggcct gcgccaagag ccctctagaa aacacttggt gggccgagca ggacagcccc    2460
ttctgcttcc tggccttctg ctttgagtac gccggagtgc agcaccacgg cctgagctac    2520
aactgcagcc tgcccctggc cttcgatggc agctgcagcg catccagca cttcagcgcc    2580 atgctgaggg acgaagtggg cggcagagcc gtgaatctgc tgccaagcga acagtgcag    2640 gacatctacg ggatcgtggc caagaaagtg aacgagatcc tgcaggccga cgccatcaac    2700
ggcaccgaca acgaggtggt gaccgtgacc gatgagaaca ccggcgagat cagcgagaaa    2760
gtgaagctcg gcaccaaggc cctggctggc cagtggctgg cctacggcgt gaccagatcc    2820
gtgaccaagc ggagcgtgat gacactggcc tatggcagca agagttcgg cttccggcag    2880 caggtgctgg aagataccat ccagcctgcc atcgacagcg gcaaggggct gatgttcacc    2940
cagcccaacc aggccgctgg ctacatggcc aagctcatat gggagagcgt gtccgtgaca    3000
gtggtggccg ccgtggaggc catgaattgg ctgaagtccg ccgccaaact gctggccgct    3060
gaagtgaagg acaaaaagac cggcgaaatc ctgcggaaga gatgcgccgt gcactgggtg    3120 accccccgatg gcttccccgt gtggcaggag tacaagaagc ccatccagac ccggctgaac    3180
ctgatgttcc tgggccagtt cagactgcag cccaccatca acaccaacaa ggactccgag    3240
atcgacgccc acaagcagga aagcggcatt gccccccaact tcgtgcacag ccaggacggc    3300
agccacctga aaagaccgt ggtgtgggct cacgagaagt acggcatcga gagcttcgcc    3360
ctgatccacg acagcttcgg caccattccc gccgacgccg ccaacctgtt caaggccgtg    3420
cgggagacaa tggtggacac ctacgagagc tgcgacgtgc tggccgactt ctacgaccag    3480
ttcgccgacc agctgcacga gagccagctg gacaagatgc ccgccctgcc cgccaagggg    3540
aacctgaacc tgcgggacat cctggaaagc gacttcgcct cgcctga                 3588
```

<210> SEQ ID NO 42
<211> LENGTH: 1195
<212> TYPE: PRT
<213> ORGANISM: Artificial
<220> FEATURE:
<223> OTHER INFORMATION: Protein sequence encoded by pD12L-T7RNAP
      plasmid

<400> SEQUENCE: 42

| Met | Glu | Phe | Asp | Glu | Ile | Val | Lys | Asn | Ile | Arg | Glu | Gly | Thr | His | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Leu | Pro | Phe | Tyr | Glu | Thr | Leu | Pro | Glu | Leu | Asn | Leu | Ser | Leu | Gly |
|     |     |     | 20  |     |     |     |     | 25  |     |     |     |     | 30  |     |     |

| Lys | Ser | Pro | Leu | Pro | Ser | Leu | Glu | Tyr | Gly | Ala | Asn | Tyr | Phe | Leu | Gln |
|     |     | 35  |     |     |     |     | 40  |     |     |     |     | 45  |     |     |     |

| Ile | Ser | Arg | Val | Asn | Asp | Leu | Asn | Arg | Met | Pro | Thr | Asp | Met | Leu | Lys |
| 50  |     |     |     |     | 55  |     |     |     |     | 60  |     |     |     |     |     |

| Leu | Phe | Thr | His | Asp | Ile | Met | Leu | Pro | Glu | Ser | Asp | Leu | Asp | Lys | Val |
| 65  |     |     |     |     | 70  |     |     |     |     | 75  |     |     |     |     | 80  |

| Tyr | Glu | Ile | Leu | Lys | Ile | Asn | Ser | Val | Lys | Tyr | Gly | Arg | Ser | Thr |
|     |     |     |     | 85  |     |     |     |     | 90  |     |     |     |     | 95  |

| Lys | Ala | Asp | Ala | Val | Val | Ala | Asp | Leu | Ser | Ala | Arg | Asn | Lys | Leu | Phe |
|     |     |     | 100 |     |     |     |     | 105 |     |     |     |     | 110 |     |     |

| Lys | Arg | Glu | Arg | Asp | Ala | Ile | Lys | Ser | Asn | Asn | His | Leu | Thr | Glu | Asn |
|     |     |     | 115 |     |     |     |     | 120 |     |     |     |     | 125 |     |     |

| Asn | Leu | Tyr | Ile | Ser | Asp | Tyr | Lys | Met | Leu | Thr | Phe | Asp | Val | Phe | Arg |
|     |     | 130 |     |     |     |     | 135 |     |     |     |     | 140 |     |     |     |

```
Pro Leu Phe Asp Phe Val Asn Glu Lys Tyr Cys Ile Ile Lys Leu Pro
145                 150                 155                 160

Thr Leu Phe Gly Arg Gly Val Ile Asp Thr Met Arg Ile Tyr Cys Ser
            165                 170                 175

Leu Phe Lys Asn Val Arg Leu Leu Lys Cys Val Ser Asp Ser Trp Leu
        180                 185                 190

Lys Asp Ser Ala Ile Met Val Ala Ser Asp Val Cys Lys Lys Asn Leu
    195                 200                 205

Asp Leu Phe Met Ser His Val Lys Ser Val Thr Lys Ser Ser Ser Trp
    210                 215                 220

Lys Asp Val Asn Ser Val Gln Phe Ser Ile Leu Asn Asn Pro Val Asp
225                 230                 235                 240

Thr Glu Phe Ile Asn Lys Phe Leu Glu Phe Ser Asn Arg Val Tyr Glu
            245                 250                 255

Ala Leu Tyr Tyr Val His Ser Leu Leu Tyr Ser Ser Met Thr Ser Asp
        260                 265                 270

Ser Lys Ser Ile Glu Asn Lys His Gln Arg Arg Leu Val Lys Leu Leu
    275                 280                 285

Leu Gly Pro Gly Gly Gly Ser Gly Gly Gly Ser Gly Gly Gly
290                 295                 300

Gly Ser Gly Gly Gly Ser Leu Glu Asn Thr Ile Asn Ile Ala Lys
305                 310                 315                 320

Asn Asp Phe Ser Asp Ile Glu Leu Ala Ala Ile Pro Phe Asn Thr Leu
            325                 330                 335

Ala Asp His Tyr Gly Glu Arg Leu Ala Arg Glu Gln Leu Ala Leu Glu
        340                 345                 350

His Glu Ser Tyr Glu Met Gly Glu Ala Arg Phe Arg Lys Met Phe Glu
    355                 360                 365

Arg Gln Leu Lys Ala Gly Glu Val Ala Asp Asn Ala Ala Lys Pro
370                 375                 380

Leu Ile Thr Thr Leu Leu Pro Lys Met Ile Ala Arg Ile Asn Asp Trp
385                 390                 395                 400

Phe Glu Glu Val Lys Ala Lys Arg Gly Lys Arg Pro Thr Ala Phe Gln
            405                 410                 415

Phe Leu Gln Glu Ile Lys Pro Glu Ala Val Ala Tyr Ile Thr Ile Lys
        420                 425                 430

Thr Thr Leu Ala Cys Leu Thr Ser Ala Asp Asn Thr Thr Val Gln Ala
    435                 440                 445

Val Ala Ser Ala Ile Gly Arg Ala Ile Glu Asp Glu Ala Arg Phe Gly
450                 455                 460

Arg Ile Arg Asp Leu Glu Ala Lys His Phe Lys Lys Asn Val Glu Glu
465                 470                 475                 480

Gln Leu Asn Lys Arg Val Gly His Val Tyr Lys Lys Ala Phe Met Gln
            485                 490                 495

Val Val Glu Ala Asp Met Leu Ser Lys Gly Leu Leu Gly Gly Glu Ala
        500                 505                 510

Trp Ser Ser Trp His Lys Glu Asp Ser Ile His Val Gly Val Arg Cys
    515                 520                 525

Ile Glu Met Leu Ile Glu Ser Thr Gly Met Val Ser Leu His Arg Gln
530                 535                 540

Asn Ala Gly Val Val Gly Gln Asp Ser Glu Thr Ile Glu Leu Ala Pro
545                 550                 555                 560

Glu Tyr Ala Glu Ala Ile Ala Thr Arg Ala Gly Ala Leu Ala Gly Ile
```

```
                565                 570                 575
Ser Pro Met Phe Gln Pro Cys Val Val Pro Lys Pro Trp Thr Gly
                580                 585                 590

Ile Thr Gly Gly Gly Tyr Trp Ala Asn Gly Arg Arg Pro Leu Ala Leu
                595                 600             605

Val Arg Thr His Ser Lys Lys Ala Leu Met Arg Tyr Glu Asp Val Tyr
610                 615                 620

Met Pro Glu Val Tyr Lys Ala Ile Asn Ile Ala Gln Asn Thr Ala Trp
625                 630                 635                 640

Lys Ile Asn Lys Lys Val Leu Ala Val Ala Asn Val Ile Thr Lys Trp
                645                 650                 655

Lys His Cys Pro Val Glu Asp Ile Pro Ala Ile Glu Arg Glu Glu Leu
                660                 665                 670

Pro Met Lys Pro Glu Asp Ile Asp Met Asn Pro Glu Ala Leu Thr Ala
                675                 680                 685

Trp Lys Arg Ala Ala Ala Val Tyr Arg Lys Asp Lys Ala Arg Lys
690                 695                 700

Ser Arg Arg Ile Ser Leu Glu Phe Met Leu Glu Gln Ala Asn Lys Phe
705                 710                 715                 720

Ala Asn His Lys Ala Ile Trp Phe Pro Tyr Asn Met Asp Trp Arg Gly
                725                 730                 735

Arg Val Tyr Ala Val Ser Met Phe Asn Pro Gln Gly Asn Asp Met Thr
                740                 745                 750

Lys Gly Leu Leu Thr Leu Ala Lys Gly Lys Pro Ile Gly Lys Glu Gly
                755                 760                 765

Tyr Tyr Trp Leu Lys Ile His Gly Ala Asn Cys Ala Gly Val Asp Lys
                770                 775                 780

Val Pro Phe Pro Glu Arg Ile Lys Phe Ile Glu Glu Asn His Glu Asn
785                 790                 795                 800

Ile Met Ala Cys Ala Lys Ser Pro Leu Glu Asn Thr Trp Trp Ala Glu
                805                 810                 815

Gln Asp Ser Pro Phe Cys Phe Leu Ala Phe Cys Phe Glu Tyr Ala Gly
                820                 825                 830

Val Gln His His Gly Leu Ser Tyr Asn Cys Ser Leu Pro Leu Ala Phe
                835                 840                 845

Asp Gly Ser Cys Ser Gly Ile Gln His Phe Ser Ala Met Leu Arg Asp
850                 855                 860

Glu Val Gly Gly Arg Ala Val Asn Leu Leu Pro Ser Glu Thr Val Gln
865                 870                 875                 880

Asp Ile Tyr Gly Ile Val Ala Lys Lys Val Asn Glu Ile Leu Gln Ala
                885                 890                 895

Asp Ala Ile Asn Gly Thr Asp Asn Glu Val Val Thr Val Thr Asp Glu
                900                 905                 910

Asn Thr Gly Glu Ile Ser Glu Lys Val Lys Leu Gly Thr Lys Ala Leu
                915                 920                 925

Ala Gly Gln Trp Leu Ala Tyr Gly Val Thr Arg Ser Val Thr Lys Arg
930                 935                 940

Ser Val Met Thr Leu Ala Tyr Gly Ser Lys Glu Phe Gly Phe Arg Gln
945                 950                 955                 960

Gln Val Leu Glu Asp Thr Ile Gln Pro Ala Ile Asp Ser Gly Lys Gly
                965                 970                 975

Leu Met Phe Thr Gln Pro Asn Gln Ala Ala Gly Tyr Met Ala Lys Leu
                980                 985                 990
```

```
Ile Trp Glu Ser Val Ser Val Thr Val Val Ala Ala Val Glu Ala Met
        995                 1000                    1005

Asn Trp Leu Lys Ser Ala Ala Lys Leu Leu Ala Ala Glu Val Lys
    1010                1015                1020

Asp Lys Lys Thr Gly Glu Ile Leu Arg Lys Arg Cys Ala Val His
    1025                1030                1035

Trp Val Thr Pro Asp Gly Phe Pro Val Trp Gln Glu Tyr Lys Lys
    1040                1045                1050

Pro Ile Gln Thr Arg Leu Asn Leu Met Phe Leu Gly Gln Phe Arg
    1055                1060                1065

Leu Gln Pro Thr Ile Asn Thr Asn Lys Asp Ser Glu Ile Asp Ala
    1070                1075                1080

His Lys Gln Glu Ser Gly Ile Ala Pro Asn Phe Val His Ser Gln
    1085                1090                1095

Asp Gly Ser His Leu Arg Lys Thr Val Val Trp Ala His Glu Lys
    1100                1105                1110

Tyr Gly Ile Glu Ser Phe Ala Leu Ile His Asp Ser Phe Gly Thr
    1115                1120                1125

Ile Pro Ala Asp Ala Ala Asn Leu Phe Lys Ala Val Arg Glu Thr
    1130                1135                1140

Met Val Asp Thr Tyr Glu Ser Cys Asp Val Leu Ala Asp Phe Tyr
    1145                1150                1155

Asp Gln Phe Ala Asp Gln Leu His Glu Ser Gln Leu Asp Lys Met
    1160                1165                1170

Pro Ala Leu Pro Ala Lys Gly Asn Leu Asn Leu Arg Asp Ile Leu
    1175                1180                1185

Glu Ser Asp Phe Ala Phe Ala
    1190                1195

<210> SEQ ID NO 43
<211> LENGTH: 21
<212> TYPE: DNA
<213> ORGANISM: Artificial
<220> FEATURE:
<223> OTHER INFORMATION: SI04364381

<400> SEQUENCE: 43
cagcggttga agggcaagga a                                         21

<210> SEQ ID NO 44
<211> LENGTH: 21
<212> TYPE: DNA
<213> ORGANISM: Artificial
<220> FEATURE:
<223> OTHER INFORMATION: SI04369344

<400> SEQUENCE: 44
atgcggaatg gaagcacgtt a                                         21

<210> SEQ ID NO 45
<211> LENGTH: 21
<212> TYPE: DNA
<213> ORGANISM: Artificial
<220> FEATURE:
<223> OTHER INFORMATION: SI04250162

<400> SEQUENCE: 45
atggtcgtgt ccggagctaa a                                         21
```

```
<210> SEQ ID NO 46
<211> LENGTH: 21
<212> TYPE: DNA
<213> ORGANISM: Artificial
<220> FEATURE:
<223> OTHER INFORMATION: SI04354420

<400> SEQUENCE: 46
cagcggcttc agcccaggtt a                                              21

<210> SEQ ID NO 47
<211> LENGTH: 21
<212> TYPE: DNA
<213> ORGANISM: Artificial
<220> FEATURE:
<223> OTHER INFORMATION: SI00055986

<400> SEQUENCE: 47
atggatttaa agggcggcta a                                              21

<210> SEQ ID NO 48
<211> LENGTH: 21
<212> TYPE: DNA
<213> ORGANISM: Artificial
<220> FEATURE:
<223> OTHER INFORMATION: SI03021508

<400> SEQUENCE: 48
ttcaaggttc tatgaccgaa a                                              21

<210> SEQ ID NO 49
<211> LENGTH: 21
<212> TYPE: DNA
<213> ORGANISM: Artificial
<220> FEATURE:
<223> OTHER INFORMATION: SI00055972

<400> SEQUENCE: 49
cagggttgtt aagttgtact a                                              21

<210> SEQ ID NO 50
<211> LENGTH: 21
<212> TYPE: DNA
<213> ORGANISM: Artificial
<220> FEATURE:
<223> OTHER INFORMATION: SI00055979

<400> SEQUENCE: 50
taccatctgc agtattataa a                                              21

<210> SEQ ID NO 51
<211> LENGTH: 47
<212> TYPE: PRT
<213> ORGANISM: artificial sequence
<220> FEATURE:
<223> OTHER INFORMATION: acidic leucine zipper

<400> SEQUENCE: 51

Leu Glu Ile Glu Ala Ala Phe Leu Glu Gln Glu Asn Thr Ala Leu Glu
1               5                   10                  15

Thr Glu Val Ala Glu Leu Glu Gln Glu Val Gln Arg Leu Glu Asn Ile
            20                  25                  30

Val Ser Gln Tyr Glu Thr Arg Tyr Gly Pro Leu Gly Gly Gly Lys
        35                  40                  45
```

```
<210> SEQ ID NO 52
<211> LENGTH: 47
<212> TYPE: PRT
<213> ORGANISM: artificial sequence
<220> FEATURE:
<223> OTHER INFORMATION: leucine zipper

<400> SEQUENCE: 52

Leu Glu Ile Arg Ala Ala Phe Leu Arg Arg Arg Asn Thr Ala Leu Arg
1               5                   10                  15

Thr Arg Val Ala Glu Leu Arg Gln Arg Val Gln Arg Leu Arg Asn Ile
            20                  25                  30

Val Ser Gln Tyr Glu Thr Arg Tyr Gly Pro Leu Gly Gly Gly Lys
        35                  40                  45
```